US012630531B2

(12) United States Patent
Hwang et al.

(10) Patent No.: US 12,630,531 B2
(45) Date of Patent: May 19, 2026

(54) QUINAZOLINE-2,4-DIAMINE DERIVATIVE AND PHARMACEUTICAL COMPOSITION FOR PREVENTING OR TREATING CANCER COMPRISING SAME AS ACTIVE INGREDIENT

(71) Applicant: OMIC Smap Inc., Seoul (KR)

(72) Inventors: Jung Jin Hwang, Seoul (KR); Sang Eun Park, Seoul (KR); Dong Eun Kim, Seoul (KR); Ji-Ye Hong, Seoul (KR); Choung-Soo Kim, Seoul (KR); Woo Chan Son, Seoul (KR); Shinae Kim, Daegu (KR); Sugyeong Kwon, Daegu (KR); Kyungjin Jung, Daegu (KR); Nayeon Kim, Daegu (KR); Jina Kim, Daegu (KR); Kyung-Hee Kim, Daegu (KR); Jung Wook Chin, Daegu (KR); Sung Jin Cho, Daegu (KR); Sehan Lee, Daegu (KR); Eunju Cha, Daegu (KR); Jeongmin Joo, Daegu (KR); Ji Sun Hwang, Daegu (KR); Jeong-Eun Park, Daegu (KR); Ji Hoon Yu, Daegu (KR); Eunmi Hong, Daegu (KR); Young-Hoon Park, Daegu (KR); Ju-Hee Lee, Daegu (KR)

(73) Assignee: OMIC Smap Inc., Seoul (KR)

( * ) Notice: Subject to any disclaimer, the term of this patent is extended or adjusted under 35 U.S.C. 154(b) by 469 days.

(21) Appl. No.: 18/246,178

(22) PCT Filed: Sep. 16, 2021

(86) PCT No.: PCT/KR2021/012661
§ 371 (c)(1),
(2) Date: Mar. 21, 2023

(87) PCT Pub. No.: WO2022/060114
PCT Pub. Date: Mar. 24, 2022

(65) Prior Publication Data

US 2023/0365530 A1 Nov. 16, 2023

(30) Foreign Application Priority Data

Sep. 21, 2020 (KR) ........................ 10-2020-0121587

(51) Int. Cl.
*C07D 401/14* (2006.01)
*A61K 45/06* (2006.01)
*A61P 35/00* (2006.01)
*C07D 239/95* (2006.01)
*C07D 401/12* (2006.01)

(52) U.S. Cl.
CPC ............ *C07D 401/14* (2013.01); *A61K 45/06* (2013.01); *A61P 35/00* (2018.01); *C07D 239/95* (2013.01); *C07D 401/12* (2013.01)

(58) Field of Classification Search
CPC .. C07D 401/14; C07D 239/95; C07D 401/12; A61K 45/06
See application file for complete search history.

(56) References Cited

U.S. PATENT DOCUMENTS

2003/0181472 A1 9/2003 Clark et al.
2020/0054635 A1* 2/2020 Campbell et al.

FOREIGN PATENT DOCUMENTS

EP 4192826 A1 6/2023
WO WO 2022/031939 A1 2/2022
WO 2022/204683 A1 9/2022

OTHER PUBLICATIONS

Leenders et al. (Bioorganic and Medicinal Chemistry Letters 2019, 29: 2516-2524) (Year: 2019).*

(Continued)

*Primary Examiner* — Brandon J Fetterolf
(74) *Attorney, Agent, or Firm* — Klarquist Sparkman, LLP

(57) ABSTRACT

A compound, a stereoisomer thereof, a hydrate thereof, or a pharmaceutically acceptable salt thereof, provided as one (Continued)

aspect of the present invention, exhibits a high inhibitory ability on euchromatic histone-lysine N-methyltransferase 2 (EHMT2), and thus, the compound can be usefully used for the treatment of cancer.

14 Claims, 2 Drawing Sheets

(56) References Cited

OTHER PUBLICATIONS

Kim et al., "BIX-01294 induces autophagy-associated cell death via EHMT2/G9a dysfunction and intracellular reactive oxygen species production", Autophagy, Dec. 2013, vol. 9, Issue 12, pp. 2126-2139.
Krivega et al., "Inhibition of G9a methyltransferase stimulates fetal hemoglobin production by facilitating LCR/?-globin looping", Blood, May 15, 2015, vol. 126, Issue 5, pp. 26.
Leenders et al., "Novel SAR for quinazoline inhibitors of EHMT1 and EHMT2", Bioorganic & Medicinal Chemistry Letters, vol. 29, Jun. 14, 2019, pp. 2516-2524.
Liu et al., "Discovery of an in Vivo Chemical Probe of the Lysine Methyltransferases G9a and GLP", J. Med. Chem., Oct. 8, 2013, vol. 56, Issue 21, pp. 8931-8942.
Park et al., "Inhibition of EHMT2/G9a epigenetically increases the transcription of Beclin-1 via an increase in ROS and activation of NF-?B", Oncotarget, May 11, 2016, vol. 7, Issue 26, pp. 39796-39808.

* cited by examiner

QUINAZOLINE-2,4-DIAMINE DERIVATIVE AND PHARMACEUTICAL COMPOSITION FOR PREVENTING OR TREATING CANCER COMPRISING SAME AS ACTIVE INGREDIENT

CROSS REFERENCE TO RELATED APPLICATIONS

This patent application is a nationalization of and claims priority to PCT Application No. PCT/KR2021/012661 filed on Sep. 16, 2021, which claims priority under 35 U.S.C. § 119 from Korean Patent Application 10-2020-0121587 filed on Sep. 21, 2020. Each of the aforementioned applications are incorporated by reference herein in their entirety.

BACKGROUND OF THE INVENTION

1. Field of the Invention

The present invention relates to a quinazoline-2,4-diamine derivative and a pharmaceutical composition for preventing or treating cancer comprising the same as an active ingredient.

2. Description of the Related Art

Methylation of protein lysine residues is an important signaling mechanism in eukaryotic cells, and the methylation status of histone lysines encodes the signals recognized by a number of proteins and protein complexes in the context of epigenetic regulation.

Histone methylation is catalyzed by histone methyltransferase (HMT), which is involved in a variety of human diseases. HMT can play a role in activating or inhibiting gene expression, and certain HMT (e.g., euchromatin histone-lysine N-methyltransferase 2 or EHMT2, also known as G9a) can methylate many nonhistone proteins, such as tumor suppressor proteins (Liu et al., Journal of Medicinal Chemistry 56:8931-8942, 2013 and Krivega et al., Blood 126(5):665-672, 2015).

Researches on substances to control the cause of cancer through inhibition of EHMT2/G9a are being conducted, as researches have revealed that EHMT2/G9a inhibits the expression of tumor-suppressing genes through autophagy, the action of eating the cell's own unnecessary substances (Sang Eun Park et al., 2016, Inhibition of EHMT2/G9a epigenetically increases the transcription of Beclin-1 via an increase in ROS and activation of NF-κB; Yunha Kim et al., 2013, BIX-01294 induces autophagy-associated cell death via EHMT2/G9a dysfunction and intracellular reactive oxygen species production).

SUMMARY OF THE INVENTION

It is an object of the present invention to provide a novel quinazoline-2,4-diamine derivative compound, a stereoisomer thereof, a hydrate thereof, or a pharmaceutically acceptable salt thereof.

It is another object of the present invention to provide a method for preparing the novel quinazoline-2,4-diamine derivative compound and the stereoisomer thereof.

It is another object of the present invention to provide a pharmaceutical composition for preventing or treating cancer comprising the compound, the stereoisomer thereof, the hydrate thereof, or the pharmaceutically acceptable salt thereof as an active ingredient.

It is another object of the present invention to provide a health functional food for preventing or ameliorating cancer comprising the compound, the stereoisomer thereof, the hydrate thereof, or the pharmaceutically acceptable salt thereof as an active ingredient.

It is another object of the present invention to provide a method for treating cancer comprising a step of administering the compound, the stereoisomer thereof, the hydrate thereof, or the pharmaceutically acceptable salt thereof to a subject in need.

It is another object of the present invention to provide the compound, the stereoisomer thereof, the hydrate thereof, or the pharmaceutically acceptable salt thereof for use in the treatment of cancer.

It is another object of the present invention to provide a use of the compound, the stereoisomer thereof, the hydrate thereof, or the pharmaceutically acceptable salt thereof for the preparation of a medicament for treating cancer.

To achieve the above objects, the present invention provides a compound represented by formula 1, a stereoisomer thereof, a hydrate thereof, or a pharmaceutically acceptable salt thereof:

[Formula 1]

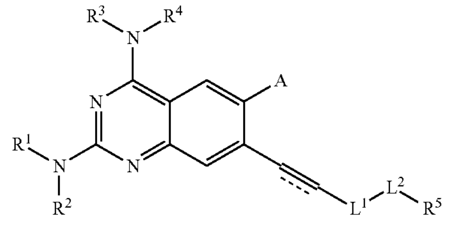

In formula 1 above,

 is a double bond or a triple bond;

$R^1$ and $R^2$ are independently hydrogen, straight or branched $C_{1-10}$ alkyl, straight or branched $C_{1-10}$ alkoxycarbonyl straight or branched $C_{1-5}$ alkyl, nonsubstituted or substituted 3-8 membered heteroaryl containing one or more heteroatoms selected from the group consisting of N, O and S, or $R^1$ and $R^2$ form nonsubstituted or substituted 3-12 membered heterocycloalkyl containing one or more heteroatoms selected from the group consisting of N, O and S along with nitrogen atom to which they are attached;

$R^3$ is hydrogen, straight or branched $C_{1-10}$ alkyl, nonsubstituted or substituted $C_{3-10}$ cycloalkyl, nonsubstituted or substituted 3-10 membered heterocycloalkyl containing one or more heteroatoms selected from the group consisting of N, O and S, nonsubstituted or substituted 3-10 membered heterocycloalkyl straight or branched 의 $C_{1-5}$ alkyl containing one or more heteroatoms selected from the group consisting of N, O and S, straight or branched di$C_{1-5}$alkylamino straight or branched $C_{1-5}$ alkyl, or nonsubstituted or substituted 3-8 membered heteroaryl straight or branched $C_{1-5}$ alkyl containing one or more heteroatoms selected from the group consisting of N, O and S;

$R^4$ is hydrogen, or straight or branched $C_{1-5}$ alkyl;

$R^5$ is straight or branched di$C_{1-5}$alkylamino, or nonsubstituted or substituted 3-10 membered heterocycloalkyl containing one or more heteroatoms selected from the group consisting of N, O and S; the substituted heterocycloalkyl, cycloalkyl or heteroaryl can be substituted with one or more substituents selected from the group consisting of —OH, —$NH_2$, —$NO_2$, halogen, straight or branched $C_{1-10}$ alkyl, straight or branched $C_{1-5}$ alkoxy, straight or branched di$C_{1-5}$alkylamino, straight or branched 의 $C_{1-5}$ haloalkyl, straight or branched $C_{1-5}$ aminoalkyl, $C_{3-8}$ cycloalkyl, $C_{6-10}$ aryl, $C_{6-8}$ aryl straight or branched $C_{1-3}$ alkyl, and straight or branched 의 $C_{1-s}$ hydroxyalkyl;

A is hydrogen, or straight or branched $C_{1-5}$ alkoxy;

$L^1$ is straight or branched $C_{1-5}$ alkyl;

$L^2$ is a bond, —C(═O)—, or —$SO_2$—.

The present invention also provides a method for preparing the compound, the stereoisomer thereof, the hydrate thereof, or the pharmaceutically acceptable salt thereof The present invention also provides a pharmaceutical composition for preventing or treating cancer comprising the compound, the stereoisomer thereof, the hydrate thereof, or the pharmaceutically acceptable salt thereof as an active ingredient.

The present invention also provides a health functional food for preventing or ameliorating cancer comprising the compound, the stereoisomer thereof, the hydrate thereof, or the pharmaceutically acceptable salt thereof as an active ingredient.

The present invention also provides a method for treating cancer comprising a step of administering the compound, the stereoisomer thereof, the hydrate thereof, or the pharmaceutically acceptable salt thereof to a subject in need.

The present invention also provides the compound, the stereoisomer thereof, the hydrate thereof, or the pharmaceutically acceptable salt thereof for use in the treatment of cancer.

In addition, the present invention provides a use of the compound, the stereoisomer thereof, the hydrate thereof, or the pharmaceutically acceptable salt thereof for the preparation of a medicament for treating cancer.

Advantageous Effect

A compound, a stereoisomer thereof, a hydrate thereof, or a pharmaceutically acceptable salt thereof, provided as one aspect of the present invention, exhibits a high inhibitory ability on euchromatic histone-lysine N-methyltransferase 2 (EHMT2), and thus, the compound can be usefully used for the treatment of cancer.

DESCRIPTION OF THE PREFERRED EMBODIMENTS

Figure 1:
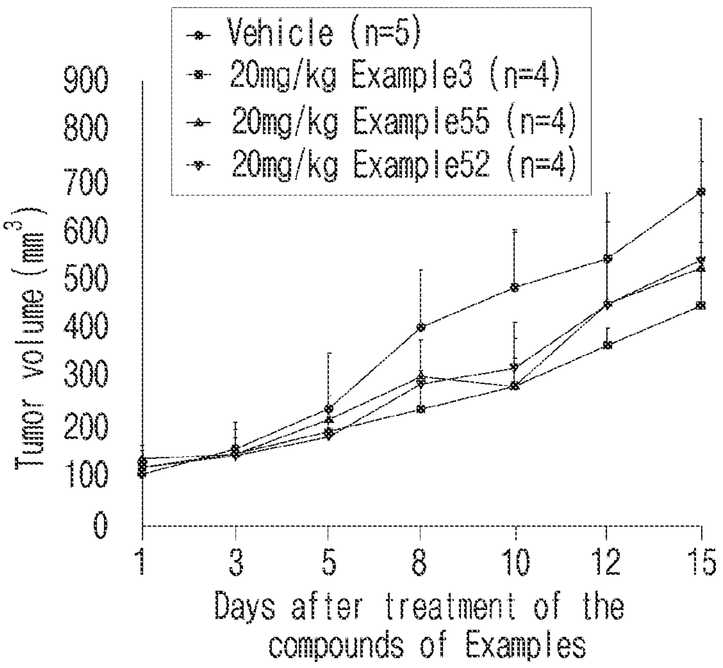
FIG. 1 is a graph showing the results of measuring tumor growth through tumor volume in the Miapaca2 xenograft model.

Hereinafter, the present invention is described in detail.

The present invention provides a compound represented by formula 1, a stereoisomer thereof, a hydrate thereof, or a pharmaceutically acceptable salt thereof:

[Formula 1]

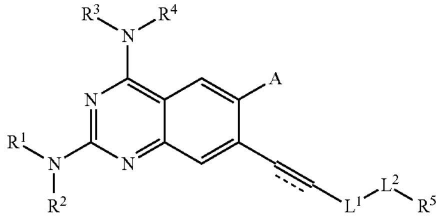

In formula 1 above,

≡ is a double bond or a triple bond;

$R^1$ and $R^2$ are independently hydrogen, straight or branched $C_{1-10}$ alkyl, straight or branched $C_{1-10}$ alkoxycarbonyl straight or branched $C_{1-5}$ alkyl, nonsubstituted or substituted 3-8 membered heteroaryl containing one or more heteroatoms selected from the group consisting of N, O and S, or $R^1$ and $R^2$ form nonsubstituted or substituted 3-12 membered heterocycloalkyl containing one or more heteroatoms selected from the group consisting of N, O and S along with nitrogen atom to which they are attached;

$R^3$ is hydrogen, straight or branched $C_{1-10}$ alkyl, nonsubstituted or substituted $C_{3-10}$ cycloalkyl, nonsubstituted or substituted 3-10 membered heterocycloalkyl containing one or more heteroatoms selected from the group consisting of N, O and S, nonsubstituted or substituted 3-10 membered heterocycloalkyl straight or branched 의 $C_{1-5}$ alkyl containing one or more heteroatoms selected from the group consisting of N, O and S, straight or branched di$C_{1-5}$alkylamino straight or branched $C_{1-5}$ alkyl, or nonsubstituted or substituted 3-8 membered heteroaryl straight or branched $C_{1-5}$ alkyl containing one or more heteroatoms selected from the group consisting of N, O and S;

$R^4$ is hydrogen, or straight or branched $C_{1-5}$ alkyl;

$R^5$ is straight or branched di$C_{1-5}$alkylamino, or nonsubstituted or substituted 3-10 membered heterocycloalkyl containing one or more heteroatoms selected from the group consisting of N, O and S;

the substituted heterocycloalkyl, cycloalkyl or heteroaryl can be substituted with one or more substituents selected from the group consisting of —OH, —$NH_2$, —$NO_2$, halogen, straight or branched $C_{1-10}$ alkyl, straight or branched $C_{1-5}$ alkoxy, straight or branched di$C_{1-5}$alkylamino, straight or branched 의 $C_{1-5}$ haloalkyl, straight or branched $C_{1-5}$ aminoalkyl, $C_{3-8}$ cycloalkyl, $C_{6-10}$ aryl, $C_{6-8}$ aryl straight or branched $C_{1-3}$ alkyl, and straight or branched 의 $C_{1-5}$ hydroxyalkyl; A is hydrogen, or straight or branched $C_{1-5}$ alkoxy;

$L^1$ is straight or branched $C_{1-5}$ alkyl; and $L^2$ is a bond, —C(═O)—, or —$SO_2$—.

At this time, $R^1$ and $R^2$ are independently hydrogen, straight or branched $C_{1-5}$ alkyl, straight or branched $C_{1-5}$ alkoxycarbonyl straight or branched $C_{1-3}$ alkyl, nonsubstituted or substituted 5 or 6 membered heteroaryl containing one or more heteroatoms selected from the group consisting of N, O and S, or $R^1$ and $R^2$ form nonsubstituted or substituted 3-9 membered heterocycloalkyl containing one or more heteroatoms selected from the group consisting of N, O and S along with nitrogen atom to which they are attached;

$R^3$ is hydrogen, straight or branched $C_{1-5}$ alkyl, nonsubstituted or substituted $C_{5-7}$ cycloalkyl, nonsubstituted or substituted 5-7 membered heterocycloalkyl containing one or more heteroatoms selected from the group consisting of N, O and S, nonsubstituted or substituted 5-7 membered heterocycloalkyl straight or branched 의 d $C_{1-3}$ alkyl containing one or more heteroatoms selected from the group consisting of N, O and S, straight or branched di$C_{1-3}$alkylamino straight or branched $C_{1-3}$ alkyl, or nonsubstituted or substituted 5-8 membered heteroaryl straight or branched $C_{1-3}$ alkyl containing one or more heteroatoms selected from the group consisting of N, O and S;

$R^4$ is hydrogen, or straight or branched $C_{1-3}$ alkyl;

$R^5$ is straight or branched di$C_{1-3}$alkylamino, or nonsubstituted or substituted 3-7 membered heterocycloalkyl containing one or more heteroatoms selected from the group consisting of N, O and S;

the substituted heterocycloalkyl, cycloalkyl or heteroaryl can be substituted with one or more substituents selected from the group consisting of —OH, —$NH_2$, —$NO_2$, halogen, straight or branched $C_{1-10}$ alkyl, straight or branched $C_{1-5}$ alkoxy, straight or branched di$C_{1-5}$alkylamino, straight or branched 의 $C_{1-5}$ haloalkyl, straight or branched $C_{1-5}$ aminoalkyl, $C_{3-8}$ cycloalkyl, $C_{6-10}$ aryl, $C_{6-8}$ aryl straight or branched $C_{1-3}$ alkyl, and straight or branched 의 $C_{1-5}$ hydroxyalkyl;

A is hydrogen, or straight or branched $C_{1-5}$ alkoxy;

$L^1$ is straight or branched $C_{1-3}$ alkyl; and $L^2$ is a bond, or —C(=O)—.

At this time, $R^1$ and $R^2$ are independently hydrogen, —$CH_3$, —$CH_2COOC(CH_3)_3$ or

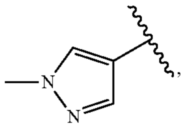, or 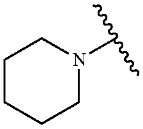,

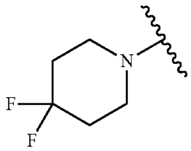, 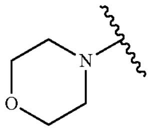,

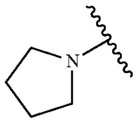, 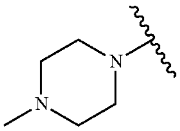,

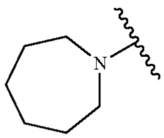, 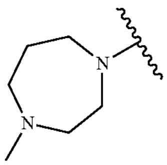,

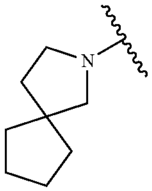, 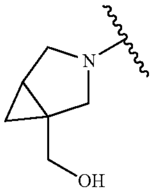,

-continued

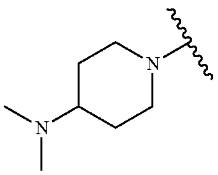, 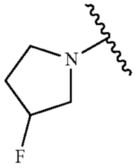,

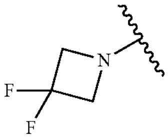 or 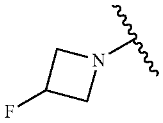

along with nitrogen atom to which they are attached;

$R^3$ is —$CH_3$,

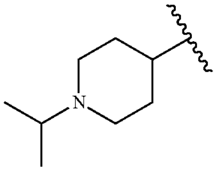, 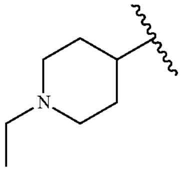,

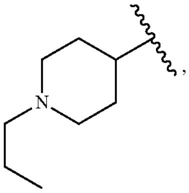, 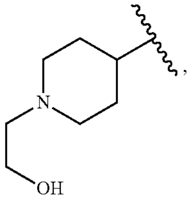,

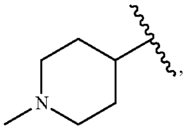, 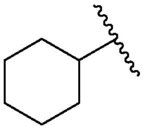,

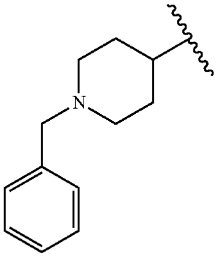, 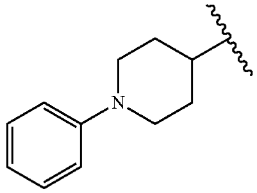,

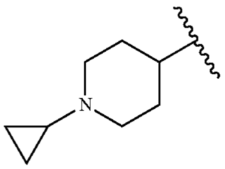, 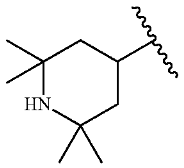,

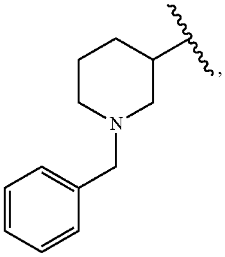, 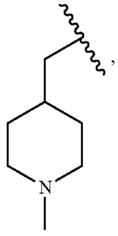, 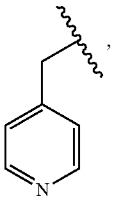,

-continued

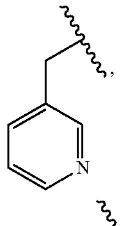, 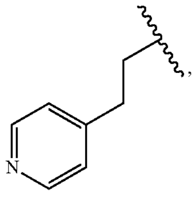, 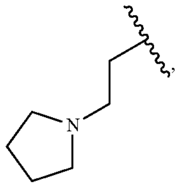,

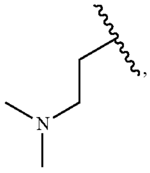, or 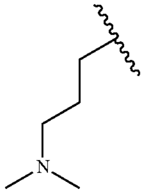;

$R^4$ is hydrogen;

$R^5$ is $-N(CH_3)_2$, $-N(CH_2CH_3)_2$,

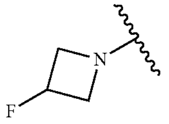, 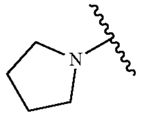,

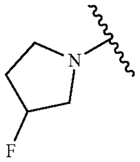, 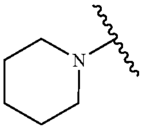, or

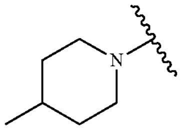;

A is $-OCH_3$;

$L^1$ is $-(CH_2CH_2)$; and $L^2$ can be a bond, or $-C(=O)-$.

At this time, the compound represented by formula 1 can be any one compound selected from group consisting of the following compounds.

(1) 5-(4-((1-isopropylpiperidine-4-yl)amino)-6-methoxy-2-(piperidine-1-yl)quinazoline-7-yl)-N,N-dimethylpentyne-4-amide;

(2) 5-(4-((1-isopropylpiperidine-4-yl)amino)-6-methoxy-2-(piperidine-1-yl)quinazoline-7-yl)-1-(pyrrolidine-1-yl)4-pentyne-1-one;

(3) 7-(4-(dimethylamino)-1-butyne-1-yl)-N-(1-isopropylpiperidine-4-yl)-6-methoxy-2-(piperidine-1-yl)quinazoline-4-amine;

(4) 2-(4,4-difluoropiperidine-1-yl)-7-(4-dimethylamino)-1-butyne-1-yl)-N-(1-isopropylpiperidine-4-yl)-6-methoxyquinazoline-4-amine;

(5) 7-(4-(dimethylamino)-1-butyne-1-yl)-N-(1-isopropylpiperidine-4-yl)-6-methoxy-2-morpholinoquinazoline-4-amine;

(6) 7-(4-(dimethylamino)-1-butyne-1-yl)-N-(2-isopropylpiperidine-4-yl)-6-methoxy-2-(pyrrolidine-1-yl)quinazoline-4-amine;

(7) 7-(4-(dimethylamino)-1-butyne-1-yl)-N-(1-isopropylpiperidine-4-yl)quinazoline-4-amine;

(8) 2-(azepane-1-yl)-7-(4-(dimethylamino)-1-butyne-1-yl)-N-(1-isopropylpiperidine-4-yl)-6-methoxyquinazoline-4-amine;

(9) 7-(4-(dimethylamino)-1-butyne-1-yl)-N-(1-isopropylpiperidine-4-yl)-6-(methoxy-2-(2-azaspiro[4.4]nonane-2-yl)quinazoline-4-amine;

(10) ((1S,2R,5R)-3-(7-(4-(dimethylamino)-1-butyne-1-yl)-4-((1-isopropylpiperidine-4-yl)amino)-6-methoxyquinazoline-2-yl)-3-azabicyclo[3.1.0]hexane-2-yl)methanol;

(11) 7-(4-(dimethylamino)-1-butyne-1-yl)-2-(4-(dimethylamino)piperidine-1-yl)-N-(1-isopropylpiperidine-4-yl)-6-methoxyquinazoline-4-amine;

(12) N-(1-isopropylpiperidine-4-yl)-6-methoxy-2-(piperidine-1-yl)-7-(4-(piperidine-1-yl)-1-butyne-1-yl)quinazoline-4-amine;

(13) 7-(4-(diethylamino)-1-butyne-1-yl)-N-(1-isopropylpiperidine-4-yl)-6-methoxy-2-(piperidine-1-yl)quinazoline-4-amine;

(14) 7-(4-dimethylamino)-1-butyne-1-yl)-N4-(1-isopropylpiperidine-4-yl)-6-methoxy-N2,N2-dimethylquinazoline-2,4-diamine;

(15) N-(1-isopropylpiperidine-4-yl)-6-methoxy-7-(4-(4-methylpiperidine-1-yl)-1-butyne-1-yl)-2-(piperidine-1-yl)quinazoline-4-amine;

(16) N-(1-isopropylpiperidine-4-yl)-6-methoxy-2-(piperidine-1-yl)-7-(4-(pyrrolidine-1-yl)-1-butyne-1-yl)quinazoline-4-amine;

(17) 7-(4-(dimethylamino)-1-butyne-1-yl)-N-(1-isopropylpiperidine-4-yl)-6-methoxy-2-(4-methyl-1,4-diazepane-1-yl)quinazoline-4-amine;

(18) N-(1-benzylpiperidine-4-yl)-7-(4-(dimethylamino)-1-butyne-1-yl)-6-methoxy-2-(piperidine-1-yl)quinazoline-4-amine;

(19) (R)—N-(1-benzylpiperidine-3-yl)-7-(4-(dimethylamino)-1-butyne-1-yl)-6-methoxy-2-(piperidine-1-yl) quinazoline-4-amine;

(20) 7-(4-(dimethylamino)-1-butyne-1-yl)-6-methoxy-2-(piperidine-1-yl)-N-(2-(pyrrolidine-1-yl)ethyl)quinazoline-4-amine;

(21) N1-(7-(4-(dimethylamino)-1-butyne-1-yl)-6-methoxy-2-(piperidine-1-yl)quinazoline-4-yl)-N3,N3-dimethylpropane-1,3-diamine;

(22) 7-(4-(dimethylamino)-1-butyne-1-yl)-6-methoxy-N-(1-methylpiperidine-4-yl)-2-(piperidine-1-yl)quinazoline-4-amine;

(23) N-cyclohexyl-7-(4-(dimethylamino)-1-butyne-1-yl)-6-methoxy-2-(piperidine-1-yl)quinazoline-4-amine;

(24) N-(1-cyclopropylpiperidine-4-yl)-7-(4-(dimethylamino)-1-butyne-1-yl)-6-methoxy-2-(piperidine-1-yl) quinazoline-4-amine;

(25) 7-(4-(dimethylamino)-1-butyne-1-yl)-6-methoxy-N-(1-phenylpiperidine-4-yl)-2-(piperidine-1-yl)quinazoline-4-amine;

(26) 7-(4-(dimethylamino)-1-butyne-1-yl)-6-methoxy-2-(piperidine-1-yl)-N-(pyridine-3-ylmethyl)quinazoline-4-amine;

(27) 7-(4-(dimethylamino)-1-butyne-1-yl)-6-methoxy-2-(piperidine-1-yl)-N-(2,2,6,6,-tetramethylpiperidine-4-yl) quinazoline-4-amine;

(28) N1-(7-(4-(dimethylamino)-1-butyne-1-yl)-6-methoxy-2-(piperidine-1-yl)quinazoline-4-yl)-N2,N2-dimethylethane-1,2-diamine;

(29) (S)-7-(4-(3-fluoropyrrolidine-1-yl)-1-butyne-1-yl)-N-(1-isopropylpiperidine-4-yl)-6-methoxy-2-(piperidine-1-yl)quinazoline-4-amine;

(30) (R)-7-(4-(3-fluoropyrrolidine-1-yl)-1-butyne-1-yl)-N-(1-isopropylpiperidine-4-yl)-6-methoxy-2-(piperidine-1-yl)quinazoline-4-amine;

(31) 7-(4-(dimethylamino)-1-butyne-1-yl)-6-methoxy-N-((1-methylpiperidine-4-yl)methyl)-2-(piperidine-1-yl)quinazoline-4-amine;

(32) 7-(4-(dimethylamino)-1-butyne-1-yl)-6-methoxy-2-(piperidine-1-yl)-N-(pyridine-4-ylmethyl)quinazoline-4-amine;

(33) 7-(4-(3-fluoroazetidine-1-yl)-1-butyne-1-yl)-N-(1-isopropylpiperidine-4-yl)-6-methoxy-2-(piperidine-1-yl)quinazoline-4-amine;

(34) 7-(4-(dimethylamino)-1-butyne-1-yl)-6-methoxy-2-(piperidine-1-yl)-N-(2-pyridine-4-yl)ethyl)quinazoline-4-amine;

(35) 2-(4,4-difluoropiperidine-1-yl)-N-(1-isopropylpiperidine-4-yl)-6-methoxy-7-(4-(pyrrolidine-1-yl)-1-butyne-1-yl)quinazoline-4-amine;

(36) 2-(azepane-1-yl)-N-(1-isopropylpiperidine-4-yl)-6-methoxy-7-(4-pyrrolidine-1-yl)-1-butyne-1-yl)quinazoline-4-amine;

(37) 2-(azepane-1-yl)-N-(1-isopropylpiperidine-4-yl)-6-methoxy-7-(4-(piperidine-1-yl)-1-butyne-1-yl)quinazoline-4-amine;

(38) N-(1-isopropylpiperidine-4-yl)-6-methoxy-2-(4-methylpiperazine-1-yl)-7-(4-(pyrrolidine-1-yl)-1-butyne-1-yl)quinazoline-4-amine;

(39) N-(1-Disopropylpiperidine-4-yl)-6-methoxy-2-(4-methylpiperazine-1-yl)-7-(4-(piperidine-1-yl)-1-butyne-1-yl)quinazoline-4-amine;

(40) N-(1-isopropylpiperidine-4-yl)-6-methoxy-7-(4-(pyrrolidine-1-yl)-1-butyne-1-yl)-2-(2-azaspiro[4.4]nonane-2-yl)quinazoline-4-amine;

(41) N-(1-isopropylpiperidine-4-yl)-6-methoxy-7-(4-(piperidine-1-yl)-1-butyne-1-yl)-2-(2-azaspiro[4.4]nonane-2-yl)quinazoline-4-amine;

(42) N-(1-isopropylpiperidine-4-yl)-6-methoxy-2-(pyrrolidine-1-yl)-7-(4-(pyrrolidine-1-yl)-1-butyne-1-yl)quinazoline-4-amine;

(43) N-(1-isopropylpiperidine-4-yl)-6-methoxy-7-(4-(piperidine-1-yl)-1-butyne-1-yl)-2-(pyrrolidine-1-yl)quinazoline-4-amine;

(44) N-(1-isopropylpiperidine-4-yl)-6-methoxy-N2,N2-dimethyl-7-(4-(piperidine-1-yl)-1-butyne-1-yl)quinazoline-2,4-diamine;

(45) N-(1-isopropylpiperidine-4-yl)-6-methoxy-2-(4-methyl1,4-diazepane-1-yl)-7-(4-(piperidine-1-yl)-1-butyne-1-yl)quinazoline-4-amine;

(46) ((1S,2R,5R)-3-(4-((1-isopropylpiperidine-4-yl)amino)-6-methoxy-7-(4-(pyrrolidine-1-yl)-1-butyne-1-yl)quinazoline-2-yl)-3-azabicyclo[3.1.0]hexane-2-yl)methanol;

(47) ((1S,2R,5R)-3-(4-((1-isopropylpiperidine-4-yl)amino)-6-methoxy-7-(4-(piperidine-1-yl)-1-butyne-1-yl)quinazoline-2-yl)-3-azabicyclo[3.1.0]hexane-2-yl)methanol;

(48) N-(1-isopropylpiperidine-4-yl)-6-methoxy-2-(4-methyl-1,4-diazepane-1-yl)-7-(4-(pyrrolidine-1-yl)-1-butyne-1-yl)quinazoline-4-amine;

(49) N4-(1-isopropylpiperidine-4-yl)-6-methoxy-N2,N2-dimethyl-7-(4-(pyrrolidine-1-yl)-1-butyne-1-yl)quinazoline-2,4-diamine;

(50) 7-(4-(dimethylamino)-1-butyne-1-yl)-N-(1-ethylpiperidine-4-yl)-6-methoxy-2-(piperidine-1-yl)quinazoline-4-amine;

(51) N-(1-ethylpiperidine-4-yl)-6-methoxy-2-(piperidine-1-yl)-7-(4-(pyrrolidine-1-yl)-1-butyne-1-yl)quinazoline-4-amine;

(52) N1-(6-methoxy-2-(pyrrolidine-1-yl)-7-(4-(pyrrolidine-1-yl)-1-butyne-1-yl)quinazoline-4-yl)-N2,N2-dimethylethane-1,2-diamine;

(53) N-(1-cyclopropylpiperidine-4-yl)-6-methoxy-2-(piperidine-1-yl)-7-(4-(pyrrolidine-1-yl)-1-butyne-1-yl)quinazoline-4-amine;

(54) N-(1-cyclopropylpiperidine-4-yl)-6-methoxy-2-(pyrrolidine-1-yl)-7-(4-(pyrrolidine-1-yl)-1-butyne-1-yl)quinazoline-4-amine;

(55) N4-(1-cyclopropylpiperidine-4-yl)-6-methoxy-N2,N2-dimethyl-7-(4-(pyrrolidine-1-yl)-1-butyne-1-yl)quinazoline-2,4-diamine;

(56) N-(1-cyclopropylpiperidine-4-yl)-6-methoxy-2-(4-methyl-1,4-diazepane-1-yl)-7-(4-(pyrrolidine-1-yl)-1-butyne-1-yl)quinazoline-4-amine;

(57) (S)-2-(3-fluoropyrrolidine-1-yl)-N-(1-isopropylpiperidine-4-yl)-6-methoxy-7-(4-(pyrrolidine-1-yl)-1-butyne-1-yl)quinazoline-4-amine;

(58) 2-(3,3-difluoroazetine-1-yl)-N-(1-isopropylpiperidine-4-yl)-6-methoxy-7-(4-(pyrrolidine-1-yl)-1-butyne-1-yl)quinazoline-4-amine;

(59) 2-(3-fluoroazetidine-1-yl)-N-(1-isopropylpiperidine-4-yl)-6-methoxy-7-(4-(pyrrolidine-1-yl)-1-butyne-1-yl)quinazoline-4-amine;

(60) (R)-2-(3-fluoropyrrolidine-1-yl)-N-(1-isopropylpiperidine-4-yl)-6-methoxy-7-(4-(pyrrolidine-1-yl)-1-butyne-1-yl)quinazoline-4-amine;

(61) N4-(2-(dimethylamino)ethyl)-6-methoxy-N2,N2-dimethyl-7-(4-(pyrrolidine-1-yl)-1-butyne-1-yl)quinazoline-2,4-diamine;

(62) N1-(6-methoxy-2-(4-methyl-1,4-diazepane-1-yl)-7-(4-(pyrrolidine-1-yl)-1-butyne-1-yl)quinazoline-4-yl)-N2,N2-dimethylethane-1,2-diamine;

(63) N4-(1-ethylpiperidine-4-yl)-6-methoxy-N2,N2-dimethyl-7-(4-(-pyrrolidine-1-yl)-1-butyne-1-yl)quinazoline-2,4-diamine;

(64) N-(1-ethylpiperidine-4-yl)-6-methoxy-2-(pyrrolidine-1-yl)-7-(4-(pyrrolidine-1-yl)-1-butyne-1-yl)quinazoline-4-amine;

(65) N-(1-ethylpiperidine-4-yl)-6-methoxy-2-(4-methyl-1,4-diazepane-1-yl)-7-(4-(pyrrolidine-1-yl)-1-butyne-1-yl)quinazoline-4-amine;

(66) (E)-N-(1-isopropylpiperidine-4-yl)-6-methoxy-2-(piperidine-1-yl)-7-(4-(piperidine-1-yl)-1-butene-1-yl)quinazoline-4-amine;

(67) 6-methoxy-2-(piperidine-1-yl)-N-(1-propylpiperidine-4-yl)-7-(4-(pyrrolidine-1-yl)-1-butyne-1-yl)quinazoline-4-amine;

(68) 6-methoxy-N-(1-propylpiperidine-4-yl)-2-(pyrrolidine-1-yl)-7-(4-(pyrrolidine-1-yl)-1-butyne-1-yl)quinazoline-4-amine;

(69) 2-(4-((6-methoxy-2-(piperidine-1-yl)-7-(4-(pyrrolidine-1-yl)-1-butyne-1-yl)quinazoline-4-yl)amino)piperidine-1-yl)ethanol;

(70) 2-(4-((6-methoxy-2-(pyrrolidine-1-yl)-7-(4-(pyrrolidine-1-yl)-1-butyne-1-yl)quinazoline-4-yl)amino)piperidine-1-yl)ethanol;

(71) 6-methoxy-N-(pyridine-3-ylmethyl)-2-(pyrrolidine-1-yl)-7-(4-(pyrrolidine-1-yl)-1-butyne-1-yl)quinazoline-4-amine;

(72) (S)—N-(1-ethylpiperidine-4-yl)-2-(3-fluoropyrrolidine-1-yl)-6-methoxy-7-(4-(pyrrolidine-1-yl)-1-butyne-1-yl)quinazoline-4-amine;

(73) 6-methoxy-2-(pyrrolidine-1-yl)-7-(4-(pyrrolidine-1-yl)-1-butyne-1-yl)-N-(2,2,6,6-tetramethylpiperidine-4-yl)quinazoline-4-amine;

(74) (R)—N-(1-cyclopropylpiperidine-4-yl)-2-(3-fluoropyrrolidine-1-yl)-6-methoxy-7-(4-(pyrrolidine-1-yl)-1-butyne-1-yl)quinazoline-4-amine;

(75) (S)—N-(1-cyclopropylpiperidine-4-yl)-2-(3-fluoropyrrolidine-1-yl)-6-methoxy-7-(4-(pyrrolidine-1-yl)-1-butyne-1-yl)quinazoline-4-amine;
(76) (R)—N-(1-cyclopropylpiperidine-4-yl)-7-(4-(dimethylamino)-1-butyne-1-yl)-2-(3-fluoropyrrolidine-1-yl)-6-methoxyquinazoline-4-amine;
(77) (R)—N-(1-ethylpiperidine-4-yl)-2-(3-fluoropyrrolidine-1-yl)-6-methoxy-7-(4-(pyrrolidine-1-yl)-1-butyne-1-yl)quinazoline-4-amine;
(78) (S)—N-(1-ethylpiperidine-4-yl)-7-(4-(3-fluoropyrrolidine-1-yl)-1-butyne-1-yl)-6-methoxy-2-(pyrrolidine-1-yl)quinazoline-4-amine;
(79) (S)—N1-(2-(3-fluoropyrrolidine-1-yl)-6-methoxy-7-(4-(pyrrolidine-1-yl)-1-butyne-1-yl)quinazoline-4-yl)-N2,N2-dimethylethane-1,2-diamine;
(80) (R)—N1-(2-(3-fluoropyrrolidine-1-yl)-6-methoxy-7-(4-(pyrrolidine-1-yl)-1-butyne-1-yl)quinazoline-4-yl)-N2,N2-dimethylethane-1,2-diamine;
(81) 6-methoxy-N-methyl-2-(pyrrolidine-1-yl)-7-(4-(pyrrolidine-1-yl)-1-butyne-1-yl)quinazoline-4-amine;
(82) tert-butene 2-((4-((1-isopropylpiperidine-4-yl)amino)-6-methoxy-7-(4-(pyrrolidine-1-yl)-1-butyne-1-yl)quinazoline-2-yl)(methyl)amino)acetate;
(83) 6-methoxy-N2,N-dimethyl-N4-(1-propylpiperidine-4-yl)-7-(4-(pyrrolidine-1-yl)-1-butyne-1-yl)quinazoline-2,4-diamine;
(84) (R)-2-(3-fluoropyrrolidine-1-yl)-6-methoxy-N-(1-propylpiperidine-4-yl)-7-(4-(pyrrolidine-1-yl)-1-butyne-1-yl)quinazoline-4-amine;
(85) (E)-N-(1-isopropylpiperidine-4-yl)-6-methoxy-2-(pyrrolidine-1-yl)-7-(4-(pyrrolidine-1-yl)-1-butene-1-yl)quinazoline-4-amine;
(86) (E)-7-(4-(dimethylamino)-1-butene-1-yl)-N-(1-isopropylpiperidine-4-yl)-6-methoxy-2-(pyrrolidine-1-yl)quinazoline-4-amine;
(87) 2-(4-((2-(dimethylamino)-6-methoxy-7-(4-(pyrrolidine-1-yl)-1-butyne-1-yl)quinazoline-4-yl)amino)piperidine-1-yl)ethanol;
(88) N4-(1-isopropylpiperidine-4-yl)-6-methoxy-N2-(1-methyl-1H-pyrazole-4-yl)-7-(4-(pyrrolidine-1-yl)-1-butyne-1-yl)quinazoline-2,4-diamine; and
(89) (R)-2-(4-((2-(3-(fluoropyrrolidine-1-yl)-6-methoxy-7-(4-(pyrrolidine-1-yl)-1-butyne-1-yl)quinazoline-4-yl)amino)piperidine-1-yl)ethanol.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the derivative represented by formula 1 is dissolved in an organic solvent such as methanol, ethanol, acetone, methylenechloride, and acetonitrile, to which organic acid or inorganic acid is added to induce precipitation. Then, the precipitate is filtered and dried to give the salt. Or the solvent and the excessive acid are distillated under reduced pressure, dried, and crystallized in an organic solvent to give the salt.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

In addition, the present invention includes not only the compound represented by formula 1 but also a pharmaceutically acceptable salt thereof, and a solvate, an optical isomer, or a hydrate possibly produced from the same.

The present invention also provides a preparation method of a compound represented by formula 1 comprising a step of preparing a compound represented by formula 1 by reacting a compound represented by formula 2, as shown in reaction formula 1 below:

[Reaction Formula 1]

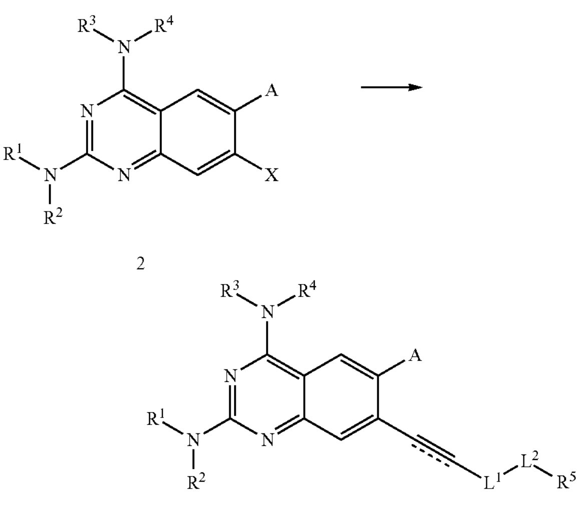

2

1

In reaction formula 1, $R^1$, $R^2$, $R^3$, $R^4$, $R^5$, A, $L^1$, and $L^2$ are as defined in formula 1 above; and X is halogen.

The present invention also provides a pharmaceutical composition for preventing or treating cancer comprising the compound, the stereoisomer thereof, the hydrate thereof, or the pharmaceutically acceptable salt thereof as an active ingredient.

In this case, the compound inhibits HMT (histone methyl transferase), and the HMT may be EHMT1 (euchromatic histone-lysine N-methyltransferase 1) or EHMT2 (euchromatic histone-lysine N-methyltransferase 2). In addition, the compound inhibits the growth of cancer cells.

The cancer is applied without limitation as long as it is a known cancer, but for some specific examples, it may be pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myeloid leukemia, acute lymphocytic leukemia, basal cell carcinoma, ovarian epithelial cancer, ovarian germ cell carcinoma, male breast cancer, brain cancer, pituitary adenoma, multiple myeloma, gallbladder cancer, biliary tract cancer, colorectal cancer, chronic myeloid leukemia, chronic lymphocytic leukemia, retinoblastoma, choroidal melanoma, ampullar of vater cancer, bladder cancer, peritoneal cancer, parathyroid cancer, adrenal cancer, rhinosinus cancer, non-small cell lung cancer, tongue cancer, astrocytoma, small cell lung cancer, pediatric brain cancer, childhood lymphoma, childhood leukemia, small intestine cancer, meningioma, esophageal cancer, glioma, renal pelvis cancer, kidney cancer, heart cancer, duodenal cancer, malignant soft tissue cancer, malignant bone cancer, malignant lymphoma, malignant mesothelioma, malignant melanoma, eye cancer, vulvar cancer, ureter cancer, urethral cancer, cancer of unknown primary site, gastric lymphoma, stomach cancer, gastric carcinoid tumor, gastrointestinal interstitial cancer, Wilms' cancer, breast cancer, sarcoma, penile cancer, pharynx cancer, choriocarcinoma of pregnancy, cervical cancer, endometrial cancer, uterine sarcoma, prostate cancer, metastatic bone cancer, metastatic brain cancer, mediastinum cancer, rectal cancer, rectal carcinoid tumor, vaginal cancer, spinal cord cancer, vestibular schwannoma, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleura cancer, or thymus cancer.

The compound represented by formula 1 or the pharmaceutically acceptable salt thereof can be administered orally or parenterally and be used in general forms of pharmaceutical formulation. That is, the composition of the present invention can be prepared for oral or parenteral administration by mixing with generally used diluents or excipients such as fillers, extenders, binders, wetting agents, disintegrating agents and surfactants. The formulations for oral administration are exemplified by tablets, pills, powders, and granules, etc. These solid formulations are prepared by mixing the compound with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, and emulsions. Water insoluble excipients and suspensions can contain, in addition to the active compound or compounds, propylene glycol, polyethylene glycol, vegetable oil like olive oil, injectable ester like ethylolate, etc.

The pharmaceutical composition comprising the compound represented by formula 1 or the pharmaceutically acceptable salt thereof as an active ingredient can be administered by parenterally and the parenteral administration includes subcutaneous injection, intravenous injection, intramuscular injection and intrathoracic injection.

At this time, to prepare the composition as a formulation for parenteral administration, the compound represented by formula 1 or the pharmaceutically acceptable salt thereof is mixed with a stabilizer or a buffering agent to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The formulations for oral administration are exemplified by tablets, pills, hard/soft capsules, solutions, suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salts or azeotropic mixtures and/or absorbents, coloring agents, flavours, and sweeteners can be additionally included thereto.

In another aspect of the present invention, the present invention provides a health functional food composition for preventing or ameliorating cancer comprising the compound represented by formula 1, the stereoisomer thereof, the hydrate thereof, or the pharmaceutically acceptable salt thereof as an active ingredient.

In another aspect of the present invention, the present invention provides an anticancer adjuvant comprising the compound represented by formula 1, the stereoisomer thereof, the hydrate thereof, or the pharmaceutically acceptable salt thereof as an active ingredient.

The anticancer adjuvant can be administered together with other anticancer treatments, and the other anticancer treatments indicate other anticancer agent therapy, radiation anticancer therapy, and the like. In one embodiment of the present invention, other anticancer agents in other anticancer therapy include chemotherapeutic drugs, targeted therapy agents, cancer immunotherapy agents, and the like.

In another aspect of the present invention, the present invention provides an anticancer combination drug comprising the compound represented by formula 1, the stereoisomer thereof, the hydrate thereof, or the pharmaceutically acceptable salt thereof; and other anticancer agent as active ingredients.

In the anticancer adjuvant or the combination drug, the compound, the stereoisomer thereof, the hydrate thereof, or the pharmaceutically acceptable salt thereof is characterized in that it enhances the anticancer activity of other anticancer agents, particularly cancer immunotherapy agents.

The cancer immunotherapy agent includes immune checkpoint inhibitors, cellular immunotherapy agents, anticancer vaccines, and antibody-drug conjugates. In the immune checkpoint inhibitor, the immune checkpoint may be a protein, and the protein includes PD-1, PD-L1, CLTA-4, A2AR, B7-H3, B7-H4, BTLA, IDO, KIR, LAG3, NOX2, TIM-3, VISTA, SIGLEC7, SIGLEC9, etc. The inhibitor can be a compound or an antibody against the immune checkpoint. The antibody can be a monoclonal or polyclonal antibody.

In the administration of the anticancer adjuvant or combination drug, the other anticancer agent and the compound, the stereoisomer thereof, the hydrate thereof, or the pharmaceutically acceptable salt thereof can be administered simultaneously or at different times, and the administration interval, administration dosage, and the like can be determined as needed.

Hereinafter, the present invention will be described in detail by the following examples and experimental examples. However, the following examples and experimental examples are only for illustrating the present invention, and the contents of the present invention are not limited thereto.

<Preparative Example 1> Preparation of N,N-dimethylpentyne-4-amide

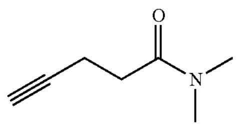

After dissolving 4-pentinoic acid (250 mg, 2.55 mmol), dimethyl amine 2.0 M in THF (1.529 ml, 3.06 mmol), EDC (537 mg, 2.80 mmol), and DMAP (31.1 mg, 0.255 mmol) in $CH_2Cl_2$ (10 ml), the mixture was stirred at room temperature. After 15 hours, the residue obtained by concentrating the reaction mixture was purified by silica gel chromatography (0~20% $MeOH/CH_2Cl_2$) to give a target compound 1-(pyrrolidine-1-yl)4-pentyne-1-one(1-(pyrrolidine-1-yl) pent-4-yn-1-one) (323 mg, yield: 100%).

$^1$H NMR (400 MHz, $CDCl_3$) δ 3.02 (s, 3H), 2.97 (s, 3H), 2.63-2.48 (m, 4H), 1.98 (t, J=2.3 Hz, 1H)

<Preparative Example 2> Preparation of 1-(pyrrolidine-1-yl)4-pentyne-1-one

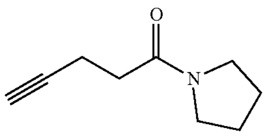

A target compound 1-(pyrrolidine-1-yl)4-pentyne-1-one (1-(pyrrolidine-1-yl)pent-4-yn-1-one) was prepared by performing the procedure of Preparative Example 1, except that pyrrolidine was used instead of dimethyl amine in Preparative Example 1 (55 mg, yield: 90%).

$^1$H NMR (400 MHz, $CDCl_3$) δ3.46 (t, J=6.9 Hz, 2H), 3.41 (t, J=6.8 Hz, 2H), 2.59-2.45 (m, 4H), 2.01-1.90 (m, 3H), 1.84 (p, J=6.6 Hz, 2H)

KSA-010-032 (354 mg, 92%).

<Preparative Example 3> Preparation of 1-(3-butyne-1-yl)pyrrolidine

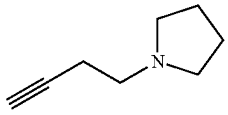

Step 1. Preparation of 3-butyne-1-yl 4-methylbenzenesulfonate

After dissolving 3-butyne-1-ol (5 g, 71.3 mmol) in dichloromethane (10 ml), triethylamine (9.38 g, 93 mmol) and DMAP (8.72 mg, 0.071 mmol) were sequentially added and stirred for 10 minutes. Then, the reaction mixture was cooled to 0° C., to which 4-methylbenzene-1-sulfonyl chloride (16.32 g, 86 mmol) was added, followed by stirring at room temperature for 3 hours. Upon completion of the reaction, water was added thereto, followed by extraction with dichloromethane. The organic layer was dried over magnesium sulfate, filtered, and concentrated. The obtained residue was purified by silica gel chromatography (0~20% EtOAc/Hexane) to give a target compound (7.5 g, yield: 46.9%).

Step 2. Preparation of 1-(but-3-yn-1-yl)pyrrolidine $K_2CO_3$ (6.16 g, 44.6 mmol) and pyrrolidine (2.75 ml, 33.4 mmol) were sequentially added to a solution of 3-butyne-1-yl 4-methylbenzenesulfonate (5 g, 22.29 mmol) dissolved in acetonitrile (40 ml), followed by refluxing at 0° C. for 15 hours. The reaction mixture was filtered through celite, and the filtrate was concentrated. The obtained residue was purified by silica gel chromatography (0~20% $MeOH/CH_2Cl_2$) to give a target compound 1-(3-butyne-1-yl)pyrrolidine(1-(but-3-yn-1-yl)pyrrolidine) (1 g, yield: 36.4%).

$^1$H NMR (400 MHz, CDCl3) δ2.67 (t, J=7.6 Hz, 1H), 2.59-2.50 (m, 2H), 2.40 (td, J=7.6, 2.6 Hz, 1H), 1.98 (t, J=2.7 Hz, 1H), 1.86-1.73 (m, 2H)

<Preparative Example 4> Preparation of 1-(3-butyne-1-yl)piperidine

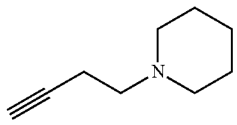

A target compound 1-(3-butyne-1-yl)piperidine(1-(but-3-yn-1-yl)piperidine) was prepared by performing the procedure of steps 1 to 2 of Preparative Example 3, except that piperidine was used instead of pyrrolidine in step 2 of Preparative Example 3 (55 mg, yield: 90%).

$^1$H NMR (400 MHz, CDCl3) δ 2.57 (t, J=7.8 Hz, 2H), 2.46-2.34 (m, 6H), 1.97 (t, J=2.7 Hz, 1H), 1.58 (dt, J=11.1, 5.6 Hz, 4H), 1.43 (dt, J=11.3, 5.8 Hz, 2H)

<Preparative Example 5> Preparation of 1-(3-butyne-1-yl)-4,4-difluoropiperidine

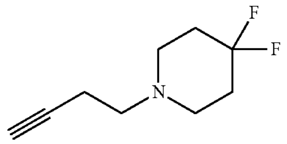

A target compound 1-(3-butyne-1-yl)-4,4-difluoropiperidine(1-(but-3-yn-1-yl)-4,4-difluoropiperidine) was prepared by performing the procedure of steps 1 to 2 of Preparative Example 3, except that 4,4-difluoropiperidine was used instead of pyrrolidine in step 2 of Preparative Example 3 (62 mg, yield: 80%).

$^1$H NMR (400 MHz, CDCl3) δ2.65 (t, J=5.3 Hz, 1H), 2.62-2.55 (m, 2H), 2.38 (td, J=7.4, 2.6 Hz, 1H), 2.06-1.94 (m, 2H)

<Preparative Example 6> Preparation of 1-(3-butyne-1-yl)-4-methylpiperidine

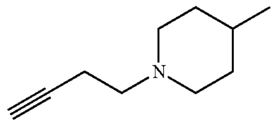

A target compound 1-(3-butyne-1-yl)-4-methylpiperidine (1-(but-3-yn-1-yl)-4-methylpiperidine) was prepared by performing the procedure of steps 1 to 2 of Preparative Example 3, except that 4-methylpiperidine was used instead of pyrrolidine in step 2 of Preparative Example 3 (34 mg, yield: 100%).

$^1$H NMR (400 MHz, CDCl3) δ 2.93-2.81 (m, 2H), 2.65-2.53 (m, 2H), 2.45-2.31 (m, 2H), 2.03-1.95 (m, 3H), 1.63-1.52 (m, 2H), 1.42-1.30 (m, 1H), 1.24 (ddd, J=15.1, 12.1, 3.6 Hz, 2H), 0.92 (d, J=6.3 Hz, 3H)

<Preparative Example 7> Preparation of 1-(3-butyne-1-yl)-N,N-dimethylpiperidine-4-amine

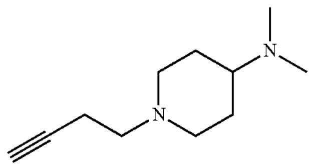

A target compound 1-(3-butyne-1-yl)-N,N-dimethylpiperidine-4-amine (1-(but-3-yn-1-yl)-N,N-dimethylpiperidine-4-amine) was prepared by performing the procedure of steps 1 to 2 of Preparative Example 3, except that N,N-dimethylpiperidine-4-amine was used instead of pyrrolidine in step 2 of Preparative Example 3 (62 mg, yield: 77%).

$^1$H NMR (400 MHz, CDCl3) δ3.02-2.91 (m, 1H), 2.58 (t, J=7.6 Hz, 1H), 2.38 (td, J=7.7, 2.6 Hz, 1H), 2.27 (s, 3H), 2.20-2.09 (m, 1H), 2.07-1.99 (m, 1H), 1.99-1.96 (m, 1H), 1.85-1.74 (m, 1H), 1.53 (qd, J=12.3, 3.7 Hz, 1H)

<Preparative Example 8> Preparation of 1-(3-butyne-1-yl)-4-methylpiperazine

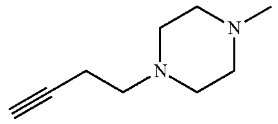

A target compound 1-(3-butyne-1-yl)-4-methylpiperazine (1-(but-3-yn-1-yl)-4-methylpiperazine) was prepared by performing the procedure of steps 1 to 2 of Preparative Example 1, except that 4-methylpiperazine was used instead of pyrrolidine in step 2 of Preparative Example 3 (41 mg, yield: 60.4%).

$^1$H NMR (400 MHz, CDCl3) δ$^1$H NMR (400 MHz, $CDCl_3$) δ2.61 (t, J=7.6 Hz, 2H), 2.52 (br s, 4H), 2.46 (br s, 4H), 2.42-2.35 (m, 2H), 2.29 (s, 3H), 1.98 (t, J=2.7 Hz, 1H)

<Preparative Example 9> Preparation of 4-(3-butyne-1-yl)morpholine

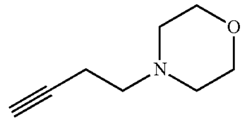

A target compound 4-(3-butyne-1-yl)morpholine(4-(but-3-yn-1-yl)morpholine) was prepared by performing the procedure of steps 1 to 2 of Preparative Example 1, except that morpholine was used instead of pyrrolidine in step 2 of Preparative Example 3 (16.4 mg, yield: 75%).

$^1$H NMR (400 MHz, CDCl3) δ 3.79-3.61 (m, 1H), 2.59 (t, J=7.5 Hz, 1H), 2.53-2.45 (m, 1H), 2.39 (td, J=7.5, 2.4 Hz, 1H), 1.99 (t, J=2.5 Hz, 1H)

<Preparative Example 10> Preparation of (S)-1-(3-butyne-1-yl)-3-fluoropyrrolidine

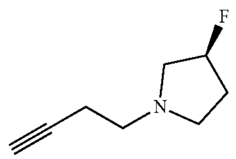

A target compound (S)-1-(3-butyne-1-yl)-3-fluoropyrrolidine((S)-1-(but-3-yn-1-yl)-3-fluoropyrrolidine) was prepared by performing the procedure of steps 1 to 2 of Preparative Example 1, except that (S)-3-fluoropyrrolidine hydrochloride was used instead of pyrrolidine in step 2 of Preparative Example 3 (20 mg, yield: 63.5%).

$^1$H NMR (400 MHz, CDCl3) δ5.27-5.03 (m, 1H), 2.96-2.84 (m, 2H), 2.84-2.74 (m, 1H), 2.71 (t, J=7.6 Hz, 2H), 2.50 (dd, J=14.0, 8.2 Hz, 1H), 2.41 (td, J=7.5, 2.6 Hz, 2H), 2.24-2.00 (m, 2H), 1.99 (t, J=2.7 Hz, 1H)

<Preparative Example 11> Preparation of (R)-1-(3-butyne-1-yl)-3-fluoropyrrolidine

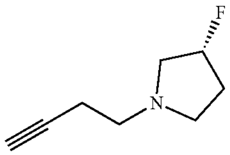

A target compound (R)-1-(3-butyne-1-yl)-3-fluoropyrrolidine((R)-1-(but-3-yn-1-yl)-3-fluoropyrrolidine) was prepared by performing the procedure of steps 1 to 2 of Preparative Example 1, except that (R)-3-fluoropyrrolidine hydrochloride was used instead of pyrrolidine in step 2 of Preparative Example 3 (19 mg, yield: 60.4%).

$^1$H NMR (400 MHz, CDCl3) $\delta^1$H NMR (400 MHz, $CDCl_3$) δ5.27-5.05 (m, 1H), 2.96-2.84 (m, 2H), 2.84-2.74 (m, 1H), 2.71 (t, J=7.6 Hz, 2H), 2.55-2.46 (m, 1H), 2.41 (td, J=7.5, 2.6 Hz, 2H), 2.25-2.00 (m, 2H), 1.99 (t, J=2.7 Hz, 1H)

<Preparative Example 12> Preparation of 1-(3-butyne-1-yl)-3-fluoroazetidine

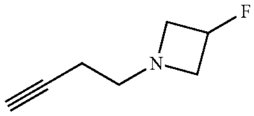

A target compound 1-(3-butyne-1-yl)-3-fluoroazetidine (1-(but-3-yn-1-yl)-3-fluoroazetidine) was prepared by performing the procedure of steps 1 to 2 of Preparative Example 1, except that 3-fluoroazetidine was used instead of pyrrolidine in step 2 of Preparative Example 3 (23 mg, yield: 81%).

$^1$H NMR (400 MHz, CDCl3) $\delta^1$H NMR (400 MHz, $CDCl_3$) δ5.25-5.00 (m, 1H), 3.83-3.65 (m, 2H), 3.23-3.08 (m, 2H), 2.67 (t, J=7.0 Hz, 2H), 2.26 (td, J=7.0, 2.7 Hz, 2H), 1.98 (t, J=2.7 Hz, 1H)

<Preparative Example 13> Preparation of 1-(3-butene-1-yl)piperidine

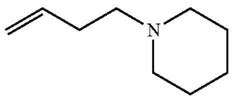

3-Bromo-1-propene (0.846 mL, 10 mmol) was dissolved in DMSO (5 mL), to which piperidine (0.494 mL, 5 mmol) was added, and the mixture was cooled below 0° C. While maintaining the temperature, an aqueous formaldehyde solution (0.787 mL, 10 mmol), Cu(I), I (0.095 g, 0.5 mmol), and Zn (0.981 g, 15 mmol) were added to the reaction mixture, followed by reaction at room temperature for 2 hours. 10% sodium hydroxide aqueous solution (50 mL) was added to the reaction mixture, followed by extraction with ethyl ether. The residue obtained by concentrating the organic layer was purified by silica gel chromatography (0~100% MC/ethyl ether) to give a target compound 1-(3-butene-1-yl)piperidine (1-(but-3-en-1-yl)piperidine) (449 mg, yield: 64.5%).

$^1$H NMR (400 MHz, $CDCl_3$) δ5.90-5.72 (m, 1H), 5.05 (dd, J=17.2, 1.7 Hz, 1H), 4.99 (dd, J=10.2, 1.0 Hz, 1H), 2.50-2.32 (m, 6H), 2.29-2.20 (m, 2H), 1.59 (dt, J=11.2, 5.6 Hz, 4H), 1.51-1.37 (m, 2H)

<Preparative Example 14> Preparation of 2,4-dichloro-7-iodo-6-methoxyquinazoline

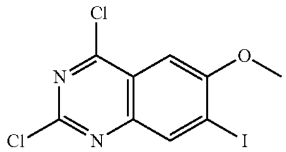

[Reaction Formula A]

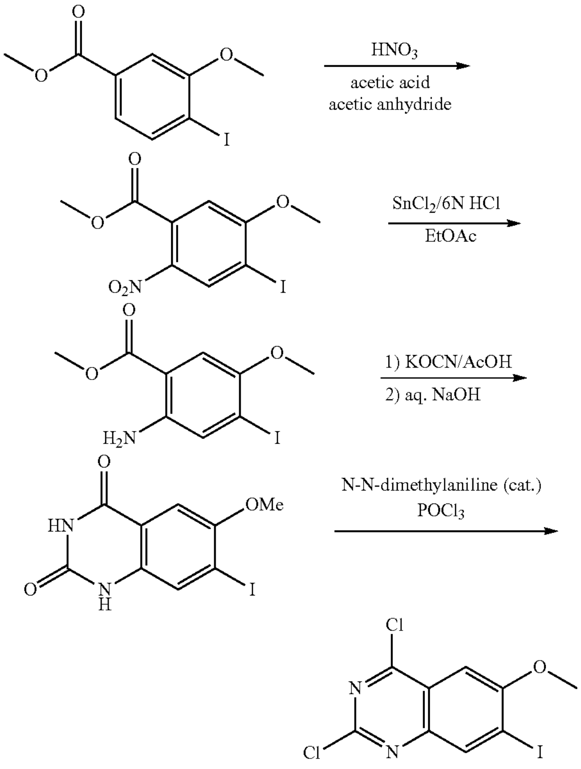

Step 1. Preparation of methyl 4-iodo-5-methoxy-2-nitrobenzonate

After dissolving methyl 4-iodo-5-methoxy-2-nitrobenzonate (10 g, 34.2 mmol) in acetic acid (70 ml, 1223 mmol) and cooling to 0° C., nitric acid (10.93 ml, 171 mmol) and acetic anhydride (35 ml, 371 mmol) were added thereto. The reaction mixture was stirred at 70° C. for 2 hours, cooled to room temperature, diluted with 1 N NaOH, and extracted twice with ethyl acetate. The organic layer was collected, washed with saturated sodium bicarbonate and brine, dried over magnesium sulfate, filtered, and concentrated. The obtained residue was purified by silica gel chromatography (0-30% EtOAc/hexane) to give a target compound (7.54 g, yield: 65.3%) as a yellow solid.

MS m/z, 336[M]+

Step 2. Preparation of methyl 2-amino-4-iodo-5-methoxybenzonate

Tin (II) chloride dehydrate (11.90 g, 52.7 mmol) and 6 N hydrochloric acid (15 ml, 90 mmol) were added to a solution of methyl 4-iodo-5-methoxy-2-nitrobenzonate (5.08 g, 15.07 mmol) dissolved in ethyl acetate (60 ml). After stirring the reaction mixture at room temperature for 15 hours, the pH was raised to with ammonia water, and the pH was adjusted to 7 with saturated sodium carbonate. The resulting solid was filtered through celite, and the filtrate was washed with brine, dried over magnesium sulfate, and concentrated. The obtained residue was purified by silica gel chromatography (0-10% EtOAc/hexane) to give a target compound (3.19 g, yield: 69%) as a yellow solid.

LCMS, 308[M+H]+

Step 3. Preparation of 7-iodo-6-methoxyquinazoline-2,4 (1H,3H)-dione

Potassium cyanate (1.497 g, 18.45 mmol) was added to a solution of methyl 2-amino-4-iodo-5-methoxybenzonate (4.722 g, 15.38 mmol) dissolved in acetic acid, and the mixture was stirred at room temperature for 1 hour. Distilled water was added to the reaction mixture, and the resulting solid was filtered and added to a mixed solution of 30% sodium hydroxide aqueous solution (15 ml) and distilled water (30 ml). The reaction mixture was stirred at 80° C. for 2 hours, cooled to room temperature, and the pH was adjusted to 2 using hydrochloric acid. The resulting solid was filtered and dried to give a target compound (4.73 g, yield: 97%) as a yellow solid.

LCMS, 319[M+H]+

Step 4. Preparation of 2,4-dichloro-7-iodo-6-methoxyquinazoline

A mixture of 7-iodo-6-methoxyquinazoline-2,4(1H,3H)-dione (2 g, 6.29 mmol), phosphoryl chloride (26 ml) and N,N-dimethylaniline (200 ul) was heated and stirred at 140° C. for 6 hours. The reaction mixture was placed in a container containing ice and extracted three times with dichloromethane. The organic layer was collected, washed twice with distilled water, dried over magnesium sulfate, and concentrated by filtration. The obtained residue was purified by silica gel chromatography (0-10% EtOAc/hexane) to give a target compound 2,4-dichloro-7-iodo-6-methoxyquinazoline (2,4-dichloro-7-iodo-6-methoxyquinazoline) (865 mg, yield: 38.8%) as a yellow solid.

LCMS, m/z 355 [M+H]+

<Example 1> Preparation of 5-(4-((1-isopropylpiperidine-4-yl)amino)-6-methoxy-2-(piperidine-1-yl) quinazoline-7-yl)-N,N-dimethylpentyne-4-amide

[Reaction Formula B]

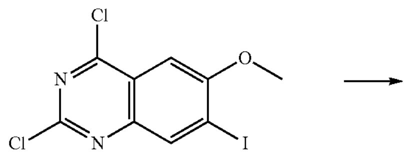

-continued

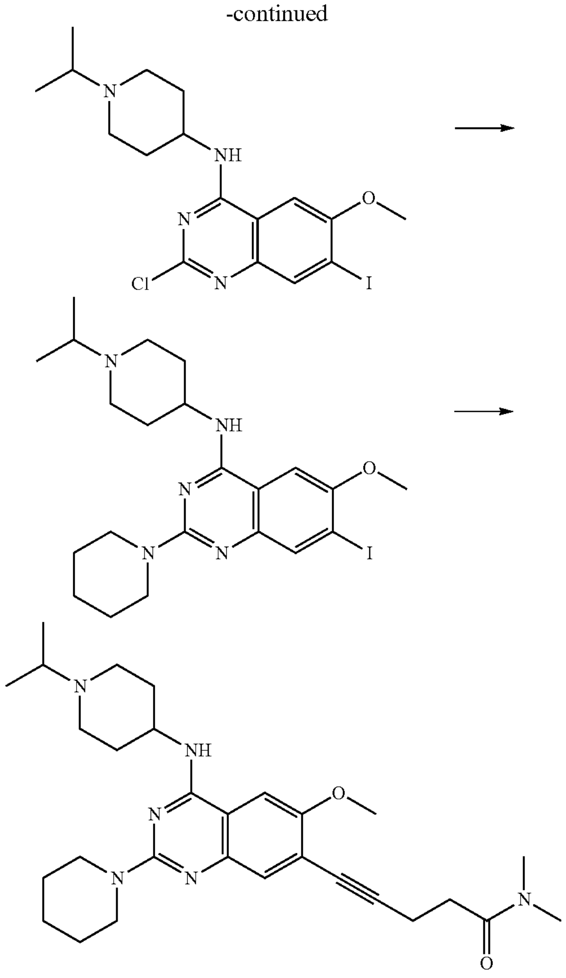

Step 1. Preparation of 2-chloro-7-iodo-N-(1-isopropylpiperidine-4-yl)-6-methoxyquinazoline-4-amine

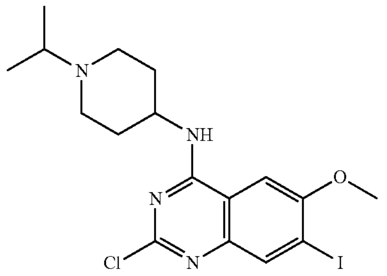 [SMILES: COc1cc2c(NC3CCN(C(C)C)CC3)nc(Cl)nc2cc1I]

After adding 1-isopropylpiperidine-4-amine (0.276 ml, 1.745 mmol) to 2,4-dichloro-7-iodo-6-methoxyquinazoline (563 mg, 1.586 mmol), the mixture was dissolved in DMF (10 ml), to which 1-isopropylpiperidine-4-amine (0.276 ml, 1.745 mmol) and DIPEA (0.304 ml, 1.745 mmol) were added, followed by stirring at room temperature for 5 hours. The residue obtained by concentrating the reaction mixture was purified by silica gel chromatography (0-5% MeOH/$CH_2Cl_2$, amine silica gel) to give a target compound (589 mg, yield: 81%) as a yellow solid.

LCMS, m/z 461 [M+H]+

Step 2. Preparation of 7-iodo-N-(1-isopropylpiperidine-4-yl)-6-methoxy-2-(piperidine-1-yl)quinazoline-4-amine

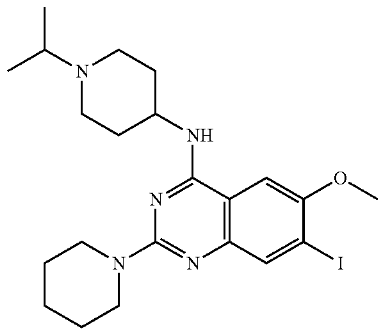 [SMILES: COc1cc2c(NC3CCN(C(C)C)CC3)nc(N3CCCCC3)nc2cc1I]

2-Chloro-7-iodo-N-(1-isopropylpiperidine-4-yl)-6-methoxyquinazoline-4-amine) (489 mg, 1.061 mmol) was dissolved in BuOH, to which piperidine (0.210 ml, 2.123 mmol) and DIPEA (3.71 ml, 21.23 mmol) were added, followed by reaction in a microwave reactor (150° C., 15 min). The residue obtained by concentrating the reaction mixture was purified by silica gel chromatography (0-5% $MeOH/CH_2Cl_2$, amine silica gel) to give a target compound (372 mg, yield: 68.8%) as a yellow solid.

LCMS, m/z 510 [M+H]+

Step 3. Preparation of 5-(4-((1-isopropylpiperidine-4-yl)amino)-6-methoxy-2-(piperidine-1-yl)quinazoline-7-yl)-N,N-dimethylpentyne-4-amide

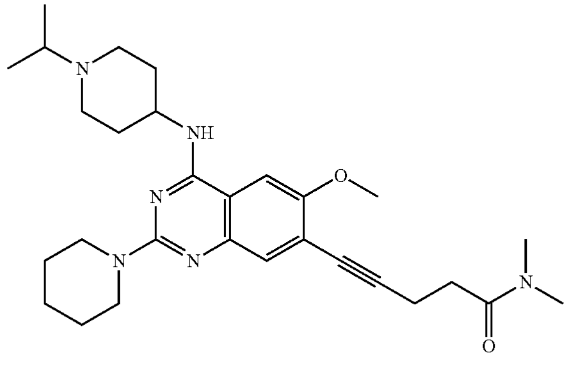 [SMILES: COc1cc2c(NC3CCN(C(C)C)CC3)nc(N3CCCCC3)nc2cc1C#CCCC(=O)N(C)C]

7-Iodo-N-(1-isopropylpiperidine-4-yl)-6-methoxy-2-methylquinazoline-4-amine (20 mg, 0.039 mmol) was dissolved in TEA (1 ml), to which N,N-dimethylpentyne-4-amide (19.66 mg, 0.157 mmol), $Pd(dppf)Cl_2CH_2Cl_2$ (1.603 mg, 1.963 umol), and Cu(I) I (0.748 mg, 3.93 umol) were added, followed by reaction at 45° C. for 6 hours. Upon completion of the reaction, the reaction mixture was cooled to room temperature and filtered through celite. The obtained filtrate was distilled under reduced pressure and purified by silica gel chromatography (0~100% EA/Hex→0~5% MeOH/DCM, amine silica gel) to give a target compound 5-(4-((1-isopropylpiperidine-4-yl)amino)-6-methoxy-2-(piperidine-1-yl)quinazoline-7-yl)-N,N-dimethylpentyne-4-amide (5-(4-((1-isopropylpiperidine-4-yl)amino)-6-methoxy-2-(piperidine-1-yl)quinazolin-7-yl)-N,N-dimethylpent-4-ynamide) (1.5 mg, yield: 7.54%) as a yellow solid.

$^1$H NMR (400 MHz, CDCl3) δ 7.52 (s, 1H), 6.63 (s, 1H), 5.02 (d, J=7.5 Hz, 1H), 4.14-4.04 (m, 1H), 3.92 (s, 3H), 3.84-3.74 (m, 4H), 3.05 (s, 3H), 2.97 (s, 3H), 2.92 (d, J=11.8 Hz, 2H), 2.87-2.81 (m, 2H), 2.81-2.76 (m, 1H), 2.71-2.64 (m, 2H), 2.35 (t, J=10.7 Hz, 2H), 2.23-2.15 (m, 2H), 2.06-1.98 (m, 2H), 1.68-1.60 (m, 6H), 1.08 (d, J=6.5 Hz, 6H).

LCMS, m/z 507[M+H]+

<Example 2> Preparation of 5-(4-((1-isopropylpiperidine-4-yl)amino)-6-methoxy-2-(piperidine-1-yl)quinazoline-7-yl)-1-(pyrrolidine-1-yl)4-pentyne-1-one Step 1. Preparation of 5-(2-chloro-4-((1-isopropylpiperidine-3-yl)amino-6-methoxyquinazoline-7-yl)-1-(pyrrolidine-1-yl)-4-pentyne-1-one

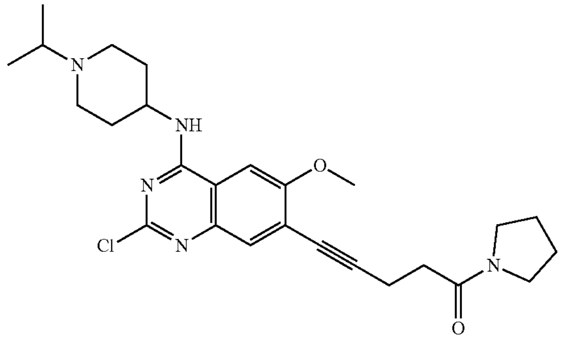 [SMILES: COc1cc2c(NC3CCN(C(C)C)CC3)nc(Cl)nc2cc1C#CCCC(=O)N1CCCC1]

1-(Pyrrolidine-1-yl)-4-pentyne-1-one (13.13 mg, 0.087 mmol), $PdCl_2$ (dppf)-$CH_2Cl_2$Adduct (0.886 mg, 1.085 μmol), and Cu(I) I (0.413 mg, 2.170 μmol) were added to a mixed solution of 2-chloro-7-iodo-N-(1-isopropylpiperidine-4-yl)-6-methoxyquinazoline-4-amine (10 mg, 0.022 mmol) and TEA (1 ml), and heated and stirred at 60° C. After 15 hours, the reaction mixture was filtered on a celite pad and washed with $CH_2Cl_2$. The resulting filtrate was distilled under reduced pressure and purified by silica gel chromatography (0-10% $MeOH/CH_2Cl_2$, amine silica gel) to give a target compound (5 mg, yield: 47.6%) as a yellow solid.

LCMS, m/z 485 [M+H]+

Step 2. Preparation of 5-(4-((1-isopropylpiperidine-4-yl)amino)-6-methoxy-2-(piperidine-1-yl)quinazoline-7-yl)-1-(pyrrolidine-1-yl)-4-pentyne-1-one

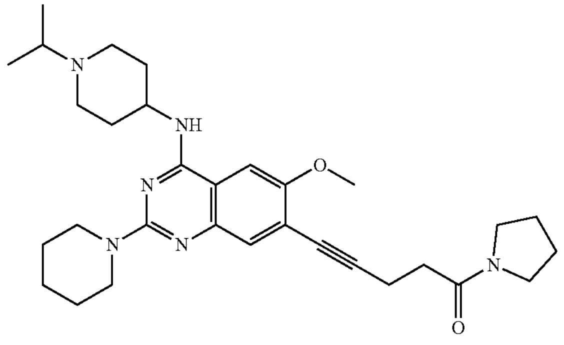 [SMILES: COc1cc2c(NC3CCN(C(C)C)CC3)nc(N3CCCCC3)nc2cc1C#CCCC(=O)N1CCCC1]

Piperidine (2.045 μl, 0.021 mmol) and DIPEA (0.1 ml, 0.573 mmol) were added to a mixed solution of 5-(2-chloro-4-((1-isopropylpiperidine-4-yl)amino)-6-methoxyquinazoline-7-yl)-1-(pyrrolidine-1-yl)-4-pentyne-1-one (5 mg, 10.33 μmol) and BuOH (0.5 ml) and reacted in a microwave reactor (150° C., 30 minutes). The residue obtained by concentrating the reaction mixture was purified by silica gel chromatography (0-5% $MeOH/CH_2Cl_2$, amine silica gel) to give a target compound 5-(4-((1-isopropylpiperidine-4-yl)amino)-6-methoxy-2-(piperidine-1-yl)quinazoline-7-yl)-1-(pyrrolidine-1-yl)4-pentyne-1-one (5-(4-((1-isopropylpiperidine-4-yl)amino)-6-methoxy-2-(piperidine-1-yl)quinazolin-7-yl)-1-(pyrrolidine-1-yl)pent-4-yn-1-one) (2.6 mg, yield: 41.6%) as a yellow solid.

$^1$H NMR (400 MHz, CDCl3) δ7.52 (s, 1H), 6.63 (s, 1H), 5.03 (d, J=7.0 Hz, 1H), 4.14-4.05 (m, 1H), 3.91 (s, 3H), 3.82-3.74 (m, 4H), 3.48 (q, J=6.3 Hz, 4H), 2.92 (d, J=11.8 Hz, 2H), 2.89-2.83 (m, 2H), 2.78 (quintet, J=6.1 Hz, 1H), 2.65-2.59 (m, 2H), 2.34 (t, J=10.7 Hz, 2H), 2.23-2.14 (m, 2H), 2.01-1.91 (m, 2H), 1.91-1.81 (m, 2H), 1.62-1.54 (m, 8H), 1.08 (d, J=6.5 Hz, 6H).

LCMS, m/z 533[M+H]+

<Example 3> Preparation of 7-(4-(dimethylamino)-1-butyne-1-yl)-N-(1-isopropylpiperidine-4-yl)-6-methoxy-2-(piperidine-1-yl)quinazoline-4-amine

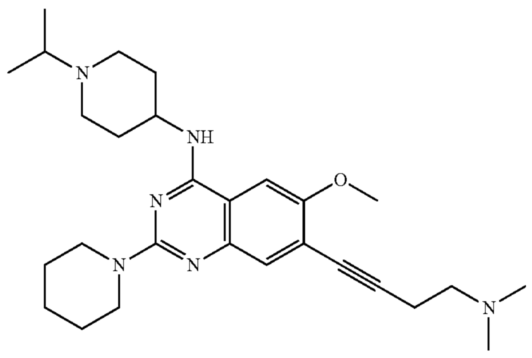

A target compound 7-(4-(dimethylamino)-1-butyne-1-yl)-N-(1-isopropylpiperidine-4-yl)-6-methoxy-2-(piperidine-1-yl)quinazoline-4-amine(7-(4-(dimethylamino)but-1-yn-1-yl)-N-(1-isopropylpiperidine-4-yl)-6-methoxy-2-(piperidine-1-yl)quinazolin-4-amine) was obtained (238 mg, yield: 53.9%) as a yellow solid by performing the procedure of step 3 of Example 1 according to reaction formula B, except that N,N-dimethyl3-butyne-1-amine was used instead of N,N-dimethyl-4-pentyneamide in step 3 of Example 1.

$^1$H NMR (400 MHz, CDCl3) δ7.53 (s, 1H), 6.64 (s, 1H), 5.04 (d, J=7.2 Hz, 1H), 4.16-4.06 (m, 1H), 3.91 (s, 3H), 3.83-3.76 (m, 4H), 2.96-2.88 (m, 2H), 2.78 (quintet, J=6.5 Hz, 1H), 2.67-2.62 (m, 4H), 2.42-2.32 (m, 2H), 2.31 (s, 6H), 2.22-2.15 (m, 2H), 1.66-1.56 (m, 8H), 1.08 (d, J=6.6 Hz, 6H).

LCMS, m/z 479[M+H]+

<Example 4> Preparation of 2-(4,4-difluoropiperidine-1-yl)-7-(4-dimethylamino)-1-butyne-1-yl)-N-(1-isopropylpiperidine-4-yl)-6-methoxyquinazoline-4-amine Step 1. Preparation of 2-(4,4-difluoropiperidine-1-yl)-7-iodo-N-(1-isopropylpiperidine-4-yl)-6-methoxyquinazoline-4-amine

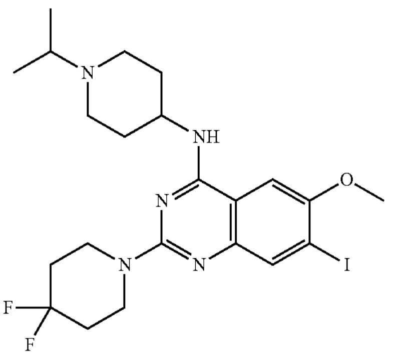 [SMILES: COc1cc2c(NC3CCN(C(C)C)CC3)nc(N3CCC(F)(F)CC3)nc2cc1I]

A target compound was obtained (92 mg, yield: 78%) as a yellow solid by performing the procedure of steps 1 to 2 of Example 1, except that 4,4-difluoropiperidine was used instead of piperidine in step 2 of Example 1.

$^1$H NMR (400 MHz, $CDCl_3$) δ8.04 (s, 1H), 6.65 (s, 1H), 5.19 (d, J=7.2 Hz, 1H), 4.15-4.04 (m, 1H), 4.03-3.95 (m, 4H), 3.94 (s, 3H), 2.99-2.87 (m, 2H), 2.79 (dt, J=13.1, 6.6 Hz, 1H), 2.35 (td, J=11.7, 2.2 Hz, 2H), 2.23-2.11 (m, 2H), 2.09-1.91 (m, 4H), 1.64-1.53 (m, 2H), 1.08 (d, J=6.6 Hz, 6H).

LCMS, m/z 546[M+H]+

Step 2. Preparation of 2-(4,4-difluoropiperidine-1-yl)-7-(4-dimethylamino)-1-butyl-1-yl)-N-(1-isopropylpiperidine-4-yl)-6-methoxyquinazoline-4-amine

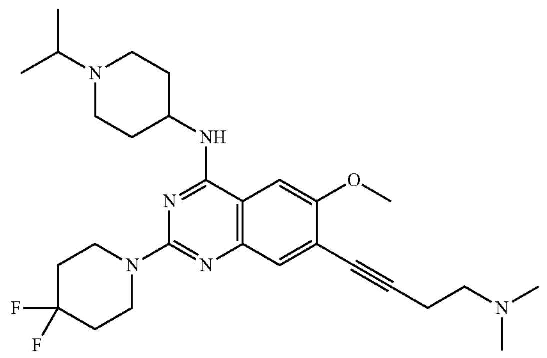 [SMILES: COc1cc2c(NC3CCN(C(C)C)CC3)nc(N3CCC(F)(F)CC3)nc2cc1C#CCCN(C)C]

A target compound 2-(4,4-difluoropiperidine-1-yl)-7-(4-dimethylamino)-1-butyne-1-yl)-N-(1-isopropylpiperidine-4-yl)-6-methoxyquinazoline-4-amine(2-(4,4-difluoropiperidine-1-yl)-7-(4-(dimethylamino)but-1-yn-1-yl)-N-(1-isopropylpiperidine-4-yl)-6-methoxyquinazolin-4-amine) was obtained (11 mg, yield: 52.3%) as a yellow solid in the same manner as described in step 3 of Example 1 that 2-(4,4-difluoropiperidine-1-yl)-7-iodo-N-(1-isopropylpiperidine-4-yl)-6-methoxyquinazoline-4-amine and N,N-dimethyl-3-butyne-1-amine were used as starting materials in step 3 of Example 1.

$^1$H NMR (400 MHz, CDCl3) δ7.54 (s, 1H), 6.67 (s, 1H), 5.16 (d, J=7.2 Hz, 1H), 4.16-4.04 (m, 4H), 3.99-3.96 (m, 4H), 3.93 (s, 3H), 2.93 (d, J=11.9 Hz, 2H), 2.81 (quintet, J=6.5 Hz, 1H), 2.66-2.64 (m, 4H), 2.38-2.35 (m, 2H), 2.31 (s, 6H), 2.17 (d, J=10.6 Hz, 2H), 2.04-1.95 (m, 4H), 1.62 (qd, J=11.6, 3.6 Hz, 2H), 1.09 (d, J=6.6 Hz, 6H).

LCMS, m/z 515[M+H]+

<Example 5> Preparation of 7-(4-(dimethylamino)-1-butyne-1-yl)-N-(1-isopropylpiperidine-4-yl)-6-methoxy-2-morpholinoquinazoline-4-amine Step 1. Preparation of 7-iodo-N-(1-isopropylpiperidine-4-yl)-6-methoxy-2-morpholinoquinazoline-4-amine

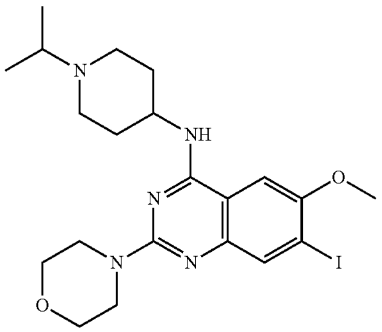

A target compound was obtained (45 mg, yield: 79%) as a yellow solid by performing the procedure of steps 1 to 2 of Example 1, except that morpholine was used instead of piperidine in step 2 of Example 1.

$^1$H NMR (400 MHz, $CDCl_3$) δ8.04 (s, 1H), 6.64 (s, 1H), 5.17 (d, J=7.3 Hz, 1H), 4.17-4.05 (m, 1H), 3.94 (s, 3H), 3.86-3.71 (m, 8H), 2.99-2.88 (m, 2H), 2.79 (quintet, J=6.7 Hz, 1H), 2.35 (td, J=11.7, 1.9 Hz, 2H), 2.22-2.12 (m, 2H), 1.69-1.62 (m, 2H), 1.09 (d, J=6.6 Hz, 6H).

LCMS, m/z 512[M+H]+

Step 2. Preparation of 7-(4-(dimethylamino)-1-butyne-1-yl)-N-(1-isopropylpiperidine-4-yl)-6-methoxy-2-morpholinoquinazoline-4-amine

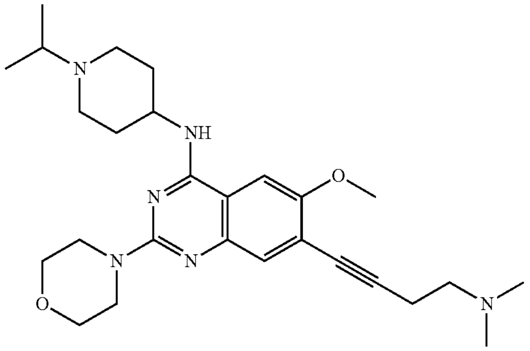

A target compound 7-(4-(dimethylamino)-1-butyne-1-yl)-N-(1-isopropylpiperidine-4-yl)-6-methoxy-2-morpholinoquinazoline-4-amine(7-(4-(dimethylamino)but-1-yn-1-yl)-N-(1-isopropylpiperidine-4-yl)-6-methoxy-2-morpholinoquinazolin-4-amine) was obtained (4.1 mg, yield: 25.4%) as a yellow oil in the same manner as described in step 3 of Example 1 that 7-iodo-N-(1-isopropylpiperidine-4-yl)-6-methoxy-2-morpholinoquinazoline-4-amine and N,N-dimethyl-3-butyne-1-amine were used as starting materials in step 3 of Example 1.

$^1$H NMR (400 MHz, CDCl3) δ7.55 (s, 1H), 6.67 (s, 1H), 5.16 (d, J=7.0 Hz, 1H), 4.15-4.04 (m, 1H), 3.93 (s, 3H), 3.84-3.72 (m, 8H), 2.98-2.87 (m, 2H), 2.79 (quintet, J=6.5 Hz, 1H), 2.68-2.61 (m, 4H), 2.41-2.33 (m, 2H), 2.31 (s, 6H), 2.22-2.11 (m, 2H), 1.67-1.54 (m, 2H), 1.08 (d, J=6.5 Hz, 6H).

LCMS, m/z 481[M+H]+

<Example 6> Preparation of 7-(4-(dimethylamino)-1-butyne-1-yl)-N-(2-isopropylpiperidine-4-yl)-6-methoxy-2-(pyrrolidine-1-yl)quinazoline-4-amine Step 1. Preparation of 7-iodo-N-(1-isopropylpiperidine-4-yl)-6-methoxy-2-(pyrrolidine-1-yl)quinazoline-4-amine

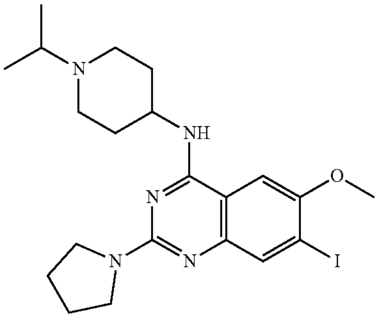 [SMILES: COc1cc2c(NC3CCN(C(C)C)CC3)nc(N3CCCC3)nc2cc1I]

A target compound was obtained (104 mg, yield: 95%) as a yellow solid by performing the procedure of steps 1 to 2 of Example 1, except that pyrrolidine was used instead of piperidine in step 2 of Example 1.

$^1$H NMR (400 MHz, $CDCl_3$) δ8.06 (s, 1H), 6.64 (s, 1H), 5.10 (d, J=7.2 Hz, 1H), 4.23-4.08 (m, 1H), 3.92 (s, 3H), 3.68-3.57 (m, 4H), 2.98-2.86 (m, 2H), 2.78 (quintet, J=6.5 Hz, 1H), 2.34 (td, J=11.6, 2.2 Hz, 2H), 2.25-2.16 (m, 2H), 2.02-1.90 (m, 4H), 1.61-1.50 (m, 2H), 1.07 (t, J=9.5 Hz, 6H).

LCMS, m/z 496[M+H]+

Step 2. Preparation of 7-(4-(dimethylamino)-1-butyne-1-yl)-N-(1-isopropylpiperidine-4-yl)-6-methoxy-2-(pyrrolidine-1-yl)quinazoline-4-amine

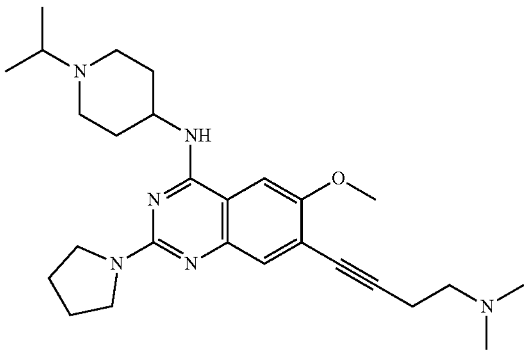 [SMILES: COc1cc2c(NC3CCN(C(C)C)CC3)nc(N3CCCC3)nc2cc1C#CCCN(C)C]

A target compound 7-(4-(dimethylamino)-1-butyne-1-yl)-N-(2-isopropylpiperidine-4-yl)-6-methoxy-2-(pyrrolidine-1-yl)quinazoline-4-amine(7-(4-(dimethylamino)but-1-yn-1-yl)-N-(1-isopropylpiperidine-4-yl)-6-methoxy-2-(pyrrolidine-1-yl)quinazolin-4-amine) was obtained (21.4 mg, yield: 56.3%) as a yellow solid in the same manner as described in step 3 of Example 1 that 7-iodo-N-(1-isopropylpiperidine-4-yl)-6-methoxy-2-(pyrrolidine-1-yl)quinazoline-4-amine and N,N-dimethyl-3-butyne-1-amine were used as starting materials in step 3 of Example 1.

$^1$H NMR (400 MHz, $CDCl_3$) δ7.58 (s, 1H), 6.67 (s, 1H), 5.12 (d, J=5.0 Hz, 1H), 4.19-4.06 (m, 1H), 3.91 (s, 3H), 3.65-3.58 (m, 4H), 2.98-2.87 (m, 2H), 2.79 (quintet, J=6.5 Hz, 1H), 2.67-2.61 (m, 4H), 2.39-2.33 (m, 2H), 2.31 (s, 6H), 2.25-2.16 (m, 2H), 1.98-1.91 (m, 4H), 1.61 (ddd, J=15.1, 11.9, 3.7 Hz, 2H), 1.08 (d, J=6.5 Hz, 6H).

LCMS, m/z 465[M+H]+

<Example 7> Preparation of 7-(4-(dimethylamino)-1-butyne-1-yl)-N-(1-isopropylpiperidine-4-yl)quinazoline-4-amine Step 1. Preparation of 7-iodo-N-(1-isopropylpiperidine-4-yl)-6-methoxy-2-(4-methylpiperazine-1-yl)quinazoline-4-amine

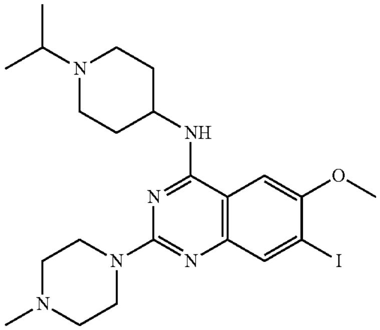 [SMILES: COc1cc2c(NC3CCN(C(C)C)CC3)nc(N3CCN(C)CC3)nc2cc1I]

A target compound was obtained (30 mg, yield: 88%) as a yellow solid by performing the procedure of steps 1 to 2 of Example 1, except that 1-methylpiperazine was used instead of piperidine in step 2 of Example 1.

LCMS, m/z 525[M+H]+

Step 2. Preparation of 7-(4-(dimethylamino)-1-butyne-1-yl)-N-(1-isopropylpiperidine-4-yl)-6-methoxy-2-(4-methylpiperazine-1-yl)quinazoline-4-amine

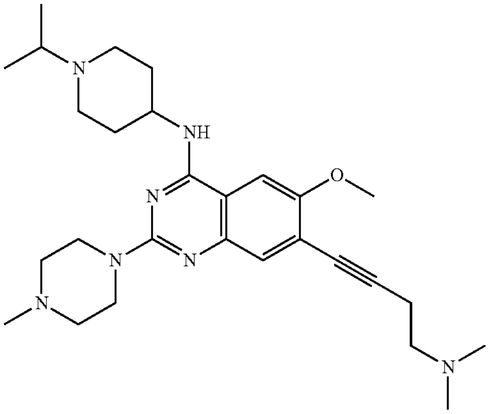 [SMILES: COc1cc2c(NC3CCN(C(C)C)CC3)nc(N3CCN(C)CC3)nc2cc1C#CCCN(C)C]

A target compound 7-(4-(dimethylamino)-1-butyne-1-yl)-N-(1-isopropylpiperidine-4-yl)quinazoline-4-amine(7-(4-(dimethylamino)but-1-yn-1-yl)-N-(1-isopropylpiperidine-4-yl)-6-methoxy-2-(4-methylpiperazin-1-yl)quinazolin-4-amine) was obtained (16 mg, yield: 53.5%) in the same manner as described in step 3 of Example 1 that 7-iodo-N-(1-isopropylpiperidine-4-yl)-6-methoxy-2-(4-methylpiperazine-1-yl)quinazoline-4-amine and N,N-dimethyl-3-butyne-1-amine were used as starting materials in step 3 of Example 1.

$^1$H NMR (400 MHz, $CDCl_3$) δ7.54 (s, 1H), 6.68 (s, 1H), 5.16 (d, J=7.3 Hz, 1H), 4.19-4.06 (m, 1H), 3.92 (s, 3H), 3.89-3.82 (m, 4H), 3.00-2.91 (m, 2H), 2.82 (quintet, J=6.5 Hz, 1H), 2.68-2.63 (m, 4H), 2.54-2.45 (m, 4H), 2.45-2.35 (m, 2H), 2.34 (s, 3H), 2.31 (s, 6H), 2.23-2.15 (m, 2H), 1.72-1.58 (m, 2H), 1.10 (d, J=6.5 Hz, 6H).

LCMS, m/z 494[M+H]+

<Example 8> Preparation of 2-(azepane-1-yl)-7-(4-(dimethylamino)-1-butyne-1-yl)-N-(1-isopropylpiperidine-4-yl)-6-methoxyquinazoline-4-amine Step 1. Preparation of 2-(azepane-1-yl)-7-iodo-N-(1-isopropylpiperidine-4-yl)-6-methoxyquinazoline-4-amine

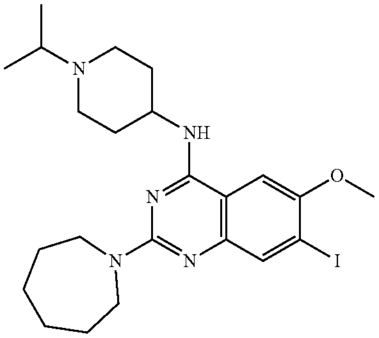 [SMILES: COc1cc2c(NC3CCN(C(C)C)CC3)nc(N3CCCCCC3)nc2cc1I]

A target compound was obtained (30 mg, yield: 52.6%) as a yellow solid by performing the procedure of steps 1 to 2 of Example 1, except that homopiperidine was used instead of piperidine in step 2 of Example 1.

$^1$H NMR (400 MHz, $CDCl_3$) δ8.02 (s, 1H), 6.64 (s, 1H), 5.10 (d, J=7.1 Hz, 1H), 4.18-4.02 (m, 1H), 3.99-3.94 (m, 2H), 3.92 (s, 3H), 3.86 (t, J=6.4 Hz, 2H), 3.00-2.88 (m, 2H), 2.78 (quintet, J=13.1, 6.6 Hz, 1H), 2.73-2.64 (m, 2H), 2.61-2.50 (m, 2H), 2.37 (s, 3H), 2.36-2.28 (m, 2H), 2.25-2.13 (m, 2H), 2.08-1.95 (m, 2H), 1.61 (ddd, J=14.9, 11.7, 3.6 Hz, 2H), 1.09 (d, J=6.6 Hz, 6H).

LCMS, m/z 524[M+H]+

Step 2. Preparation of 2-(azepane-1-yl)-7-(4-(dimethylamino)-1-butyne-1-yl)-N-(1-isopropylpiperidine-4-yl)-6-methoxyquinazoline-4-amine

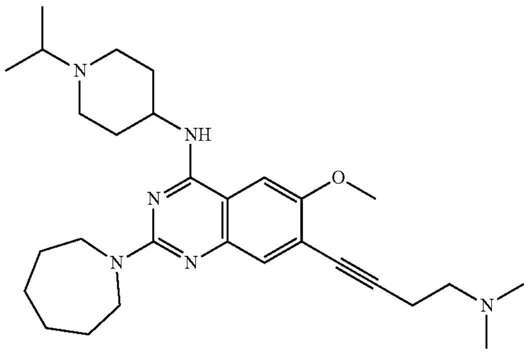 [SMILES: COc1cc2c(NC3CCN(C(C)C)CC3)nc(N3CCCCCC3)nc2cc1C#CCCN(C)C]

A target compound 2-(azepane-1-yl)-7-(4-(dimethylamino)-1-butyne-1-yl)-N-(1-isopropylpiperidine-4-yl)-6-methoxyquinazoline-4-amine(2-(azepane-1-yl)-7-(4-(dimethylamino)but-1-yn-1-yl)-N-(1-isopropylpiperidine-4-yl)-6-methoxyquinazolin-4-amine) was obtained (3 mg, yield: 10.6%) in the same manner as described in step 3 of Example 1 that 2-(azepane-1-yl)-7-iodo-N-(1-isopropylpiperidine-4-yl)-6-methoxyquinazoline-4-amine and N,N-dimethyl-3-butyne-1-amine were used as starting materials in step 3 of Example 1.

$^1$H NMR (400 MHz, $CDCl_3$) δ7.53 (s, 1H), 6.65 (s, 1H), 5.04 (d, J=6.7 Hz, 1H), 4.13-4.03 (m, 1H), 3.91 (s, 3H), 3.78 (t, J=6.0 Hz, 4H), 2.93 (d, J=11.7 Hz, 2H), 2.78 (quintet, J=6.5 Hz, 1H), 2.65 (s, 4H), 2.36-2.33 (m, 2H), 2.30 (s, 6H), 2.20 (d, J=12.5 Hz, 2H), 2.03 (d, J=7.8 Hz, 2H), 1.78 (s, 2H), 1.62-1.59 (m, 2H), 1.55-1.53 (m, 4H), 1.08 (d, J=6.5 Hz, 6H).

LCMS, m/z 493[M+H]+

<Example 9> Preparation of 7-(4-(dimethylamino)-1-butyne-1-yl)-N-(1-isopropylpiperidine-4-yl)-6-(methoxy-2-(2-azaspiro[4.4]nonane-2-yl)quinazoline-4-amine Step 1. Preparation of 7-iodo-N-(1-isopropylpiperidine-4-yl)-6-methoxy-2-(2-azaspiro[4.4]nonane-2-yl)quinazoline-4-amine

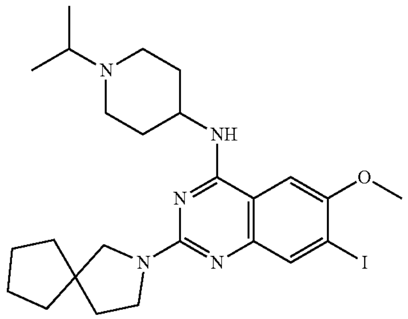 [SMILES: COc1cc2c(NC3CCN(C(C)C)CC3)nc(N3CCC4(CCCC4)C3)nc2cc1I]

A target compound was obtained (23 mg, yield: 38.6%) as a yellow solid by performing the procedure of steps 1 to 2 of Example 1, except that 2-azaspiro[4.4]nonane was used instead of piperidine in step 2 of Example 1.

$^1$H NMR (400 MHz, $CDCl_3$) δ8.05 (s, 1H), 6.63 (s, 1H), 5.09 (d, J=7.1 Hz, 1H), 4.22-4.07 (m, 1H), 3.92 (s, 3H), 3.67 (t, J=6.9 Hz, 2H), 3.47 (s, 2H), 2.96-2.88 (m, 2H), 2.78 (quintet, J=13.1, 6.5 Hz, 1H), 2.42-2.28 (m, J=11.5 Hz, 2H), 2.25-2.14 (m, J=9.9 Hz, 2H), 1.84 (t, J=6.9 Hz, 2H), 1.74-1.66 (m, 4H), 1.60-1.49 (m, 6H), 1.09 (d, J=6.6 Hz, 6H).

LCMS, m/z 550[M+H]+

Step 2. Preparation of 7-(4-(dimethylamino)-1-butyne-1-yl)-N-(1-isopropylpiperidine-4-yl)-6-methoxy-2-(2-azaspiro[4.4]nonane-2-yl)quinazoline-4-amine

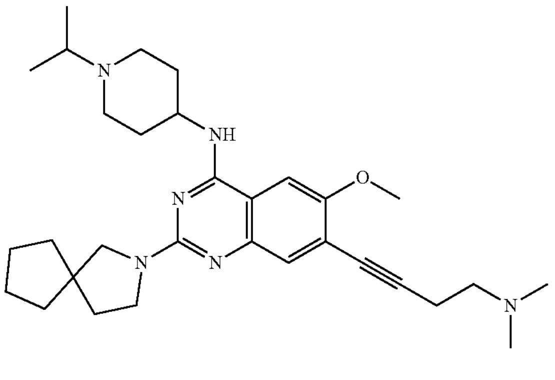 [SMILES: COc1cc2c(NC3CCN(C(C)C)CC3)nc(N3CCC4(CCCC4)C3)nc2cc1C#CCCN(C)C]

A target compound 7-(4-(dimethylamino)-1-butyne-1-yl)-N-(1-isopropylpiperidine-4-yl)-6-(methoxy-2-(2-azaspiro[4.4]nonane-2-yl)quinazoline-4-amine (7-(4-(dimethylamino)but-1-yn-1-yl)-N-(1-isopropylpiperidine-4-yl)-6-methoxy-2-(2-azaspiro[4.4]nonan-2-yl)quinazolin-4-amine) was obtained (15 mg, yield: 78%) in the same manner as described in step 3 of Example 1 that 7-iodo-N-(1-isopropylpiperidine-4-yl)-6-methoxy-2-(2-azaspiro[4.4]nonane-2- yl)quinazoline-4-amine and N,N-dimethyl-3-butyne-1-amine were used as starting materials in step 3 of Example 1.

$^1$H NMR (400 MHz, $CDCl_3$) δ7.56 (s, 1H), 6.67 (s, 1H), 5.11 (d, J=7.0 Hz, 1H), 4.19-4.06 (m, 1H), 3.91 (s, 3H), 3.66 (t, J=6.9 Hz, 2H), 3.51-3.40 (m, 2H), 2.96-2.86 (m, 2H), 2.78 (quintet, J=6.4 Hz, 1H), 2.67-2.60 (m, 4H), 2.39-2.33 (m, 2H), 2.30 (s, 6H), 2.23-2.14 (m, 2H), 1.99-1.89 (m, 4H), 1.83 (t, J=6.9 Hz, 2H), 1.66-1.63 (m, 2H), 1.63-1.53 (m, 4H), 1.08 (d, J=6.5 Hz, 6H).

LCMS, m/z 519[M+H]+

<Example 10> Preparation of ((1S,2R,5R)-3-(7-(4-(dimethylamino)-1-butyne-1-yl)-4-((1-isopropylpiperidine-4-yl)amino)-6-methoxyquinazoline-2-yl)-3-azabicyclo[3.1.0]hexane-2-yl)methanol Step 1. Preparation of ((1S,2R,5R)-3-(7-iodo-4-((1-isopropylpiperidine-4-yl)amino)-6-methoxyquinazoline-2-yl)-3-azabicyclo[3.1.0]hexane-2-yl)methanol

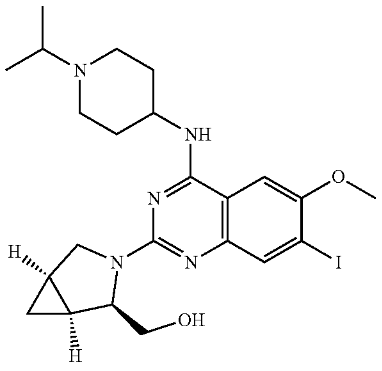 [SMILES: COc1cc2c(NC3CCN(C(C)C)CC3)nc(N3C[C@@H]4C[C@@H]4[C@@H]3CO)nc2cc1I]

A target compound was obtained (25 mg, yield: 42.9%) as a yellow solid by performing the procedure of steps 1 to 2 of Example 1, except that ((1S,2R,5R)-3-azabicyclo[3.1.0]hexane-2-yl)methanol was used instead of piperidine in step 2 of Example 1.

$^1$H NMR (400 MHz, $CDCl_3$) δ7.95 (s, 1H), 6.61 (s, 1H), 5.28-5.19 (m, 1H), 4.55-4.46 (m, 1H), 4.18 (d, J=11.1 Hz, 1H), 4.13-4.03 (m, 1H), 3.92 (s, 3H), 3.80-3.70 (m, 1H), 3.57 (dd, J=11.1, 4.1 Hz, 1H), 3.52-3.38 (m, 2H), 3.24-3.07 (m, 3H), 2.99-2.95 (m, 1H), 2.95-2.92 (m, 1H), 2.92-2.89 (m, 1H), 2.87 (s, 1H), 2.85-2.76 (m, 2H), 2.37 (t, J=11.6 Hz, 2H), 1.42-1.33 (m, 2H), 1.33-1.27 (m, 2H), 1.21-1.12 (m, 2H), 1.10 (d, J=6.6 Hz, 6H), 0.78-0.66 (m, 1H), 0.57 (td, J=7.8, 5.4 Hz, 2H), 0.23-0.15 (m, 1H), 0.12 (dd, J=9.0, 4.2 Hz, 2H).

LCMS, m/z 538[M+H]+

Step 2. Preparation of ((1S,2R,5R)-3-(7-(4-dimethylamino)-1-butyne-1-yl)-4-((1-isopropylpiperidine-4-yl)amino)-6-methoxyquinazoline-2-yl)-3-azabicyclo[3.1.0]hexane-2-yl)methanol

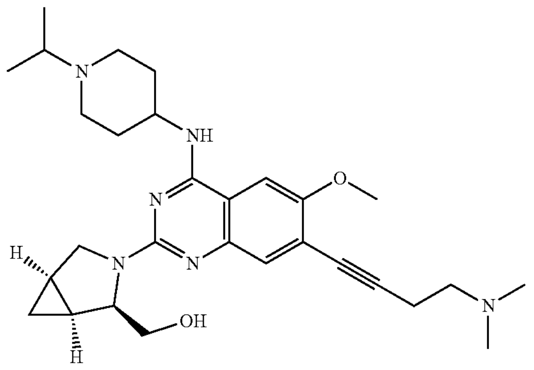 [SMILES: COc1cc2c(NC3CCN(C(C)C)CC3)nc(N3C[C@@H]4C[C@@H]4[C@@H]3CO)nc2cc1C#CCCN(C)C]

A target compound ((1S,2R,5R)-3-(7-(4-(dimethylamino)-1-butyne-1-yl)-4-((1-isopropylpiperidine-4-yl)amino)-6-methoxyquinazoline-2-yl)-3-azabicyclo[3.1.0]hexane-2-yl)methanol(((1S,2R,5R)-3-(7-(4-(dimethylamino)but-1-yn-1-yl)-4-((1-isopropylpiperidine-4-yl)amino)-6-methoxyquinazolin-2-yl)-3-azabicyclo[3.1.0]hexan-2-yl)methanol) was obtained (9 mg, yield: 36.8%) in the same manner as described in step 3 of Example 1 that ((1S,2R,5R)-3-(7-iodo-4-((1-isopropylpiperidine-4-yl)amino)-6-methoxyquinazoline-2-yl)-3-azabicyclo[3.1.0]hexane-2-yl)methanol and N,N-dimethyl-3-butyne-1-amine were used as starting materials in step 3 of Example 1.

$^1$H NMR (400 MHz, $CDCl_3$) δ7.46 (s, 1H), 6.67 (s, 1H), 5.31 (d, J=6.3 Hz, 1H), 4.50 (dd, J=9.2, 1.8 Hz, 1H), 4.16 (d, J=11.0 Hz, 1H), 3.78-3.69 (m, 1H), 3.56 (dd, J=11.1, 4.2 Hz, 1H), 2.98-2.87 (m, 3H), 2.81-2.76 (m, 1H), 2.64 (s, 3H), 2.39-2.31 (m, 3H), 2.30 (s, 6H), 2.22-2.10 (m, 5H), 1.30-1.25 (m, 2H), 1.19-1.15 (m, 2H), 1.09 (d, J=6.5 Hz, 6H), 0.89-0.85 (m, 2H), 0.72 (dt, J=12.7, 6.4 Hz, 1H), 0.19 (q, J=4.2 Hz, 1H).

LCMS, m/z 507[M+H]+

<Example 11> Preparation of 7-(4-(dimethylamino)-1-butyne-1-yl)-2-(4-(dimethylamino)piperidine-1-yl)-N-(1-isopropylpiperidine-4-yl)-6-methoxyquinazoline-4-amine Step 1. Preparation of 2-(4-(dimethylamino)piperidine-1-yl)-7-iodo-N-(1-isopropylpiperidine-4-yl)-6-methoxyquinazoline-4-amine

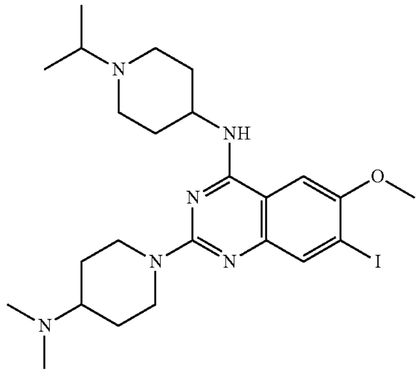

A target compound was obtained (46 mg, yield: 77%) as a yellow solid by performing the procedure of steps 1 to 2 of Example 1, except that N,N-dimethylpiperidine-4-amine was used instead of piperidine in step 2 of Example 1.

$^1$H NMR (400 MHz, $CDCl_3$) δ8.02 (s, 1H), 6.64 (s, 1H), 5.14 (d, J=7.3 Hz, 1H), 4.98-4.77 (m, 2H), 4.21-4.02 (m, 1H), 3.93 (s, 3H), 2.97-2.90 (m, 2H), 2.89-2.73 (m, 3H), 2.45-2.34 (m, 3H), 2.31 (s, 6H), 2.24-2.15 (m, 2H), 1.95-1.87 (m, 2H), 1.61 (ddd, J=15.0, 12.0, 3.9 Hz, 2H), 1.47 (ddd, J=24.3, 12.3, 4.2 Hz, 2H), 1.09 (d, J=6.6 Hz, 6H).

LCMS, m/z 553[M+H]+

Step 2. Preparation of 7-(4-dimethylamino)-1-butyne-1-yl)-2-(4-(dimethylamino)piperidine-1-yl)-N-(1-isopropylpiperidine-4-yl)-6-methoxyquinazoline-4-amine

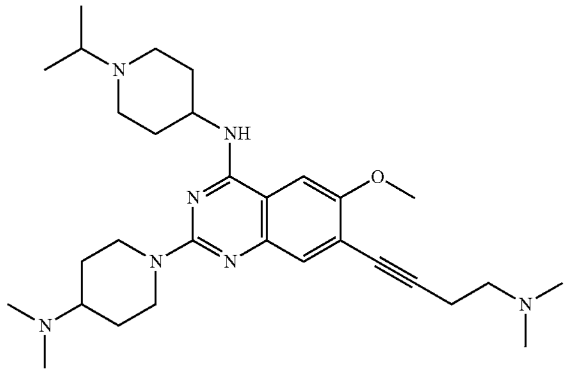

A target compound 7-(4-(dimethylamino)-1-butyne-1-yl)-2-(4-(dimethylamino)piperidine-1-yl)-N-(1-isopropylpiperidine-4-yl)-6-methoxyquinazoline-4-amine(7-(4-(dimethylamino)but-1-yn-1-yl)-2-(4-(dimethylamino)piperidine-1-yl)-N-(1-isopropylpiperidine-4-yl)-6-methoxyquinazolin-4-amine) was obtained (2.4 mg, yield: 9.76%) as a yellow solid in the same manner as described in step 3 of Example 1 that 2-(4-(dimethylamino)piperidine-1-yl)-7-iodo-N-(1-isopropylpiperidine-4-yl)-6-methoxyquinazoline-4-amine and N,N-dimethyl-3-butyne-1-amine were used as starting materials in step 3 of Example 1.

$^1$H NMR (400 MHz, $CDCl_3$) δ7.54 (s, 1H), 6.70 (s, 1H), 5.27-5.26 (m, 1H), 4.90 (d, J=12.8 Hz, 2H), 4.21-4.13 (m, 1H), 3.93 (s, 3H), 3.05 (d, J=11.6 Hz, 2H), 2.98-2.91 (m, 1H), 2.83 (t, J=12.0 Hz, 2H), 2.53-2.44 (m, 3H), 2.22 (d, J=15.2 Hz, 2H), 2.03 (d, J=7.4 Hz, 2H), 1.94 (d, J=12.0 Hz, 2H), 1.55-1.45 (m, 2H), 1.16 (d, J=6.5 Hz, 6H).

LCMS, m/z 522[M+H]+

<Example 12> Preparation of N-(1-isopropylpiperidine-4-yl)-6-methoxy-2-(piperidine-1-yl)-7-(4-(piperidine-1-yl)-1-butyne-1-yl)quinazoline-4-amine

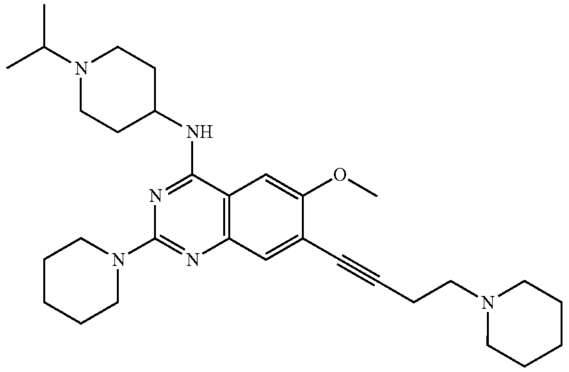 [SMILES: COc1cc2c(NC3CCN(C(C)C)CC3)nc(N3CCCCC3)nc2cc1C#CCCN1CCCCC1]

A target compound N-(1-isopropylpiperidine-4-yl)-6-methoxy-2-(piperidine-1-yl)-7-(4-(piperidine-1-yl)-1-butyne-1-yl)quinazoline-4-amine(N-(1-isopropylpiperidine-4-yl)-6-methoxy-2-(piperidine-1-yl)-7-(4-(piperidine-1-yl) but-1-yn-1-yl)quinazolin-4-amine) was obtained (10 mg, yield: 48.9%) as a solid by performing the procedure of steps 1 to 3 of Example 1, except that 1-(3-butyne-1-yl)piperidine was used instead of N,N-dimethyl-4-pentyneamide in step 3 of Example 1.

$^1$H NMR (400 MHz, $CDCl_3$) δ7.52 (s, 1H), 6.65 (s, 1H), 5.05 (d, J=7.2 Hz, 1H), 4.13-4.06 (m, 1H), 3.91 (s, 3H), 3.80-3.78 (m, 4H), 2.92 (d, J=11.9 Hz, 2H), 2.78 (quintet, J=6.5 Hz, 1H), 2.68 (s, 4H), 2.48 (s, 4H), 2.35 (t, J=10.6 Hz, 2H), 2.18 (d, J=12.2 Hz, 2H), 1.63-1.59 (m, 12H), 1.47-1.43 (m, 2H), 1.08 (d, J=6.6 Hz, 6H).

LCMS, m/z 519[M+H]+

<Example 13> Preparation of 7-(4-(diethylamino)-1-butyne-1-yl)-N-(1-isopropylpiperidine-4-yl)-6-methoxy-2-(piperidine-1-yl)quinazoline-4-amine

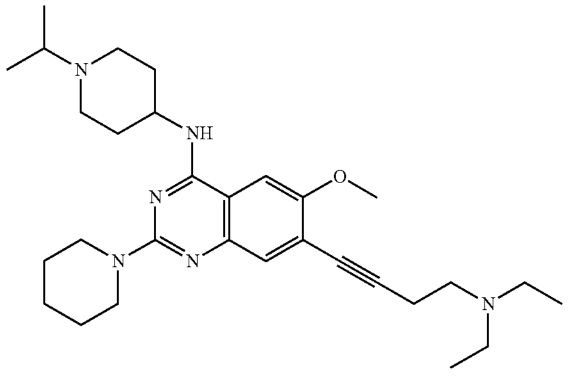 [SMILES: CCN(CC)CCC#Cc1cc2nc(N3CCCCC3)nc(NC3CCN(C(C)C)CC3)c2cc1OC]

A target compound 7-(4-(diethylamino)-1-butyne-1-yl)-N-(1-isopropylpiperidine-4-yl)-6-methoxy-2-(piperidine-1-yl)quinazoline-4-amine(7-(4-(diethylamino)but-1-yn-1-yl)-N-(1-isopropylpiperidine-4-yl)-6-methoxy-2-(piperidine-1-yl)quinazolin-4-amine) was obtained (10 mg, yield: 76%) as a yellow solid by performing the procedure of steps 1 to 3 of Example 1, except that N,N-diethyl-3-butyne-1-amide was used instead of N,N-dimethyl-4-pentyneamide in step 3 of Example 1.

$^1$H NMR (400 MHz, $CDCl_3$) δ7.53 (s, 1H), 6.65 (s, 1H), 5.06 (d, J=7.2 Hz, 1H), 4.15-4.06 (m, 1H), 3.91 (s, 3H), 3.80-3.79 (m, 4H), 2.92 (d, J=11.8 Hz, 2H), 2.85-2.81 (m, 2H), 2.80-2.75 (m, 1H), 2.63-2.57 (m, 6H), 2.35 (t, J=10.7 Hz, 2H), 2.19 (d, J=10.5 Hz, 2H), 1.63-1.55 (m, 8H), 1.09-1.05 (m, 12H).

LCMS, m/z 507[M+H]+

<Example 14> Preparation of 7-(4-dimethylamino)-1-butyne-1-yl)-N4-(1-isopropylpiperidine-4-yl)-6-methoxy-N2,N2-dimethylquinazoline-2,4-diamine Step 1. Preparation of 7-io-N4-(1-isopropylpiperidine-4-yl)-6-methoxyN2,N2-dimethylquinazoline-2,4-diamine

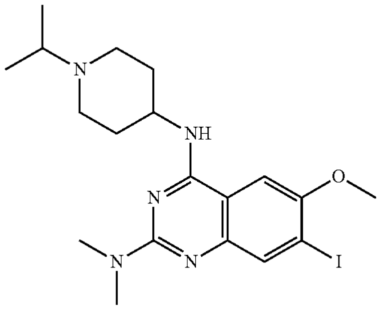 [SMILES: COc1cc2c(NC3CCN(C(C)C)CC3)nc(N(C)C)nc2cc1I]

A target compound was obtained (15 mg, yield: 68.6%) as a yellow solid by performing the procedure of steps 1 to 2 of Example 1, except that dimethylamine was used instead of piperidine in step 2 of Example 1.

$^1$H NMR (400 MHz, $CDCl_3$) δ8.04 (s, 1H), 6.63 (s, 1H), 5.09 (d, J=6.9 Hz, 1H), 4.23-4.04 (m, 1H), 3.92 (s, 3H), 3.21 (s, 6H), 2.98-2.88 (m, 2H), 2.81 (quintet, J=6.5 Hz, 1H), 2.36 (td, J=11.7, 2.1 Hz, 2H), 2.28-2.13 (m, 2H), 1.62-1.51 (m, 2H), 1.09 (d, J=6.6 Hz, 6H).

LCMS, m/z 469[M]+

Step 2. Preparation of 7-(4-(dimethylamino)-1-butyne-1-yl)-N4-(1-isopropylpiperidine-4-yl)-6-methoxy-N2,N2-dimethylquinazoline-2,4-diamine

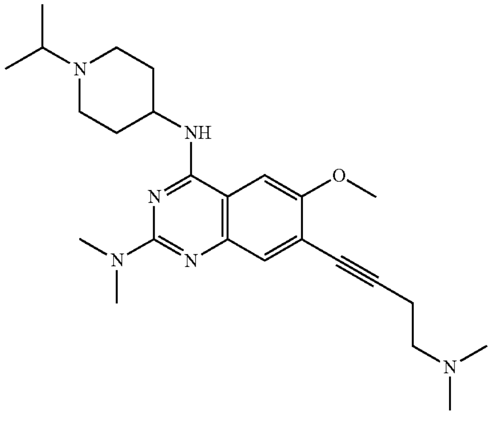 [SMILES: COc1cc2c(NC3CCN(C(C)C)CC3)nc(N(C)C)nc2cc1C#CCCN(C)C]

A target compound 7-(4-dimethylamino)-1-butyne-1-yl)-N4-(1-isopropylpiperidine-4-yl)-6-methoxy-N2,N2-dimethylquinazoline-2,4-diamine(7-(4-(dimethylamino)but-1-yn-1-yl)-N4-(1-isopropylpiperidine-4-yl)-6-methoxy-N2,N2-dimethylquinazoline-2,4-diamine) was obtained (1.3 mg, yield: 24%) as a yellow solid in the same manner as described in step 3 of Example 1 that 7-iodo-N4-(1-isopropylpiperidine-4-yl)-6-methoxy-N2,N2-dimethylquinazoline-2,4-diamine and N,N-dimethyl-3-butyne-1-amine were used as starting materials in step 3 of Example 1.

$^1$H NMR (400 MHz, $CDCl_3$) δ7.56 (s, 1H), 6.66 (s, 1H), 5.07 (d, J=7.1 Hz, 1H), 4.19-4.07 (m, 1H), 3.92 (s, 3H), 3.20 (s, 6H), 2.98-2.89 (m, 2H), 2.78 (quintet, J=6.5 Hz, 1H), 2.70-2.59 (m, 4H), 2.40-2.32 (m, 2H), 2.31 (s, 6H), 2.27-2.16 (m, J=10.6 Hz, 2H), 1.60 (qd, J=11.9, 3.6 Hz, 2H), 1.08 (d, J=6.5 Hz, 6H).

LCMS, m/z 439[M+H]+

<Example 15> Preparation of N-(1-isopropylpiperidine-4-yl)-6-methoxy-7-(4-(4-methylpiperidine-1-yl)-1-butyne-1-yl)-2-(piperidine-1-yl)quinazoline-4-amine

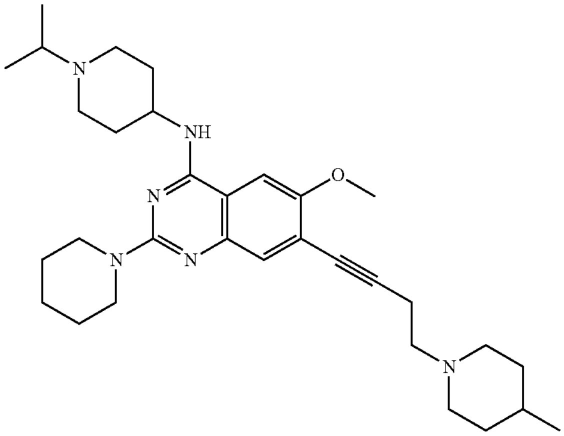 [SMILES: COc1cc2c(NC3CCN(C(C)C)CC3)nc(N3CCCCC3)nc2cc1C#CCCN1CCC(C)CC1]

A target compound N-(1-isopropylpiperidine-4-yl)-6-methoxy-7-(4-(4-methylpiperidine-1-yl)-1-butyne-1-yl)-2-(piperidine-1-yl)quinazoline-4-amine(N-(1-isopropylpiperidine-4-yl)-6-methoxy-7-(4-(4-methylpiperidine-1-yl)but-1-yn-1-yl)-2-(piperidine-1-yl)quinazolin-4-amine) was obtained (8 mg, yield: 55.7%) by performing the procedure of steps 1 to 3 of Example 1, except that 1-(3-butyne-1-yl)-4-methylpiperidine was used instead of N,N-dimethyl-4-pentyneamide in step 3 of Example 1.

$^1$H NMR (400 MHz, $CDCl_3$) δ7.53 (s, 1H), 6.66 (s, 1H), 5.07 (d, J=6.3 Hz, 1H), 4.18-4.03 (m, 1H), 3.92 (s, 3H), 3.85-3.72 (m, 4H), 3.01-2.87 (m, 4H), 2.79 (quintet, J=12.9, 6.4 Hz, 1H), 2.75-2.63 (m, 4H), 2.43-2.29 (m, 2H), 2.26-2.13 (m, 2H), 2.12-1.98 (m, 2H), 1.69-1.53 (m, 8H), 1.42-1.31 (m, 1H), 1.31-1.18 (m, 4H), 1.09 (d, J=6.5 Hz, 6H), 0.93 (d, J=6.3 Hz, 3H).

LCMS, m/z 533[M+H]+

<Example 16> Preparation of N-(1-isopropylpiperidine-4-yl)-6-methoxy-2-(piperidine-1-yl)-7-(4-(pyrrolidine-1-yl)-1-butyne-1-yl)quinazoline-4-amine

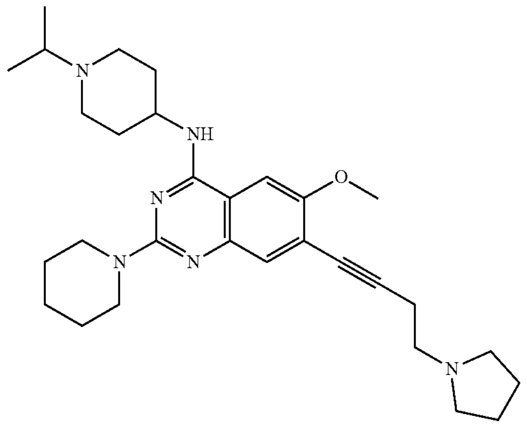 [SMILES: COc1cc2c(NC3CCN(C(C)C)CC3)nc(N3CCCCC3)nc2cc1C#CCCN1CCCC1]

A target compound N-(1-isopropylpiperidine-4-yl)-6-methoxy-2-(piperidine-1-yl)-7-(4-(pyrrolidine-1-yl)-1-butyne-1-yl)quinazoline-4-amine(N-(1-isopropylpiperidine-4-yl)-6-methoxy-2-(piperidine-1-yl)-7-(4-(pyrrolidine-1-yl) but-1-yn-1-yl)quinazolin-4-amine) was obtained (8 mg, yield: 60.1%) by performing the procedure of steps 1 to 3 of Example 1, except that 1-(3-butyne-1-yl)pyrrolidine was used instead of N,N-dimethyl-4-pentyneamide in step 3 of Example 1.

$^1$H NMR (400 MHz, $CDCl_3$) δ7.53 (s, 1H), 6.67 (s, 1H), 5.11 (d, J=6.8 Hz, 1H), 4.19-4.02 (m, 1H), 3.92 (s, 3H), 3.85-3.72 (m, 4H), 2.99-2.89 (m, 2H), 2.85-2.75 (m, 3H), 2.74-2.67 (m, 2H), 2.64-2.56 (m, 4H), 2.41-2.30 (m, 2H), 2.25-2.14 (m, 2H), 1.86-1.74 (m, 4H), 1.69-1.55 (m, 8H), 1.09 (d, J=6.5 Hz, 6H).

LCMS, m/z 505[M+H]+

<Example 17> Preparation of 7-(4-(dimethylamino)-1-butyne-1-yl)-N-(1-isopropylpiperidine-4-yl)-6-methoxy-2-(4-methyl-1,4-diazepane-1-yl)quinazoline-4-amine Step 1. Preparation of 7-iodo-N-(1-isopropylpiperidine-4-yl)-6-methoxy-2-(4-methyl-1,4-diazepane-1-yl)quinazoline-4-amine

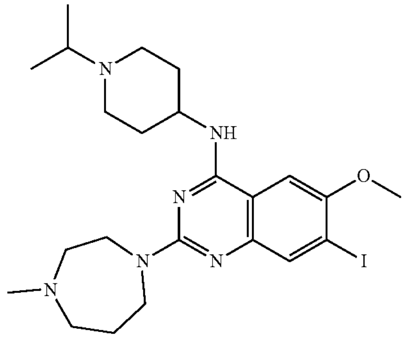

A target compound was obtained (14 mg, yield: 57.6%) as a yellow solid by performing the procedure of steps 1 to 2 of Example 1, except that 1-methylhomopiperazine was used instead of piperidine in step 2 of Example 1.

$^1$H NMR (400 MHz, $CDCl_3$) δ8.02 (s, 1H), 6.64 (s, 1H), 5.10 (d, J=7.1 Hz, 1H), 4.14-4.02 (m, 1H), 3.99-3.94 (m, 2H), 3.92 (s, 3H), 3.86 (t, J=6.4 Hz, 2H), 2.99-2.89 (m, 2H), 2.78 (quintet, J=6.6 Hz, 1H), 2.72-2.65 (m, 2H), 2.61-2.51 (m, 2H), 2.37 (s, 3H), 2.36-2.28 (m, 2H), 2.25-2.13 (m, 2H), 2.08-1.95 (m, 2H), 1.61 (ddd, J=14.9, 11.7, 3.6 Hz, 2H), 1.09 (d, J=6.6 Hz, 6H).

LCMS, 539 m/z [M+H]+

Step 2. Preparation of 7-(4-(dimethylamino)-1-butyne-1-yl)-N-(1-isopropylpiperidine-4-yl)-6-methoxy-2-(4-methoxy-1,4-diazepane-1-yl)quinazoline-4-amine

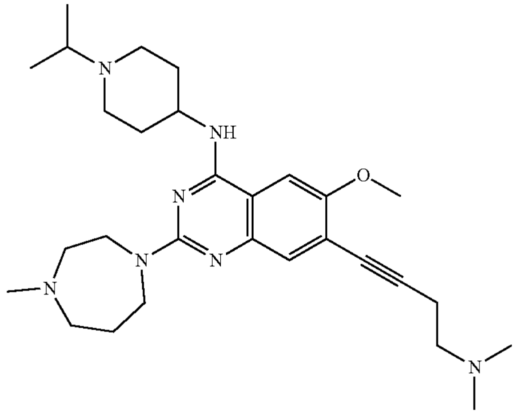

A target compound 7-(4-(dimethylamino)-1-butyne-1-yl)-N-(1-isopropylpiperidine-4-yl)-6-methoxy-2-(4-methyl-1,4-diazepane-1-yl)quinazoline-4-amine(7-(4-(dimethylamino)but-1-yn-1-yl)-N-(1-isopropylpiperidine-4-yl)-6-methoxy-2-(4-methyl-1,4-diazepane-1-yl)quinazolin-4-amine) was obtained (13 mg, yield: 58.8%) as a yellow solid in the same manner as described in step 3 of Example 1 that 7-iodo-N-(1-isopropylpiperidine-4-yl)-6-methoxy-2-(4-methyl-1,4-diazepane-1-yl)quinazoline-4-amine and N,N-dimethyl-3-butyne-1-amine were used as starting materials in step 3 of Example 1.

$^1$H NMR (400 MHz, $CDCl_3$) δ7.53 (s, 1H), 6.65 (s, 1H), 5.06 (d, J=7.1 Hz, 1H), 4.12-4.02 (m, 1H), 3.99-3.93 (m, 2H), 3.92 (s, 3H), 3.86 (t, J=6.4 Hz, 2H), 2.93 (d, J=11.9 Hz, 2H), 2.78 (quintet, J=6.6 Hz, 1H), 2.72-2.67 (m, 2H), 2.65 (s, 4H), 2.59-2.53 (m, 2H), 2.37 (s, 3H), 2.36-2.32 (m, 2H), 2.31 (s, 6H), 2.19 (d, J=12.2 Hz, 2H), 2.04-1.96 (m, 2H), 1.67-1.53 (m, 2H), 1.08 (d, J=6.5 Hz, 6H).

LCMS, m/z 508[M+H]+

<Example 18> Preparation of N-(1-benzylpiperidine-4-yl)-7-(4-(dimethylamino)-1-butyne-1-yl)-6-methoxy-2-(piperidine-1-yl)quinazoline-4-amine Step 1. Preparation of N-(1-benzylpiperidine-4-yl)-2-chloro-7-iodo-6-methoxyquinazoline-4-amine

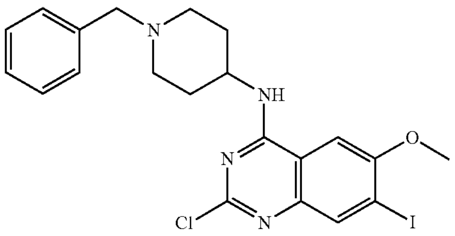 [SMILES: COc1cc2c(NC3CCN(Cc4ccccc4)CC3)nc(Cl)nc2cc1I]

A target compound was obtained (147 mg, yield: 100%) as a yellow solid by performing the procedure of step 1 of Example 1, except that 1-benzylpiperidine-4-amine was used instead of 1-isopropylpiperidine-4-amine in step 1 of Example 1.

LCMS, m/z 509[M+H]+

Step 2. Preparation of N-(1-benzylpiperidine-4-yl)-7-iodo-6-methoxy-2-(piperidine-1-yl)quinazoline-4-amine

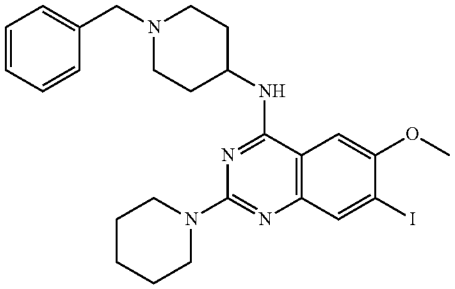 [SMILES: COc1cc2c(NC3CCN(Cc4ccccc4)CC3)nc(N3CCCCC3)nc2cc1I]

A target compound was obtained (54 mg, yield: 75%) as a yellow solid in the same manner as described in step 2 of Example 1 that N-(1-benzylpiperidine-4-yl)-2-chloro-7-iodo-6-methoxyquinazoline-4-amine was used as a starting material in step 2 of Example 1.

$^1$H NMR (400 MHz, $CDCl_3$) δ8.02 (s, 1H), 7.38-7.32 (m, 3H), 7.32-7.26 (m, 2H), 6.61 (s, 1H), 5.05 (d, J=4.6 Hz, 1H), 4.23-4.05 (m, 1H), 3.91 (s, 3H), 3.85-3.71 (m, 4H), 3.56 (s, 2H), 3.04-2.79 (m, 2H), 2.37-2.07 (m, 4H), 1.75-1.55 (m, 8H).

LCMS, m/z 558[M+H]+

Step 3. Preparation of N-(1-benzylpiperidine-4-yl)-7-(4-dimethylamino)-1-butyne-1-yl)-6-methoxy-2-(piperidine-1-yl)quinazoline-4-amine

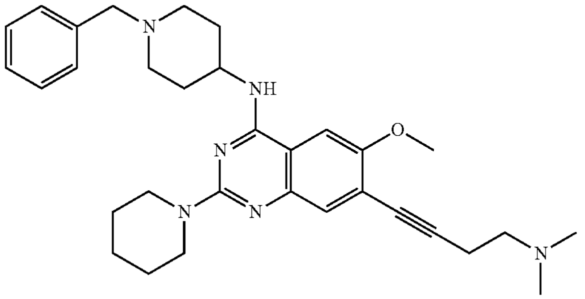 [SMILES: COc1cc2c(NC3CCN(Cc4ccccc4)CC3)nc(N3CCCCC3)nc2cc1C#CCCN(C)C]

A target compound N-(1-benzylpiperidine-4-yl)-7-(4-(dimethylamino)-1-butyne-1-yl)-6-methoxy-2-(piperidine-1-yl)quinazoline-4-amine(N-(1-benzylpiperidine-4-yl)-7-(4-(dimethylamino)but-1-yn-1-yl)-6-methoxy-2-(piperidine-1-yl)quinazolin-4-amine) was obtained (12 mg, yield: 47.3%) as a yellow solid in the same manner as described in step 3 of Example 1 that N-(1-benzylpiperidine-4-yl)-7-iodo-6-methoxy-2-(piperidine-1-yl)quinazoline-4-amine and N,N-dimethyl-3-butyne-1-amine were used as starting materials in step 3 of Example 1. 1H NMR (400 MHz, $CDCl_3$) δ7.53 (s, 1H), 7.34 (s, 2H), 7.33 (d, J=2.4 Hz, 2H), 7.31-7.27 (m, 1H), 6.63 (s, 1H), 5.02 (d, J=5.9 Hz, 1H), 4.18-4.08 (m, 1H), 3.91 (s, 3H), 3.83-3.75 (m, 4H), 3.56 (s, 2H), 2.91 (d, J=11.8 Hz, 2H), 2.65 (s, 4H), 2.31 (s, 6H), 2.22 (t, J=11.9 Hz, 2H), 2.18-2.10 (m, 2H), 1.67-1.60 (m, 8H).

LCMS, m/z 527[M+H]+

<Example 19> Preparation of (R)—N-(1-benzylpiperidine-3-yl)-7-(4-(dimethylamino)-1-butyne-1-yl)-6-methoxy-2-(piperidine-1-yl)quinazoline-4-amine Step 1. Preparation of (R)—N-(1-benzylpiperidine-3-yl)-2-chloro-7-iodo-6-methoxyquinazoline-4-amine

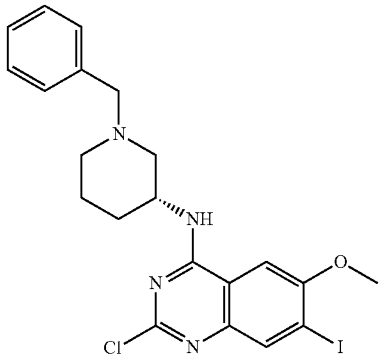 [SMILES: COc1cc2c(N[C@@H]3CCCN(Cc4ccccc4)C3)nc(Cl)nc2cc1I]

A target compound was obtained (78 mg, yield: 100%) as a yellow solid by performing the procedure of step 1 of Example 1, except that (R)-1-benzylpiperidine-3-amine was used instead of 1-isopropylpiperidine-4-amine in step 1 of Example 1.

LCMS, m/z 509[M+H]+

Step 2. Preparation of (R)—N-(1-benzylpiperidine-3-yl)-7-iodo-6-methoxy-2-(piperidine-1-yl)quinazoline-4-amine

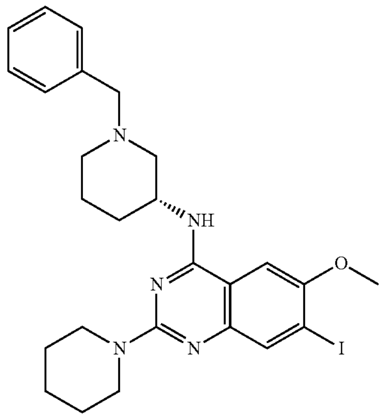 [SMILES: COc1cc2c(N[C@@H]3CCCN(Cc4ccccc4)C3)nc(N3CCCCC3)nc2cc1I]

A target compound was obtained (63 mg, yield: 80%) as a yellow solid in the same manner as described in step 2 of Example 1 that (R)—N-(1-benzylpiperidine-3-yl)-2-chloro-7-iodo-6-methoxyquinazoline-4-amine was used as a starting material in step 2 of Example 1.

$^{1}$H NMR (400 MHz, $CDCl_3$) δ8.00 (s, 1H), 7.38-7.26 (m, 5H), 6.69 (s, 1H), 6.01 (br s, 1H), 4.45-4.29 (m, 1H), 3.97 (s, 3H), 3.83-3.68 (m, 4H), 3.55 (q, J=13.2 Hz, 2H), 2.84-2.68 (m, 1H), 2.68-2.53 (m, 2H), 2.41-2.21 (m, 1H), 2.06-1.89 (m, 1H), 1.86-1.71 (m, 1H), 1.68-1.57 (m, 8H).

LCMS, m/z 558 [M+H]+

Step 3. Preparation of (R)—N-(1-benzylpiperidine-3-yl)-7-(4-dimethylamino)-1-butyne-1-yl)-6-methoxy-2-(piperidine-1-yl)quinazoline-4-amine

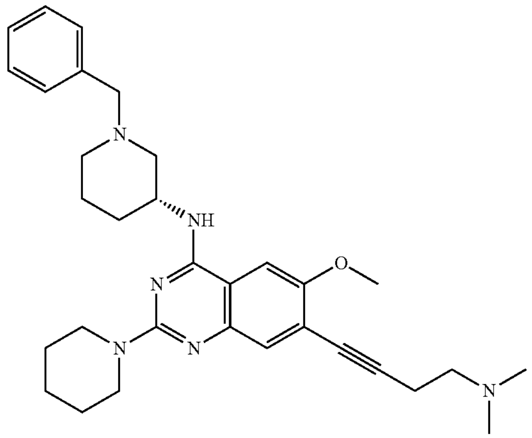 [SMILES: COc1cc2c(N[C@@H]3CCCN(Cc4ccccc4)C3)nc(N3CCCCC3)nc2cc1C#CCCN(C)C]

A target compound (R)—N-(1-benzylpiperidine-3-yl)-7-(4-(dimethylamino)-1-butyne-1-yl)-6-methoxy-2-(piperidine-1-yl)quinazoline-4-amine ((R)—N-(1-benzylpiperidine-3-yl)-7-(4-(dimethylamino)but-1-yn-1-yl)-6-methoxy-2-(piperidine-1-yl)quinazolin-4-amine) was obtained (16 mg, yield: 28.6%) as a yellow solid in the same manner as described in step 3 of Example 1 that (R)—N-(1-benzylpiperidine-3-yl)-7-iodo-6-methoxy-2-(piperidine-1-yl)quinazoline-4-amine and N,N-dimethyl-3-butyne-1-amine were used as starting materials in step 3 of Example 1.

$^{1}$H NMR (400 MHz, $CDCl_3$) δ7.52 (s, 1H), 7.36-7.25 (m, 5H), 6.71 (s, 1H), 5.94 (s, 1H), 4.41-4.35 (m, 1H), 3.97 (s, 3H), 3.78-3.76 (m, 4H), 3.55 (q, J=14.4 Hz, 2H), 2.74-2.70 (m, 1H), 2.66 (s, 4H), 2.62-2.56 (m, 2H), 2.32 (s, 6H), 2.24 (s, 2H), 1.97-1.93 (m, 1H), 1.80-1.74 (m, 1H), 1.63-1.58 (m, 8H).

LCMS, m/z 527[M+H]+

<Example 20> Preparation of 7-(4-(dimethylamino)-1-butyne-1-yl)-6-methoxy-2-(piperidine-1-yl)-N-(2-(pyrrolidine-1-yl)ethyl)quinazoline-4-amine Step 1. Preparation of 2-chloro-7-iodo-6-methoxy-N-(2-pyrrolidine-1-yl)ethyl)quinazoline-4-amine

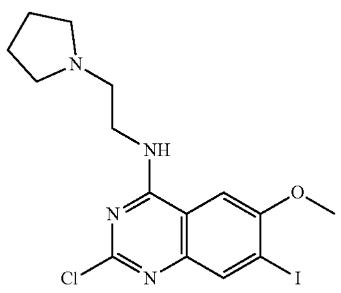 [SMILES: COc1cc2c(NCCN3CCCC3)nc(Cl)nc2cc1I]

A target compound was obtained (21 mg, yield: 34.5%) as a yellow solid by performing the procedure of step 1 of Example 1, except that 2-(pyrrolidine-1-yl)ethaneamine was used instead of 1-isopropylpiperidine-4-amine in step 1 of Example 1.

LCMS, m/z 433[M+H]+

Step 2. Preparation of 7-iodo-6-methoxy-2-(piperidine-1-yl)-N-(2-(pyrrolidine-1-yl)ethyl)quinazoline-4-amine

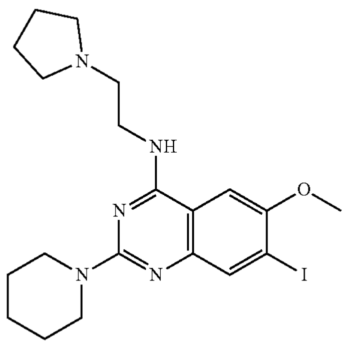 [SMILES: COc1cc2c(NCCN3CCCC3)nc(N3CCCCC3)nc2cc1I]

A target compound was obtained (21 mg, yield: 89%) as a yellow solid in the same manner as described in step 2 of Example 1 that 2-chloro-7-iodo-6-methoxy-N-(2-(pyrrolidine-1-yl)quinazoline-4-amine was used as a starting material in step 2 of Example 1.

$^{1}$H NMR (400 MHz, $CDCl_3$) δ8.01 (s, 1H), 6.75 (s, 1H), 6.10 (s, 1H), 3.90 (s, 3H), 3.86-3.78 (m, 4H), 3.74-3.61 (m, 2H), 2.81 (t, J=6.2 Hz, 2H), 2.67-2.55 (m, 4H), 1.90-1.77 (m, 4H), 1.70-1.55 (m, 6H).

LCMS, m/z 482[M+H]+

Step 3. Preparation of 7-(4-(dimethylamino)-1-butyne-1-yl)-6-methoxy-2-(piperidine-1-yl)-N-(2-(pyrrolidine-1-yl)ethyl)quinazoline-4-amine

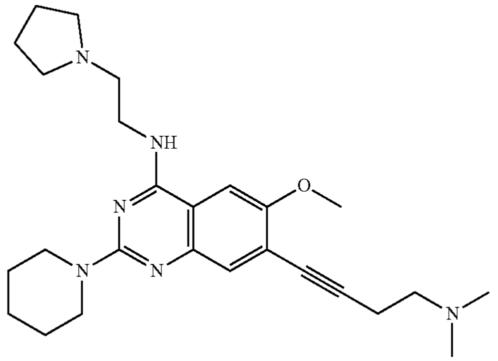 [SMILES: COc1cc2c(NCCN3CCCC3)nc(N3CCCCC3)nc2cc1C#CCCN(C)C]

A target compound 7-(4-(dimethylamino)-1-butyne-1-yl)-6-methoxy-2-(piperidine-1-yl)-N-(2-(pyrrolidine-1-yl)ethyl)quinazoline-4-amine(7-(4-(dimethylamino)but-1-yn-1-yl)-6-methoxy-2-(piperidine-1-yl)-N-(2-(pyrrolidine-1-yl)ethyl)quinazolin-4-amine) was obtained (2 mg, yield: 10.7%) as a yellow solid in the same manner as described in step 3 of Example 1 that 7-iodo-6-methoxy-2-(piperidine-1-yl)-N-(2-(pyrrolidine-1-yl)ethyl)quinazoline-4-amine and N,N-dimethyl-3-butyne-1-amine were used as starting materials in step 3 of Example 1.

$^1$H NMR (400 MHz, $CDCl_3$) δ7.53 (s, 1H), 6.92 (s, 1H), 6.39 (s, 1H), 3.93 (s, 3H), 3.83-3.78 (m, 4H), 3.78-3.71 (m, 2H), 3.00-2.86 (m, 2H), 2.86-2.68 (m, 4H), 2.68-2.60 (m, 4H), 2.31 (s, 6H), 1.95-1.82 (m, 4H), 1.69-1.55 (m, 6H).

LCMS, m/z 451[M+H]+

<Example 21> Preparation of N1-(7-(4-(dimethylamino)-1-butyne-1-yl)-6-methoxy-2-(piperidine-1-yl)quinazoline-4-yl)-N3,N3-dimethylpropane-1,3-diamine Step 1. Preparation of N1-(2-chloro-7-iodo-6-methoxyquinazoline-4-yl)-N3,N3-dimethylpropane-1,3-diamine

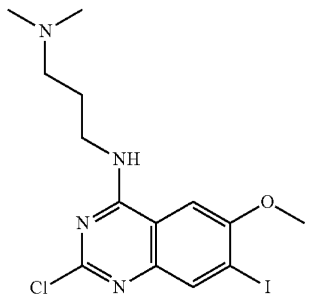

A target compound was obtained (51 mg, yield: 86%) as a yellow solid by performing the procedure of step 1 of Example 1, except that N1,N1-dimethylpropane-1,3-diamine was used instead of 1-isopropylpiperidine-4-amine in step 1 of Example 1.

LCMS, m/z 421[M+H]+

Step 2. Preparation of N1-(7-iodo-6-methoxy-2-(piperidine-1-yl)quinazoline-4-yl)-N3,N3-dimethylpropane-1,3-diamine

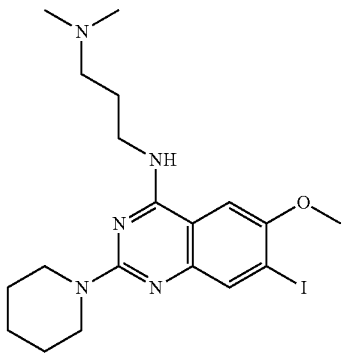 [SMILES: COc1cc2c(NCCCN(C)C)nc(N3CCCCC3)nc2cc1I]

A target compound was obtained (41 mg, yield: 70.6%) as a yellow solid in the same manner as described in step 2 of Example 1 that N1-(2-chloro-7-iodo-6-methoxyquinazoline-4-yl)-N3,N3-dimethylpropane-1,3-diamine was used as a starting material in step 2 of Example 1. 1H NMR (400 MHz, $CDCl_3$) δ8.22 (s, 1H), 7.99 (s, 1H), 6.67 (s, 1H), 3.88 (s, 3H), 3.85-3.78 (m, 4H), 3.67 (dd, J=10.3, 5.8 Hz, 2H), 2.61-2.52 (m, 2H), 2.35 (s, 6H), 1.83 (dt, J=11.5, 5.8 Hz, 2H), 1.69-1.54 (m, 6H).

LCMS, m/z 470[M+H]+

Step 3. Preparation of N1-(7-(4-(dimethylamino)-1-butyne-1-yl)-6-methoxy-2-(piperidine-1-yl)quinazoline-4-yl)-N3,N3-dimethylpropane-1,3-diamine

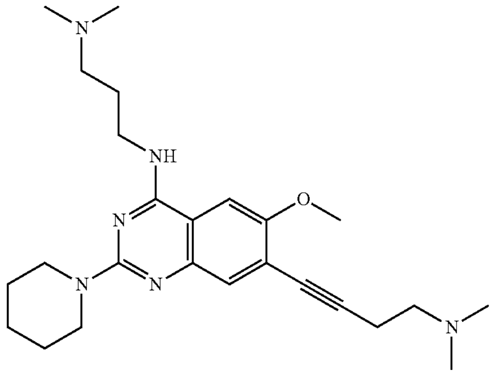 [SMILES: COc1cc2c(NCCCN(C)C)nc(N3CCCCC3)nc2cc1C#CCCN(C)C]

A target compound N1-(7-(4-(dimethylamino)-1-butyne-1-yl)-6-methoxy-2-(piperidine-1-yl)quinazoline-4-yl)-N3,N3-dimethylpropane-1,3-diamine(N1-(7-(4-(dimethylamino)but-1-yn-1-yl)-6-methoxy-2-(piperidine-1-yl)quinazolin-4-yl)-N3,N3-dimethylpropane-1,3-diamine) was obtained (5 mg, yield: 13.5%) as a yellow solid in the same manner as described in step 3 of Example 1 that N1-(7-iodo-6-methoxy-2-(piperidine-1-yl)quinazoline-4-yl)-N3,N3-dimethylpropane-1,3-diamine and N,N-dimethyl-3-butyne-1-amine were used as starting materials in step 3 of Example 1.

$^1$H NMR (400 MHz, $CDCl_3$) δ8.08 (s, 1H), 7.53 (s, 1H), 6.70 (s, 1H), 3.88 (s, 3H), 3.83-3.81 (m, 4H), 3.70-3.66 (m, 2H), 2.65 (s, 4H), 2.61-2.52 (m, 2H), 2.35 (s, 6H), 2.31 (s, 6H), 1.87-1.81 (m, 2H), 1.62-1.60 (m, 6H).

LCMS, m/z 439[M+H]+

<Example 22> Preparation of 7-(4-(dimethylamino)-1-butyne-1-yl)-6-methoxy-N-(1-methylpiperidine-4-yl)-2-(piperidine-1-yl)quinazoline-4-amine Step 1. Preparation of 2-chloro-7-iodo-6-methoxy-N-(1-methylpiperidine-4-yl)quinazoline-4-amine

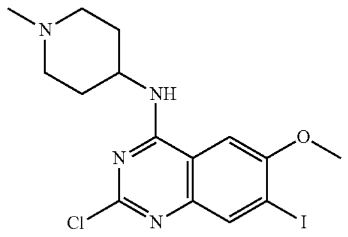

A target compound was obtained (100 mg, yield: 82%) as a yellow solid by performing the procedure of step 1 of Example 1, except that 1-methylpiperidine-4-amine was used instead of 1-isopropylpiperidine-4-amine in step 1 of Example 1.

LCMS, m/z 433[M+H]+

Step 2. Preparation of 7-iodo-6-methyl-N-(1-methylpiperidine-4-yl)-2-(piperidine-1-yl)quinazoline-4-amine

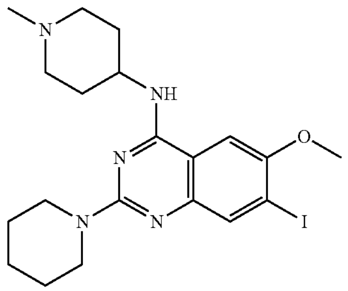

A target compound was obtained (36 mg, yield: 73.5%) as a yellow solid in the same manner as described in step 2 of Example 1 that 2-chloro-7-iodo-6-methoxy-N-(1-methylpiperidine-4-yl)quinazoline-4-amine was used as a starting material in step 2 of Example 1.

$^1$H NMR (400 MHz, $CDCl_3+D_2O$) 58.02 (s, 1H), 6.64 (s, 1H), 4.18-4.06 (m, 1H), 3.93 (s, 3H), 3.84-3.73 (m, 4H), 2.97-2.82 (m, 2H), 2.33 (s, 3H), 2.26-2.11 (m, 4H), 1.74-1.61 (m, 8H).

LCMS, m/z 482 [M+H]+

Step 3. Preparation of 7-(4-(dimethylamino)-1-butyne-1-yl)-6-methoxy-N-(1-methylpiperidine-4-yl)-2-(piperidine-1-yl)quinazoline-4-amine

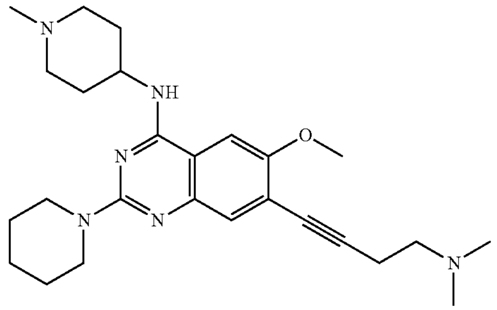 [SMILES: COc1cc2c(NC3CCN(C)CC3)nc(N3CCCCC3)nc2cc1C#CCCN(C)C]

A target compound 7-(4-(dimethylamino)-1-butyne-1-yl)-6-methoxy-N-(1-methylpiperidine-4-yl)-2-(piperidine-1-yl) quinazoline-4-amine(7-(4-(dimethylamino)but-1-yn-1-yl)-6-methoxy-N-(1-methylpiperidine-4-yl)-2-(piperidine-1-yl) quinazolin-4-amine) was obtained (1.3 mg, yield: 3.81%) as a yellow solid in the same manner as described in step 3 of Example 1 that 7-iodo-6-methoxy-N-(1-methylpiperidine-4-yl)-2-(piperidine-1-yl)quinazoline-4-amine and N,N-dimethyl-3-butyne-1-amine were used as starting materials in step 3 of Example 1.

$^1$H NMR (400 MHz, $CDCl_3$) δ7.54 (s, 1H), 6.65 (s, 1H), 5.06-4.93 (m, 1H), 4.19-4.04 (m, 1H), 3.93 (s, 3H), 3.86-3.66 (m, 4H), 2.94-2.79 (m, 2H), 2.75-2.56 (m, 4H), 2.34 (s, 3H), 2.31 (s, 6H), 2.25-2.11 (m, 4H), 1.71-1.56 (m, 8H).

LCMS, m/z 451[M+H]+

<Example 23> Preparation of N-cyclohexyl-7-(4-(dimethylamino)-1-butyne-1-yl)-6-methoxy-2-(piperidine-1-yl)quinazoline-4-amine Step 1. Preparation of 2-chloro-N-cyclohexyl-7-iodo-6-methoxyquinazoline-4-amine

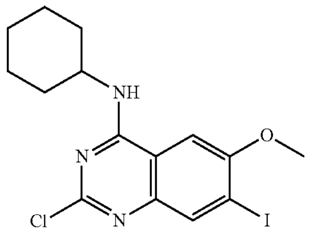 [SMILES: COc1cc2c(NC3CCCCC3)nc(Cl)nc2cc1I]

A target compound was obtained (72 mg, yield: 87%) as a yellow solid by performing the procedure of step 1 of Example 1, except that cyclohexaneamine was used instead of 1-isopropylpiperidine-4-amine in step 1 of Example 1.

LCMS, m/z 418[M+H]+

Step 2. Preparation of N-cyclohexyl-7-iodo-6-methoxy-2-(piperidine-1-yl)quinazoline-4-amine

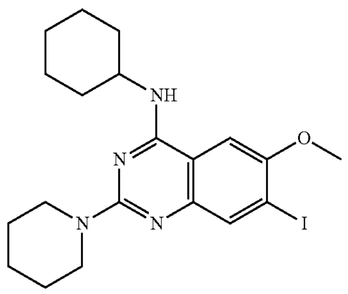 [SMILES: COc1cc2c(NC3CCCCC3)nc(N3CCCCC3)nc2cc1I]

A target compound was obtained (41 mg, yield: 51%) as a yellow solid in the same manner as described in step 2 of Example 1 that 2-chloro-N-cyclohexyl-7-iodo-6-methoxy-quinazoline-4-amine was used as a starting material in step 2 of Example 1.

LCMS, m/z 467[M+H]+

Step 3. Preparation of N-cyclohexyl-7-(4-(dimethyl-amino)-1-butyne-1-yl)-6-methoxy-2-(piperidine-1-yl)quinazoline-4-amine

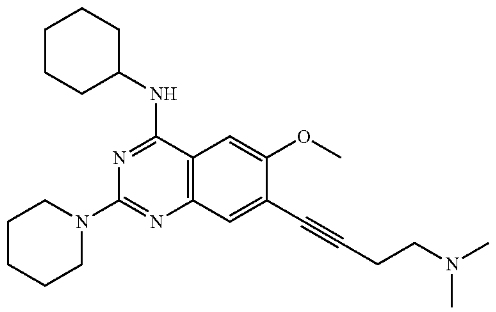 [SMILES: COc1cc2c(NC3CCCCC3)nc(N3CCCCC3)nc2cc1C#CCCN(C)C]

A target compound N-cyclohexyl-7-(4-(dimethylamino)-1-butyne-1-yl)-6-methoxy-2-(piperidine-1-yl)quinazoline-4-amine (N-cyclohexyl-7-(4-(dimethylamino)but-1-yn-1-yl)-6-methoxy-2-(piperidine-1-yl)quinazolin-4-amine) was obtained (9 mg, yield: 23.4%) as a yellow solid in the same manner as described in step 3 of Example 1 that N-cyclohexyl-7-iodo-6-methoxy-2-(piperidine-1-yl)quinazoline-4-amine and N,N-dimethyl-3-butyne-1-amine were used as starting materials in step 3 of Example 1.

$^1H$ NMR (400 MHz, $CDCl_3$) δ7.53 (s, 1H), 6.65 (s, 1H), 5.04 (s, 1H), 4.17-4.03 (m, 1H), 3.91 (s, 3H), 3.81-3.80 (m, 4H), 2.65 (s, 4H), 2.31 (s, 6H), 2.21-2.08 (m, 2H), 1.86-1.76 (m, 2H), 1.63-1.61 (m, 6H), 1.52-1.36 (m, 2H), 1.36-1.19 (m, 4H).

LCMS, m/z 436[M+H]+

<Example 24> Preparation of N-(1-cyclopropylpiperidine-4-yl)-7-(4-(dimethylamino)-1-butyne-1-yl)-6-methoxy-2-(piperidine-1-yl)quinazoline-4-amine Step 1. Preparation of 2-chloro-N-(1-cyclopropylpiperidine-4-yl)-7-iodo-6-methoxyquinazoline-4-amine A target compound was obtained (59 mg, yield: 91%) as a yellow solid by performing the procedure of step 1 of Example 1, except that 1-cyclopropylpiperidine-4-amine was used instead of 1-isopropylpiperidine-4-amine in step 2 of Example 1.

LCMS, m/z 459[M+H]+

Step 2. Preparation of N-(1-cyclopropylpiperidine-4-yl)-7-iodo-6-methoxy-2-(piperidine-1-yl)quinazoline-4-amine

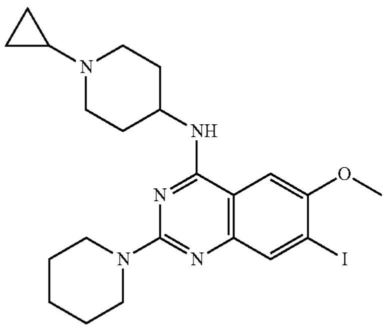 [SMILES: COc1cc2c(NC3CCN(C4CC4)CC3)nc(N3CCCCC3)nc2cc1I]

A target compound was obtained (24 mg, yield: 35.5%) as a yellow solid in the same manner as described in step 2 of Example 1 that 2-chloro-N-(1-cyclopropylpiperidine-4-yl)-7-iodo-6-methoxyquinazoline-4-amine was used as a starting material in step 2 of Example 1.

$^1H$ NMR (400 MHz, $CDCl_3$) δ8.01 (s, 1H), 6.65 (s, 1H), 5.18 (s, 1H), 4.21-4.01 (m, 1H), 3.89 (s, 3H), 3.85-3.71 (m, 4H), 3.13-2.97 (m, 2H), 2.50-2.34 (m, 2H), 2.20-2.09 (m, 2H), 1.71-1.54 (m, 8H), 0.93-0.80 (m, 1H), 0.56-0.37 (m, 4H).

LCMS, m/z 508[M+H]+

Step 3. Preparation of N-(1-cyclopropylpiperidine-4-yl)-7-(4-dimethylamino)-1-butyne-1-yl)-6-methoxy-2-(piperidine-1-yl)quinazoline-4-amine

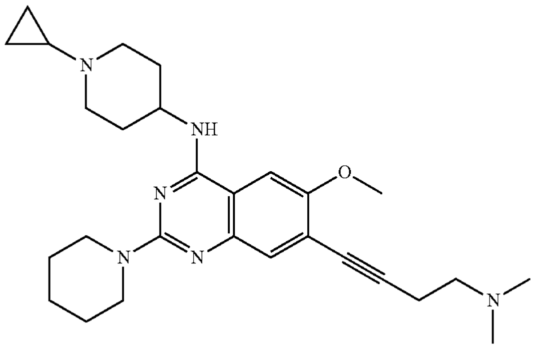 [SMILES: COc1cc2c(NC3CCN(C4CC4)CC3)nc(N3CCCCC3)nc2cc1C#CCCN(C)C]

A target compound N-(1-cyclopropylpiperidine-4-yl)-7-(4-(dimethylamino)-1-butyne-1-yl)-6-methoxy-2-(piperidine-1-yl)quinazoline-4-amine(N-(1-cyclopropylpiperidine-4-yl)-7-(4-(dimethylamino)but-1-yn-1-yl)-6-methoxy-2-(piperidine-1-yl)quinazolin-4-amine) was obtained (0.5 mg, yield: 2.05%) as a yellow solid in the same manner as described in step 3 of Example 1 that N-(1-cyclopropylpiperidine-4-yl)-7-iodo-6-methoxy-2-(piperidine-1-yl)quinazoline-4-amine and N,N-dimethyl-3-butyne-1-amine were used as starting materials in step 3 of Example 1.

$^1$H NMR (400 MHz, $CDCl_3$) δ7.53 (s, 1H), 6.62 (s, 1H), 4.98 (d, J=5.7 Hz, 1H), 4.19-4.09 (m, 1H), 3.91 (s, 3H), 3.85-3.73 (m, 4H), 3.11-2.98 (m, 2H), 2.70-2.59 (m, 4H), 2.47-2.36 (m, 2H), 2.31 (s, 6H), 2.20-2.10 (m, 2H), 1.69-1.58 (m, 8H), 0.92-0.83 (m, 1H), 0.51-0.39 (m, 4H).

LCMS, m/z 477[M+H]+

<Example 25> Preparation of 7-(4-(dimethylamino)-1-butyne-1-yl)-6-methoxy-N-(1-phenylpiperidine-4-yl)-2-(piperidine-1-yl)quinazoline-4-amine

Step 1. Preparation of 2-chloro-7-iodo-6-methoxy-N-(1-phenylpiperidine-4-yl)quinazoline-4-amine

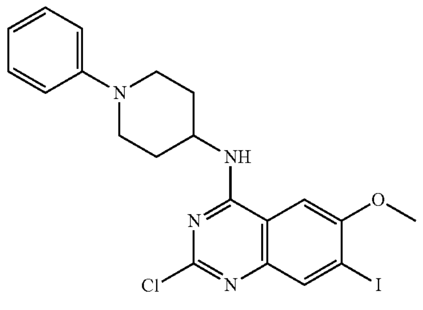 [SMILES: COc1cc2c(NC3CCN(c4ccccc4)CC3)nc(Cl)nc2cc1I]

A target compound was obtained (65 mg, yield: 93%) as a yellow solid by performing the procedure of step 1 of Example 1, except that 1-phenylpiperidine-4-amine was used instead of 1-isopropylpiperidine-4-amine in step 1 of Example 1.

LCMS, m/z 495[M+H]+

Step 2. Preparation of 7-iodo-6-methoxy-N-(1-phenylpiperidine-4-yl)-2-(piperidine-1-yl)quinazoline-4-amine

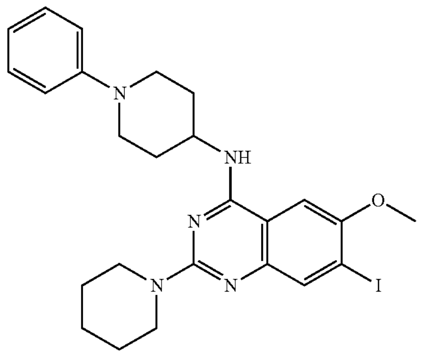 [SMILES: COc1cc2c(NC3CCN(c4ccccc4)CC3)nc(N3CCCCC3)nc2cc1I]

A target compound was obtained (61 mg, yield: 84%) as a yellow solid in the same manner as described in step 2 of Example 1 that 2-chloro-7-iodo-6-methoxy-N-(1-phenylpiperidine-4-yl)quinazoline-4-amine was used as a starting material in step 2 of Example 1.

LCMS, m/z 544[M+H]+

Step 3. Preparation of 7-(4-(dimethylamino)-1-butyne-1-yl)-6-methoxy-N-(1-phenylpiperidine-4-yl)-2-(piperidine-1-yl)quinazoline-4-amine

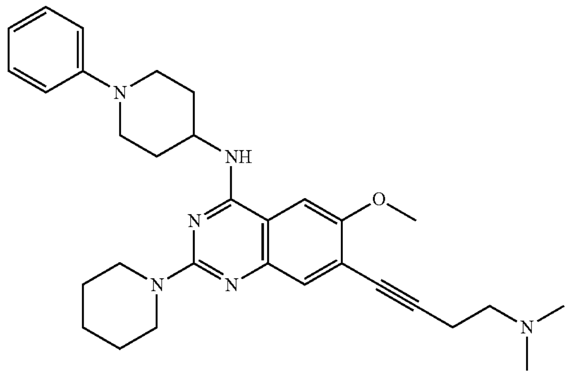 [SMILES: COc1cc2c(NC3CCN(c4ccccc4)CC3)nc(N3CCCCC3)nc2cc1C#CCCN(C)C]

A target compound 7-(4-(dimethylamino)-1-butyne-1-yl)-6-methoxy-N-(1-phenylpiperidine-4-yl)-2-(piperidine-1-yl)quinazoline-4-amine(7-(4-(dimethylamino)but-1-yn-1-yl)-6-methoxy-N-(1-phenylpiperidine-4-yl)-2-(piperidine-1-yl)quinazolin-4-amine) was obtained (5.6 mg, yield: 23.5%) as a yellow solid in the same manner as described in step 3 of Example 1 that 7-iodo-6-methoxy-N-(1-phenylpiperidine-4-yl)-2-(piperidine-1-yl)quinazoline-4-amine and N,N-dimethyl-3-butyne-1-amine were used as starting materials in step 3 of Example 1.

$^1$H NMR (400 MHz, $CDCl_3$) δ7.54 (s, 1H), 7.32-7.26 (m, 2H), 6.98 (d, J=8.0 Hz, 2H), 6.86 (t, J=7.3 Hz, 1H), 6.65 (s, 1H), 5.08 (d, J=7.1 Hz, 1H), 4.37-4.25 (m, 1H), 3.91 (s, 3H), 3.84-3.78 (m, 4H), 3.76-3.69 (m, 2H), 3.08-2.91 (m, 2H), 2.71-2.61 (m, 4H), 2.31 (s, 6H), 2.30-2.21 (m, 2H), 1.81-1.68 (m, 2H), 1.67-1.57 (m, 6H).

LCMS, m/z 513[M+H]+

<Example 26> Preparation of 7-(4-(dimethylamino)-1-butyne-1-yl)-6-methoxy-2-(piperidine-1-yl)-N-(pyridine-3-ylmethyl)quinazoline-4-amine

Step 1. Preparation of 2-chloro-7-iodo-6-methoxy-N-(pyridine-3-ylmethyl)quinazoline-4-amine

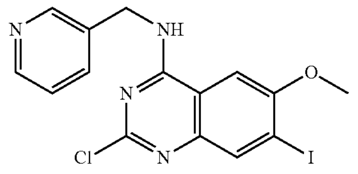

A target compound was obtained (55 mg, yield: 92%) as a yellow solid by performing the procedure of step 1 of Example 1, except that pyridine-3-ylmethaneamine was used instead of 1-isopropylpiperidine-4-amine in step 1 of Example 1.

LCMS, m/z 427[M+H]+

Step 2. Preparation of 7-iodo-6-methoxy-2-(piperidine-1-yl)-N-(pyridine-3-ylmethyl)quinazoline-4-amine

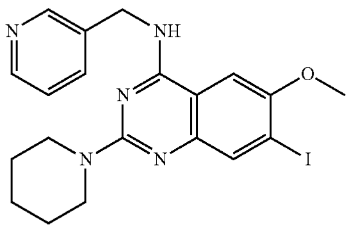 [SMILES: COc1cc2c(NCc3cccnc3)nc(N3CCCCC3)nc2cc1I]

A target compound was obtained (41 mg, yield: 66.9%) as a yellow solid in the same manner as described in step 2 of Example 1 that 2-chloro-7-iodo-6-methoxy-N-(pyridine-3-ylmethyl)quinazoline-4-amine was used as a starting material in step 2 of Example 1.

LCMS, m/z 476[M+H]+

Step 3. Preparation of 7-(4-(dimethylamino)-1-butyne-1-yl)-6-methoxy-2-(piperidine-1-yl)-N-(pyridine-3-ylmethyl)quinazoline-4-amine

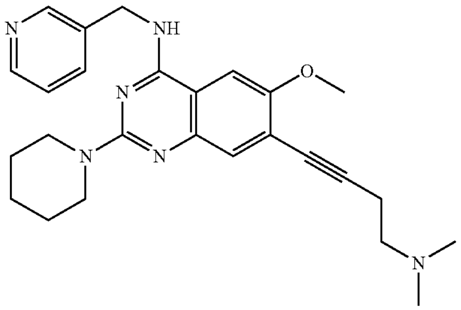 [SMILES: COc1cc2c(NCc3cccnc3)nc(N3CCCCC3)nc2cc1C#CCCN(C)C]

A target compound 7-(4-(dimethylamino)-1-butyne-1-yl)-6-methoxy-2-(piperidine-1-yl)-N-(pyridine-3-ylmethyl)quinazoline-4-amine(7-(4-(dimethylamino)but-1-yn-1-yl)-6-methoxy-2-(piperidine-1-yl)-N-(pyridin-3-ylmethyl)quinazolin-4-amine) was obtained (7.1 mg, yield: 29.8%) as a yellow solid in the same manner as described in step 3 of Example 1 that 7-iodo-6-methoxy-2-(piperidine-1-yl)-N-(pyridine-3-ylmethyl)quinazoline-4-amine and N,N-dimethyl-3-butyne-1-amine were used as starting materials in step 3 of Example 1.

$^1$H NMR (400 MHz, $CDCl_3$) δ8.63 (s, 1H), 8.52 (d, J=3.72, 1H), 7.74 (dt, J=7.9, 2.0 Hz, 1H), 7.55 (s, 1H), 7.25-7.23 (m, 1H), 6.76 (s, 1H), 5.85 (s, 1H), 4.80 (d, J=5.4 Hz, 2H), 3.85 (s, 3H), 3.79 (t, J=5.1 Hz, 4H), 2.64 (s, 4H), 2.30 (s, 6H), 1.63-1.62 (m, 2H), 1.56-1.55 (m, 4H).

LCMS, m/z 445[M+H]+

<Example 27> Preparation of 7-(4-(dimethylamino)-1-butyne-1-yl)-6-methoxy-2-(piperidine-1-yl)-N-(2,2,6,6,-tetramethylpiperidine-4-yl)quinazoline-4-amine Step 1. Preparation of 2-chloro-7-iodo-6-methoxy-N-(2,2,6,6-tetramethylpiperidine-4-yl)quinazoline-4-amine

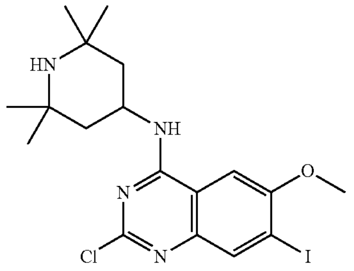

A target compound was obtained (39 mg, yield: 58.3%) as a yellow solid by performing the procedure of step 1 of Example 1, except that 2,2,6,6-tetramethylpiperidine-4-amine was used instead of 1-isopropylpiperidine-4-amine in step 1 of Example 1.

LCMS, m/z 475[M+H]+

Step 2. Preparation of 7-iodo-6-methoxy-2-(piperidine-1-yl)-N-(2,2,6,6-tetramethylpiperidine-4-yl)quinazoline-4-amine

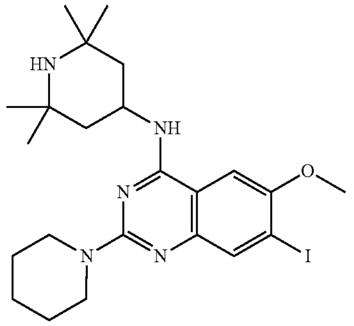

A target compound was obtained (27 mg, yield: 62.8%) as a yellow solid in the same manner as described in step 2 of Example 1 that 2-chloro-7-iodo-6-methoxy-N-(pyridine-3-ylmethyl)quinazoline-4-amine was used as a starting material in step 2 of Example 1.

LCMS, m/z 524[M+H]+KSA-009-098

Step 3. Preparation of 7-(4-(dimethylamino)-1-butyne-1-yl)-6-methoxy-2-(piperidine-1-yl)-N-(2,2,6,6-tetramethylpiperidine-4-yl)quinazoline-4-amine

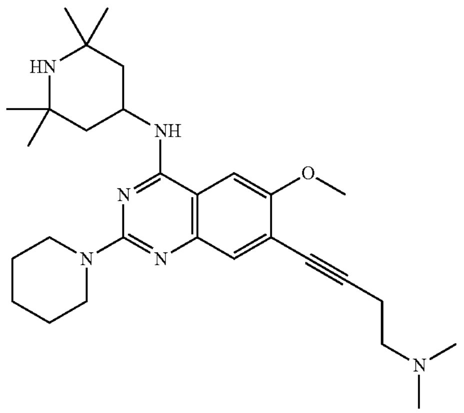

A target compound 7-(4-(dimethylamino)-1-butyne-1-yl)-6-methoxy-2-(piperidine-1-yl)-N-(2,2,6,6,-tetramethylpiperidine-4-yl)quinazoline-4-amine (7-(4-(dimethylamino) but-1-yn-1-yl)-6-methoxy-2-(piperidine-1-yl)-N-(2,2,6,6-tetramethylpiperidine-4-yl)quinazolin-4-amine) was obtained (4 mg, yield: 14.3%) as a yellow solid in the same manner as described in step 3 of Example 1 that 7-iodo-6-methoxy-2-(piperidine-1-yl)-N-(2,2,6,6-tetramethylpiperidine-4-yl)quinazoline-4-amine and N,N-dimethyl-3-butyne-1-amine were used as starting materials in step 3 of Example 1.

$^1$H NMR (400 MHz, $CDCl_3$) δ7.54 (s, 1H), 6.63 (s, 1H), 4.94 (d, J=6.9 Hz, 1H), 4.71-4.59 (m, 1H), 3.91 (s, 3H), 3.88-3.79 (m, 4H), 2.67-2.63 (m, 4H), 2.31 (s, 6H), 2.17 (dd, J=12.3, 3.5 Hz, 2H), 1.69-1.55 (m, 6H), 1.34 (s, 6H), 1.19 (s, 6H), 1.11 (t, J=12.1 Hz, 2H).

LCMS, m/z 493[M+H]+

<Example 28> Preparation of N1-(7-(4-(dimethylamino)-1-butyne-1-yl)-6-methoxy-2-(piperidine-1-yl)quinazoline-4-yl)-N2,N2-dimethylethane-1,2-diamine Step 1. Preparation of N1-(2-chloro-7-iodo-6-methoxyquinazoline-4-yl)-N2,N2-dimethylethane-1,2-diamine

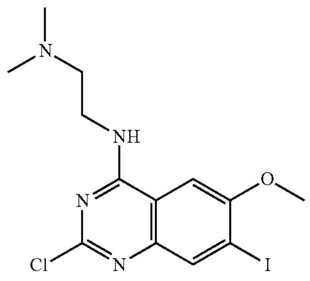

A target compound was obtained (48 mg, yield: 84%) as a yellow solid by performing the procedure of step 1 of Example 1, except that N1,N1-dimethylethane-1,2-diamine was used instead of 1-isopropylpiperidine-4-amine in step 1 of Example 1.

LCMS, m/z 407 [M+H]+

Step 2. Preparation of N1-(7-iodo-6-methoxy-2-(piperidine-1-yl)quinazoline-4-yl)-N2,N2-dimethylethane-1,2-diamine

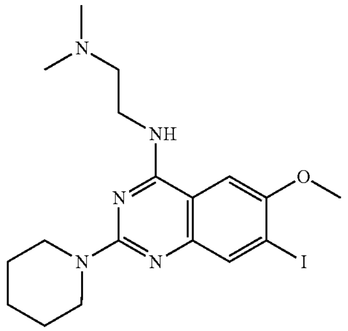 [SMILES: COc1cc2c(NCCN(C)C)nc(N3CCCCC3)nc2cc1I]

A target compound was obtained (27 mg, yield: 50.2%) as a yellow solid in the same manner as described in step 2 of Example 1 that N1-(2-chloro-7-iodo-6-methoxyquinazoline-4-yl)-N2,N2-dimethylethane-1,2-diamine was used as a starting material in step 2 of Example 1.

LCMS, m/z 456[M+H]+

Step 3. N1-(7-(4-(dimethylamino)-1-butyne-1-yl)-6-methoxy-2-(piperidine-1-yl)quinazoline-4-yl)-N2,N2-dimethylethane-1,2-diamine

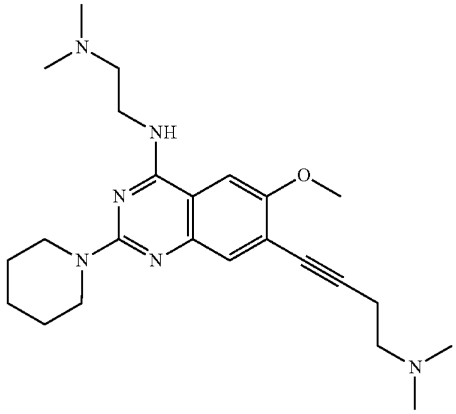 [SMILES: COc1cc2c(NCCN(C)C)nc(N3CCCCC3)nc2cc1C#CCCN(C)C]

A target compound N1-(7-(4-(dimethylamino)-1-butyne-1-yl)-6-methoxy-2-(piperidine-1-yl)quinazoline-4-yl)-N2,N2-dimethylethane-1,2-diamine(N1-(7-(4-(dimethylamino) but-1-yn-1-yl)-6-methoxy-2-(piperidine-1-yl)quinazolin-4-yl)-N2,N2-dimethylethane-1,2-diamine) was obtained (3.9 mg, yield: 20.5%) as a yellow solid in the same manner as described in step 3 of Example 1 that N1-(7-iodo-6-methoxy-2-(piperidine-1-yl)quinazoline-4-yl)-N2,N2-dimethylethane-1,2-diamine and N,N-dimethyl-3-butyne-1-amine were used as starting materials in step 3 of Example 1.

$^1$H NMR (400 MHz, $CDCl_3$) δ7.52 (s, 1H), 6.75 (s, 1H), 5.97 (s, 1H), 3.90 (s, 3H), 3.84-3.76 (m, 4H), 3.68-3.55 (m, 2H), 2.64 (s, 4H), 2.61 (t, J=6.0 Hz, 2H), 2.31 (s, 12H), 1.68-1.55 (m, 6H).

LCMS, m/z 425[M+H]+

<Example 29> Preparation of (S)-7-(4-(3-fluoropyrrolidine-1-yl)-1-butyne-1-yl)-N-(1-isopropylpiperidine-4-yl)-6-methoxy-2-(piperidine-1-yl)quinazoline-4-amine

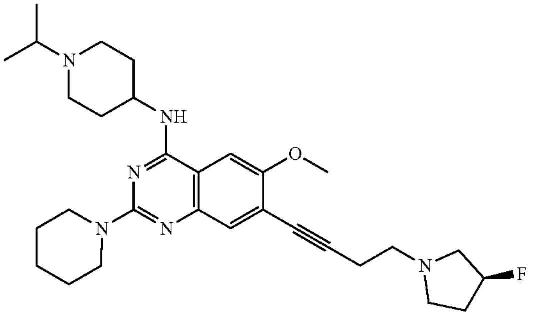 [SMILES: COc1cc2c(NC3CCN(C(C)C)CC3)nc(N3CCCCC3)nc2cc1C#CCCN1CC[C@H](F)C1]

A target compound (S)-7-(4-(3-fluoropyrrolidine-1-yl)-1-butyne-1-yl)-N-(1-isopropylpiperidine-4-yl)-6-methoxy-2-(piperidine-1-yl)quinazoline-4-amine((S)-7-(4-(3-fluoropyrrolidine-1-yl)but-1-yn-1-yl)-N-(1-isopropylpiperidine-4-yl)-6-methoxy-2-(piperidine-1-yl)quinazolin-4-amine) was obtained (13.7 mg, yield: 50.7%) as a yellow solid by performing the procedure of steps 1 to 3 of Example 1, except that (S)-1-(3-butyne-1-yl)-3-fluoropyrrolidine was used instead of N,N-dimethyl-4-pentyneamide in step 3 of Example 1.

$^1$H NMR (400 MHz, $CDCl_3$) δ7.52 (s, 1H), 6.64 (s, 1H), 5.26-5.09 (m, 1H), 5.01 (d, J=7.1 Hz, 1H), 4.16-4.03 (m, 1H), 3.91 (s, 3H), 3.84-3.74 (m, 4H), 3.03-2.88 (m, 4H), 2.87-2.73 (m, 4H), 2.72-2.69 (m, 2H), 2.56-2.51 (m, 1H), 2.37-2.31 (m, 2H), 2.24-2.17 (m, 2H), 2.15-2.08 (m, 1H), 2.04 (s, 1H), 1.63-1.53 (m, 8H), 1.08 (d, J=6.5 Hz, 6H).

LCMS, m/z 523[M+H]+

<Example 30> Preparation of (R)-7-(4-(3-fluoropyrrolidine-1-yl)-1-butyne-1-yl)-N-(1-isopropylpiperidine-4-yl)-6-methoxy-2-(piperidine-1-yl)quinazoline-4-amine

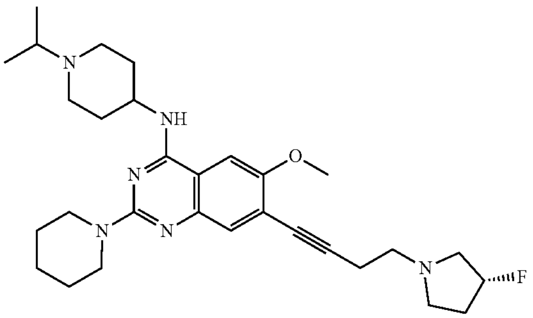 [SMILES: COc1cc2c(NC3CCN(C(C)C)CC3)nc(N3CCCCC3)nc2cc1C#CCCN1CC[C@@H](F)C1]

A target compound (R)-7-(4-(3-fluoropyrrolidine-1-yl)-1-butyne-1-yl)-N-(1-isopropylpiperidine-4-yl)-6-methoxy-2-(piperidine-1-yl)quinazoline-4-amine((R)-7-(4-(3-fluoropyrrolidine-1-yl)but-1-yn-1-yl)-N-(1-isopropylpiperidine-4-yl)-6-methoxy-2-(piperidine-1-yl)quinazolin-4-amine) was obtained (12.5 mg, yield: 48.2%) as a yellow solid by performing the procedure of steps 1 to 3 of Example 1, except that (R)-1-(3-butyne-1-yl)-3-fluoropyrrolidine was used instead of N,N-dimethyl-4-pentyneamide in step 3 of Example 1.

$^1$H NMR (400 MHz, $CDCl_3$) δ7.52 (s, 1H), 6.64 (s, 1H), 5.26-5.09 (m, 1H), 5.01 (d, J=7.1 Hz, 1H), 4.15-4.02 (m, 1H), 3.91 (s, 3H), 3.81-3.79 (m, 4H), 3.05-2.88 (m, 4H), 2.88-2.73 (m, 4H), 2.72-2.69 (m, 2H), 2.56-2.51 (m, 1H), 2.37-2.32 (m, 2H), 2.24-2.17 (m, 2H), 2.15-2.08 (m, 1H), 2.05-1.99 (m, 1H), 1.69-1.51 (m, 8H), 1.08 (d, J=6.5 Hz, 6H).

LCMS, m/z 523[M+H]+

<Example 31> Preparation of 7-(4-(dimethylamino)-1-butyne-1-yl)-6-methoxy-N-((1-methylpiperidine-4-yl)methyl)-2-(piperidine-1-yl)quinazoline-4-amine Step 1. Preparation of 2-chloro-7-iodo-6-methoxy-N-((1-methylpiperidine-4-yl)methyl)quinazoline-4-amine

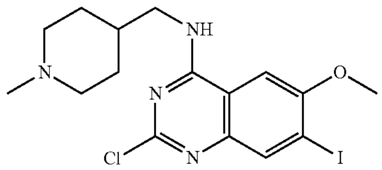

A target compound was obtained (59 mg, yield: 94%) as a yellow solid by performing the procedure of step 1 of Example 1, except that (1-methylpiperidine-4-yl)methaneamine was used instead of 1-isopropylpiperidine-4-amine in step 1 of Example 1.

LCMS, m/z 447[M+H]+

Step 2. Preparation of 7-iodo-6-methoxy-N-((1-methylpiperidine-4-yl)methyl)-2-(piperidine-1-yl)quinazoline-4-amine

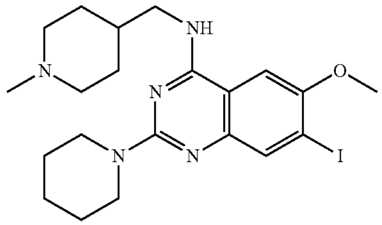

A target compound was obtained (47 mg, yield: 71.8%) as a yellow solid in the same manner as described in step 2 of Example 1 that 2-chloro-7-iodo-6-methoxy-N-((1-methylpiperidine-4-yl)methyl)quinazoline-4-amine was used as a starting material in step 2 of Example 1.

LCMS, m/z 496[M+H]+

Step 3. Preparation of 7-(4-(dimethylamino)-1-butyne-1-yl)-6-methoxy-N-((1-methylpiperidine-4-yl)methyl)-2-(piperidine-1-yl)quinazoline-4-amine

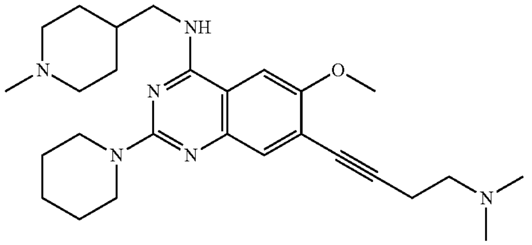

A target compound 7-(4-(dimethylamino)-1-butyne-1-yl)-6-methoxy-N-((1-methylpiperidine-4-yl)methyl)-2-(piperidine-1-yl)quinazoline-4-amine(7-(4-(dimethylamino)but-1-yn-1-yl)-6-methoxy-N-((1-methylpiperidine-4-yl)methyl)-2-(piperidine-1-yl)quinazolin-4-amine) was obtained (17 mg, yield: 42.7%) as a yellow solid in the same manner as described in step 3 of Example 1 that 7-iodo-6-methoxy-N-((1-methylpiperidine-4-yl)methyl)-2-(piperidine-1-yl)quinazoline-4-amine and N,N-dimethyl-3-butyne-1-amine were used as starting materials in step 3 of Example 1.

$^1$H NMR (400 MHz, MeOD) δ7.29 (s, 1H), 7.20 (s, 1H), 3.79 (s, 3H), 3.69 (t, J=5.3 Hz, 4H), 3.38 (d, J=6.4 Hz, 2H), 3.22 (m, 2H), 2.80 (dd, J=11.5, 3.6 Hz, 2H), 2.56 (s, 4H), 2.23 (s, 6H), 2.15 (s, 3H), 1.91-1.86 (m, 2H), 1.71-1.67 (m, 2H), 1.59-1.57 (m, 2H), 1.52-1.47 (m, 4H), 1.29-1.26 (m, 2H).

LCMS, m/z 465[M+H]+

<Example 32> Preparation of 7-(4-(dimethylamino)-1-butyne-1-yl)-6-methoxy-2-(piperidine-1-yl)-N-(pyridine-4-ylmethyl)quinazoline-4-amine Step 1. Preparation of 2-chloro-7-iodo-6-methoxy-N-(pyridine-4-ylmethyl)quinazoline-4-amine

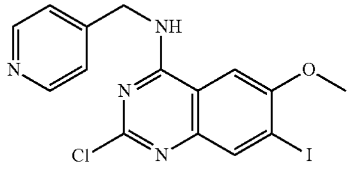 [SMILES: COc1cc2c(NCc3ccncc3)nc(Cl)nc2cc1I]

A target compound was obtained (42 mg, yield: 69.9%) as a yellow solid by performing the procedure of step 1 of Example 1, except that pyridine-4-ylmethaneamine was used instead of 1-isopropylpiperidine-4-amine in step 1 of Example 1.

LCMS, m/z 427[M+H]+

Step 2. Preparation of 7-iodo-6-methoxy-2-(piperidine-1-yl)-N-(pyridine-4-ylmethyl)quinazoline-4-amine

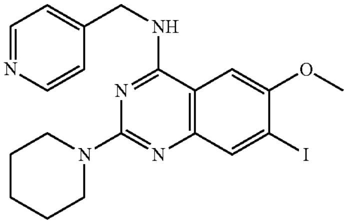 [SMILES: COc1cc2c(NCc3ccncc3)nc(N3CCCCC3)nc2cc1I]

A target compound was obtained (14 mg, yield: 29.8%) as a yellow solid in the same manner as described in step 2 of Example 1 that 2-chloro-7-iodo-6-methoxy-N-(pyridine-4-ylmethyl)quinazoline-4-amine was used as a starting material in step 2 of Example 1.

LCMS, m/z 476[M+H]+

Step 3. Preparation of 7-(4-(dimethylamino)-1-butyne-1-yl)-6-methoxy-2-(piperidine-1-yl)-N-(pyridine-4-ylmethyl)quinazoline-4-amine

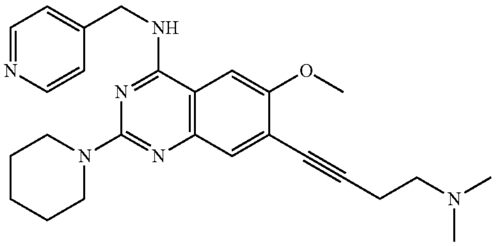 [SMILES: COc1cc2c(NCc3ccncc3)nc(N3CCCCC3)nc2cc1C#CCCN(C)C]

A target compound 7-(4-(dimethylamino)-1-butyne-1-yl)-6-methoxy-2-(piperidine-1-yl)-N-(pyridine-4-ylmethyl)quinazoline-4-amine(7-(4-(dimethylamino)but-1-yn-1-yl)-6-methoxy-2-(piperidine-1-yl)-N-(pyridin-4-ylmethyl)quinazolin-4-amine) was obtained (4.9 mg, yield: 43.7%) as a yellow solid in the same manner as described in step 3 of Example 1 that 7-iodo-6-methoxy-2-(piperidine-1-yl)-N-(pyridine-4-ylmethyl)quinazoline-4-amine and N,N-dimethyl-3-butyne-1-amine were used as starting materials in step 3 of Example 1.

$^1$H NMR (400 MHz, $CDCl_3$) δ8.53 (d, J=5.9 Hz, 2H), 7.56 (s, 1H), 7.28 (d, J=5.8 Hz, 2H), 6.78 (s, 1H), 5.92-5.80 (m, 1H), 4.80 (d, J=5.6 Hz, 2H), 3.88 (s, 3H), 3.77-3.63 (m, 4H), 2.72-2.61 (m, 4H), 2.31 (s, 6H), 1.65-1.56 (m, 2H), 1.54-1.44 (m, 4H).

LCMS, m/z 445[M+H]+

<Example 33> Preparation of 7-(4-(3-fluoroazetidine-1-yl)-1-butyne-1-yl)-N-(1-isopropylpiperidine-4-yl)-6-methoxy-2-(piperidine-1-yl)quinazoline-4-amine

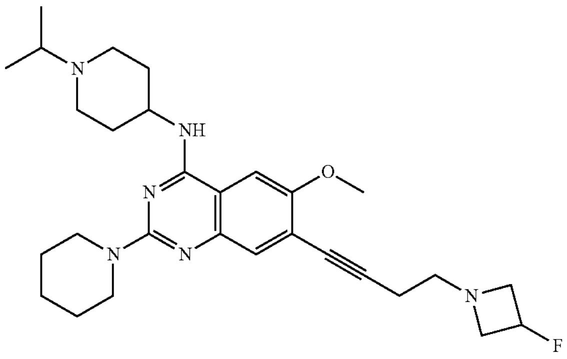 [SMILES: COc1cc2c(NC3CCN(C(C)C)CC3)nc(N3CCCCC3)nc2cc1C#CCCN1CC(F)C1]

A target compound 7-(4-(3-fluoroazetidine-1-yl)-1-butyne-1-yl)-N-(1-isopropylpiperidine-4-yl)-6-methoxy-2-(piperidine-1-yl)quinazoline-4-amine(7-(4-(3-fluoroazetidin-1-yl)but-1-yn-1-yl)-N-(1-isopropylpiperidine-4-yl)-6-methoxy-2-(piperidine-1-yl)quinazolin-4-amine) was obtained (0.6 mg, yield: 1.97%) as a yellow solid by performing the procedure of steps 1 to 3 of Example 1, except that 1-(3-butyne-1-yl)-3-fluoroazetine was used instead of N,N-dimethyl-4-pentyneamide in step 3 of Example 1.

$^1$H NMR (400 MHz, $CDCl_3$) δ7.52 (s, 1H), 6.64 (s, 1H), 5.24-5.17 (m, 1H), 5.07-5.02 (m, 1H), 4.16-4.07 (m, 1H), 3.91 (s, 3H), 3.85-3.69 (m, 6H), 3.31-3.19 (m, 2H), 2.99-2.93 (m, 2H), 2.85-2.82 (m, 1H), 2.78 (t, J=7.0 Hz, 2H), 2.57 (t, J=7.0 Hz, 2H), 2.44-2.33 (m, 2H), 2.27-2.14 (m, 2H), 1.65-1.64 (m, 8H), 1.10 (d, J=6.5 Hz, 6H).

LCMS, m/z 509[M+H]+

<Example 34> Preparation of 7-(4-(dimethylamino)-1-butyne-1-yl)-6-methoxy-2-(piperidine-1-yl)-N-(2-pyridine-4-yl)ethyl)quinazoline-4-amine Step 1. Preparation of 2-chloro-7-iodo-6-methoxy-N-(2-(pyridine-4-yl)ethyl)quinazoline-4-amine

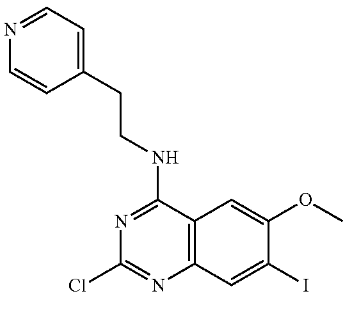 [SMILES: COc1cc2c(NCCc3ccncc3)nc(Cl)nc2cc1I]

A target compound was obtained (44 mg, yield: 70.9%) as a yellow solid by performing the procedure of step 1 of Example 1, except that 2-(pyridine-4-yl)ethaneamine was used instead of 1-isopropylpiperidine-4-amine in step 1 of Example 1.

LCMS, m/z 441[M+H]+

Step 2. Preparation of 7-iodo-6-methoxy-2-(piperidine-1-yl)-N-(2-(pyridine-4-yl)ethyl)quinazoline-4-amine

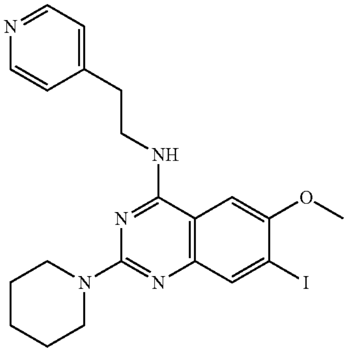 [SMILES: COc1cc2c(NCCc3ccncc3)nc(N3CCCCC3)nc2cc1I]

A target compound was obtained (19 mg, yield: 38.1%) as a yellow solid in the same manner as described in step 2 of Example 1 that 2-chloro-7-iodo-6-methoxy-N-(2-(pyridine-4-yl)ethyl)quinazoline-4-amine was used as a starting material in step 2 of Example 1.

LCMS, m/z 490[M+H]+

Step 3. Preparation of 7-(4-(dimethylamino)-1-butyne-1-yl)-6-methoxy-2-(piperidine-1-yl)-N-(2-(pyridine-4-yl)ethyl)quinazoline-4-amine

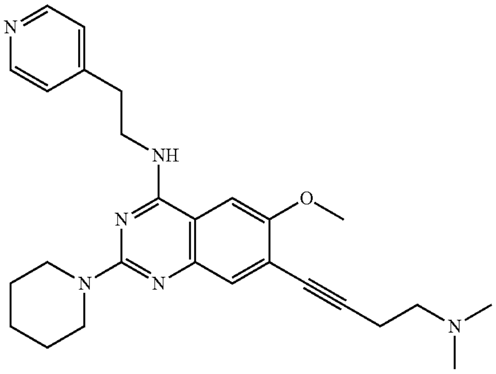 [SMILES: COc1cc2c(NCCc3ccncc3)nc(N3CCCCC3)nc2cc1C#CCCN(C)C]

A target compound 7-(4-(dimethylamino)-1-butyne-1-yl)-6-methoxy-2-(piperidine-1-yl)-N-(2-pyridine-4-yl)ethyl) quinazoline-4-amine(7-(4-(dimethylamino)but-1-yn-1-yl)-6-methoxy-2-(piperidine-1-yl)-N-(2-(pyridin-4-yl)ethyl) quinazolin-4-amine) was obtained (1.5 mg, yield: 8.21%) as a yellow solid in the same manner as described in step 3 of Example 1 that 7-iodo-6-methoxy-2-(piperidine-1-yl)-N-(2-(pyridine-4-yl)ethyl)quinazoline-4-amine and N,N-dimethyl-3-butyne-1-amine were used as starting materials in step 3 of Example 1.

$^1$H NMR (400 MHz, $CDCl_3$) δ8.54-8.53 (m, 2H), 7.56 (s, 1H), 7.17-7.15 (m, 2H), 6.59 (s, 1H), 5.34 (s, 1H), 3.98-3.67 (m, 9H), 3.04 (t, J=7.1 Hz, 2H), 2.64 (s, 4H), 2.31 (s, 6H), 4.66-1.64 (m, 6H).

LCMS, m/z 459[M+H]+

<Example 35> Preparation of 2-(4,4-difluoropiperidine-1-yl)-N-(1-isopropylpiperidine-4-yl)-6-methoxy-7-(4-(pyrrolidine-1-yl)-1-butyne-1-yl)quinazoline-4-amine

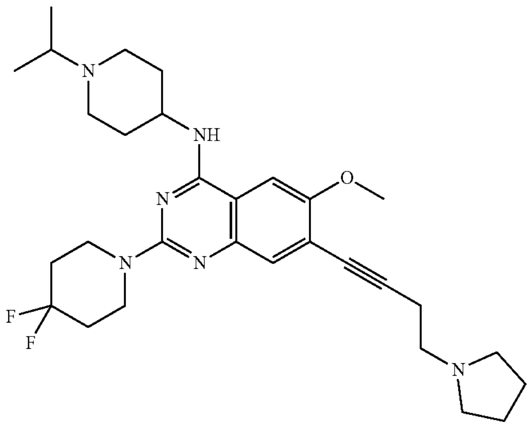 [SMILES: COc1cc2c(NC3CCN(C(C)C)CC3)nc(N3CCC(F)(F)CC3)nc2cc1C#CCCN1CCCC1]

2-(4,4-Difluoropiperidine-1-yl)-7-iodo-N-(1-isopropylpiperidine-4-yl)-6-methoxyquinazoline-4-amine was prepared in the same manner as described in step 1 of Example 4, and a target compound 2-(4,4-difluoropiperidine-1-yl)-N-(1-isopropylpiperidine-4-yl)-6-methoxy-7-(4-(pyrrolidine-1-yl)-1-butyne-1-yl)quinazoline-4-amine(2-(4,4-difluoropiperidine-1-yl)-N-(1-isopropylpiperidine-4-yl)-6-methoxy-7-(4-(pyrrolidine-1-yl)but-1-yn-1-yl)quinazolin-4-amine) was obtained (2.9 mg, yield: 24.3%) in the same manner as described in step 3 of Example 1 using 1-(3-butyne-1-yl) pyrrolidine as a starting material in step 3 of Example 1.

$^1$H NMR (400 MHz, $CDCl_3$) δ7.53 (s, 1H), 6.66 (s, 1H), 5.10 (d, J=7.1 Hz, 1H), 4.14-4.03 (m, 1H), 4.03-3.95 (m, 2H), 3.93 (s, 3H), 2.92 (d, J=12.0 Hz, 2H), 2.83-2.76 (m, 2H), 2.74-2.66 (m, 2H), 2.64-2.55 (m, 4H), 2.35 (t, J=10.5 Hz, 2H), 2.18 (d, J=10.0 Hz, 2H), 2.07-1.92 (m, 5H), 1.85-1.77 (m, 6H), 1.66-1.54 (m, 2H), 1.08 (d, J=6.6 Hz, 6H).

LCMS, m/z 541[M+H]+

<Example 36> Preparation of 2-(azepane-1-yl)-N-(1-isopropylpiperidine-4-yl)-6-methoxy-7-(4-pyrrolidine-1-yl)-1-butyne-1-yl)quinazoline-4-amine

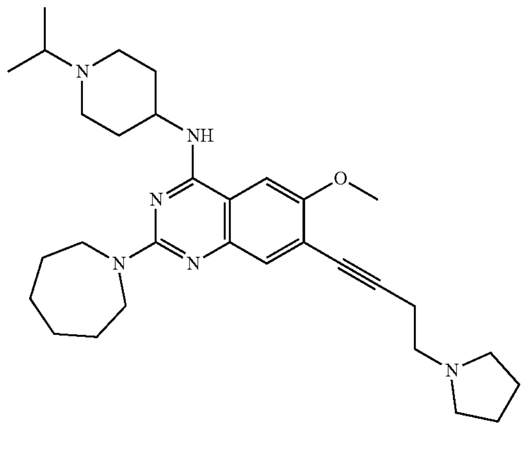 [SMILES: COc1cc2c(NC3CCN(C(C)C)CC3)nc(N3CCCCCC3)nc2cc1C#CCCN1CCCC1]

2-(Azepane-1-yl)-7-iodo-N-(1-isopropylpiperidine-4-yl)-6-methoxyquinazoline-4-amine was prepared in the same manner as described in step 1 of Example 8, and a target compound 2-(azepane-1-yl)-N-(1-isopropylpiperidine-4-yl)-6-methoxy-7-(4-pyrrolidine-1-yl)-1-butyne-1-yl)quinazoline-4-amine(2-(azepane-1-yl)-N-(1-isopropylpiperidine-4-yl)-6-methoxy-7-(4-(pyrrolidine-1-yl)but-1-yn-1-yl) quinazolin-4-amine) was obtained (1.9 mg, yield: 11.8%) in the same manner as described in step 3 of Example 1 using 1-(3-butyne-1-yl)pyrrolidine as a starting material in step 3 of Example 1.

$^1$H NMR (400 MHz, $CDCl_3$) δ7.53 (s, 1H), 6.65 (s, 1H), 5.02 (s, 1H), 4.18-4.00 (m, 1H), 3.91 (s, 3H), 3.82-3.75 (m, 4H), 2.98-2.90 (m, 2H), 2.83-2.76 (m, 2H), 2.74-2.67 (m, 2H), 2.64-2.59 (m, 4H), 2.39-2.30 (m, 2H), 2.24-2.14 (m, 2H), 2.02-1.86 (m, 2H), 1.83-1.76 (m, 7H), 1.69-1.59 (m, 2H), 1.57-1.52 (m, 4H), 1.09 (d, J=6.6 Hz, 6H).

LCMS, m/z 519[M+H]+

<Example 37> Preparation of 2-(azepane-1-yl)-N-(1-isopropylpiperidine-4-yl)-6-methoxy-7-(4-(piperidine-1-yl)-1-butyne-1-yl)quinazoline-4-amine

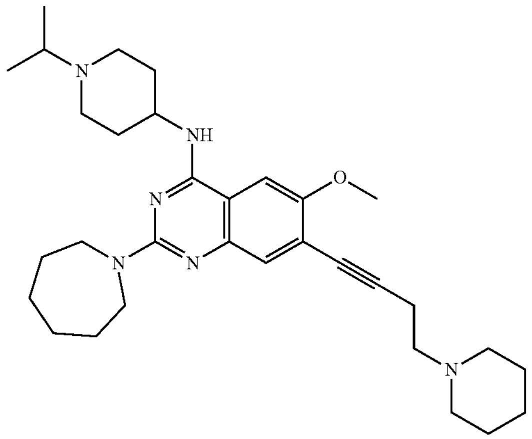 [SMILES: COc1cc2c(NC3CCN(C(C)C)CC3)nc(N3CCCCCC3)nc2cc1C#CCCN1CCCCC1]

2-(Azepane-1-yl)-7-iodo-N-(1-isopropylpiperidine-4-yl)-6-methoxyquinazoline-4-amine was prepared in the same manner as described in step 1 of Example 8, and a target compound 2-(azepane-1-yl)-N-(1-isopropylpiperidine-4-yl)-6-methoxy-7-(4-(piperidine-1-yl)-1-butyne-1-yl)quinazoline-4-amine(2-(azepane-1-yl)-N-(1-isopropylpiperidine-4-yl)-6-methoxy-7-(4-(piperidine-1-yl)but-1-yn-1-yl) quinazolin-4-amine) was obtained (6 mg, yield: 39.3%) in the same manner as described in step 3 of Example 1 using 1-(3-butyne-1-yl)piperidine as a starting material in step 3 of Example 1.

$^1$H NMR (400 MHz, $CDCl_3$) δ 7.53 (s, 1H), 6.65 (s, J=5.9 Hz, 1H), 5.01 (d, J=6.9 Hz, 1H), 4.13-4.01 (m, 1H), 3.91 (s, 3H), 3.82-3.74 (m, 4H), 2.98-2.89 (m, 2H), 2.81-2.74 (m, 1H), 2.71-2.65 (m, 4H), 2.52-2.44 (m, 4H), 2.37-2.29 (m, 2H), 2.23-2.17 (m, 2H), 2.00-1.90 (m, 2H), 1.82-1.75 (m, 4H), 1.65-1.52 (m, 8H), 1.48-1.40 (m, 2H), 1.08 (d, J=6.6 Hz, 6H).

LCMS, m/z 533[M+H]+

<Example 38> Preparation of N-(1-isopropylpiperidine-4-yl)-6-methoxy-2-(4-methylpiperazine-1-yl)-7-(4-(pyrrolidine-1-yl)-1-butyne-1-yl)quinazoline-4-amine

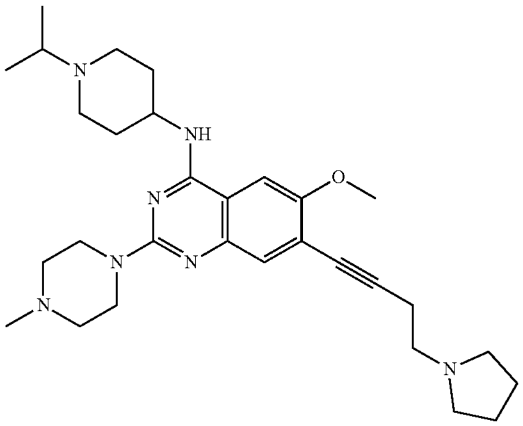 [SMILES: COc1cc2c(NC3CCN(C(C)C)CC3)nc(N3CCN(C)CC3)nc2cc1C#CCCN1CCCC1]

7-Iodo-N-(1-isopropylpiperidine-4-yl)-6-methoxy-2-(4-methylpiperazine-1-yl)quinazoline-4-amine was prepared in the same manner as described in step 1 of Example 7, and a target compound N-(1-isopropylpiperidine-4-yl)-6-methoxy-2-(4-methylpiperazine-1-yl)-7-(4-(pyrrolidine-1-yl)-1-butyne-1-yl)quinazoline-4-amine(N-(1-isopropylpiperidine-4-yl)-6-methoxy-2-(4-methylpiperazin-1-yl)-7-(4-(pyrrolidine-1-yl)but-1-yn-1-yl)quinazolin-4-amine) was obtained (1.3 mg, yield: 7.2%) in the same manner as described in step 3 of Example 1 using 1-(3-butyne-1-yl) pyrrolidine as a starting material in step 3 of Example 1.

$^1$H NMR (400 MHz, $CDCl_3$) δ7.54 (s, 1H), 6.65 (s, 1H), 5.05 (d, J=7.2 Hz, 1H), 4.18-4.02 (m, 1H), 3.92 (s, 3H), 3.88-3.80 (m, 4H), 2.98-2.89 (m, 2H), 2.83-2.76 (m, 2H), 2.74-2.68 (m, 2H), 2.64-2.57 (m, 2H), 2.52-2.46 (m, 2H), 2.41-2.32 (m, 5H), 2.23-2.15 (m, 2H), 1.84-1.76 (m, 4H), 1.70-1.57 (m, 7H), 1.09 (d, J=6.6 Hz, 6H).

LCMS, m/z 520[M+H]+

<Example 39> Preparation of N-(1-Disopropylpiperidine-4-yl)-6-methoxy-2-(4-methylpiperazine-1-yl)-7-(4-(piperidine-1-yl)-1-butyne-1-yl)quinazoline-4-amine

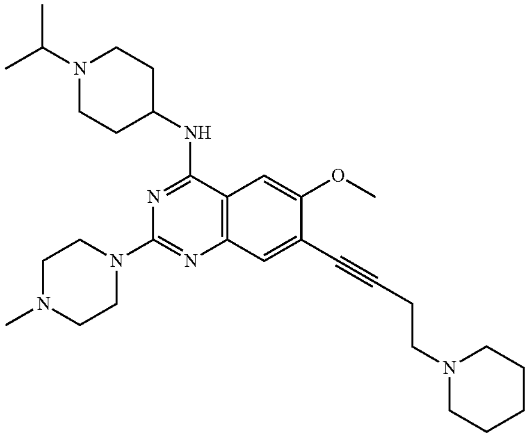 [SMILES: COc1cc2c(NC3CCN(C(C)C)CC3)nc(N3CCN(C)CC3)nc2cc1C#CCCN1CCCCC1]

7-Iodo-N-(1-isopropylpiperidine-4-yl)-6-methoxy-2-(4-methylpiperazine-1-yl)quinazoline-4-amine was prepared in the same manner as described in step 1 of Example 7, and a target compound N-(1-Disopropylpiperidine-4-yl)-6-methoxy-2-(4-methylpiperazine-1-yl)-7-(4-(piperidine-1-yl)-1-butyne-1-yl)quinazoline-4-amine(N-(1-isopropylpiperidine-4-yl)-6-methoxy-2-(4-methylpiperazin-1-yl)-7-(4-(piperidine-1-yl)but-1-yn-1-yl)quinazolin-4-amine) was obtained (6 mg, yield: 39.3%) in the same manner as described in step 3 of Example 1 using 1-(3-butyne-1-yl) piperidine as a starting material in step 3 of Example 1.

$^1$H NMR (400 MHz, $CDCl_3$) δ7.54 (s, 1H), 6.67 (s, 1H), 5.12 (d, J=7.0 Hz, 1H), 4.18-4.05 (m, 1H), 3.92 (s, 3H), 3.89-3.82 (m, 4H), 3.01-2.90 (m, 2H), 2.88-2.79 (m, 1H), 2.71-2.67 (m, 4H), 2.60-2.54 (m, 2H), 2.53-2.46 (m, 4H), 2.46-2.37 (m, 4H), 2.35 (s, 3H), 2.23-2.16 (m, 2H), 1.65-1.53 (m, 6H), 1.48-1.38 (m, 2H), 1.10 (d, J=6.6 Hz, 6H).

LCMS, m/z 534[M+H]+

<Example 40> Preparation of N-(1-isopropylpiperidine-4-yl)-6-methoxy-7-(4-(pyrrolidine-1-yl)-1-butyne-1-yl)-2-(2-azaspiro[4.4]nonane-2-yl)quinazoline-4-amine

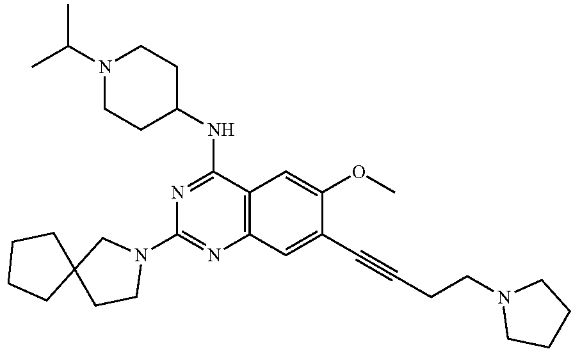 [SMILES: COc1cc2c(NC3CCN(C(C)C)CC3)nc(N3CCC4(CCCC4)C3)nc2cc1C#CCCN1CCCC1]

7-Iodo-N-(1-isopropylpiperidine-4-yl)-6-methoxy-2-(2-azaspiro[4.4]nonane-2-yl)quinazoline-4-amine was prepared in the same manner as described in step 1 of Example 9, and a target compound N-(1-isopropylpiperidine-4-yl)-6-methoxy-7-(4-(pyrrolidine-1-yl)-1-butyne-1-yl)-2-(2-azaspiro[4.4]nonane-2-yl)quinazoline-4-amine(N-(1-isopropylpiperidine-4-yl)-6-methoxy-7-(4-(pyrrolidine-1-yl) but-1-yn-1-yl)-2-(2-azaspiro[4.4]nonan-2-yl)quinazolin-4-amine) was obtained (29.7 mg, yield: 74.1%) in the same manner as described in step 3 of Example 1 using 1-(3-butyne-1-yl)pyrrolidine as a starting material in step 3 of Example 1.

$^1$H NMR (400 MHz, $CDCl_3$) δ7.56 (s, 1H), 6.66 (s, 1H), 5.06 (d, J=5.5 Hz, 1H), 4.21-4.03 (m, 1H), 3.91 (s, 3H), 3.67 (t, J=6.9 Hz, 2H), 3.47 (s, 2H), 2.92 (d, J=11.8 Hz, 2H), 2.82-2.74 (m, 3H), 2.74-2.65 (m, 2H), 2.64-2.54 (m, 4H), 2.37-2.32 (m, 2H), 2.21 (d, J=11.4 Hz, 2H), 1.87-1.74 (m, 6H), 1.69-1.68 (m, 4H), 1.67-1.62 (m, 2H), 1.60-1.55 (m, 4H), 1.08 (d, J=6.5 Hz, 6H).

LCMS, m/z 545[M+H]+

<Example 41> Preparation of N-(1-isopropylpiperidine-4-yl)-6-methoxy-7-(4-(piperidine-1-yl)-1-butyne-1-yl)-2-(2-azaspiro[4.4]nonane-2-yl)quinazoline-4-amine

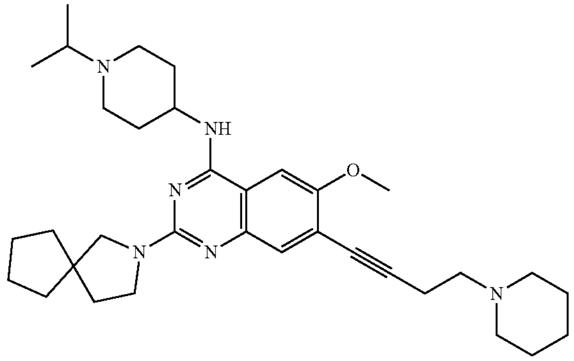 [SMILES: COc1cc2c(NC3CCN(C(C)C)CC3)nc(N3CCC4(CCCC4)C3)nc2cc1C#CCCN1CCCCC1]

7-Iodo-N-(1-isopropylpiperidine-4-yl)-6-methoxy-2-(2-azaspiro[4.4]nonane-2-yl)quinazoline-4-amine was prepared in the same manner as described in step 1 of Example 9, and a target compound N-(1-isopropylpiperidine-4-yl)-6-methoxy-7-(4-(piperidine-1-yl)-1-butyne-1-yl)-2-(2-azaspiro[4.4]nonane-2-yl)quinazoline-4-amine(N-(1-isopropylpiperidine-4-yl)-6-methoxy-7-(4-(piperidine-1-yl) but-1-yn-1-yl)-2-(2-azaspiro[4.4]nonan-2-yl)quinazolin-4-amine) was obtained (25.4 mg, yield: 60.6%) in the same manner as described in step 3 of Example 1 using 1-(3-butyne-1-yl)piperidine as a starting material in step 3 of Example 1.

$^1$H NMR (400 MHz, $CDCl_3$) δ 7.55 (s, 1H), 6.66 (s, 1H), 5.14-4.96 (m, 1H), 4.17-4.06 (m, 1H), 3.90 (s, 3H), 3.66 (t, J=6.9 Hz, 2H), 3.47 (s, 2H), 2.98-2.85 (m, 2H), 2.77 (quintet, J=6.5 Hz, 1H), 2.73-2.61 (m, 4H), 2.54-2.41 (m, 4H), 2.34 (t, J=10.6 Hz, 2H), 2.25-2.14 (m, 2H), 1.83 (t, J=6.9 Hz, 2H), 1.73-1.67 (m, 6H), 1.66-1.53 (m, 8H), 1.48-1.38 (m, 2H), 1.07 (d, J=6.5 Hz, 6H).

LCMS, m/z 559[M+H]+

<Example 42> Preparation of N-(1-isopropylpiperidine-4-yl)-6-methoxy-2-(pyrrolidine-1-yl)-7-(4-(pyrrolidine-1-yl)-1-butyne-1-yl)quinazoline-4-amine

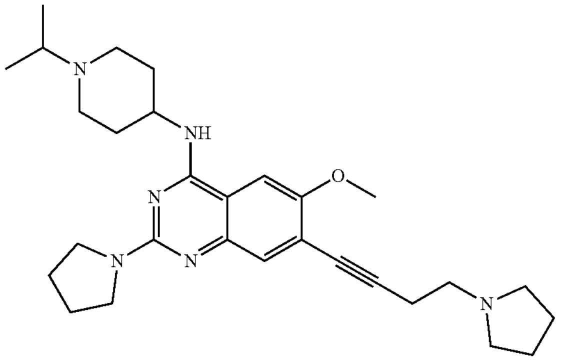 [SMILES: COc1cc2c(NC3CCN(C(C)C)CC3)nc(N3CCCC3)nc2cc1C#CCCN1CCCC1]

7-Iodo-N-(1-isopropylpiperidine-4-yl)-6-methoxy-2-(pyrrolidine-1-yl)quinazoline-4-amine was prepared in the same manner as described in step 1 of Example 6, and a target compound N-(1-isopropylpiperidine-4-yl)-6-methoxy-2-(pyrrolidine-1-yl)-7-(4-(pyrrolidine-1-yl)-1-butyne-1-yl)quinazoline-4-amine(N-(1-isopropylpiperidine-4-yl)-6-methoxy-2-(pyrrolidine-1-yl)-7-(4-(pyrrolidine-1-yl)but-1-yn-1-yl)quinazolin-4-amine) was obtained (1.5 mg, yield: 7.73%) in the same manner as described in step 3 of Example 1 using 1-(3-butyne-1-yl)pyrrolidine as a starting material in step 3 of Example 1.

1H NMR (400 MHz, CDCl3) δ 7.58 (s, 1H), 6.66 (s, 1H), 5.08-5.00 (m, 1H), 4.21-4.04 (m, 1H), 3.92 (s, 3H), 3.72-3.53 (m, 4H), 2.99-2.87 (m, 2H), 2.84-2.76 (m, 3H), 2.74-2.67 (m, 2H), 2.66-2.56 (m, 4H), 2.40-2.30 (m, 2H), 2.26-2.17 (m, 2H), 2.00-1.93 (m, 4H), 1.86-1.77 (m, 4H), 1.66-1.54 (m, 2H), 1.08 (d, J=6.5 Hz, 6H).

LCMS, m/z 491[M+H]+

<Example 43> Preparation of N-(1-isopropylpiperidine-4-yl)-6-methoxy-7-(4-(piperidine-1-yl)-1-butyne-1-yl)-2-(pyrrolidine-1-yl)quinazoline-4-amine

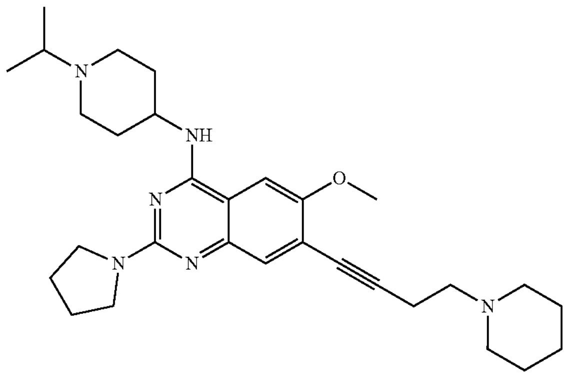 [SMILES: COc1cc2c(NC3CCN(C(C)C)CC3)nc(N3CCCC3)nc2cc1C#CCCN1CCCCC1]

7-Iodo-N-(1-isopropylpiperidine-4-yl)-6-methoxy-2-(pyrrolidine-1-yl)quinazoline-4-amine was prepared in the same manner as described in step 1 of Example 6, and a target compound N-(1-isopropylpiperidine-4-yl)-6-methoxy-7-(4-(piperidine-1-yl)-1-butyne-1-yl)-2-(pyrrolidine-1-yl)quinazoline-4-amine(N-(1-isopropylpiperidine-4-yl)-6-methoxy-7-(4-(piperidine-1-yl)but-1-yn-1-yl)-2-(pyrrolidine-1-yl)quinazolin-4-amine) was obtained (2 mg, yield: 9.72%) in the same manner as described in step 3 of Example 1 using 1-(3-butyne-1-yl)piperidine as a starting material in step 3 of Example 1.

$^1$H NMR (400 MHz, $CDCl_3$) δ7.57 (s, 1H), 6.65 (s, 1H), 5.02 (d, J=6.9 Hz, 1H), 4.18-4.09 (m, 1H), 3.91 (s, 3H), 3.62 (t, J=6.7 Hz, 4H), 2.92 (d, J=11.9 Hz, 2H), 2.78 (dt, J=13.1, 6.5 Hz, 1H), 2.69 (t, J=3.6 Hz, 4H), 2.47 (d, J=4.8 Hz, 4H), 2.39-2.30 (m, 2H), 2.21 (d, J=11.1 Hz, 2H), 1.98-1.92 (m, 4H), 1.60 (dt, J=10.9, 5.6 Hz, 6H), 1.45 (dd, J=11.5, 6.0 Hz, 2H), 1.08 (d, J=6.6 Hz, 6H).

LCMS, m/z 505[M+H]+

<Example 44> Preparation of N-(1-isopropylpiperidine-4-yl)-6-methoxy-N2,N2-dimethyl-7-(4-(piperidine-1-yl)-1-butyne-1-yl)quinazoline-2,4-diamine

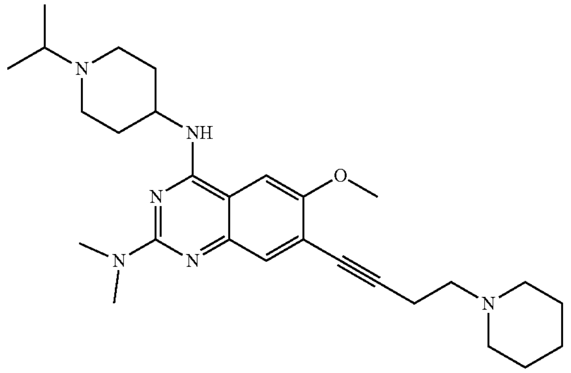 [SMILES: COc1cc2c(NC3CCN(C(C)C)CC3)nc(N(C)C)nc2cc1C#CCCN1CCCCC1]

7-Iodo-N4-(1-isopropylpiperidine-4-yl)-6-methoxy-N2, N2-dimethylquinazoline-2,4-diamine was prepared in the same manner as described in step 1 of Example 14, and a target compound N-(1-isopropylpiperidine-4-yl)-6-methoxy-N2,N2-dimethyl-7-(4-(piperidine-1-yl)-1-butyne-1-yl)quinazoline-2,4-diamine(N-(1-isopropylpiperidine-4-yl)-6-methoxy-N2,N2-dimethyl-7-(4-(piperidine-1-yl)but-1-yn-1-yl)quinazoline-2,4-diamine) was obtained (2 mg, yield: 9.72%) in the same manner as described in step 3 of Example 1 using 1-(3-butyne-1-yl)piperidine as a starting material in step 3 of Example 1.

$^1$H NMR (400 MHz, $CDCl_3$) δ7.55 (s, 1H), 6.65 (s, 1H), 5.03 (d, J=6.9 Hz, 1H), 4.20-4.08 (m, 1H), 3.91 (s, 3H), 3.20 (s, 6H), 2.95-2.89 (m, 2H), 2.78 (quintet, J=6.5 Hz, 1H), 2.73-2.66 (m, 4H), 2.54-2.41 (m, 4H), 2.35 (t, J=10.7 Hz, 2H), 2.27-2.17 (m, 2H), 1.68-1.53 (m, 6H), 1.52-1.38 (m, 2H), 1.08 (d, J=6.5 Hz, 6H).

LCMS, m/z 479[M+H]+

<Example 45> Preparation of N-(1-isopropylpiperidine-4-yl)-6-methoxy-2-(4-methyl1,4-diazepane-1-yl)-7-(4-(piperidine-1-yl)-1-butyne-1-yl)quinazoline-4-amine

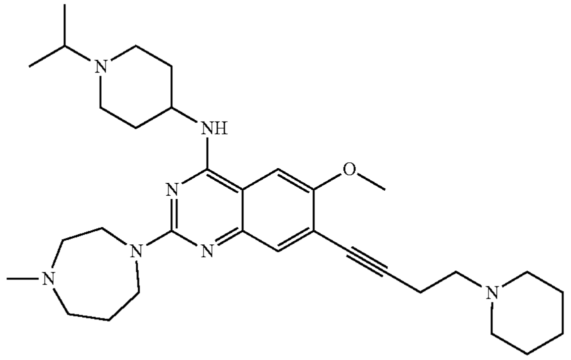 [SMILES: COc1cc2c(NC3CCN(C(C)C)CC3)nc(N3CCCN(C)CC3)nc2cc1C#CCCN1CCCCC1]

7-Iodo-N-(1-isopropylpiperidine-4-yl)-6-methoxy-2-(4-methyl-1,4-diazepane-1-yl)quinazoline-4-amine was prepared in the same manner as described in step 1 of Example 17, and a target compound N-(1-isopropylpiperidine-4-yl)-6-methoxy-2-(4-methyl1,4-diazepane-1-yl)-7-(4-(piperidine-1-yl)-1-butyne-1-yl)quinazoline-4-amine(N-(1-isopropylpiperidine-4-yl)-6-methoxy-2-(4-methyl-1,4-diazepane-1-yl)-7-(4-(piperidine-1-yl)but-1-yn-1-yl)quinazolin-4-amine) was obtained (8 mg, yield: 24.3%) in the same manner as described in step 3 of Example 1 using 1-(3-butyne-1-yl)piperidine as a starting material in step 3 of Example 1.

$^1$H NMR (400 MHz, $CDCl_3$) δ7.53 (s, 1H), 6.66 (s, 1H), 5.03 (d, J=7.0 Hz, 1H), 4.11-4.01 (m, 1H), 3.99-3.94 (m, 2H), 3.91 (s, 3H), 3.87 (t, J=6.4 Hz, 2H), 2.98-2.86 (m, 2H), 2.83-2.74 (m, 1H), 2.73-2.64 (m, 6H), 2.61-2.53 (m, 2H), 2.53-2.43 (m, 4H), 2.37 (s, 3H), 2.36-2.27 (m, 2H), 2.24-2.13 (m, 2H), 2.03-1.99 (m, 2H), 1.68-1.54 (m, 6H), 1.50-1.39 (m, 2H), 1.08 (d, J=6.5 Hz, 6H).

LCMS, m/z 548[M+H]+

<Example 46> Preparation of ((1S,2R,5R)-3-(4-((1-isopropylpiperidine-4-yl)amino)-6-methoxy-7-(4-(pyrrolidine-1-yl)-1-butyne-1-yl)quinazoline-2-yl)-3-azabicyclo[3.1.0]hexane-2-yl)methanol

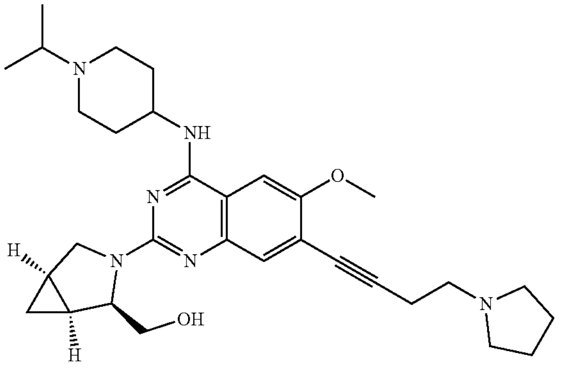 [SMILES: COc1cc2c(NC3CCN(C(C)C)CC3)nc(N3C[C@@H]4C[C@@H]4[C@@H]3CO)nc2cc1C#CCCN1CCCC1]

((1S,2R,5R)-3-(7-iodo-4-((1-isopropylpiperidine-4-yl)amino)-6-methoxyquinazoline-2-yl)-3-azabicyclo[3.1.0]hexane-2-yl)methanol was prepared in the same manner as described in step 1 of Example 10, and a target compound ((1S,2R,5R)-3-(4-((1-isopropylpiperidine-4-yl)amino)-6-methoxy-7-(4-(pyrrolidine-1-yl)-1-butyne-1-yl)quinazoline-2-yl)-3-azabicyclo[3.1.0]hexane-2-yl)methanol(((1S,2R,5R)-3-(4-((1-isopropylpiperidine-4-yl)amino)-6-methoxy-7-(4-(pyrrolidine-1-yl)but-1-yn-1-yl)quinazolin-2-yl)-3-azabicyclo[3.1.0]hexan-2-yl)methanol) was obtained (15.4 mg, yield: 23.6%) in the same manner as described in step 3 of Example 1 using 1-(3-butyne-1-yl)pyrrolidine as a starting material in step 3 of Example 1.

$^1$H NMR (400 MHz, $CDCl_3$) δ7.46 (s, 1H), 6.62 (s, 1H), 5.17-5.08 (m, 1H), 4.88 (br s, 1H), 4.54-4.46 (m, 1H), 4.21-4.14 (m, 1H), 4.14-4.02 (m, 1H), 3.91 (s, 3H), 3.78-3.71 (m, 1H), 3.57 (dd, J=11.0, 4.0 Hz, 1H), 2.98-2.87 (m, 2H), 2.85-2.66 (m, 4H), 2.65-2.55 (m, 4H), 2.36 (t, J=11.5 Hz, 2H), 2.24-2.12 (m, 2H), 1.83-1.77 (m, 8H), 1.09 (d, J=6.5 Hz, 6H), 0.91-0.81 (m, 2H), 0.77-0.65 (m, 1H), 0.23-0.15 (m, 1H).

LCMS, m/z 533[M+H]+

<Example 47> Preparation of ((1S,2R,5R)-3-(4-((1-isopropylpiperidine-4-yl)amino)-6-methoxy-7-(4-(piperidine-1-yl)-1-butyne-1-yl)quinazoline-2-yl)-3-azabicyclo[3.1.0]hexane-2-yl)methanol

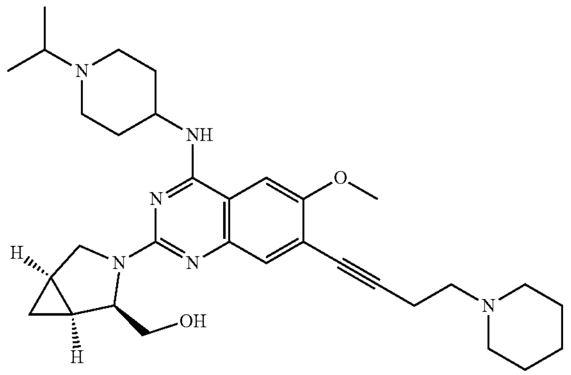 [SMILES: COc1cc2c(NC3CCN(C(C)C)CC3)nc(N3C[C@@H]4C[C@@H]4[C@@H]3CO)nc2cc1C#CCCN1CCCCC1]

((1S,2R,5R)-3-(7-iodo-4-((1-isopropylpiperidine-4-yl)amino)-6-methoxyquinazoline-2-yl)-3-azabicyclo[3.1.0]hexane-2-yl)methanol was prepared in the same manner as described in step 1 of Example 10, and a target compound ((1S,2R,5R)-3-(4-((1-isopropylpiperidine-4-yl)amino)-6-methoxy-7-(4-(piperidine-1-yl)-1-butyne-1-yl)quinazoline-2-yl)-3-azabicyclo[3.1.0]hexane-2-yl)methanol(((1S,2R,5R)-3-(4-((1-isopropylpiperidine-4-yl)amino)-6-methoxy-7-(4-(piperidine-1-yl)but-1-yn-1-yl)quinazolin-2-yl)-3-azabicyclo[3.1.0]hexan-2-yl)methanol) was obtained (5.1 mg, yield: 8.1%) in the same manner as described in step 3 of Example 1 using 1-(3-butene-1-yl)piperidine as a starting material in step 3 of Example 1.

$^1$H NMR (400 MHz, $CDCl_3$) δ7.46 (s, 1H), 6.63 (s, 1H), 5.16 (d, J=7.2 Hz, 1H), 4.88 (br s, 1H), 4.55-4.46 (m, 1H), 4.21-4.15 (m, 1H), 4.11-4.04 (m, 1H), 3.91 (s, 3H), 3.80-3.70 (m, 2H), 3.56 (dd, J=11.0, 4.2 Hz, 1H), 2.98-2.88 (m, 2H), 2.80 (quintet, J=6.6 Hz, 1H), 2.70-2.66 (m, 4H), 2.52-2.44 (m, 5H), 2.41-2.31 (m, 2H), 2.24-2.11 (m, 2H), 1.64-1.56 (m, 8H), 1.09 (d, J=6.6 Hz, 6H), 0.92-0.80 (m, 2H), 0.77-0.66 (m, 1H), 0.24-0.14 (m, 1H).

LCMS, m/z 547[M+H]+

<Example 48> Preparation of N-(1-isopropylpiperidine-4-yl)-6-methoxy-2-(4-methyl-1,4-diazepane-1-yl)-7-(4-(pyrrolidine-1-yl)-1-butyne-1-yl)quinazoline-4-amine

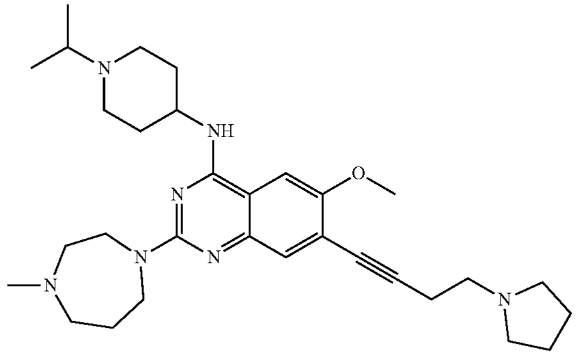 [SMILES: COc1cc2c(NC3CCN(C(C)C)CC3)nc(N3CCCN(C)CC3)nc2cc1C#CCCN1CCCC1]

7-Iodo-N-(1-isopropylpiperidine-4-yl)-6-methoxy-2-(4-methyl-1,4-diazepane-1-yl)quinazoline-4-amine was prepared in the same manner as described in step 1 of Example 17, and a target compound N-(1-isopropylpiperidine-4-yl)-6-methoxy-2-(4-methyl-1,4-diazepane-1-yl)-7-(4-(pyrrolidine-1-yl)-1-butyne-1-yl)quinazoline-4-amine(N-(1-isopropylpiperidine-4-yl)-6-methoxy-2-(4-methyl-1,4-diazepane-1-yl)-7-(4-(pyrrolidine-1-yl)but-1-yn-1-yl)quinazolin-4-amine) was obtained (2 mg, yield: 9.48%) in the same manner as described in step 3 of Example 1 using 1-(3-butyne-1-yl)pyrrolidine as a starting material in step 3 of Example 1.

$^1$H NMR (400 MHz, $CDCl_3$) δ7.53 (s, 1H), 6.65 (s, 1H), 5.03 (d, J=6.9 Hz, 1H), 4.11-4.04 (m, 1H), 4.01-3.94 (m, 2H), 3.92 (s, 3H), 3.87 (t, J=6.4 Hz, 2H), 2.99-2.88 (m, 2H), 2.85-2.76 (m, 3H), 2.74-2.67 (m, 4H), 2.65-2.55 (m, 6H), 2.38 (s, 3H), 2.36-2.30 (m, 2H), 2.23-2.15 (m, 2H), 2.07-2.00 (m, 2H), 1.84-1.77 (m, 4H), 1.66-1.57 (m, 2H), 1.09 (d, J=6.5 Hz, 6H).

LCMS, m/z 534[M+H]+

<Example 49> Preparation of N4-(1-isopropylpiperidine-4-yl)-6-methoxy-N2,N2-dimethyl-7-(4-(pyrrolidine-1-yl)-1-butyne-1-yl)quinazoline-2,4-diamine

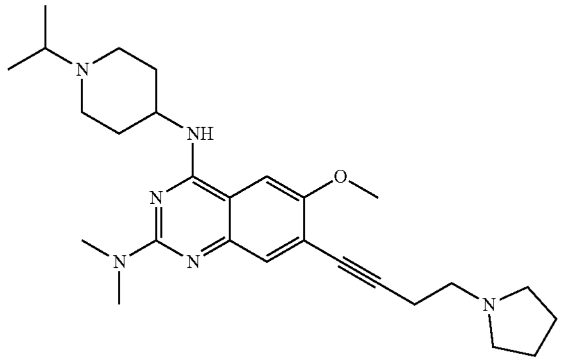 [SMILES: COc1cc2c(NC3CCN(C(C)C)CC3)nc(N(C)C)nc2cc1C#CCCN1CCCC1]

7-Iodo-N4-(1-isopropylpiperidine-4-yl)-6-methoxy-N2,N2-dimethylquinazoline-2,4-diamine was prepared in the same manner as described in step 1 of Example 15, and a target compound N4-(1-isopropylpiperidine-4-yl)-6-methoxy-N2,N2-dimethyl-7-(4-(pyrrolidine-1-yl)-1-butyne-1-yl)quinazoline-2,4-diamine(N4-(1-isopropylpiperidine-4-yl)-6-methoxy-N2,N2-dimethyl-7-(4-(pyrrolidine-1-yl)but-1-yn-1-yl)quinazoline-2,4-diamine) was obtained (15 mg, yield: 35.8%) in the same manner as described in step 3 of Example 1 using 1-(3-butyne-1-yl)pyrrolidine as a starting material in step 3 of Example 1.

$^1$H NMR (400 MHz, $CDCl_3$) δ7.56 (s, 1H), 6.68 (s, 1H), 5.11 (d, J=6.7 Hz, 1H), 4.24-4.05 (m, 1H), 3.91 (s, 3H), 3.20 (s, 6H), 2.93 (d, J=11.8 Hz, 2H), 2.85-2.74 (m, 3H), 2.74-2.67 (m, 2H), 2.65-2.53 (m, 4H), 2.40-2.29 (m, 2H), 2.21 (d, J=11.5 Hz, 2H), 1.90-1.75 (m, 4H), 1.61 (qd, J=11.9, 3.5 Hz, 2H), 1.08 (d, J=6.6 Hz, 6H).

LCMS, m/z 465[M+H]+

<Example 50> Preparation of 7-(4-(dimethylamino)-1-butyne-1-yl)-N-(1-ethylpiperidine-4-yl)-6-methoxy-2-(piperidine-1-yl)quinazoline-4-amine Step 1. Preparation of 2-chloro-N-(1-ethylpiperidine-4-yl)-7-iodo-6-methoxyquinazoline-4-amine

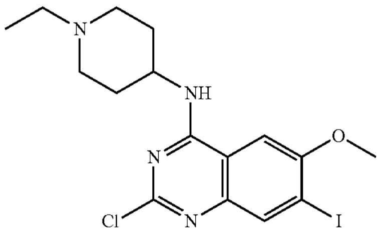 [SMILES: CCN1CCC(Nc2nc(Cl)nc3cc(I)c(OC)cc23)CC1]

A target compound was obtained (160 mg, yield: 85%) as a yellow solid by performing the procedure of step 1 of Example 1, except that 1-ethylpiperidine-4-amine was used instead of 1-isopropylpiperidine-4-amine in step 1 of Example 1.

LCMS, m/z 447[M+H]+

Step 2. Preparation of N-(1-ethylpiperidine-3-yl)-7-iodo-6-methoxy-2-(piperidine-1-yl)quinazoline-4-amine

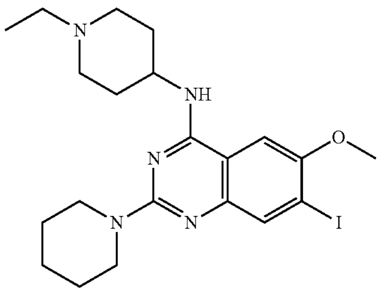 [SMILES: CCN1CCC(Nc2nc(N3CCCCC3)nc3cc(I)c(OC)cc23)CC1]

A target compound was obtained (62 mg, yield: 80%) as a yellow solid in the same manner as described in step 2 of Example 1 that 2-chloro-N-(1-ethylpiperidine-4-yl)-7-iodo-6-methoxyquinazoline-4-amine was used as a starting material in step 2 of Example 1.

LCMS, m/z 496[M+H]+

Step 3. Preparation of 7-(4-(dimethylamino)-1-butyne-1-yl)-N-(1-ethylpiperidine-4-yl)-6-methoxy-2-(piperidine-1-yl)quinazoline-4-amine

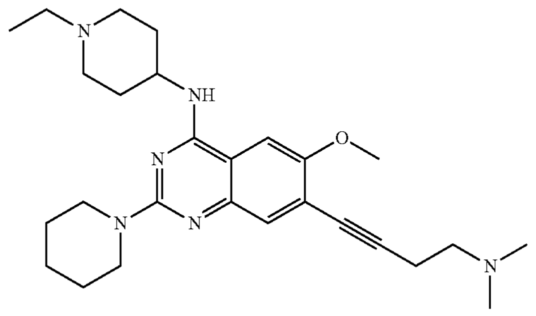 [SMILES: CCN1CCC(Nc2nc(N3CCCCC3)nc3cc(C#CCCN(C)C)c(OC)cc23)CC1]

A target compound 7-(4-(dimethylamino)-1-butyne-1-yl)-N-(1-ethylpiperidine-4-yl)-6-methoxy-2-(piperidine-1-yl) quinazoline-4-amine(7-(4-(dimethylamino)but-1-yn-1-yl)-N-(1-ethylpiperidine-4-yl)-6-methoxy-2-(piperidine-1-yl) quinazolin-4-amine) was obtained (5 mg, yield: 17.6%) as a yellow solid in the same manner as described in step 3 of Example 1 that N-(1-ethylpiperidine-4-yl)-7-iodo-6-methoxy-2-(piperidine-1-yl)quinazoline-4-amine and N,N-dimethyl-3-butyne-1-amine were used as starting materials in step 3 of Example 1.

$^1$H NMR (400 MHz, $CDCl_3$) δ7.53 (s, 1H), 6.65 (s, 1H), 5.04 (d, J=7.0 Hz, 1H), 4.21-4.08 (m, 1H), 3.92 (s, 3H), 3.87-3.75 (m, 4H), 3.03-2.91 (m, 2H), 2.70-2.60 (m, 4H), 2.47 (q, J=7.2 Hz, 2H), 2.31 (s, 6H), 2.27-2.13 (m, 4H), 1.71-1.55 (m, 8H), 1.12 (t, J=7.2 Hz, 3H).

LCMS, m/z 465[M+H]+

<Example 51> Preparation of N-(1-ethylpiperidine-4-yl)-6-methoxy-2-(piperidine-1-yl)-7-(4-(pyrrolidine-1-yl)-1-butyne-1-yl)quinazoline-4-amine

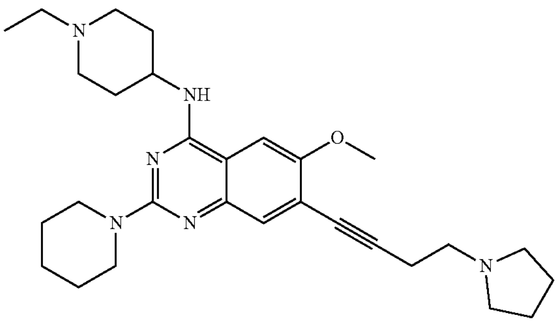 [SMILES: CCN1CCC(Nc2nc(N3CCCCC3)nc3cc(C#CCCN4CCCC4)c(OC)cc23)CC1]

N-(1-ethylpiperidine-4-yl)-7-iodo-6-methoxy-2-(piperidine-1-yl)quinazoline-4-amine was prepared in the same manner as described in step 1 of Example 50, and a target compound N-(1-ethylpiperidine-4-yl)-6-methoxy-2-(piperidine-1-yl)-7-(4-(pyrrolidine-1-yl)-1-butyne-1-yl) quinazoline-4-amine (N-(1-ethylpiperidine-4-yl)-6-methoxy-2-(piperidine-1-yl)-7-(4-(pyrrolidine-1-yl)but-1-yn-1-yl) quinazolin-4-amine) was obtained (5.5 mg, yield: 18.1%) in the same manner as described in step 3 of Example 1 using 1-(3-butyne-1-yl)pyrrolidine as a starting material in step 3 of Example 1.

$^{1}$H NMR (400 MHz, $CDCl_3$) δ7.53 (s, 1H), 6.66 (s, 1H), 5.05 (d, J=7.1 Hz, 1H), 4.19-4.07 (m, 1H), 3.92 (s, 3H), 3.86-3.74 (m, 4H), 3.02-2.92 (m, 2H), 2.83-2.67 (m, 4H), 2.66-2.54 (m, 4H), 2.46 (q, J=7.2 Hz, 2H), 2.24-2.10 (m, 4H), 1.84-1.75 (m, 4H), 1.71-1.53 (m, 8H), 1.12 (t, J=7.2 Hz, 3H).

LCMS, m/z 491[M+H]+

<Example 52> Preparation of N1-(6-methoxy-2-(pyrrolidine-1-yl)-7-(4-(pyrrolidine-1-yl)-1-butyne-1-yl)quinazoline-4-yl)-N2,N2-dimethylethane-1,2-diamine

Step 1. Preparation of N1-(7-iodo-6-methoxy-2-(pyrrolidine-1-yl)quinazoline-4-yl)-N2,N2-dimethylethane-1,2-diamine

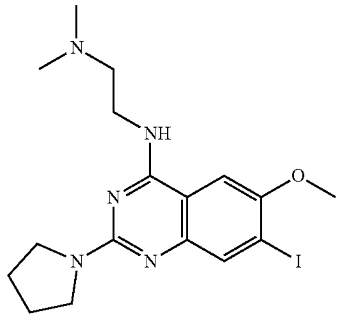 [SMILES: COc1cc2c(NCCN(C)C)nc(N3CCCC3)nc2cc1I]

N1-(2-chloro-7-iodo-6-methoxyquinazoline-4-yl)-N2,N2-dimethylethane-1,2-diamine was prepared in the same manner as described in step 1 of Example 28, and a target compound was obtained (28.8 mg, yield: 93%) as a yellow solid in the same manner as described in step 2 of Example 1 using pyrrolidine as a starting material in step 2 of Example 1.

LCMS, m/z 442[M+H]+

Step 2. Preparation of N1-(6-methoxy-2-(pyrrolidine-1-yl)-7-(4-(pyrrolidine-1-yl)-1-butyne-1-yl) quinazoline-4-yl)-N2,N2-dimethylethane-1,2-diamine

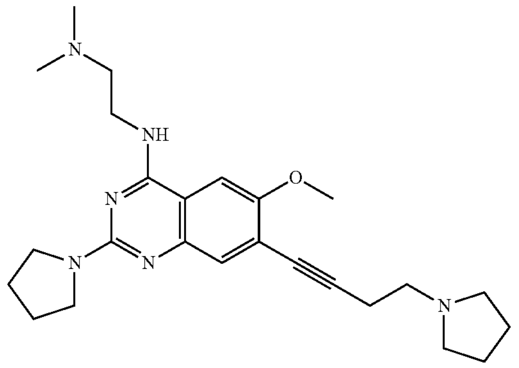 [SMILES: COc1cc2c(NCCN(C)C)nc(N3CCCC3)nc2cc1C#CCCN1CCCC1]

A target compound N1-(6-methoxy-2-(pyrrolidine-1-yl)-7-(4-(pyrrolidine-1-yl)-1-butyne-1-yl)quinazoline-4-yl)-N2,N2-dimethylethane-1,2-diamine(N1-(6-methoxy-2-(pyrrolidine-1-yl)-7-(4-(pyrrolidine-1-yl)but-1-yn-1-yl)quinazolin-4-yl)-N2,N2-dimethylethane-1,2-diamine) was obtained (2.3 mg, yield: 8.23%) in the same manner as described in step 3 of Example 1 that N1-(7-iodo-6-methoxy-2-(pyrrolidine-1-yl)quinazoline-4-yl)-N2,N2-dimethylethane-1,2-diamine and 1-(3-butyne-1-yl)pyrrolidine were used as starting materials in step 3 of Example 1.

$^{1}$H NMR (400 MHz, $CDCl_3$) δ7.57 (s, 1H), 6.83 (s, 1H), 6.06 (s, 1H), 3.91 (s, 3H), 3.71-3.51 (m, 6H), 2.83-2.76 (m, 2H), 2.76-2.67 (m, 2H), 2.66-2.54 (m, 6H), 2.31 (s, 6H), 1.99-1.91 (m, 4H), 1.85-1.77 (m, 4H).

LCMS, m/z 437[M+H]+

<Example 53> Preparation of N-(1-cyclopropylpiperidine-4-yl)-6-methoxy-2-(piperidine-1-yl)-7-(4-(pyrrolidine-1-yl)-1-butyne-1-yl)quinazoline-4-amine

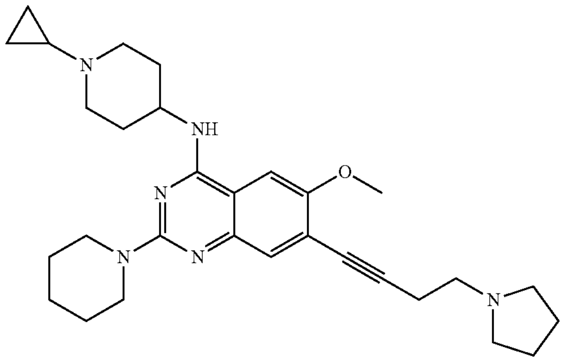 [SMILES: COc1cc2c(NC3CCN(C4CC4)CC3)nc(N3CCCCC3)nc2cc1C#CCCN1CCCC1]

N-(1-cyclopropylpiperidine-4-yl)-7-iodo-6-methoxy-2-(piperidine-1-yl)quinazoline-4-amine was prepared in the same manner as described in step 2 of Example 24, and a target compound N-(1-cyclopropylpiperidine-4-yl)-6-methoxy-2-(piperidine-1-yl)-7-(4-(pyrrolidine-1-yl)-1-butyne-1-yl)quinazoline-4-amine (N-(1-cyclopropylpiperidine-4-yl)-6-methoxy-2-(piperidine-1-yl)-7-(4-(pyrrolidine-1-yl)but-1-yn-1-yl)quinazolin-4-amine) was obtained (4.1 mg, yield: 11.7%) in the same manner as described in step 3 of Example 1 using 1-(3-butyne-1-yl)pyrrolidine as a starting material in step 3 of Example 1.

$^{1}$H NMR (400 MHz, $CDCl_3$) δ7.53 (s, 1H), 6.63 (s, 1H), 5.01 (d, J=7.0 Hz, 1H), 4.20-4.07 (m, 1H), 3.91 (s, 3H), 3.83-3.77 (m, 4H), 3.10-3.02 (m, 2H), 2.84-2.75 (m, 2H), 2.74-2.66 (m, 2H), 2.65-2.57 (m, 4H), 2.47-2.35 (m, 2H), 2.20-2.08 (m, 2H), 1.84-1.77 (m, 4H), 1.67-1.58 (m, 7H), 1.57-1.48 (m, 2H), 0.53-0.45 (m, 2H), 0.45-0.35 (m, 2H).

LCMS, m/z 503[M+H]+

<Example 54> Preparation of N-(1-cyclopropylpiperidine-4-yl)-6-methoxy-2-(pyrrolidine-1-yl)-7-(4-(pyrrolidine-1-yl)-1-butyne-1-yl)quinazoline-4-amine Step 1. Preparation of N-(1-cyclopropylpiperidine-4-yl)-7-iodo-6-methoxy-2-(pyrrolidine-1-yl)quinazoline-4-amine

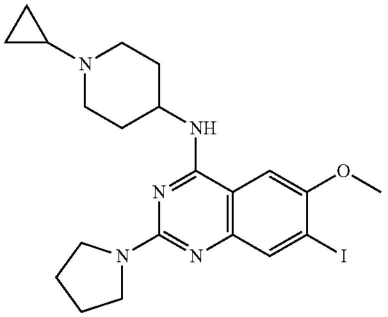 [SMILES: COc1cc2c(NC3CCN(C4CC4)CC3)nc(N3CCCC3)nc2cc1I]

2-Chloro-N-(1-cyclopropylpiperidine-4-yl)-7-iodo-6-methoxyquinazoline-4-amine was prepared in the same manner as described in step 1 of Example 24, and a target compound was obtained (37 mg, yield: 52.9%) as a yellow solid in the same manner as described in step 2 of Example 1 using pyrrolidine as a starting material in step 2 of Example 1.

LCMS, m/z 494[M+H]+

Step 2. Preparation of N-(1-cyclopropylpiperidine-4-yl)-6-methoxy-2-(pyrrolidine-1-yl)-7-(4-(pyrrolidine-1-yl)-1-butyne-1-yl)quinazoline-4-amine

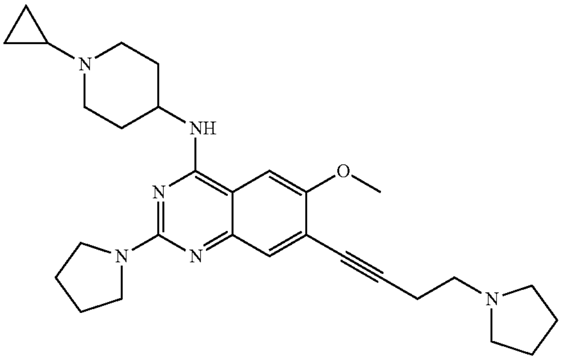 [SMILES: COc1cc2c(NC3CCN(C4CC4)CC3)nc(N3CCCC3)nc2cc1C#CCCN1CCCC1]

A target compound N-(1-cyclopropylpiperidine-4-yl)-6-methoxy-2-(pyrrolidine-1-yl)-7-(4-(pyrrolidine-1-yl)-1-butyne-1-yl)quinazoline-4-amine(N-(1-cyclopropylpiperidine-4-yl)-6-methoxy-2-(pyrrolidine-1-yl)-7-(4-(pyrrolidine-1-yl)but-1-yn-1-yl)quinazolin-4-amine) was obtained (7.1 mg, yield: 20.2%) as a yellow solid in the same manner as described in step 3 of Example 1 that N-(1-cyclopropylpiperidine-4-yl)-7-iodo-6-methoxy-2-(pyrrolidine-1-yl)quinazoline-4-amine and 1-(3-butyne-1-yl)pyrrolidine were used as starting materials in step 3 of Example 1.

$^1$H NMR (400 MHz, $CDCl_3$) δ7.57 (s, 1H), 6.66 (s, 1H), 5.06 (d, J=5.9 Hz, 1H), 4.23-4.13 (m, 1H), 3.90 (s, 3H), 3.66-3.58 (m, 4H), 3.10-2.99 (m, 2H), 2.84-2.76 (m, 2H), 2.75-2.66 (m, 2H), 2.66-2.55 (m, 4H), 2.47-2.36 (m, 2H), 2.22-2.08 (m, 2H), 2.01-1.90 (m, 4H), 1.84-1.78 (m, 4H), 1.67-1.61 (m, 1H), 1.61-1.47 (m, 2H), 0.52-0.45 (m, 2H), 0.44-0.37 (m, 2H).

LCMS, m/z 489[M+H]+

<Example 55> Preparation of N4-(1-cyclopropylpiperidine-4-yl)-6-methoxy-N2,N2-dimethyl-7-(4-(pyrrolidine-1-yl)-1-butyne-1-yl)quinazoline-2,4-diamine Step 1. Preparation of N4-(1-cyclopropylpiperidine-4-yl)-7-iodo-6-methoxy-N2,N2-dimethylquinazoline-2,4-diamine

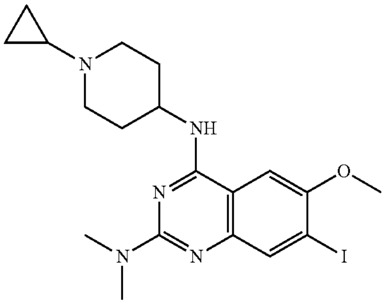 [SMILES: COc1cc2c(NC3CCN(C4CC4)CC3)nc(N(C)C)nc2cc1I]

2-Chloro-N-(1-cyclopropylpiperidine-4-yl)-7-iodo-6-methoxyquinazoline-4-amine was prepared in the same manner as described in step 1 of Example 24, and a target compound was obtained (12 mg, yield: 39.3%) as a yellow solid in the same manner as described in step 2 of Example 1 using dimethylamine as a starting material in step 2 of Example 1.

LCMS, m/z 468[M+H]+

Step 2. Preparation of N4-(1-cyclopropylpiperidine-4-yl)-6-methoxy-N2,N2-dimethyl-7-(4-(pyrrolidine-1-yl)-1-butyne-1-yl)quinazoline-2,4-diamine

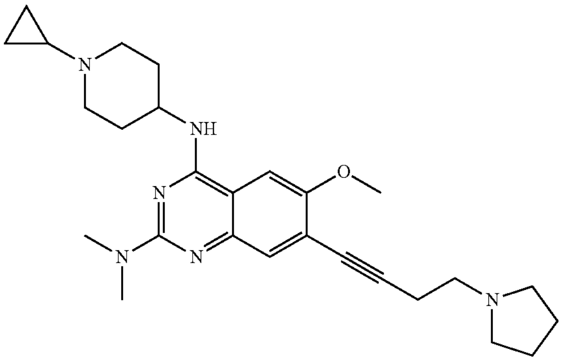 [SMILES: COc1cc2c(NC3CCN(C4CC4)CC3)nc(N(C)C)nc2cc1C#CCCN1CCCC1]

A target compound N4-(1-cyclopropylpiperidine-4-yl)-6-methoxy-N2,N2-dimethyl-7-(4-(pyrrolidine-1-yl)-1-butyne-1-yl)quinazoline-2,4-diamine(N4-(1-cyclopropylpiperidine-4-yl)-6-methoxy-N2,N2-dimethyl-7-(4-(pyrrolidine-1-yl)but-1-yn-1-yl)quinazoline-2,4-diamine) was obtained (4.9 mg, yield: 19.4%) as a yellow solid in the same manner as described in step 3 of Example 1 that N4-(1-cyclopropylpiperidine-4-yl)-7-iodo-6-methoxy-N2, N2-dimethylquinazoline-2,4-diamine and 1-(3-butyne-1-yl) pyrrolidine were used as starting materials in step 3 of Example 1.

$^1$H NMR (400 MHz, $CDCl_3$) δ7.56 (s, 1H), 6.65 (s, 1H), 5.04 (d, J=6.4 Hz, 1H), 4.22-4.10 (m, 1H), 3.91 (s, 3H), 3.20 (s, 6H), 3.10-3.01 (m, 2H), 2.83-2.76 (m, 2H), 2.76-2.66 (m, 2H), 2.67-2.56 (m, 4H), 2.49-2.35 (m, 2H), 2.21-2.11 (m, 2H), 1.86-1.74 (m, 4H), 1.68-1.60 (m, 1H), 1.60-1.46 (m, 2H), 0.52-0.45 (m, 2H), 0.45-0.34 (m, 2H). LCMS, m/z 463[M+H]+

<Example 56> Preparation of N-(1-cyclopropylpiperidine-4-yl)-6-methoxy-2-(4-methyl-1,4-diazepane-1-yl)-7-(4-(pyrrolidine-1-yl)-1-butyne-1-yl)quinazoline-4-amine Step 1. Preparation of N-(1-cyclopropylpiperidine-4-yl)-7-iodo-6-methoxy-2-(4-methyl-1,4-diazepane-1-yl)quinazoline-4-amine

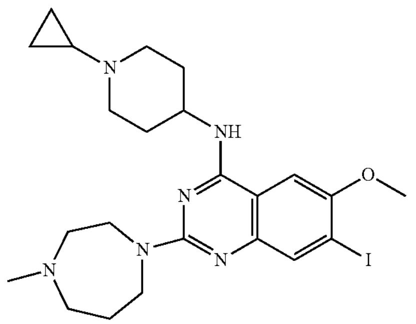

2-Chloro-N-(1-cyclopropylpiperidine-4-yl)-7-iodo-6-methoxyquinazoline-4-amine was prepared in the same manner as described in step 1 of Example 24, and a target compound was obtained (68 mg, yield: 83%) as a yellow solid in the same manner as described in step 2 of Example 1 using 1-methylhomopiperazine as a starting material in step 2 of Example 1.

LCMS, m/z 537[M+H]+

Step 2. Preparation of N-(1-cyclopiperidine-4-yl)-6-methoxy-2-(4-methyl-1,4-diazepane-1-yl)-7-(4-(pyrrolidine-1-yl)-1-butyne-1-yl)quinazoline-4-amine

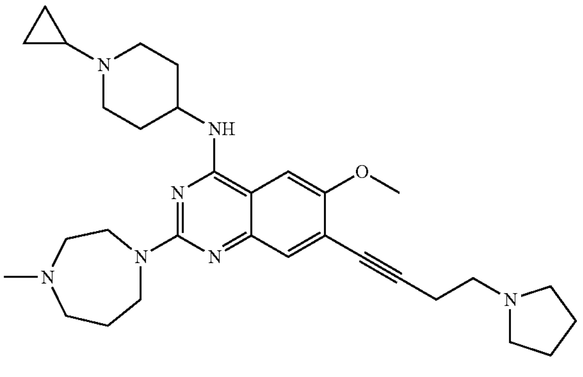 [SMILES: COc1cc2c(NC3CCN(C4CC4)CC3)nc(N3CCCN(C)CC3)nc2cc1C#CCCN1CCCC1]

A target compound N-(1-cyclopropylpiperidine-4-yl)-6-methoxy-2-(4-methyl-1,4-diazepane-1-yl)-7-(4-(pyrrolidine-1-yl)-1-butyne-1-yl)quinazoline-4-amine(N-(1-cyclopropylpiperidine-4-yl)-6-methoxy-2-(4-methyl-1,4-diazepane-1-yl)-7-(4-(pyrrolidine-1-yl)but-1-yn-1-yl) quinazolin-4-amine) was obtained (3.5 mg, yield: 17.1%) in the same manner as described in step 3 of Example 1 that N-(1-cyclopropylpiperidine-4-yl)-7-iodo-6-methoxy-2-(4-methyl-1,4-diazepane-yl)quinazoline-4-amine and 1-(3-butyne-1-yl)pyrrolidine were used as starting materials in step 3 of Example 1.

$^1$H NMR (400 MHz, $CDCl_3$) δ7.54 (s, 1H), 6.65 (s, 1H), 5.03 (d, J=6.5 Hz, 1H), 4.18-4.05 (m, 1H), 4.01-3.95 (m, 2H), 3.91 (s, 3H), 3.87 (t, J=6.4 Hz, 2H), 3.13-2.97 (m, 2H), 2.85-2.75 (m, 2H), 2.75-2.66 (m, 4H), 2.66-2.53 (m, 6H), 2.45-2.32 (m, 5H), 2.19-2.11 (m, 2H), 2.06-1.97 (m, 2H), 1.88-1.74 (m, 4H), 1.68-1.62 (m, 1H), 1.62-1.46 (m, 2H), 0.52-0.45 (m, 2H), 0.45-0.34 (m, 2H).

LCMS, m/z 532[M+H]+

<Example 57> Preparation of (S)-2-(3-fluoropyrrolidine-1-yl)-N-(1-isopropylpiperidine-4-yl)-6-methoxy-7-(4-(pyrrolidine-1-yl)-1-butyne-1-yl)quinazoline-4-amine Step 1. Preparation of (S)-2-(3-fluoropyrrolidine-1-yl)-7-iodo-N-(1-isopropylpiperidine-4-yl)-6-methoxyquinazoline-4-amine

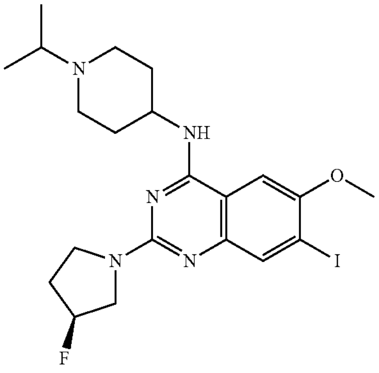 [SMILES: COc1cc2c(NC3CCN(C(C)C)CC3)nc(N3CC[C@H](F)C3)nc2cc1I]

2-Chloro-7-iodo-N-(1-isopropylpiperidine-4-yl)-6-methoxyquinazoline-4-amine was prepared in the same manner as described in step 1 of Example 1, and a target compound was obtained (55 mg, yield: 36.8%) as a yellow solid in the same manner as described in step 2 of Example 1 using (S)-3-fluoropyrrolidine hydrochloride as a starting material in step 1 of Example 1.

LCMS, m/z 514[M+H]+

Step 2. Preparation of (S)-2-(3-fluoropyrrolidine-1-yl)-N-(1-isopropylpiperidine-4-yl)-6-methoxy-7-(4-pyrrolidine-1-yl)-1-butyne-1-yl)quinazoline-4-amine

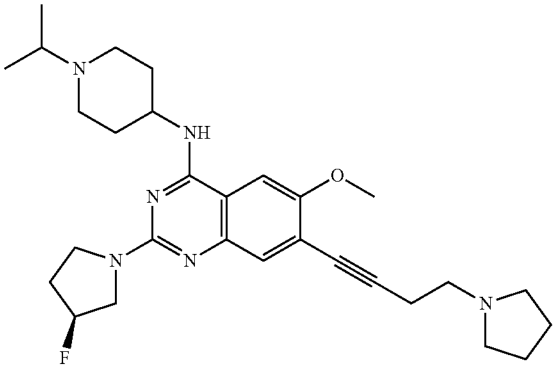 [SMILES: COc1cc2c(NC3CCN(C(C)C)CC3)nc(N3CC[C@H](F)C3)nc2cc1C#CCCN1CCCC1]

A target compound (S)-2-(3-fluoropyrrolidine-1-yl)-N-(1-isopropylpiperidine-4-yl)-6-methoxy-7-(4-(pyrrolidine-1-yl)-1-butyne-1-yl)quinazoline-4-amine ((S)-2-(3-fluoro-pyrrolidine-1-yl)-N-(1-isopropylpiperidine-4-yl)-6-methoxy-7-(4-(pyrrolidine-1-yl)but-1-yn-1-yl)quinazolin-4-amine) was obtained (26.4 mg, yield: 59.2%) as a yellow solid in the same manner as described in step 3 of Example 1 that (S)-2-(3-fluoropyrrolidine-1-yl)-7-iodo-N-(1-isopropylpiperidine-4-yl)-6-methoxyquinazoline-4-amine and 1-(3-butyne-1-yl)pyrrolidine were used as starting materials in step 3 of Example 1.

$^1$H NMR (400 MHz, $CDCl_3$) δ 7.58 (s, 1H), 6.68 (s, 1H), 5.45-5.23 (m, 1H), 5.12 (d, J=7.0 Hz, 1H), 4.20-4.08 (m, 1H), 4.07-3.99 (m, 1H), 3.98-3.94 (m, 1H), 3.92 (s, 3H), 3.85-3.62 (m, 2H), 2.98-2.88 (m, 2H), 2.85-2.74 (m, 3H), 2.74-2.67 (m, 2H), 2.64-2.55 (m, 4H), 2.39-2.30 (m, 3H), 2.25-2.17 (m, 2H), 2.11-1.99 (m, 1H), 1.83-1.77 (m, 4H), 1.67-1.54 (m, 2H), 1.08 (d, J=6.5 Hz, 6H).

LCMS, m/z 509[M+H]+

<Example 58> Preparation of 2-(3,3-difluoro-azetine-1-yl)-N-(1-isopropylpiperidine-4-yl)-6-methoxy-7-(4-(pyrrolidine-1-yl)-1-butyne-1-yl)quinazoline-4-amine Step 1. Preparation of 2-(3,3-difluoroazetidine-1-yl)-7-iodo-N-(1-diisopropylpiperidine-4-yl)-6-methoxyquinazoline-4-amine

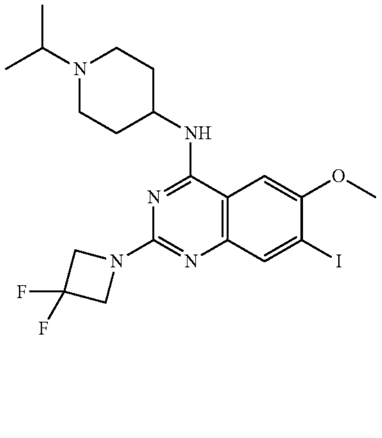 [SMILES: COc1cc2c(NC3CCN(C(C)C)CC3)nc(N3CC(F)(F)C3)nc2cc1I]

2-Chloro-7-iodo-N-(1-isopropylpiperidine-4-yl)-6-methoxyquinazoline-4-amine was prepared in the same manner as described in step 1 of Example 1, and a target compound was obtained (48 mg, yield: 46.3%) as a yellow solid in the same manner as described in step 2 of Example 1 using 3,3-difluoroazetidine as a starting material in step 2 of Example 1.

$^1$H NMR (400 MHz, $CDCl_3$) δ8.10 (s, 1H), 6.65 (s, 1H), 5.22 (d, J=7.3 Hz, 1H), 4.45 (t, J=12.3 Hz, 4H), 4.21-4.05 (m, 1H), 3.96 (s, 3H), 2.97-2.88 (m, 2H), 2.78 (dt, J=13.1, 6.6 Hz, 1H), 2.33 (td, J=11.7, 2.1 Hz, 2H), 2.22-2.09 (m, 2H), 1.64-1.49 (m, 2H), 1.08 (d, J=6.6 Hz, 6H).

LCMS, m/z 518[M+H]+

Step 2. Preparation of 2-(3,3-difluoroazetidine-1-yl)-N-(1-isopropylpiperidine-4-yl)-6-methoxy-7-(4-(pyrrolidine-1-yl)-1-butyne-1-yl)quinazoline-4-amine

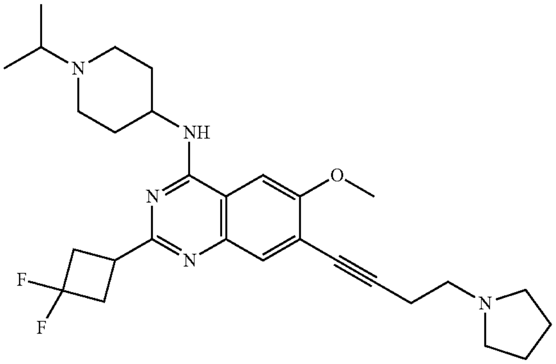 [SMILES: COc1cc2c(NC3CCN(C(C)C)CC3)nc(C3CC(F)(F)C3)nc2cc1C#CCCN1CCCC1]

A target compound 2-(3,3-difluoroazetine-1-yl)-N-(1-isopropylpiperidine-4-yl)-6-methoxy-7-(4-(pyrrolidine-1-yl)-1-butyne-1-yl)quinazoline-4-amine(2-(3,3-difluoroazetidin-1-yl)-N-(1-isopropylpiperidine-4-yl)-6-methoxy-7-(4-(pyrrolidine-1-yl)but-1-yn-1-yl)quinazolin-4-amine) was obtained (28.7 mg, yield: 66.5%) as a yellow solid in the same manner as described in step 3 of Example 1 that 2-(3,3-difluoroazetidine-1-yl)-7-iodo-N-(1-isopropylpiperidine-4-yl)-6-methoxyquinazoline-4-amine and 1-(3-butyne-1-yl)pyrrolidine were used as starting materials in step 3 of Example 1.

$^1$H NMR (400 MHz, $CDCl_3$) δ7.60 (s, 1H), 6.70 (s, 1H), 5.26 (d, J=7.3 Hz, 1H), 4.44 (t, J=12.3 Hz, 4H), 4.18-4.05 (m, 1H), 3.93 (s, 3H), 2.97-2.84 (m, 2H), 2.82-2.74 (m, 3H), 2.75-2.66 (m, 2H), 2.65-2.54 (m, 4H), 2.33 (t, J=10.7 Hz, 2H), 2.22-2.10 (m, 2H), 1.84-1.74 (m, 4H), 1.66-1.51 (m, 2H), 1.07 (d, J=6.5 Hz, 6H).

LCMS, m/z 513[M+H]+

<Example 59> Preparation of 2-(3-fluoroazetidine-1-yl)-N-(1-isopropylpiperidine-4-yl)-6-methoxy-7-(4-(pyrrolidine-1-yl)-1-butyne-1-yl)quinazoline-4-amine Step 1. Preparation of 2-(3-fluoroazetidine-1-yl)-7-iodo-N-(1-isopropylpiperidine-4-yl)-6-methoxyquinazoline-4-amine

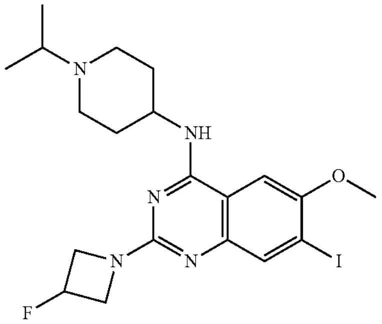 [SMILES: COc1cc2c(NC3CCN(C(C)C)CC3)nc(N3CC(F)C3)nc2cc1I]

2-Chloro-7-iodo-N-(1-isopropylpiperidine-4-yl)-6-methoxyquinazoline-4-amine was prepared in the same manner as described in step 1 of Example 1, and a target compound was obtained (53 mg, yield: 52%) as a yellow solid in the same manner as described in step 2 of Example 1 using 3-fluoroazetidine as a starting material in step 2 of Example 1.

LCMS, m/z 500[M+H]+

Step 2. Preparation of 2-(3-fluoroazetidine-1-yl)-N-(1-isopropylpiperidine-4-yl)-6-methoxy-7-(4-pyrrolidine-1-yl)-1-butyne-1-yl)quinazoline-4-amine

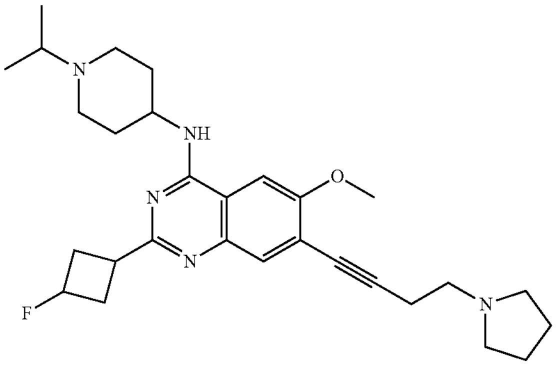 [SMILES: COc1cc2c(NC3CCN(C(C)C)CC3)nc(C3CC(F)C3)nc2cc1C#CCCN1CCCC1]

A target compound 2-(3-fluoroazetidine-1-yl)-N-(1-isopropylpiperidine-4-yl)-6-methoxy-7-(4-(pyrrolidine-1-yl)-1-butyne-1-yl)quinazoline-4-amine(2-(3-fluoroazetidin-1-yl)-N-(1-isopropylpiperidine-4-yl)-6-methoxy-7-(4-(pyrrolidine-1-yl)but-1-yn-1-yl)quinazolin-4-amine) was obtained (26.5 mg, yield: 49.2%) as a yellow solid in the same manner as described in step 3 of Example 1 that 2-(3-fluoroazetidine-1-yl)-7-iodo-N-(1-isopropylpiperidine-4-yl)-6-methoxyquinazoline-4-amine and 1-(3-butyne-1-yl) pyrrolidine were used as starting materials in step 3 of Example 1.

$^1$H NMR (400 MHz, $CDCl_3$) δ7.59 (s, 1H), 6.68 (s, 1H), 5.49-5.27 (m, 1H), 5.16 (d, J=7.3 Hz, 1H), 4.48-4.34 (m, 2H), 4.30-4.17 (m, 2H), 4.17-4.07 (m, 1H), 3.92 (s, 3H), 2.98-2.85 (m, 2H), 2.84-2.66 (m, 5H), 2.66-2.55 (m, 4H), 2.39-2.26 (m, 2H), 2.23-2.11 (m, 2H), 1.85-1.77 (m, 4H), 1.66-1.50 (m, 2H), 1.07 (d, J=6.5 Hz, 6H).

LCMS, m/z 495[M+H]+

<Example 60> Preparation of (R)-2-(3-fluoropyrrolidine-1-yl)-N-(1-isopropylpiperidine-4-yl)-6-methoxy-7-(4-(pyrrolidine-1-yl)-1-butyne-1-yl)quinazoline-4-amine Step 1. Preparation of (R)-2-(3-fluoropyrrolidine-1-yl)-7-iodo-N-(1-isopropylpiperidine-4-yl)-6-methoxyquinazoline-4-amine

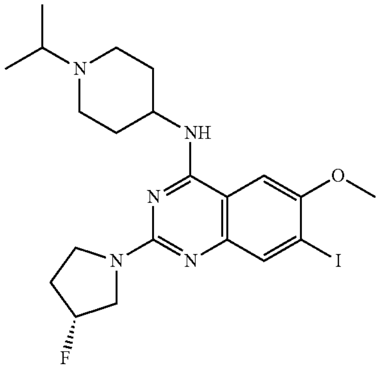 [SMILES: COc1cc2c(NC3CCN(C(C)C)CC3)nc(N3CC[C@@H](F)C3)nc2cc1I]

2-Chloro-7-iodo-N-(1-isopropylpiperidine-4-yl)-6-methoxyquinazoline-4-amine was prepared in the same manner as described in step 1 of Example 1, and a target compound was obtained (49 mg, yield: 32.6%) as a yellow solid in the same manner as described in step 1 of Example 1 using (R)-3-fluoropyrrolidine hydrochloride as a starting material in step 2 of Example 1.

LCMS, m/z 514[M+H]+

Step 2. Preparation of (R)-2-(3-fluoropyrrolidine-1-yl)-N-(1-isopropylpiperidine-4-yl)-6-methoxy-7-(4-(pyrrolidine-1-yl)-1-butyne-1-yl)quinazoline-4-amine

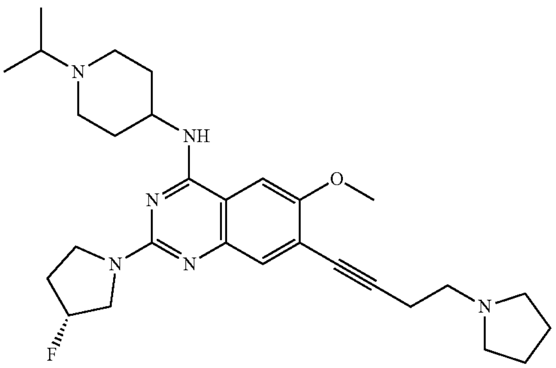 [SMILES: COc1cc2c(NC3CCN(C(C)C)CC3)nc(N3CC[C@@H](F)C3)nc2cc1C#CCCN1CCCC1]

A target compound (R)-2-(3-fluoropyrrolidine-1-yl)-N-(1-isopropylpiperidine-4-yl)-6-methoxy-7-(4-(pyrrolidine-1-yl)-1-butyne-1-yl)quinazoline-4-amine ((R)-2-(3-fluoropyrrolidine-1-yl)-N-(1-isopropylpiperidine-4-yl)-6- methoxy-7-(4-(pyrrolidine-1-yl)but-1-yn-1-yl)quinazolin-4-amine) was obtained (24.9 mg, yield: 57.1%) as a yellow solid in the same manner as described in step 3 of Example 1 that (R)-2-(3-fluoropyrrolidine-1-yl)-7-iodo-N-(1-isopropylpiperidine-4-yl)-6-methoxyquinazoline-4-amine and 1-(3-butyne-1-yl)pyrrolidine were used as starting materials.

$^1$H NMR (400 MHz, $CDCl_3$) δ 7.58 (s, 1H), 6.67 (s, 1H), 5.45-5.23 (m, 1H), 5.09 (d, J=7.1 Hz, 1H), 4.20-4.08 (m, 1H), 4.07-3.98 (m, 1H), 3.97-3.88 (m, 1H), 3.92 (s, 3H), 3.85-3.63 (m, 2H), 2.98-2.86 (m, 2H), 2.83-2.74 (m, 3H), 2.74-2.67 (m, 2H), 2.64-2.55 (m, 4H), 2.40-2.27 (m, 3H), 2.25-2.15 (m, 2H), 2.10-1.97 (m, 1H), 1.84-1.79 (m, 4H), 1.67-1.50 (m, 2H), 1.08 (d, J=6.5 Hz, 6H).

LCMS, m/z 509[M+H]+

<Example 61> Preparation of N4-(2-(dimethylamino)ethyl)-6-methoxy-N2,N2-dimethyl-7-(4-(pyrrolidine-1-yl)-1-butyne-1-yl)quinazoline-2,4-diamine

Step 1. Preparation of N4-(2-dimethylamino)ethyl)-7-iodo-6-methoxy-N2,N2-dimethylquinazoline-2,4-diamine

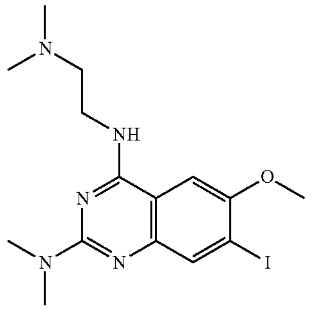

N1-(2-chloro-7-iodo-6-methoxyquinazoline-4-yl)-N2,N2-dimethylethane-1,2-diamine was prepared in the same manner as described in step 1 of Example 28, and a target compound was obtained (20 mg, yield: 65.3%) as a yellow solid in the same manner as described in step 2 of Example 1 using dimethylamine as a starting material in step 2 of Example 1.

LCMS, m/z 416[M+H]+

Step 2. Preparation of N4-(2-(dimethylamino)ethyl)-6-methoxy-N2,N2-dimethyl-7-(4-pyrrolidine-1-yl)-1-butyne-1-yl)quinazoline-2,4-diamine

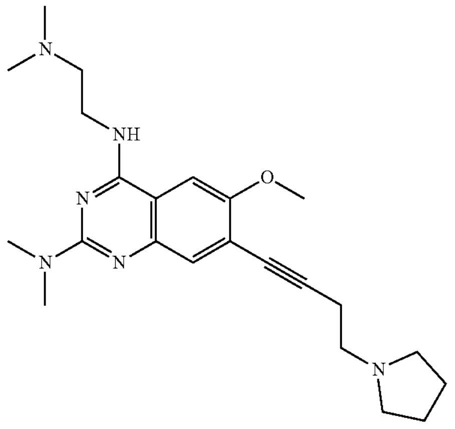 [SMILES: COc1cc2c(NCCN(C)C)nc(N(C)C)nc2cc1C#CCCN1CCCC1]

A target compound N4-(2-(dimethylamino)ethyl)-6-methoxy-N2,N2-dimethyl-7-(4-(pyrrolidine-1-yl)-1-butyne-1-yl)quinazoline-2,4-diamine(N4-(2-(dimethylamino)ethyl)-6-methoxy-N2,N2-dimethyl-7-(4-(pyrrolidine-1-yl)but-1-yn-1-yl)quinazoline-2,4-diamine) was obtained (1.1 mg, yield: 5.26%) as a yellow solid in the same manner as described in step 3 of Example 1 that N4-(2-(dimethylamino)ethyl)-7-iodo-6-methoxy-N2,N2-dimethylquinazoline-2,4-diamine and 1-(3-butyne-1-yl)pyrrolidine were used as starting materials in step 3 of Example 1.

$^1$H NMR (400 MHz, $CDCl_3$) δ7.56 (s, 1H), 6.83 (s, 1H), 6.10 (s, 1H), 3.92 (s, 3H), 3.67 (d, J=5.5 Hz, 2H), 3.21 (s, 6H), 2.85-2.77 (m, 2H), 2.75-2.68 (m, 2H), 2.67-2.56 (m, 6H), 2.32 (s, 6H), 1.87-1.77 (m, 4H).

LCMS, m/z 411 [M+H]+

<Example 62> Preparation of N1-(6-methoxy-2-(4-methyl-1,4-diazepane-1-yl)-7-(4-(pyrrolidine-1-yl)-1-butyne-1-yl)quinazoline-4-yl)-N2,N2-dimethylethane-1,2-diamine

Step 1. Preparation of N1-(7-iodo-6-methoxy-2-(4-methyl-1,4-diazepane-1-yl)quinazoline-4-yl)-N2,N2-dimethylethane-1,2-diamine

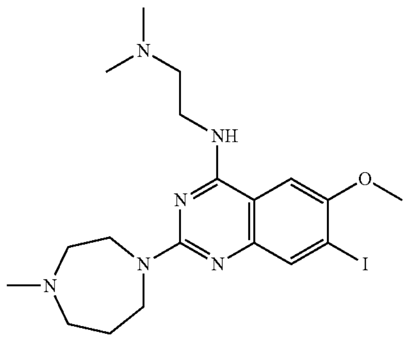

N1-(2-chloro-7-iodo-6-methoxyquinazoline-4-yl)-N2,N2-dimethylethane-1,2-diamine was prepared in the same manner as described in step 1 of Example 28, and a target compound was obtained (22.8 mg, yield: 66.6%) as a yellow solid in the same manner as described in step 2 of Example 1 using 1-methylhomopiperazine as a starting material in step 2 of Example 1.

LCMS, m/z 485[M+H]+

Step 2. Preparation of N1-(6-methoxy-2-(4-methyl-1,4-diazepane-1-yl)-7-(4-(pyrrolidine-1-yl)-1-butyne-1-yl)quinazoline-4-yl)-N2,N2-dimethyl-ethane-1,2-diamine

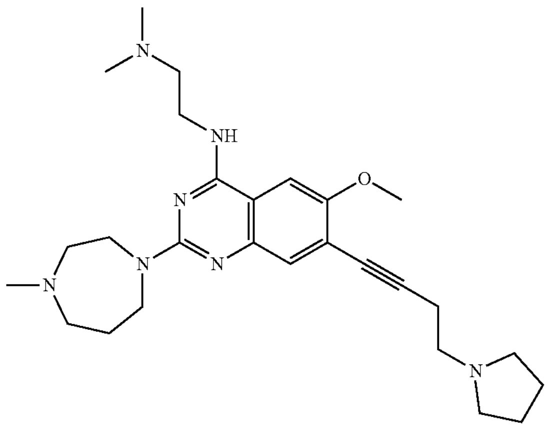 [SMILES: COc1cc2c(NCCN(C)C)nc(N3CCCN(C)CC3)nc2cc1C#CCCN1CCCC1]

A target compound N1-(6-methoxy-2-(4-methyl-1,4-diazepane-1-yl)-7-(4-(pyrrolidine-1-yl)-1-butyne-1-yl)quinazoline-4-yl)-N2,N2-dimethylethane-1,2-diamine(N1-(6-methoxy-2-(4-methyl-1,4-diazepane-1-yl)-7-(4-(pyrrolidine-1-yl)but-1-yn-1-yl)quinazolin-4-yl)-N2,N2-dimethylethane-1,2-diamine) was obtained (3.6 mg, yield: 17.6%) as a yellow solid in the same manner as described in step 3 of Example 1 that N1-(7-iodo-6-methoxy-2-(4-methyl-1,4-diazepane-1-yl)quinazoline-4-yl)-N2,N2-dimethylethane-1,2-diamine and 1-(3-butyne-1-yl)pyrrolidine were used as starting materials in step 3 of Example 1.

$^1$H NMR (400 MHz, $CDCl_3$) δ7.54 (s, 1H), 6.82 (s, 1H), 6.03 (s, 1H), 4.04-3.96 (m, 1H), 3.92 (s, 3H), 3.90-3.84 (m, 2H), 3.68-3.59 (m, 2H), 2.84-2.76 (m, 2H), 2.75-2.67 (m, 3H), 2.66-2.50 (m, 6H), 2.37 (s, 3H), 2.32 (s, 6H), 2.12-1.93 (m, 6H), 1.87-1.74 (m, 4H).

LCMS, m/z 481[M+H]+

<Example 63> Preparation of N4-(1-ethylpiperidine-4-yl)-6-methoxy-N2,N2-dimethyl-7-(4-(-pyrrolidine-1-yl)-1-butyne-1-yl)quinazoline-2,4-diamine Step 1. Preparation of N4-(1-ethylpiperidine-4-yl)-7-iodo-6-methoxy-N2,N2-dimethylquinazoline-2,4-diamine

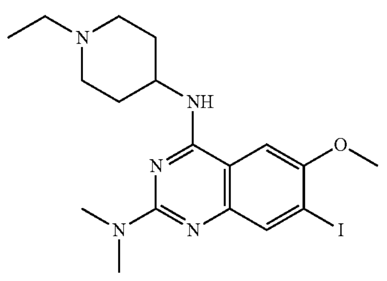 [SMILES: CCN1CCC(Nc2nc(N(C)C)nc3cc(I)c(OC)cc23)CC1]

2-Chloro-N-(1-ethylpiperidine-4-yl)-7-iodo-6-methoxy-quinazoline-4-amine was prepared in the same manner as described in step 1 of Example 50, and a target compound was obtained (68 mg, yield: 80%) as a yellow solid in the same manner as described in step 2 of Example 1 using dimethylamine as a starting material in step 2 of Example 1.

LCMS, m/z 456[M+H]+

Step 2. Preparation of N4-(1-ethylpiperidine-4-yl)-6-methoxy-N2,N2-dimethyl-7-(4-(pyrrolidine-1-yl)-1-butyne-1-yl)quinazoline-2,4-diamine

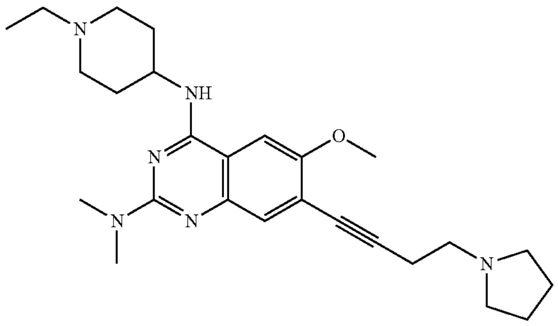 [SMILES: CCN1CCC(Nc2nc(N(C)C)nc3cc(C#CCCN4CCCC4)c(OC)cc23)CC1]

A target compound N4-(1-ethylpiperidine-4-yl)-6-methoxy-N2,N2-dimethyl-7-(4-(-pyrrolidine-1-yl)-1-butyne-1-yl)quinazoline-2,4-diamine(N4-(1-ethylpiperidine-4-yl)-6-methoxy-N2,N2-dimethyl-7-(4-(pyrrolidine-1-yl)but-1-yn-1-yl)quinazoline-2,4-diamine) was obtained (34 mg, yield: 50.2%) as a yellow solid in the same manner as described in step 3 of Example 1 that N4-(1-ethylpiperidine-4-yl)-7-iodo-6-methoxy-N2,N2-dimethylquinazoline-2,4-diamine and 1-(3-butyne-1-yl)pyrrolidine were used as starting materials in step 3 of Example 1.

$^1$H NMR (400 MHz, $CDCl_3$) δ 7.56 (s, 1H), 6.67 (s, 1H), 5.19-5.02 (m, 1H), 4.23-4.06 (m, 1H), 3.92 (s, 3H), 3.19 (s, 6H), 3.02-2.91 (m, 2H), 2.84-2.68 (m, 4H), 2.63-2.56 (m, 5H), 2.56-2.49 (m, 4H), 2.24-2.09 (m, 4H), 1.70-1.56 (m, 2H), 1.11 (t, J=7.1 Hz, 4H).

LCMS, m/z 451[M+H]+

<Example 64> Preparation of N-(1-ethylpiperidine-4-yl)-6-methoxy-2-(pyrrolidine-1-yl)-7-(4-(pyrrolidine-1-yl)-1-butyne-1-yl)quinazoline-4-amine Step 1. Preparation of N-(1-ethylpiperidine-4-yl)-7-iodo-6-methoxy-2-(pyrrolidine-1-yl)quinazoline-4-amine

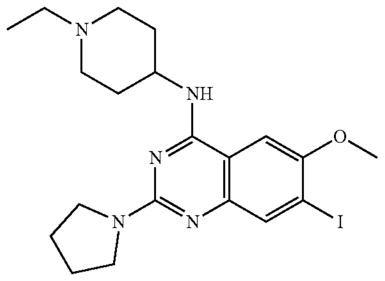 [SMILES: CCN1CCC(Nc2nc(N3CCCC3)nc3cc(I)c(OC)cc23)CC1]

2-Chloro-N-(1-ethylpiperidine-4-yl)-7-iodo-6-methoxy-quinazoline-4-amine was prepared in the same manner as described in step 1 of Example 50, and a target compound was obtained (82 mg, yield: 92%) as a yellow solid in the same manner as described in step 2 of Example 1 using pyrrolidine as a starting material in step 2 of Example 1.

LCMS, m/z 482[M+H]+

Step 2. Preparation of N-(1-ethylpiperidine-4-yl)-6-methoxy-2-(pyrrolidine-1-yl)-7-(4-(pyrrolidine-1-yl)-1-butyne-1-yl)quinazoline-4-amine

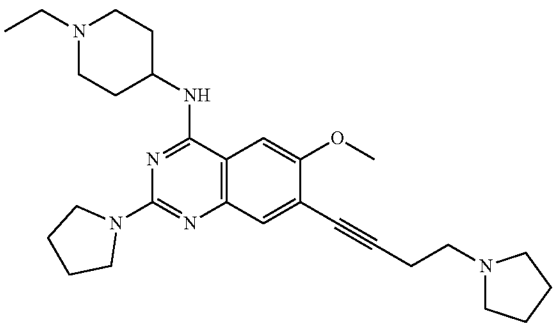 [SMILES: CCN1CCC(Nc2nc(N3CCCC3)nc3cc(C#CCCN4CCCC4)c(OC)cc23)CC1]

A target compound N-(1-ethylpiperidine-4-yl)-6-methoxy-2-(pyrrolidine-1-yl)-7-(4-(pyrrolidine-1-yl)-1-butyne-1-yl)quinazoline-4-amine(N-(1-ethylpiperidine-4-yl)-6-methoxy-2-(pyrrolidine-1-yl)-7-(4-(pyrrolidine-1-yl)but-1-yn-1-yl)quinazolin-4-amine) was obtained (27.1 mg, yield: 32.9%) as a yellow solid in the same manner as described in step 3 of Example 1 that N-(1-ethylpiperidine-4-yl)-7-iodo-6-methoxy-2-(pyrrolidine-1-yl)quinazoline-4-amine and 1-(3-butyne-1-yl)pyrrolidine were used as starting materials in step 3 of Example 1.

$^1$H NMR (400 MHz, $CDCl_3$) δ7.58 (s, 1H), 6.67 (s, 1H), 5.16-4.99 (m, 1H), 4.24-4.11 (m, 1H), 3.92 (s, 3H), 3.70-3.53 (m, 4H), 3.04-2.88 (m, 2H), 2.84-2.67 (m, 4H), 2.64-2.56 (m, 4H), 2.46 (q, J=7.2 Hz, 2H), 2.27-2.07 (m, 4H), 2.00-1.91 (m, 4H), 1.84-1.79 (m, 4H), 1.69-1.56 (m, 2H), 1.12 (t, J=7.2 Hz, 3H).

LCMS, m/z 477[M+H]+

<Example 65> Preparation of N-(1-ethylpiperidine-4-yl)-6-methoxy-2-(4-methyl-1,4-diazepane-1-yl)-7-(4-(pyrrolidine-1-yl)-1-butyne-1-yl) quinazoline-4-amine 의

Step 1. Preparation of N-(1-ethylpiperidine-4-yl)-7-iodo-6-methoxy-2-(4-methyl-1,4-diazepane-1-yl) quinazoline-4-amine

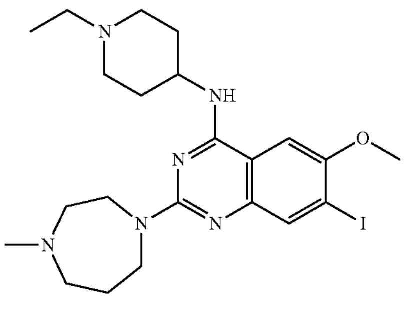

2-Chloro-N-(1-ethylpiperidine-4-yl)-7-iodo-6-methoxy-quinazoline-4-amine was prepared in the same manner as described in step 1 of Example 50, and a target compound was obtained (79 mg, yield: 75%) as a yellow solid in the same manner as described in step 2 of Example 1 using 1-methylhomopiperazine as a starting material in step 2 of Example 1.

LCMS, m/z 525[M+H]+

Step 2. Preparation of N-(1-ethylpiperidine-4-yl)-6-methoxy-2-(4-methyl-1,4-diazepane-1-yl)-7-(4-(pyrrolidine-1-yl)-1-butyne-1-yl)quinazoline-4-amine

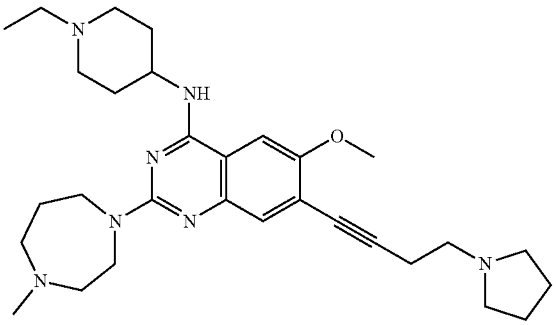 [SMILES: CCN1CCC(Nc2nc(N3CCCN(C)CC3)nc3cc(C#CCCN4CCCC4)c(OC)cc23)CC1]

A target compound N-(1-ethylpiperidine-4-yl)-6-methoxy-2-(4-methyl-1,4-diazepane-1-yl)-7-(4-(pyrrolidine-1-yl)-1-butyne-1-yl)quinazoline-4-amine(N-(1-ethylpiperidine-4-yl)-6-methoxy-2-(4-methyl-1,4-diazepane-1-yl)-7-(4-(pyrrolidine-1-yl)but-1-yn-1-yl)quinazolin-4-amine) was obtained (49.5 mg, yield: 62.9%) as a yellow solid in the same manner as described in step 3 of Example 1 that N-(1-ethylpiperidine-4-yl)-7-iodo-6-methoxy-2-(4-methyl-1,4-diazepane-1-yl)quinazoline-4-amine and 1-(3-butyne-1-yl)pyrrolidine were used as starting materials in step 3 of Example 1.

$^1$H NMR (400 MHz, $CDCl_3$) δ7.54 (s, 1H), 6.66 (s, 1H), 5.07 (d, J=7.0 Hz, 1H), 4.17-4.02 (m, 1H), 3.99-3.94 (m, 2H), 3.92 (s, 3H), 3.86 (t, J=6.4 Hz, 2H), 3.05-2.88 (m, 2H), 2.83-2.76 (m, 2H), 2.74-2.64 (m, 4H), 2.63-2.53 (m, 6H), 2.49-2.41 (m, 2H), 2.36 (s, 3H), 2.22-2.08 (m, 4H), 2.05-1.94 (m, 2H), 1.80-1.76 (m, 4H), 1.70-1.56 (m, 2H), 1.12 (t, J=7.2 Hz, 3H).

LCMS, m/z 520[M+H]+

<Example 66> Preparation of (E)-N-(1-isopropylpiperidine-4-yl)-6-methoxy-2-(piperidine-1-yl)-7-(4-(piperidine-1-yl)-1-butene-1-yl)quinazoline-4-amine

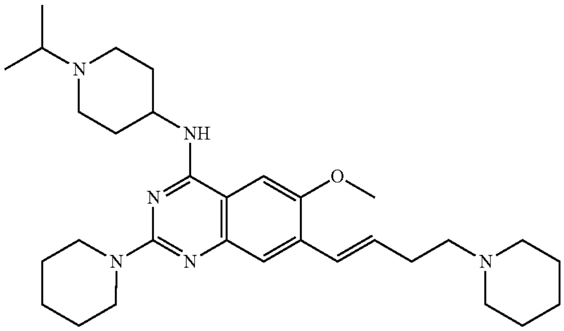 [SMILES: COc1cc2c(NC3CCN(C(C)C)CC3)nc(N3CCCCC3)nc2cc1/C=C/CCN1CCCCC1]

After dissolving 7-iodo-N-(1-isopropylpiperidine-4-yl)-6-methoxy-2-(piperidine-1-yl)quinazoline-4-amine (13.6 mg, 0.027 mmol), 1-(3-butene-1-yl)piperidine (7.43 mg, 0.053 mmol), $PdOAc_2$ (0.6 mg, 2.67 μmol), and tri-o-tolylphosphine (1.6 mg, 5.34 μmol) in TEA (1 mL), the mixture was stirred at 95° C. for 12 hours. Upon completion of the reaction, the solvent was concentrated under reduced pressure, and the obtained residue was purified by prep-HPLC to give a target compound (E)-N-(1-isopropylpiperidine-4-yl)-6-methoxy-2-(piperidine-1-yl)-7-(4-(piperidine-1-yl)-1-butene-1-yl)quinazoline-4-amine((E)-N-(1-isopropylpiperidine-4-yl)-6-methoxy-2-(piperidine-1-yl)-7-(4-(piperidine-1-yl)but-1-en-1-yl)quinazolin-4-amine) (2.8 mg, yield: 19.7%).

$^1H$ NMR (400 MHz, MeOD) δ7.74 (d, J=12.0 Hz, 2H), 6.99 (d, J=16.1 Hz, 1H), 6.52-6.42 (m, 1H), 4.66-4.52 (m, 1H), 4.04-3.95 (m, 3H), 3.95-3.88 (m, 4H), 3.68-3.55 (m, 6H), 3.30-3.25 (m, 2H), 3.06-2.96 (m, 2H), 2.82-2.71 (m, 2H), 2.51-2.40 (m, 2H), 2.16-1.95 (m, 6H), 1.93-1.71 (m, 10H), 1.43 (d, J=6.6 Hz, 6H).

LCMS, m/z 521 [M+H]+

<Example 67> Preparation of 6-methoxy-2-(piperidine-1-yl)-N-(1-propylpiperidine-4-yl)-7-(4-(pyrrolidine-1-yl)-1-butyne-1-yl)quinazoline-4-amine Step 1. Preparation of 2-chloro-7-iodo-6-methoxy-N-(1-propylpiperidine-4-yl)quinazoline-4-amine

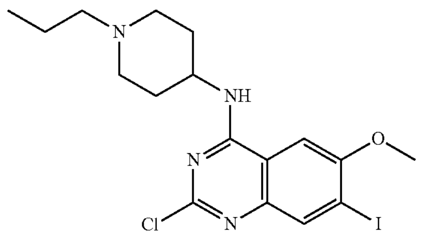 [SMILES: CCCN1CCC(Nc2nc(Cl)nc3cc(I)c(OC)cc23)CC1]

A target compound was obtained (250 mg, yield: 77%) as a yellow solid by performing the procedure of step 1 of Example 1, except that 1-propylpiperidine-4-amine dihydrochloride was used instead of 1-isopropylpiperidine-4-amine in step 1 of Example 1.

LCMS, m/z 461[M+H]+

Step 2. Preparation of 7-iodo-6-methoxy-2-(piperidine-1-yl)-N-(1-propylpiperidine-4-yl)quinazoline-4-amine

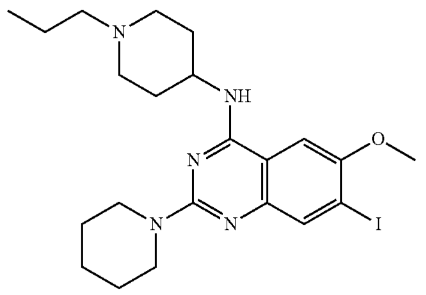 [SMILES: CCCN1CCC(Nc2nc(N3CCCCC3)nc3cc(I)c(OC)cc23)CC1]

A target compound was obtained (45 mg, yield: 40.7%) as a yellow solid in the same manner as described in step 2 of Example 1 that 2-chloro-7-iodo-6-methoxy-N-(1-propylpiperidine-4-yl)quinazoline-4-amine and piperidine were used as starting materials in step 2 of Example 1.

LCMS, m/z 510[M+H]+

Step 3. Preparation of 6-methoxy-2-(piperidine-1-yl)-N-(1-propylpiperidine-4-yl)-7-(4-(pyrrolidine-1-yl)-1-butyne-1-yl)quinazoline-4-amine

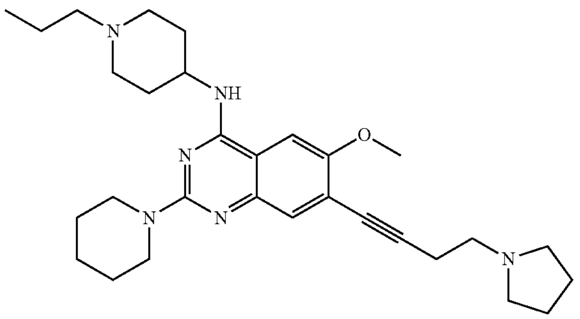 [SMILES: CCCN1CCC(Nc2nc(N3CCCCC3)nc3cc(C#CCCN4CCCC4)c(OC)cc23)CC1]

A target compound 6-methoxy-2-(piperidine-1-yl)-N-(1-propylpiperidine-4-yl)-7-(4-(pyrrolidine-1-yl)-1-butyne-1-yl)quinazoline-4-amine(6-methoxy-2-(piperidine-1-yl)-N-(1-propylpiperidine-4-yl)-7-(4-(pyrrolidine-1-yl)but-1-yn-1-yl)quinazolin-4-amine) was obtained (14 mg, yield: 46.6%) as a yellow solid in the same manner as described in step 3 of Example 1 that 7-iodo-6-methoxy-2-(piperidine-1-yl)-N-(1-propylpiperidine-4-yl)quinazoline-4-amine and 1-(3-butyne-1-yl)pyrrolidine were used as starting materials in step 3 of Example 1.

$^1H$ NMR (400 MHz, $CDCl_3$) δ 7.53 (s, 1H), 6.67 (s, 1H), 5.08 (d, J=7.0 Hz, 1H), 4.18-4.07 (m, 1H), 3.91 (s, 3H), 3.84-3.76 (m, 4H), 2.98-2.90 (m, 2H), 2.82-2.75 (m, 2H), 2.74-2.67 (m, 2H), 2.64-2.56 (m, 4H), 2.37-2.30 (m, 2H), 2.21-2.12 (m, 4H), 1.84-1.76 (m, 4H), 1.69-1.48 (m, 10H), 0.92 (t, J=7.4 Hz, 3H).

LCMS, m/z 505[M+H]+

<Example 68> Preparation of 6-methoxy-N-(1-propylpiperidine-4-yl)-2-(pyrrolidine-1-yl)-7-(4-(pyrrolidine-1-yl)-1-butyne-1-yl)quinazoline-4-amine Step 1. Preparation of 7-iodo-6-methoxy-N-(1-propylpiperidine-4-yl)-2-(pyrrolidine-1-yl)quinazoline-4-amine

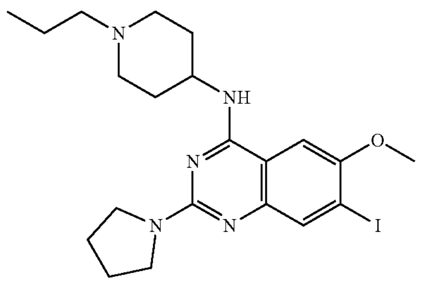 [SMILES: CCCN1CCC(Nc2nc(N3CCCC3)nc3cc(I)c(OC)cc23)CC1]

2-Chloro-7-iodo-6-methoxy-N-(1-propylpiperidine-4-yl) quinazoline-4-amine was prepared in the same manner as described in step 1 of Example 67, and a target compound was obtained (47 mg, yield: 43.7%) as a yellow solid in the same manner as described in step 2 of Example 1 using pyrrolidine as a starting material in step 2 of Example 1.

LCMS, m/z 496[M+H]+

Step 2. Preparation of 6-methoxy-N-(1-propylpiperidine-4-yl)-2-(pyrrolidine-1-yl)-7-(4-(pyrrolidine-1-yl)-1-butyne-1-yl)quinazoline-4-amine

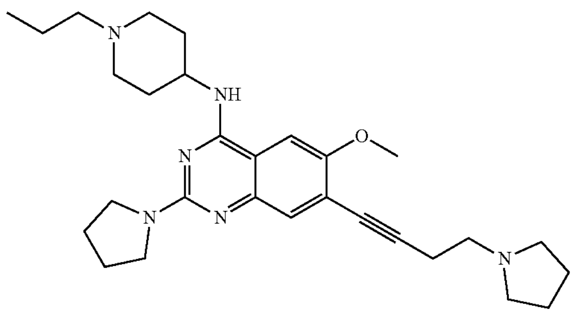 [SMILES: CCCN1CCC(Nc2nc(N3CCCC3)nc3cc(C#CCCN4CCCC4)c(OC)cc23)CC1]

A target compound 6-methoxy-N-(1-propylpiperidine-4-yl)-2-(pyrrolidine-1-yl)-7-(4-(pyrrolidine-1-yl)-1-butyne-1-yl)quinazoline-4-amine(6-methoxy-N-(1-propylpiperidine-4-yl)-2-(pyrrolidine-1-yl)-7-(4-(pyrrolidine-1-yl)but-1-yn-1-yl)quinazolin-4-amine) was obtained (16 mg, yield: 40%) in the same manner as described in step 3 of Example 1 that 7-iodo-6-methoxy-N-(1-propylpiperidine-4-yl)-2-(pyrrolidine-1-yl)quinazoline-4-amine and 1-(3-butyne-1-yl)pyrrolidine were used as starting materials in step 3 of Example 1.

$^1$H NMR (400 MHz, $CDCl_3$) δ7.58 (s, 1H), 6.73 (s, 1H), 5.21 (s, 1H), 4.23-4.08 (m, 1H), 3.90 (s, 3H), 3.67-3.55 (m, 4H), 2.94 (d, J=11.8 Hz, 2H), 2.82-2.74 (m, 2H), 2.74-2.66 (m, 2H), 2.64-2.56 (m, 4H), 2.39-2.28 (m, 2H), 2.24-2.12 (m, 4H), 2.01-1.89 (m, 4H), 1.84-1.75 (m, 4H), 1.69-1.58 (m, 2H), 1.57-1.44 (m, 2H), 0.91 (t, J=7.4 Hz, 3H).

LCMS, m/z 491[M+H]+

<Example 69> Preparation of 2-(4-((6-methoxy-2-(piperidine-1-yl)-7-(4-(pyrrolidine-1-yl)-1-butyne-1-yl)quinazoline-4-yl)amino)piperidine-1-yl)ethanol Step 1. Preparation of 2-(4-((2-chloro-7-iodo-6-methoxyquinazoline-4-yl)amino)piperidine-1-yl) ethanol

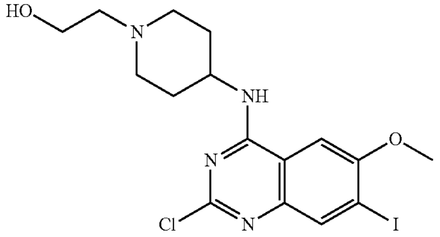 [SMILES: COc1cc2c(NC3CCN(CCO)CC3)nc(Cl)nc2cc1I]

A target compound was obtained (60 mg, yield: 23%) as a yellow solid by performing the procedure of step 1 of Example 1, except that 2-(4-aminopiperidine-1-yl)ethan-1-ol dihydrochloride was used instead of 1-isopropylpiperidine-4-amine in step 1 of Example 1.

LCMS, m/z 463[M+H]+

Step 2. Preparation of 2-(4-((7-iodo-6-methoxy-2-(piperidine-1-yl)quinazoline-4-yl)amino)piperidine-1-yl) ethanol

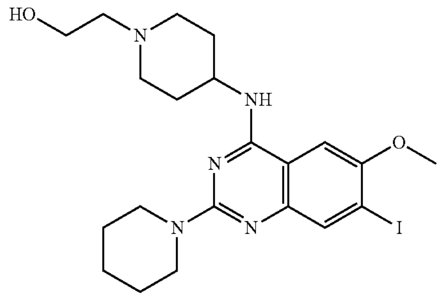 [SMILES: COc1cc2c(NC3CCN(CCO)CC3)nc(N3CCCCC3)nc2cc1I]

A target compound was obtained (38 mg, yield: 57.3%) as a yellow solid in the same manner as described in step 2 of Example 1 that 2-(4-((2-chloro-7-iodo-6-methoxyquinazoline-4-yl)amino)piperidine-1-yl)ethanol was used as a starting material in step 2 of Example 1.

LCMS, m/z 512[M+H]+

Step 3. Preparation of 2-(4-((6-methoxy-2-(piperidine-1-yl)-7-(4-(pyrrolidine-1-yl)-1-butyne-1-yl) quinazoline-4-yl)amino)piperidine-1-yl)ethanol

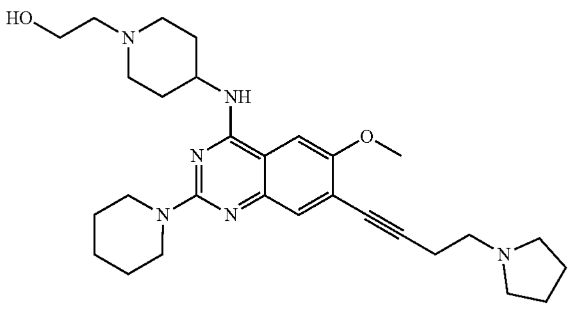 [SMILES: COc1cc2c(NC3CCN(CCO)CC3)nc(N3CCCCC3)nc2cc1C#CCCN1CCCC1]

A target compound 2-(4-((6-methoxy-2-(piperidine-1-yl)-7-(4-(pyrrolidine-1-yl)-1-butyne-1-yl)quinazoline-4-yl) amino)piperidine-1-yl)ethanol(2-(4-((6-methoxy-2-(piperidine-1-yl)-7-(4-(pyrrolidine-1-yl)but-1-yn-1-yl)quinazolin-4-yl)amino)piperidine-1-yl)ethanol) was obtained (7.6 mg, yield: 21.5%) as a yellow solid in the same manner as described in step 3 of Example 1 that 2-(4-((7-iodo-6-methoxy-2-(piperidine-1-yl)quinazoline-4-yl)amino)piperidine-1-yl)ethanol and 1-(3-butyne-1-yl)pyrrolidine were used as starting materials in step 3 of Example 1.

$^1$H NMR (400 MHz, $CDCl_3$) δ7.54 (s, 1H), 6.68 (s, 1H), 5.09 (d, J=6.5 Hz, 1H), 4.21-4.09 (m, 1H), 3.91 (s, 3H), 3.84-3.76 (m, 4H), 3.63 (t, J=5.4 Hz, 2H), 3.01-2.91 (m, 2H), 2.83-2.76 (m, 2H), 2.73-2.67 (m, 2H), 2.63-2.56 (m, 7H), 2.37-2.26 (m, 2H), 2.22-2.15 (m, 2H), 1.85-1.75 (m, 4H), 1.70-1.53 (m, 8H).

LCMS, m/z 507[M+H]+

<Example 70> Preparation of 2-(4-((6-methoxy-2-(pyrrolidine-1-yl)-7-(4-(pyrrolidine-1-yl)-1-butyne-1-yl)quinazoline-4-yl)amino)piperidine-1-yl)ethanol Step 1. Preparation of 2-(4-((7-iodo-6-methoxy-2-(pyrrolidine-1-yl)quinazoline-4-yl)amino)piperidine-1-yl) ethan-1-ol

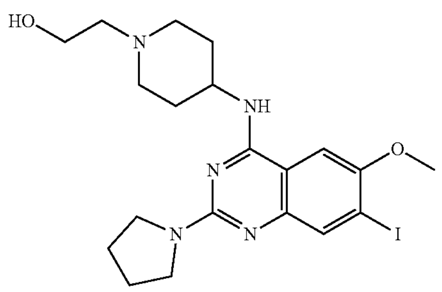 [SMILES: COc1cc2c(NC3CCN(CCO)CC3)nc(N3CCCC3)nc2cc1I]

2-(4-((2-Chloro-7-iodo-6-methoxyquinazoline-4-yl)amino)piperidine-1-yl)ethanol was prepared in the same manner as described in step 1 of Example 69, and a target compound was obtained (40 mg, yield: 62%) in the same manner as described in step 2 of Example 1 using pyrrolidine as a starting material.

LCMS, m/z 498[M+H]+

Step 2. Preparation of 2-(4-((6-methoxy-2-(pyrrolidine-1-yl)-7-(4-(pyrrolidine-1-yl)-1-butyne-1-yl)quinazoline-4-yl)amino)piperidine-1-yl)ethanol

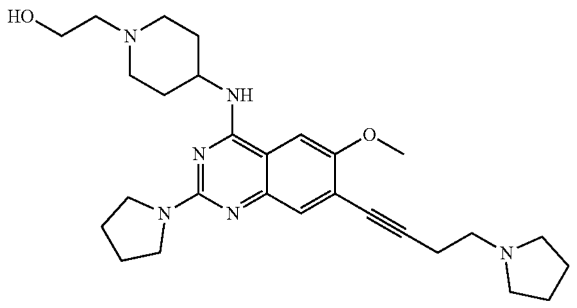 [SMILES: COc1cc2c(NC3CCN(CCO)CC3)nc(N3CCCC3)nc2cc1C#CCCN1CCCC1]

A target compound 2-(4-((6-methoxy-2-(pyrrolidine-1-yl)-7-(4-(pyrrolidine-1-yl)-1-butyne-1-yl)quinazoline-4-yl)amino)piperidine-1-yl)ethanol(2-(4-((6-methoxy-2-(pyrrolidine-1-yl)-7-(4-(pyrrolidine-1-yl)but-1-yn-1-yl)quinazolin-4-yl)amino)piperidine-1-yl)ethanol) was obtained (10.5 mg, yield: 33.6%) as a yellow solid in the same manner as described in step 3 of Example 1 that 2-(4-((7-iodo-6-methoxy-2-(pyrrolidine-1-yl)quinazoline-4-yl)amino)piperidine-1-yl)ethan-1-ol) and 1-(3-butyne-1-yl)pyrrolidine were used as starting materials in step 3 of Example 1.

$^1$H NMR (400 MHz, $CDCl_3$) δ7.58 (s, 1H), 6.71 (s, 1H), 5.13 (d, J=6.2 Hz, 1H), 4.25-4.12 (m, 1H), 3.92 (d, J=9.6 Hz, 3H), 3.67-3.56 (m, 6H), 3.03-2.89 (m, 2H), 2.82-2.75 (m, 2H), 2.74-2.67 (m, 2H), 2.64-2.55 (m, 7H), 2.36-2.25 (m, 2H), 2.25-2.14 (m, 2H), 2.01-1.92 (m, 4H), 1.86-1.75 (m, 4H), 1.66-1.54 (m, 2H).

LCMS, m/z 493[M+H]+

<Example 71> Preparation of 6-methoxy-N-(pyridine-3-ylmethyl)-2-(pyrrolidine-1-yl)-7-(4-(pyrrolidine-1-yl)-1-butyne-1-yl)quinazoline-4-amine Step 1. Preparation of 7-iodo-6-methoxy-N-(pyridine-3-ylmethyl)-2-(pyrrolidine-1-yl)quinazoline-4-amine

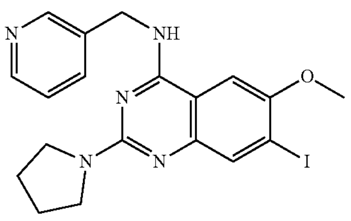 [SMILES: COc1cc2c(NCc3cccnc3)nc(N3CCCC3)nc2cc1I]

7-Iodo-6-methoxy-N-(pyridine-3-ylmethyl)-2-(pyrrolidine-1-yl)quinazoline-4-amine was prepared in the same manner as described in step 1 of Example 26, and a target compound was obtained (47 mg, yield: 79%) in the same manner as described in step 2 of Example 1 using pyrrolidine as a starting material in step 2 of Example 1.

LCMS, m/z 462 [M+H]+

Step 2. Preparation of 6-methoxy-N-(pyridine-3-ylmethyl)-2-(pyrrolidine-1-yl)-7-(4-(pyrrolidine-1-yl)-1-butyne-1-yl)quinazoline-4-amine

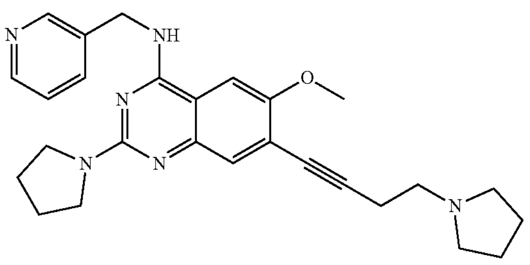 [SMILES: COc1cc2c(NCc3cccnc3)nc(N3CCCC3)nc2cc1C#CCCN1CCCC1]

A target compound 6-methoxy-N-(pyridine-3-ylmethyl)-2-(pyrrolidine-1-yl)-7-(4-(pyrrolidine-1-yl)-1-butyne-1-yl)quinazoline-4-amine(6-methoxy-N-(pyridin-3-ylmethyl)-2-(pyrrolidine-1-yl)-7-(4-(pyrrolidine-1-yl)but-1-yn-1-yl)quinazolin-4-amine) was obtained (18 mg, yield: 38.5%) as a yellow solid in the same manner as described in step 3 of Example 1 that 7-iodo-6-methoxy-N-(pyridine-3-ylmethyl)-2-(pyrrolidine-1-yl)quinazoline-4-amine and 1-(3-butyne-1-yl)pyrrolidine were used as starting materials in step 3 of Example 1.

$^1$H NMR (400 MHz, $CDCl_3$) δ 8.69 (s, 1H), 8.60-8.48 (m, 1H), 7.77 (d, J=7.8 Hz, 1H), 7.62 (s, 1H), 7.28-7.21 (m, 1H), 6.79 (s, 1H), 5.89 (s, 1H), 4.84 (d, J=5.1 Hz, 2H), 3.89 (s, 3H), 3.70-3.53 (m, 4H), 2.85-2.77 (m, 2H), 2.76-2.68 (m, 2H), 2.67-2.52 (m, 4H), 2.06-1.90 (m, 4H), 1.87-1.79 (m, 4H).

LCMS, m/z 457[M+H]+

<Example 72> Preparation of (S)—N-(1-ethylpiperidine-4-yl)-2-(3-fluoropyrrolidine-1-yl)-6-methoxy-7-(4-(pyrrolidine-1-yl)-1-butyne-1-yl)quinazoline-4-amine Step 1. Preparation of (S)—N-(1-ethylpiperidine-4-yl)-2-(3-fluoropyrrolidine-1-yl)-7-iodo-6-methoxyquinazoline-4-amine

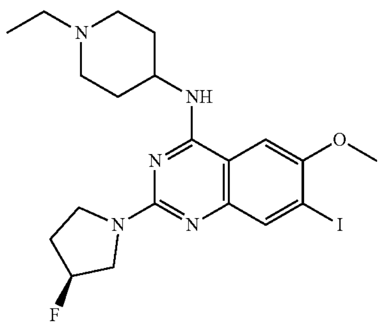 [SMILES: CCN1CCC(Nc2nc(N3CC[C@H](F)C3)nc3cc(I)c(OC)cc23)CC1]

2-Chloro-N-(1-ethylpiperidine-4-yl)-7-iodo-6-methoxyquinazoline-4-amine was prepared in the same manner as described in step 1 of Example 50, and a target compound was obtained (42 mg, yield: 85%) in the same manner as described in step 2 of Example 1 using (S)-3-fluoropyrrolidine hydrochloride as a starting material in step 2 of Example 1.

LCMS, m/z 500[M+H]+

Step 2. Preparation of (S)—N-(1-ethylpiperidine-4-yl)-2-(3-fluoropyrrolidine-1-yl)-6-methoxy-7-(4-(pyrrolidine-1-yl)-1-butyne-1-yl)quinazoline-4-amine

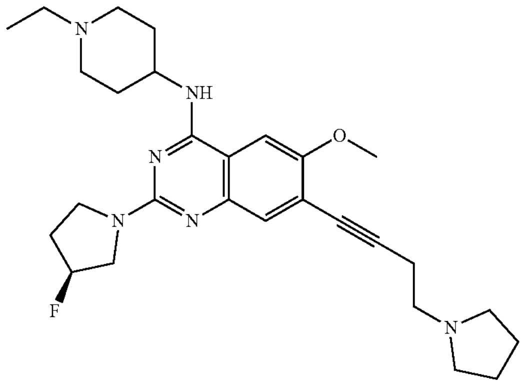 [SMILES: CCN1CCC(Nc2nc(N3CC[C@H](F)C3)nc3cc(C#CCCN4CCCC4)c(OC)cc23)CC1]

A target compound (S)—N-(1-ethylpiperidine-4-yl)-2-(3-fluoropyrrolidine-1-yl)-6-methoxy-7-(4-(pyrrolidine-1-yl)-1-butyne-1-yl)quinazoline-4-amine ((S)—N-(1-ethylpiperidine-4-yl)-2-(3-fluoropyrrolidine-1-yl)-6-methoxy-7-(4-(pyrrolidine-1-yl)but-1-yn-1-yl)quinazolin-4-amine) was obtained (16 mg, yield: 38.1%) as a yellow solid in the same manner as described in step 3 of Example 1 that (S)—N-(1-ethylpiperidine-4-yl)-2-(3-fluoropyrrolidine-1-yl)-7-iodo-6-methoxyquinazoline-4-amine and 1-(3-butyne-1-yl) pyrrolidine were used as starting materials in step 3 of Example 1.

$^1$H NMR (400 MHz, $CDCl_3$) δ 7.58 (s, 1H), 6.70 (s, 1H), 5.44-5.22 (m, 1H), 5.18 (d, J=7.1 Hz, 1H), 4.22-4.10 (m, 1H), 4.08-3.98 (m, 1H), 3.97-3.89 (m, 1H), 3.91 (s, 3H), 3.83-3.62 (m, 2H), 3.03-2.90 (m, 2H), 2.82-2.65 (m, 4H), 2.64-2.53 (m, 4H), 2.46 (q, J=7.2 Hz, 2H), 2.39-2.26 (m, 1H), 2.18 (m, 4H), 2.07-1.95 (m, 1H), 1.85-1.73 (m, 4H), 1.70-1.55 (m, 2H), 1.11 (t, J=7.2 Hz, 3H).

LCMS, m/z 495[M+H]+

<Example 73> Preparation of 6-methoxy-2-(pyrrolidine-1-yl)-7-(4-(pyrrolidine-1-yl)-1-butyne-1-yl)-N-(2,2,6,6-tetramethylpiperidine-4-yl)quinazoline-4-amine Step 1. Preparation of 7-iodo-6-methoxy-2-(pyrrolidine-1-yl)-N-(2,2,6,6-tetramethylpiperidine-4-yl) quinazoline-4-amine

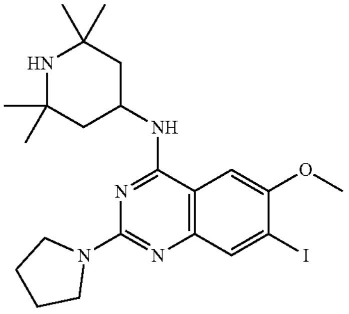

2-Chloro-7-iodo-6-methoxy-N-(2,2,6,6-tetramethylpiperidine-4-yl)quinazoline-4-amine was prepared in the same manner as described in step 1 of Example 27, and a target compound was obtained (44 mg, yield: 79%) as a yellow solid in the same manner as described in step 2 of Example 1 using pyrrolidine as a starting material.

LCMS, m/z 510[M+H]+

Step 2. Preparation of 6-methoxy-2-(pyrrolidine-1-yl)-7-(4-(pyrrolidine-1-yl)-1-butyne-1-yl)-N-(2,2,6,6-tetramethylpiperidine-4-yl)quinazoline-4-amine

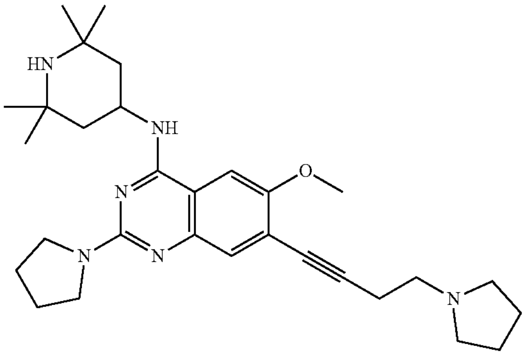 [SMILES: COc1cc2c(NC3CC(C)(C)NC(C)(C)C3)nc(N3CCCC3)nc2cc1C#CCCN1CCCC1]

A target compound 6-methoxy-2-(pyrrolidine-1-yl)-7-(4-(pyrrolidine-1-yl)-1-butyne-1-yl)-N-(2,2,6,6-tetramethylpiperidine-4-yl)quinazoline-4-amine (6-methoxy-2-(pyrrolidine-1-yl)-7-(4-(pyrrolidine-1-yl)but-1-yn-1-yl)-N-(2,2,6,6-tetramethylpiperidine-4-yl)quinazolin-4-amine) was obtained (19 mg, yield: 43.1%) in the same manner as described in step 3 of Example 1 that 7-iodo-6-methoxy-2-(pyrrolidine-1-yl)-N-(2,2,6,6-tetramethylpiperidine-4-yl) quinazoline-4-amine and 1-(3-butyne-1-yl)pyrrolidine were used as starting materials in step 3 of Example 1.

$^1$H NMR (400 MHz, $CDCl_3$) δ7.58 (s, 1H), 6.68 (s, 1H), 5.10-4.95 (m, 1H), 4.78-4.65 (m, 1H), 3.90 (s, 3H), 3.68-3.56 (m, 4H), 2.82-2.65 (m, 4H), 2.65-2.54 (m, 4H), 2.15 (dd, J=12.2, 3.4 Hz, 2H), 2.00-1.90 (m, 4H), 1.82-1.76 (m, 5H), 1.33 (s, 6H), 1.17 (s, 6H), 1.08 (t, J=12.1 Hz, 2H).

LCMS, m/z 505[M+H]+

<Example 74> Preparation of (R)—N-(1-cyclopropylpiperidine-4-yl)-2-(3-fluoropyrrolidine-1-yl)-6-methoxy-7-(4-(pyrrolidine-1-yl)-1-butyne-1-yl)quinazoline-4-amine Step 1. Preparation of (R)—N-(1-cyclopropylpiperidine-4-yl)-2-(3-fluoropyrrolidine-1-yl)-7-iodo-6-methoxyquinazoline-4-amine

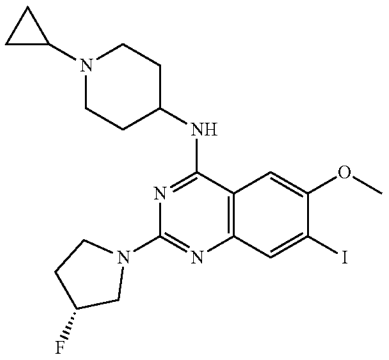 [SMILES: COc1cc2c(NC3CCN(C4CC4)CC3)nc(N3CC[C@@H](F)C3)nc2cc1I]

2-Chloro-N-(1-cyclopropylpiperidine-4-yl)-7-iodo-6-methoxyquinazoline-4-amine was prepared in the same manner as described in step 2 of Example 1, and a target compound was obtained (65 mg, yield: 83%) as a yellow solid in the same manner as described in step 2 of Example 1 using (R)-3-fluoropyrrolidine hydrochloride as a starting material.

LCMS, m/z 512[M+H]+

Step 2. Preparation of (R)—N-(1-cyclopropylpiperidine-4-yl)-2-(3-fluoropyrrolidine-1-yl)-6-methoxy-7-(4-(pyrrolidine-1-yl)-1-butyne-1-yl)quinazoline-4-amine

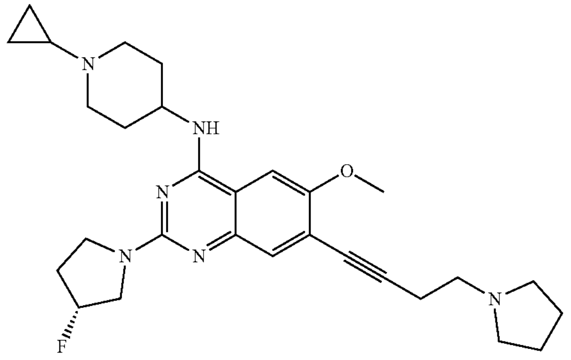 [SMILES: COc1cc2c(NC3CCN(C4CC4)CC3)nc(N3CC[C@@H](F)C3)nc2cc1C#CCCN1CCCC1]

A target compound (R)—N-(1-cyclopropylpiperidine-4-yl)-2-(3-fluoropyrrolidine-1-yl)-6-methoxy-7-(4-(pyrrolidine-1-yl)-1-butyne-1-yl)quinazoline-4-amine((R)—N-(1-cyclopropylpiperidine-4-yl)-2-(3-fluoropyrrolidine-1-yl)-6-methoxy-7-(4-(pyrrolidine-1-yl)but-1-yn-1-yl)quinazolin-4-amine) was obtained (7 mg, yield: 27.7%) in the same manner as described in step 3 of Example 1 that (R)—N-(1-cyclopropylpiperidine-4-yl)-2-(3-fluoropyrrolidine-1-yl)-7-iodo-6-methoxyquinazoline-4-amine and 1-(3-butyne-1-yl)pyrrolidine were used as starting materials in step 3 of Example 1.

$^1$H NMR (400 MHz, $CDCl_3$) δ 7.58 (s, 1H), 6.68 (s, 1H), 5.43-5.25 (m, 1H), 5.13 (s, 1H), 4.23-4.13 (m, 1H), 4.09-3.93 (m, 2H), 3.91 (s, 3H), 3.85-3.64 (m, 2H), 3.11-3.01 (m, 2H), 2.86-2.69 (m, 4H), 2.66-2.58 (m, 4H), 2.45-2.35 (m, 2H), 2.35-2.26 (m, 1H), 2.21-2.11 (m, 2H), 2.06-1.97 (m, 1H), 1.87-1.77 (m, 4H), 1.67-1.61 (m, 1H), 1.61-1.49 (m, 2H), 0.53-0.45 (m, 2H), 0.45-0.37 (m, 2H).

LCMS, m/z 507[M+H]+

<Example 75> Preparation of (S)—N-(1-cyclopropylpiperidine-4-yl)-2-(3-fluoropyrrolidine-1-yl)-6-methoxy-7-(4-(pyrrolidine-1-yl)-1-butyne-1-yl)quinazoline-4-amine Step 1. Preparation of (S)—N-(1-cyclopropylpiperidine-4-yl)-2-(3-fluoropyrrolidine-1-yl)-7-iodo-6-methoxyquinazoline-4-amine

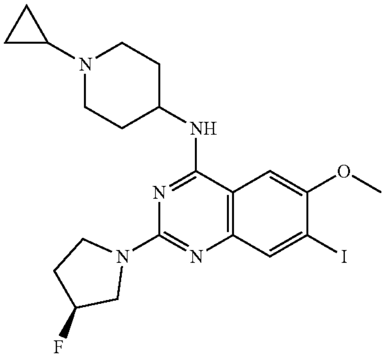 [SMILES: COc1cc2c(NC3CCN(C4CC4)CC3)nc(N3CC[C@H](F)C3)nc2cc1I]

2-Chloro-N-(1-cyclopropylpiperidine-4-yl)-7-iodo-6-methoxyquinazoline-4-amine was prepared in the same manner as described in step 1 of Example 24, and a target compound was obtained (55 mg, yield: 82%) in the same manner as described in step 2 of Example 1 using (S)-3-fluoropyrrolidine hydrochloride as a starting material.

LCMS, m/z 512[M+H]+

Step 2. Preparation of (S)—N-(1-cyclopropylpiperidine-4-yl)-2-(3-fluoropyrrolidine-1-yl)-6-methoxy-7-(4-pyrrolidine-1-yl)-1-butyne-1-yl)quinazoline-4-amine

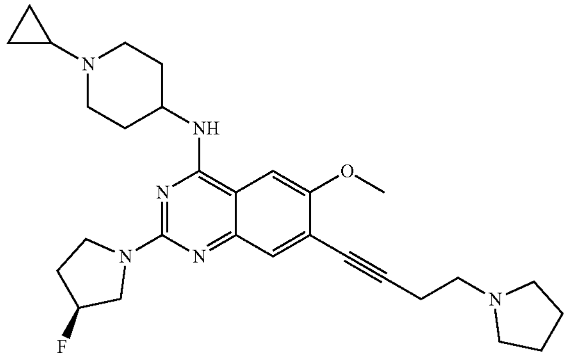 [SMILES: COc1cc2c(NC3CCN(C4CC4)CC3)nc(N3CC[C@H](F)C3)nc2cc1C#CCCN1CCCC1]

A target compound (S)—N-(1-cyclopropylpiperidine-4-yl)-2-(3-fluoropyrrolidine-1-yl)-6-methoxy-7-(4-(pyrrolidine-1-yl)-1-butyne-1-yl)quinazoline-4-amine ((S)—N-(1-cyclopropylpiperidine-4-yl)-2-(3-fluoropyrrolidine-1-yl)-6-methoxy-7-(4-(pyrrolidine-1-yl)but-1-yn-1-yl)quinazolin-4-amine) was obtained (13.7 mg, yield: 46.1%) in the same manner as described in step 3 of Example 1 that (S)—N-(1-cyclopropylpiperidine-4-yl)-2-(3-fluoropyrrolidine-1-yl)-7-iodo-6-methoxyquinazoline-4-amine and 1-(3-butyne-1-yl)pyrrolidine were used as starting materials in step 3 of Example 1.

$^1$H NMR (400 MHz, $CDCl_3$) δ 7.58 (s, 1H), 6.68 (s, 1H), 5.44-5.25 (m, 1H), 5.16-5.09 (m, 1H), 4.24-4.13 (m, 1H), 4.13-3.92 (m, 2H), 3.91 (s, 3H), 3.85-3.65 (m, 2H), 3.11-3.01 (m, 2H), 2.83-2.76 (m, 2H), 2.74-2.67 (m, 2H), 2.64-2.56 (m, 4H), 2.45-2.35 (m, 2H), 2.35-2.27 (m, 1H), 2.21-2.12 (m, 2H), 2.10-1.99 (m, 1H), 1.84-1.76 (m, 4H), 1.68-1.60 (m, 1H), 1.60-1.48 (m, 2H), 0.53-0.45 (m, 2H), 0.44-0.35 (m, 2H).

LCMS, m/z 507[M+H]+

<Example 76> Preparation of (R)—N-(1-cyclopropylpiperidine-4-yl)-7-(4-(dimethylamino)-1-butyne-1-yl)-2-(3-fluoropyrrolidine-1-yl)-6-methoxyquinazoline-4-amine

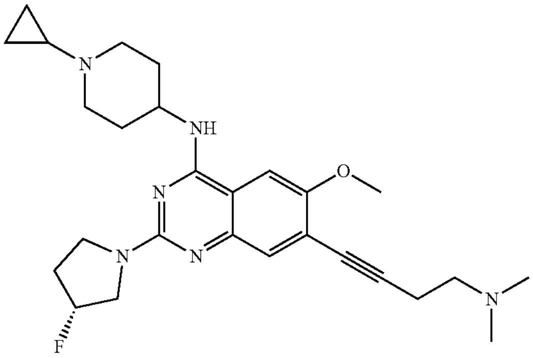 [SMILES: COc1cc2c(NC3CCN(C4CC4)CC3)nc(N3CC[C@@H](F)C3)nc2cc1C#CCCN(C)C]

(R)—N-(1-cyclopropylpiperidine-4-yl)-2-(3-fluoropyrrolidine-1-yl)-7-iodo-6-methoxyquinazoline-4-amine was prepared in the same manner as described in step 1 of Example 74, and a target compound (R)—N-(1-cyclopropylpiperidine-4-yl)-7-(4-(dimethylamino)-1-butyne-1-yl)-2-(3-fluoropyrrolidine-1-yl)-6-methoxyquinazoline-4-amine ((R)—N-(1-cyclopropylpiperidine-4-yl)-7-(4-(dimethylamino)but-1-yn-1-yl)-2-(3-fluoropyrrolidine-1-yl)-6-methoxyquinazolin-4-amine) was obtained (12.6 mg, yield: 52.6%) as a yellow solid in the same manner as described in step 3 of Example 1 using N,N-dimethyl-3-butyne-1-amine as a starting material in step 3 of Example 1.

$^1$H NMR (400 MHz, $CDCl_3$) δ 7.58 (s, 1H), 6.66 (s, 1H), 5.43-5.24 (m, 1H), 5.07 (d, J=6.5 Hz, 1H), 4.25-4.14 (m, 1H), 4.14-3.94 (m, 2H), 3.91 (s, 3H), 3.85-3.64 (m, 2H), 3.11-3.00 (m, 2H), 2.70-2.59 (m, 4H), 2.45-2.35 (m, 2H), 2.35-2.26 (m, 1H), 2.31 (s, 6H), 2.22-2.11 (m, 2H), 2.07-2.02 (m, 1H), 1.68-1.60 (m, 1H), 1.60-1.48 (m, 2H), 0.53-0.45 (m, 2H), 0.45-0.36 (m, 2H).

LCMS, m/z 481[M+H]+

<Example 77> Preparation of (R)—N-(1-ethylpiperidine-4-yl)-2-(3-fluoropyrrolidine-1-yl)-6-methoxy-7-(4-(pyrrolidine-1-yl)-1-butyne-1-yl)quinazoline-4-amine Step 1. Preparation of (R)—N-(1-ethylpiperidine-4-yl)-2-(3-fluoropyrrolidine-1-yl)-7-iodo-6-methoxyquinazoline-4-amine

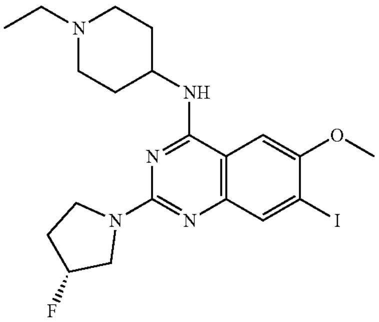 [SMILES: CCN1CCC(Nc2nc(N3CC[C@@H](F)C3)nc3cc(I)c(OC)cc23)CC1]

2-Chloro-N-(1-ethylpiperidine-4-yl)-7-iodo-6-methoxyquinazoline-4-amine was prepared in the same manner as described in step 1 of Example 50, and a target compound was obtained (45 mg, yield: 89%) as a yellow solid in the same manner as described in step 2 of Example 1 using (S)-3-fluoropyrrolidine hydrochloride as a starting material.

LCMS, m/z 500[M+H]+

Step 2. Preparation of (R)—N-(1-ethylpiperidine-4-yl)-2-(3-fluoropyrrolidine-1-yl)-6-methoxy-7-(4-(pyrrolidine-1-yl)-1-butyne-1-yl)quinazoline-4-amine

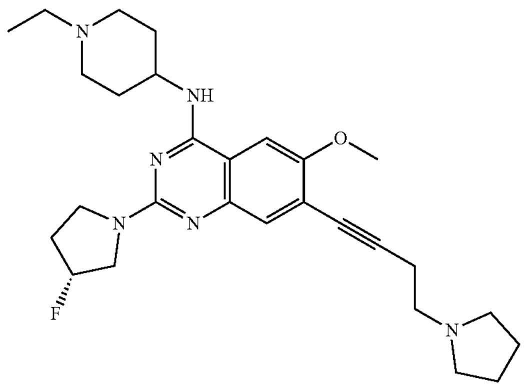 [SMILES: CCN1CCC(Nc2nc(N3CC[C@@H](F)C3)nc3cc(C#CCCN4CCCC4)c(OC)cc23)CC1]

A target compound (R)—N-(1-ethylpiperidine-4-yl)-2-(3-fluoropyrrolidine-1-yl)-6-methoxy-7-(4-(pyrrolidine-1-yl)-1-butyne-1-yl)quinazoline-4-amine ((R)—N-(1-ethylpiperidine-4-yl)-2-(3-fluoropyrrolidine-1-yl)-6-methoxy-7-(4-(pyrrolidine-1-yl)but-1-yn-1-yl)quinazolin-4-amine) was obtained (23.3 mg, yield: 52.8%) in the same manner as described in step 3 of Example 1 that (R)—N-(1-ethylpiperidine-4-yl)-2-(3-fluoropyrrolidine-1-yl)-7-iodo-6-methoxyquinazoline-4-amine and 1-(3-butyne-1-yl)pyrrolidine were used as starting materials in step 3 of Example 1.

$^1$H NMR (400 MHz, $CDCl_3$) δ 7.58 (s, 1H), 6.71 (s, 1H), 5.43-5.24 (m, J=53.2 Hz, 1H), 5.24-5.10 (m, 1H), 4.23-4.10 (m, 1H), 4.07-3.97 (m, 1H), 3.97-3.89 (m, 1H), 3.91 (s, 3H), 3.84-3.61 (m, 2H), 3.05-2.90 (m, 2H), 2.83-2.66 (m, 4H), 2.65-2.54 (m, 4H), 2.47 (q, J=7.2 Hz, 2H), 2.39-2.25 (m, 2H), 2.25-2.10 (m, 4H), 1.85-1.72 (m, 4H), 1.72-1.57 (m, 2H), 1.12 (t, J=7.2 Hz, 3H).

LCMS, m/z 495[M+H]+

<Example 78> Preparation of (S)—N-(1-ethylpiperidine-4-yl)-7-(4-(3-fluoropyrrolidine-1-yl)-1-butyne-1-yl)-6-methoxy-2-(pyrrolidine-1-yl)quinazoline-4-amine

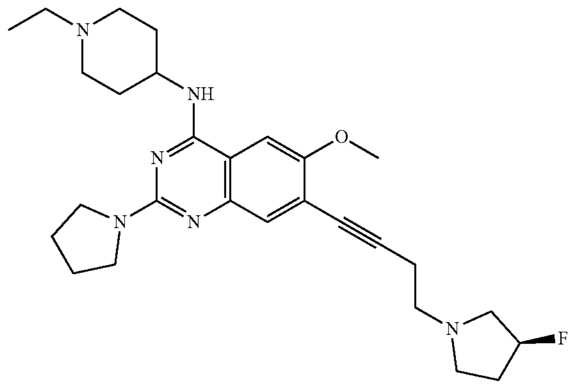 [SMILES: CCN1CCC(Nc2nc(N3CCCC3)nc3cc(C#CCCN4CC[C@H](F)C4)c(OC)cc23)CC1]

N-(1-ethylpiperidine-4-yl)-7-iodo-6-methoxy-2-(pyrrolidine-1-yl)quinazoline-4-amine was prepared in the same manner as described in step 1 of Example 64, and a target compound (S)—N-(1-ethylpiperidine-4-yl)-7-(4-(3-fluoropyrrolidine-1-yl)-1-butyne-1-yl)-6-methoxy-2-(pyrrolidine-1-yl)quinazoline-4-amine((S)—N-(1-ethylpiperidine-4-yl)-7-(4-(3-fluoropyrrolidine-1-yl)but-1-yn-1-yl)-6-methoxy-2-(pyrrolidine-1-yl)quinazolin-4-amine) was obtained (12.8 mg, yield: 30%) in the same manner as described in step 3 of Example 1 using (S)-1-(3-butyne-1-yl)-3-fluoropyrrolidine as a starting material in step 3 of Example 1.

$^1$H NMR (400 MHz, $CDCl_3$) δ7.58 (s, 1H), 6.69 (s, 1H), 5.30-5.04 (m, 2H), 4.24-4.09 (m, 1H), 3.92 (s, 3H), 3.68-3.52 (m, 4H), 3.06-2.89 (m, 4H), 2.90-2.74 (m, 3H), 2.74-2.64 (m, 2H), 2.59-2.50 (m, 1H), 2.46 (q, J=7.2 Hz, 2H), 2.25-2.14 (m, 4H), 2.14-1.99 (m, 2H), 1.99-1.92 (m, 4H), 1.71-1.56 (m, 2H), 1.12 (t, J=7.2 Hz, 3H).

LCMS, m/z 495[M+H]+

<Example 79> Preparation of (S)—N1-(2-(3-fluoropyrrolidine-1-yl)-6-methoxy-7-(4-(pyrrolidine-1-yl)-1-butyne-1-yl)quinazoline-4-yl)-N2,N2-dimethylethane-1,2-diamine Step 1. Preparation of (S)—N1-(2-(3-fluoropyrrolidine-1-yl)-7-iodo-6-methoxyquinazoline-4-yl)-N2,N2-dimethylethane-1,2-diamine

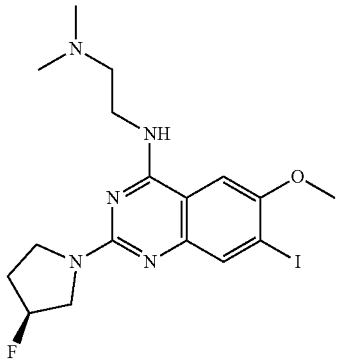 [SMILES: COc1cc2c(NCCN(C)C)nc(N3CC[C@H](F)C3)nc2cc1I]

N1-(2-chloro-7-iodo-6-methoxyquinazoline-4-yl)-N2,N2-dimethylethane-1,2-diamine was prepared in the same manner as described in step 1 of Example 28, and a target compound was obtained (58 mg, yield: 76%) in the same manner as described in step 2 of Example 1 using (S)-3-fluoropyrrolidine hydrochloride as a starting material.

LCMS, m/z 460[M+H]+

Step 2. Preparation of (S)—N1-(2-(3-fluoropyrrolidine-1-yl)-6-methoxy-7-(4-(pyrrolidine-1-yl)-1-butyne-1-yl)quinazoline-4-yl)-N2,N2-dimethylethane-1,2-diamine

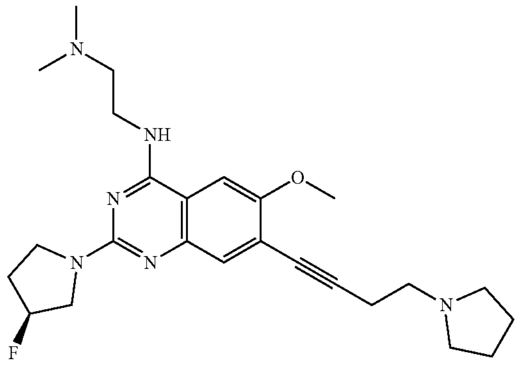 [SMILES: COc1cc2c(NCCN(C)C)nc(N3CC[C@H](F)C3)nc2cc1C#CCCN1CCCC1]

A target compound (S)—N1-(2-(3-fluoropyrrolidine-1-yl)-6-methoxy-7-(4-(pyrrolidine-1-yl)-1-butyne-1-yl)quinazoline-4-yl)-N2,N2-dimethylethane-1,2-diamine ((S)—N1-(2-(3-fluoropyrrolidine-1-yl)-6-methoxy-7-(4-(pyrrolidine-1-yl)but-1-yn-1-yl)quinazolin-4-yl)-N2,N2-dimethylethane-1,2-diamine) was obtained (17 mg, yield: 28.1%) in the same manner as described in step 3 of Example 1 that (S)—N1-(2-(3-fluoropyrrolidine-1-yl)-7-iodo-6-methoxyquinazoline-4-yl)-N2,N2-dimethylethane-1,2-diamine and 1-(3-butyne-1-yl)pyrrolidine were used as starting materials in step 3 of Example 1.

$^{1}$H NMR (400 MHz, $CDCl_3$) δ 7.58 (s, 1H), 6.86 (s, 1H), 6.22-6.05 (m, 1H), 5.44-5.22 (m, 1H), 4.14-3.94 (m, 2H), 3.92 (s, 3H), 3.85-3.70 (m, 2H), 3.69-3.62 (m, 2H), 2.84-2.75 (m, 2H), 2.74-2.68 (m, 2H), 2.66-2.54 (m, 6H), 2.32 (s, 6H), 2.20-2.08 (m, 1H), 2.07-1.98 (m, 1H), 1.85-1.73 (m, 4H).

LCMS, m/z 455[M+H]+

<Example 80> Preparation of (R)—N1-(2-(3-fluoropyrrolidine-1-yl)-6-methoxy-7-(4-(pyrrolidine-1-yl)-1-butyne-1-yl)quinazoline-4-yl)-N2,N2-dimethylethane-1,2-diamine Step 1. Preparation of (R)—N1-(2-(3-fluoropyrrolidine-1-yl)-7-iodo-7-methoxyquinazoline-4-yl)-N2,N2-dimethylethane-1,2-diamine

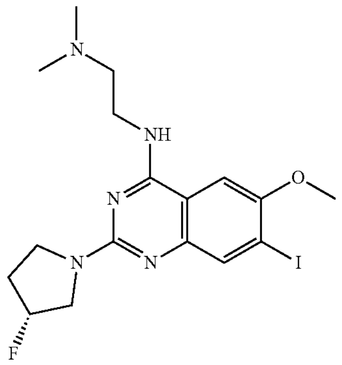 [SMILES: COc1cc2c(NCCN(C)C)nc(N3CC[C@@H](F)C3)nc2cc1I]

N1-(2-chloro-7-iodo-6-methoxyquinazoline-4-yl)-N2,N2-dimethylethane-1,2-diamine was prepared in the same manner as described in step 1 of Example 28, and a target compound was obtained (60 mg, yield: 79%) as a yellow solid in the same manner as described in step 2 of Example 1 using (R)-3-fluoropyrrolidine hydrochloride as a starting material.

LCMS, m/z 460[M+H]+

Step 2. Preparation of (R)—N1-(2-(3-fluoropyrrolidine-1-yl)-6-methoxy-7-(4-(pyrrolidine-1-yl)-1-butyne-1-yl)quinazoline-4-yl)-N2,N2-dimethylethane-1,2-diamine

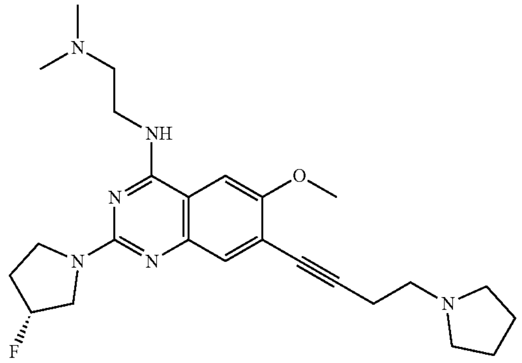 [SMILES: COc1cc2c(NCCN(C)C)nc(N3CC[C@@H](F)C3)nc2cc1C#CCCN1CCCC1]

A target compound (R)—N1-(2-(3-fluoropyrrolidine-1-yl)-6-methoxy-7-(4-(pyrrolidine-1-yl)-1-butyne-1-yl)quinazoline-4-yl)-N2,N2-dimethylethane-1,2-diamine ((R)—N1-(2-(3-fluoropyrrolidine-1-yl)-6-methoxy-7-(4-(pyrrolidine-1-yl)but-1-yn-1-yl)quinazolin-4-yl)-N2,N2-dimethylethane-1,2-diamine) was obtained (8.7 mg, yield: 13.8%) in the same manner as described in step 3 of Example 1 that (R)—N1-(2-(3-fluoropyrrolidine-1-yl)-7-iodo-6-methoxyquinazoline-4-yl)-N2,N2-dimethylethane-1,2-diamine and 1-(3-butyne-1-yl)pyrrolidine were used as starting materials in step 3 of Example 1.

$^{1}$H NMR (400 MHz, $CDCl_3$) δ 7.58 (s, 1H), 6.86 (s, 1H), 6.22-6.05 (m, 1H), 5.44-5.22 (m, 1H), 4.14-3.94 (m, 2H), 3.92 (s, 3H), 3.85-3.70 (m, 2H), 3.69-3.62 (m, 2H), 2.84-2.75 (m, 2H), 2.74-2.68 (m, 2H), 2.66-2.54 (m, 6H), 2.32 (s, 6H), 2.20-2.08 (m, 1H), 2.07-1.98 (m, 1H), 1.85-1.73 (m, 4H).

LCMS, m/z 455[M+H]+

<Example 81> Preparation of 6-methoxy-N-methyl-2-(pyrrolidine-1-yl)-7-(4-(pyrrolidine-1-yl)-1-butyne-1-yl)quinazoline-4-amine Step 1. Preparation of 2-chloro-7-iodo-6-methoxy-N-methoxyquinazoline-4-amine

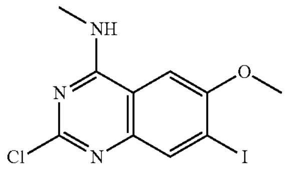 [SMILES: CNc1nc(Cl)nc2cc(I)c(OC)cc12]

A target compound was obtained (34 mg, yield: 69.1%) as a white solid by performing the procedure of step 1 of Example 1, except that methylamine was used instead of 1-isopropylpiperidine-4-amine in step 1 of Example 1.

LCMS, m/z 350[M+H]+

Step 2. Preparation of 7-iodo-6-methoxy-N-methyl-2-(pyrrolidine-1-yl)quinazoline-4-amine

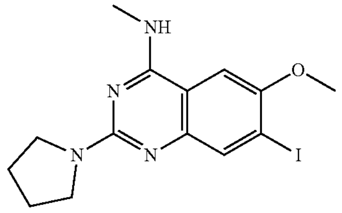 [SMILES: CNc1nc(N2CCCC2)nc2cc(I)c(OC)cc12]

A target compound was obtained (29 mg, yield: 78%) as a yellow solid in the same manner as described in step 2 of Example 1 that 2-chloro-7-iodo-6-methoxy-N-methylquinazoline-4-amine)-pyrrolidine was used as a starting material in step 2 of Example 1.

LCMS, m/z 385[M+H]+

Step 3. Preparation of 6-methoxy-N-methyl-2-(pyrrolidine-1-yl)-7-(4-(pyrrolidine-1-yl)-1-butyne-1-yl) quinazoline-4-amine

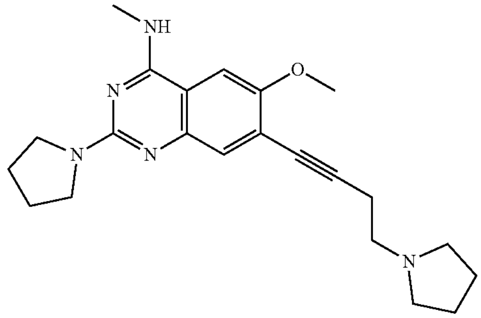 [SMILES: CNc1nc(N2CCCC2)nc2cc(C#CCCN3CCCC3)c(OC)cc12]

A target compound 6-methoxy-N-methyl-2-(pyrrolidine-1-yl)-7-(4-(pyrrolidine-1-yl)-1-butyne-1-yl)quinazoline-4-amine(6-methoxy-N-methyl-2-(pyrrolidine-1-yl)-7-(4-(pyrrolidine-1-yl)but-1-yn-1-yl)quinazolin-4-amine) was obtained (14 mg, yield: 48.7%) in the same manner as described in step 3 of Example 1 that 7-iodo-6-methoxy-N-methyl-2-(pyrrolidine-1-yl)quinazoline-4-amine and 1-(3-butyne-1-yl) were used as starting materials in step 3 of Example 1.

$^1$H NMR (400 MHz, $CDCl_3$) δ 7.56 (s, 1H), 6.79 (s, 1H), 5.93-5.27 (m, 1H), 3.85 (s, 3H), 3.69-3.60 (m, 4H), 3.21-3.00 (m, 3H), 2.83-2.64 (m, 4H), 2.63-2.52 (m, 4H), 2.00-1.87 (m, 4H), 1.85-1.69 (m, 4H).

LCMS, m/z 380[M+H]+

<Example 82> Preparation of tert-butene 2-((4-((1-isopropylpiperidine-4-yl)amino)-6-methoxy-7-(4-(pyrrolidine-1-yl)-1-butyne-1-yl)quinazoline-2-yl)(methyl)amino)acetate Step 1. Preparation of tert-butyl N-(7-iodo-4-((1-isopropylpiperidine-4-yl)amino)-6-methoxyquinazoline-2-yl)-N-methylglycinate

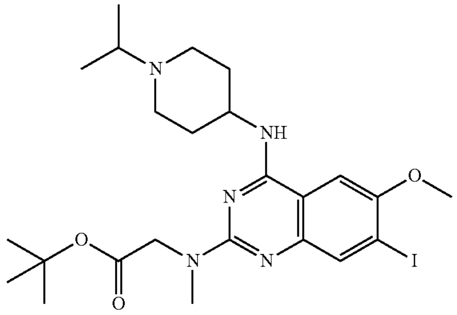 [SMILES: COc1cc2c(NC3CCN(C(C)C)CC3)nc(N(C)CC(=O)OC(C)(C)C)nc2cc1I]

2-Chloro-7-iodo-N-(1-isopropylpiperidine-4-yl)-6-methoxyquinazoline-4-amine was prepared in the same manner as described in step 1 of Example 1, and a target compound was obtained (13 mg, yield: 28.4%) as a yellow solid in the same manner as described in step 2 of Example 1 using tert-butyl 2-(methylamino)acetate hydrochloride as a starting material.

LCMS, m/z 570[M+H]+

Step 2. Preparation of tert-butyl 2-((4-(1-isopropylpiperidine-4-yl)amino)-6-methoxy-7-(4-(pyrrolidine-1-yl)-1-butyne-1-yl)quinazoline-2-yl)(methyl) amino)acetate

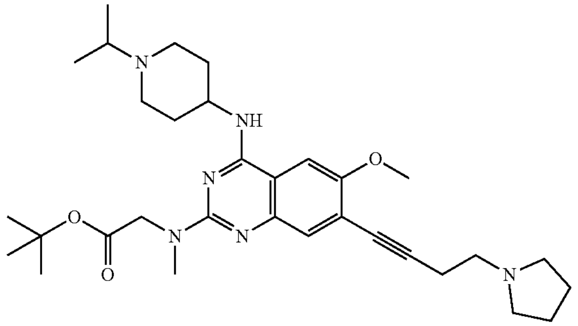 [SMILES: COc1cc2c(NC3CCN(C(C)C)CC3)nc(N(C)CC(=O)OC(C)(C)C)nc2cc1C#CCCN1CCCC1]

A target compound tert-butene 2-((4-((1-isopropylpiperidine-4-yl)amino)-6-methoxy-7-(4-(pyrrolidine-1-yl)-1-butyne-1-yl)quinazoline-2-yl)(methyl)amino)acetate (tert-butyl 2-((4-((1-isopropylpiperidine-4-yl)amino)-6-methoxy-7-(4-(pyrrolidine-1-yl)but-1-yn-1-yl)quinazolin-2-yl)(methyl)amino)acetate) was obtained (4.2 mg, yield: 26.7%) in the same manner as described in step 3 of Example 1 that tert-butyl N-(7-iodo-4-((1-isopropylpiperidine-4-yl)amino)-6-methoxyquinazoline-2-yl)-N-methylglycinate and 1-(3-butyne-1-yl)pyrrolidine were used as starting materials in step 3 of Example 1.

$^1$H NMR (400 MHz, $CDCl_3$) δ7.57 (s, 1H), 6.65 (s, 1H), 5.09 (d, J=7.4 Hz, 1H), 4.23 (s, 1H), 4.16-4.02 (m, 1H), 3.92

(s, 3H), 3.26 (s, 3H), 3.19 (s, 1H), 2.94 (d, J=11.3 Hz, 2H), 2.86-2.65 (m, 5H), 2.65-2.56 (m, 4H), 2.36 (t, J=10.6 Hz, 2H), 2.17 (d, J=11.9 Hz, 2H), 1.85-1.76 (m, 4H), 1.65-1.53 (m, 2H), 1.43 (s, 9H), 1.09 (d, J=6.5 Hz, 6H).

LCMS, m/z 565[M+H]+

<Example 83> Preparation of 6-methoxy-N2,N-dimethyl-N4-(1-propylpiperidine-4-yl)-7-(4-(pyrrolidine-1-yl)-1-butyne-1-yl)quinazoline-2,4-diamine Step 1. Preparation of 7-iodo-6-methoxy-N2,N2-dimethyl-N4-(1-propylpiperidine-4-yl)quinazoline-2,4-diamine

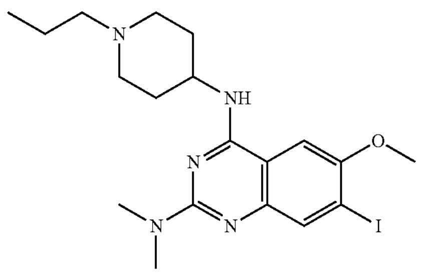 [SMILES: CCCN1CCC(Nc2nc(N(C)C)nc3cc(I)c(OC)cc23)CC1]

2-Chloro-7-iodo-6-methoxy-N-(1-propylpiperidine-4-yl)quinazoline-4-amine was prepared in the same manner as described in step 1 of Example 1, and a target compound was obtained (46 mg, yield: 75%) as a yellow solid in the same manner as described in step 2 of Example 1 using dimethylamine as a starting material in step 2 of Example 1.

LCMS, m/z 470[M+H]+

Step 2. Preparation of 6-methoxy-N2,N2-dimethyl-N4-(1-propylpiperidine-4-yl)-7-(4-(pyrrolidine-1-yl)-1-butyne-1-yl)quinazoline-2,4-diamine

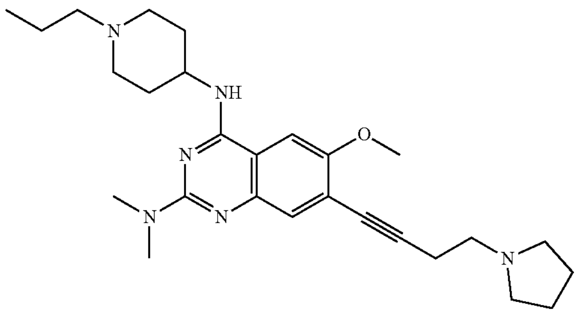 [SMILES: CCCN1CCC(Nc2nc(N(C)C)nc3cc(C#CCCN4CCCC4)c(OC)cc23)CC1]

A target compound 6-methoxy-N2,N-dimethyl-N4-(1-propylpiperidine-4-yl)-7-(4-(pyrrolidine-1-yl)-1-butyne-1-yl)quinazoline-2,4-diamine(6-methoxy-N2,N2-dimethyl-N4-(1-propylpiperidine-4-yl)-7-(4-(pyrrolidine-1-yl)but-1-yn-1-yl)quinazoline-2,4-diamine) was obtained (22 mg, yield: 48.3%) in the same manner as described in step 3 of Example 1 that 7-iodo-6-methoxy-N2,N2-dimethyl-N4-(1-propylpiperidine-4-yl)quinazoline-2,4-diamine and 1-(3-butyne-1-yl)pyrrolidine were used as starting materials in step 3 of Example 1.

$^1$H NMR (400 MHz, $CDCl_3$) δ 7.55 (s, 1H), 6.67 (s, 1H), 5.10 (d, J=7.0 Hz, 1H), 4.22-4.04 (m, 1H), 3.91 (s, 3H), 3.19 (s, 6H), 2.95 (d, J=11.7 Hz, 2H), 2.84-2.65 (m, 4H), 2.65-2.51 (m, 4H), 2.41-2.27 (m, 2H), 2.17-2.15 (m, 4H), 1.86-1.72 (m, 4H), 1.68-1.46 (m, 4H), 0.91 (t, J=7.3 Hz, 3H).

LCMS, m/z 465[M+H]+

<Example 84> Preparation of (R)-2-(3-fluoropyrrolidine-1-yl)-6-methoxy-N-(1-propylpiperidine-4-yl)-7-(4-(pyrrolidine-1-yl)-1-butyne-1-yl)quinazoline-4-amine Step 1. Preparation of (R)-2-(3-(fluoropyrrolidine-1-yl)-7-iodo-6-methoxy-N-(1-propylpiperidine-4-yl)quinazoline-4-amine

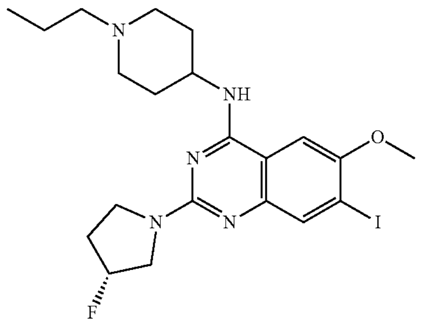 [SMILES: CCCN1CCC(Nc2nc(N3CC[C@@H](F)C3)nc3cc(I)c(OC)cc23)CC1]

2-Chloro-7-iodo-6-methoxy-N-(1-propylpiperidine-4-yl)quinazoline-4-amine was prepared in the same manner as described in step 1 of Example 67, and a target compound was obtained (42 mg, yield: 62.8%) as a yellow solid in the same manner as described in step 2 of Example 1 using (R)-3-fluoropyrrolidine hydrochloride as a starting material.

LCMS, m/z 514[M+H]+

Step 2. Preparation of (R)-2-(3-fluoropyrrolidine-1-yl)-6-methoxy-N-(1-propylpiperidine-4-yl)-7-(4-(pyrrolidine-1-yl)-1-butyne-1-yl)quinazoline-4-amine

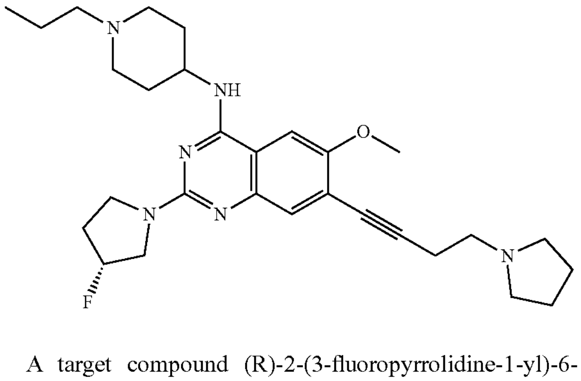

A target compound (R)-2-(3-fluoropyrrolidine-1-yl)-6-methoxy-N-(1-propylpiperidine-4-yl)-7-(4-(pyrrolidine-1-yl)-1-butyne-1-yl)quinazoline-4-amine ((R)-2-(3-fluoropyrrolidine-1-yl)-6-methoxy-N-(1-propylpiperidine-4-yl)-7-(4-(pyrrolidine-1-yl)but-1-yn-1-yl)quinazolin-4-amine) was obtained (27 mg, yield: 64.6%) in the same manner as described in step 3 of Example 1 that (R)-2-(3-fluoropyrrolidine-1-yl)-7-iodo-6-methoxy-N-(1-propylpiperidine-4-yl)quinazoline-4-amine and 1-(3-butyne-1-yl)pyrrolidine were used as starting materials in step 3 of Example 1.

$^{1}H$ NMR (400 MHz, $CDCl_3$) δ 7.59 (s, 1H), 6.70 (s, 1H), 5.46-5.23 (m, 1H), 5.16 (d, J=6.9 Hz, 1H), 4.22-4.11 (m, 1H), 4.10-3.94 (m, 1H), 3.98-3.87 (m, 1H), 3.92 (s, 3H), 3.85-3.64 (m, 2H), 3.04-2.90 (m, 2H), 2.84-2.67 (m, 4H), 2.64-2.52 (m, 4H), 2.43-2.25 (m, 3H), 2.23-2.10 (m, 4H), 2.08-1.99 (m, 1H), 1.88-1.73 (m, 4H), 1.70-1.58 (m, 2H), 1.54 (td, J=14.9, 7.3 Hz, 2H), 0.92 (t, J=7.3 Hz, 3H).

LCMS, m/z 509[M+H]+

<Example 85> Preparation of (E)-N-(1-isopropylpiperidine-4-yl)-6-methoxy-2-(pyrrolidine-1-yl)-7-(4-(pyrrolidine-1-yl)-1-butene-1-yl)quinazoline-4-amine

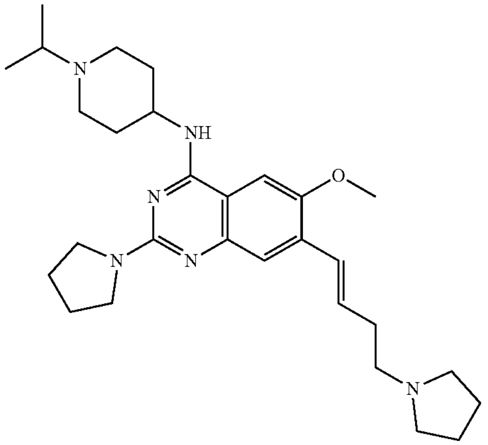 [SMILES: COc1cc2c(NC3CCN(C(C)C)CC3)nc(N3CCCC3)nc2cc1/C=C/CCN1CCCC1]

7-Iodo-N-(1-isopropylpiperidine-4-yl)-6-methoxy-2-(pyrrolidine-1-yl)quinazoline-4-amine was prepared in the same manner as described in step 1 of Example 6, and a target compound (E)-N-(1-isopropylpiperidine-4-yl)-6-methoxy-2-(pyrrolidine-1-yl)-7-(4-(pyrrolidine-1-yl)-1-butene-1-yl)quinazoline-4-amine ((E)-N-(1-isopropylpiperidine-4-yl)-6-methoxy-2-(pyrrolidine-1-yl)-7-(4-(pyrrolidine-1-yl)but-1-en-1-yl)quinazolin-4-amine) was obtained (8 mg, yield: 53.6%) in the same manner as described in Example 66 using 1-(3-butene-1-yl)quinazoline-4-amine as a starting material.

$^{1}H$ NMR (400 MHz, $CDCl_3$) δ7.57 (s, 1H), 6.77 (d, J=16.0 Hz, 1H), 6.65 (s, 1H), 6.47-6.35 (m, 1H), 5.01 (d, J=6.8 Hz, 1H), 4.21-4.06 (m, 1H), 3.88 (s, 3H), 3.72-3.52 (m, 4H), 2.92 (d, J=11.5 Hz, 2H), 2.78 (quintet, J=6.5 Hz, 1H), 2.66-2.40 (m, 6H), 2.34 (t, J=11.3 Hz, 2H), 2.28-2.12 (m, 2H), 2.00-1.90 (m, 4H), 1.89-1.82 (m, 1H), 1.85-1.72 (m, 4H), 1.76-1.69 (m, 1H), 1.65-1.49 (m, 2H), 1.08 (d, J=6.5 Hz, 6H).

LCMS, m/z 493[M+H]+

<Example 86> Preparation of (E)-7-(4-(dimethylamino)-1-butene-1-yl)-N-(1-isopropylpiperidine-4-yl)-6-methoxy-2-(pyrrolidine-1-yl)quinazoline-4-amine

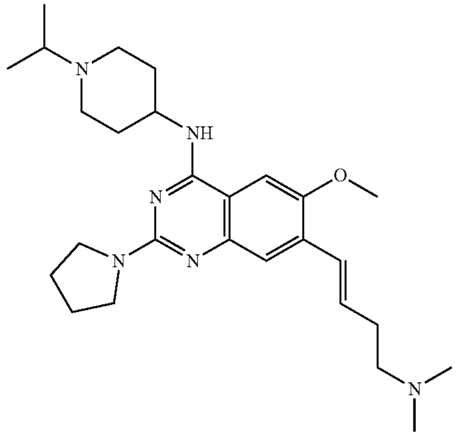 [SMILES: COc1cc2c(NC3CCN(C(C)C)CC3)nc(N3CCCC3)nc2cc1/C=C/CCN(C)C]

7-Iodo-N-(1-isopropylpiperidine-4-yl)-6-methoxy-2-(pyrrolidine-1-yl)quinazoline-4-amine was prepared in the same manner as described in step 1 of Example 6, and a target compound (E)-7-(4-(dimethylamino)-1-butene-1-yl)-N-(1-isopropylpiperidine-4-yl)-6-methoxy-2-(pyrrolidine-1-yl)quinazoline-4-amine((E)-7-(4-(dimethylamino)but-1-en-1-yl)-N-(1-isopropylpiperidine-4-yl)-6-methoxy-2-(pyrrolidine-1-yl)quinazolin-4-amine) was obtained (11 mg, yield: 56.9%) in the same manner as described in Example 66 using N,N-dimethyl-3-butene-1-amine as a starting material.

$^{1}H$ NMR (400 MHz, $CDCl_3$) δ 7.58 (s, 1H), 6.77 (d, J=15.7 Hz, 1H), 6.64 (s, 1H), 6.43-6.36 (m, 1H), 5.01 (d, J=5.1 Hz, 1H), 4.18-4.10 (m, 1H), 3.88 (s, 3H), 3.65-3.62 (m, 4H), 2.92 (d, J=11.7 Hz, 2H), 2.78 (quintet, J=6.5 Hz, 1H), 2.53-2.38 (m, 4H), 2.34 (t, J=11.4 Hz, 2H), 2.27 (s, 4H), 2.22 (d, J=12.8 Hz, 2H), 2.19 (s, 2H), 1.98-1.95 (m, 4H), 1.63-1.54 (m, 2H), 1.08 (d, J=6.5 Hz, 6H).

LCMS, m/z 467[M+H]+

<Example 87> Preparation of 2-(4-((2-(dimethylamino)-6-methoxy-7-(4-(pyrrolidine-1-yl)-1-butyne-1-yl)quinazoline-4-yl)amino)piperidine-1-yl) ethanol Step 1. Preparation of 2-(4-((2-(dimethylamino)-7-iodo-6-methoxyquinazoline-4-yl)amino)piperidine-1-yl) ethan-1-ol

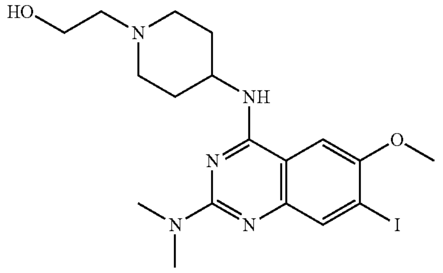 [SMILES: COc1cc2c(NC3CCN(CCO)CC3)nc(N(C)C)nc2cc1I]

2-(4-((2-Chloro-7-iodo-6-methoxyquinazoline-4-yl)amino)piperidine-1-yl)ethan-1-ol was prepared in the same manner as described in step 1 of Example 69, and a target compound was obtained (35 mg, yield: 57.3%) as a yellow solid in the same manner as described in step 2 of Example 1 using dimethylamine as a starting material.

LCMS, m/z 472[M+H]+

Step 2. Preparation of 2-(4-((2-(dimethylamino)-6-methoxy-7-(4-(pyrrolidine-1-yl)-1-butyne-1-yl)quinazoline-4-yl)amino)piperidine-1-yl)ethanol

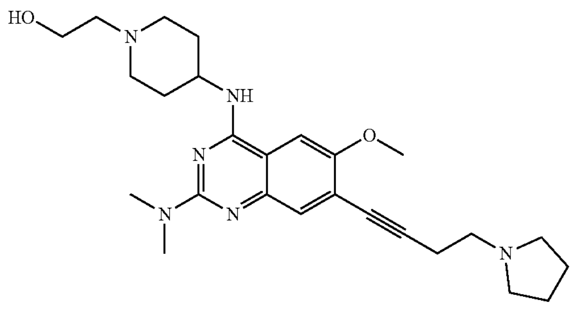 [SMILES: COc1cc2c(NC3CCN(CCO)CC3)nc(N(C)C)nc2cc1C#CCCN1CCCC1]

A target compound 2-(4-((2-(dimethylamino)-6-methoxy-7-(4-(pyrrolidine-1-yl)-1-butyne-1-yl)quinazoline-4-yl)amino)piperidine-1-yl)ethanol(2-(4-((2-(dimethylamino)-6-methoxy-7-(4-(pyrrolidine-1-yl)but-1-yn-1-yl)quinazolin-4-yl)amino)piperidine-1-yl)ethanol) was obtained (4.8 mg, yield: 13.7%) in the same manner as described in step 3 of Example 1 that 2-(4-((2-(dimethylamino)-7-iodo-6-methoxyquinazoline-4-yl)amino)piperidine-1-yl)ethan-1-ol and 1-(3-butyne-1-yl)pyrrolidine were used as starting materials in step 3 of Example 1.

$^1$H NMR (400 MHz, $CDCl_3$) δ7.57 (s, 1H), 6.67 (s, 1H), 5.09 (d, J=6.7 Hz, 1H), 4.28-4.14 (m, 1H), 3.93 (s, 3H), 3.63 (t, J=5.3 Hz, 2H), 3.20 (s, 6H), 3.02-2.91 (m, 2H), 2.83-2.68 (m, 4H), 2.64-2.55 (m, 7H), 2.30 (t, J=11.3 Hz, 2H), 2.25-2.17 (m, 2H), 1.81 (s, 4H), 1.69-1.54 (m, 2H).

LCMS, m/z 467[M+H]+

<Example 88> Preparation of N4-(1-isopropylpiperidine-4-yl)-6-methoxy-N2-(1-methyl-1H-pyrazole-4-yl)-7-(4-(pyrrolidine-1-yl)-1-butyne-1-yl)quinazoline-2,4-diamine Step 1. Preparation of 7-iodo-N4-(1-isopropylpiperidine-4-yl)-6-methoxy-N2-(1-methyl-1H-pyrazole-4-yl)quinazoline-2,4-diamine

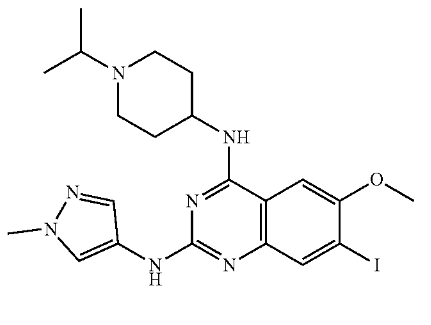

A mixed solution of 2-chloro-7-iodo-N-(1-isopropylpiperidine-4-yl)-6-methoxyquinazoline-4-amine (15 mg, 0.033 mmol) prepared in step 1 of Example 1, p-TsOH (12.39 mg, 0.065 mmol) and n-BuOH (0.5 ml) was dehydrated, replaced with nitrogen gas, and heated and stirred at 160° C. for 2 hours. The reaction mixture was concentrated, diluted with $CH_2Cl_2$, and washed with a saturated aqueous sodium hydrogen carbonate solution. The organic layer was dried over magnesium sulfate and concentrated, and then the obtained residue was purified by silica gel chromatography (0~5% MeOH/$CH_2Cl_2$, amine silica gel) to give a target compound (10 mg, yield: 58.9%) as a yellow solid.

LCMS, m/z 522[M+H]+

Step 2. Preparation of N4-(1-isopropylpiperidine-4-yl)-6-methoxy-N2-(1-methyl-1H-pyrazole-4-yl)-7-(4-(pyrrolidine-1-yl)-1-butyne-1-yl)quinazoline-2,4-diamine

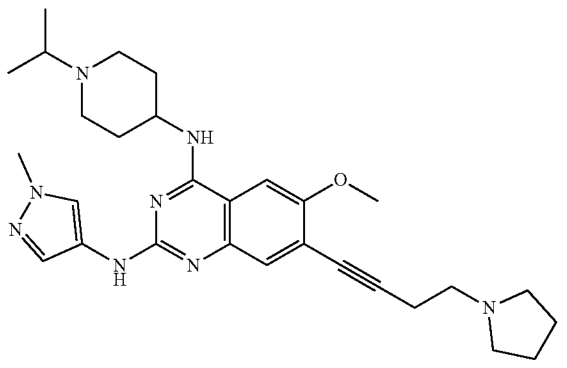 [SMILES: COc1cc2c(NC3CCN(C(C)C)CC3)nc(Nc3cnn(C)c3)nc2cc1C#CCCN1CCCC1]

A target compound N4-(1-isopropylpiperidine-4-yl)-6-methoxy-N2-(1-methyl-1H-pyrazole-4-yl)-7-(4-(pyrrolidine-1-yl)-1-butyne-1-yl)quinazoline-2,4-diamine (N4-(1-isopropylpiperidine-4-yl)-6-methoxy-N2-(1-methyl-1H-pyrazol-4-yl)-7-(4-(pyrrolidine-1-yl)but-1-yn-1-yl)quinazoline-2,4-diamine) was obtained (5.9 mg, yield: 60%) in the same manner as described in step 3 of Example 1 that 7-iodo-N4-(1-isopropylpiperidine-4-yl)-6-methoxy-N2-(1-methyl-1H-pyrazole-4-yl)quinazoline-2,4-diamine and 1-(3-butyne-1-yl)pyrrolidine were used as starting materials in step 3 of Example 1.

$^1$H NMR (400 MHz, $CDCl_3$) δ 7.90 (s, 1H), 7.62 (s, 1H), 7.57-7.52 (m, 1H), 6.73 (s, 1H), 5.45 (s, 1H), 4.22-4.10 (m, 1H), 3.98-3.92 (m, 1H), 3.94 (s, 3H), 3.89 (s, 3H), 3.03-2.92 (m, 2H), 2.89-2.77 (m, 3H), 2.77-2.68 (m, 2H), 2.67-2.56 (m, 4H), 2.39 (t, J=11.1 Hz, 2H), 2.26-2.15 (m, 2H), 1.86-1.76 (m, 4H), 1.74-1.60 (m, 2H), 1.10 (d, J=6.5 Hz, 6H).

LCMS, m/z 517[M+H]+

<Example 89> Preparation of (R)-2-(4-((2-(3-(fluoropyrrolidine-1-yl)-6-methoxy-7-(4-(pyrrolidine-1-yl)-1-butyne-1-yl)quinazoline-4-yl)amino)piperidine-1-yl) ethanol Step 1. Preparation of (R)-2-(4-((2-(3-fluoropyrrolidine-1-yl)-7-iodo-6-methoxyquinazoline-4-yl) amino)piperidine-1-yl)ethan-1-ol

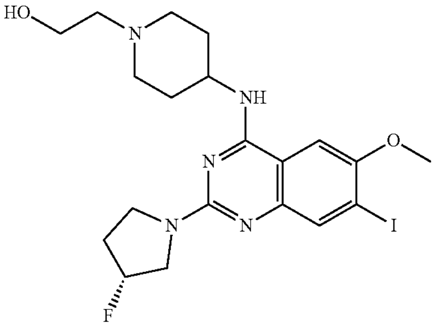 [SMILES: COc1cc2c(NC3CCN(CCO)CC3)nc(N3CC[C@@H](F)C3)nc2cc1I]

2-(4-((2-Chloro-7-iodo-6-methoxyquinazoline-4-yl)piperidine-1-yl)ethan-1-ol was prepared in the same manner as described in step 1 of Example 69, and a target compound was obtained (7 mg, yield: 15.7%) as a yellow solid in the same manner as described in step 2 of Example 1 using (R)-3-fluoropyrrolidine hydrochloride as a starting material.

LCMS, m/z 516[M+H]+

Step 2. Preparation of (R)-2-(4-((2-(3-fluoropyrrolidine-1-yl)-6-methoxy-7-(4-(pyrrolidine-1-yl)-1-butyne-1-yl)quinazoline-4-yl)amino)piperidine-1-yl) ethanol

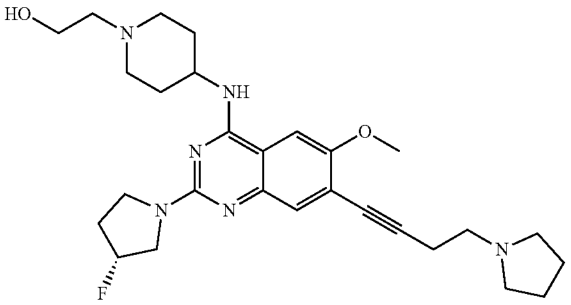 [SMILES: COc1cc2c(NC3CCN(CCO)CC3)nc(N3CC[C@@H](F)C3)nc2cc1C#CCCN1CCCC1]

A target compound (R)-2-(4-((2-(3-(fluoropyrrolidine-1-yl)-6-methoxy-7-(4-(pyrrolidine-1-yl)-1-butyne-1-yl)quinazoline-4-yl)amino)piperidine-1-yl) ethanol ((R)-2-(4-((2-(3-fluoropyrrolidine-1-yl)-6-methoxy-7-(4-(pyrrolidine-1-yl)but-1-yn-1-yl)quinazolin-4-yl)amino)piperidine-1-yl) ethanol) was obtained (15 mg, yield: 37.5%) in the same manner as described in step 3 of Example 1 that (R)-2-(4-((2-(3-fluoropyrrolidine-1-yl)-7-iodo-6-methoxyquinazoline-4-yl)amino)piperidine-1-yl)ethan-1-ol and 1-(3-butyne-1-yl)pyrrolidine were used as starting materials in step 3 of Example 1.

$^1$H NMR (400 MHz, $CDCl_3$) δ 7.60 (s, 1H), 6.77 (s, 1H), 5.43-5.25 (m, 1H), 5.36 (d, J=7.0 Hz, 1H), 4.25-4.12 (m, 1H), 4.08-3.98 (m, 1H), 3.98-3.87 (m, 1H), 3.92 (s, 3H) 3.84-3.66 (m, 2H), 3.64 (t, J=5.2 Hz, 2H), 3.02-2.93 (m, 2H), 2.83-2.67 (m, 4H), 2.63-2.55 (m, 7H), 2.39-2.24 (m, 3H), 2.23-2.14 (m, 2H), 2.08-1.99 (m, 1H), 1.85-1.75 (m, 4H), 1.68-1.53 (m, 2H).

LCMS, m/z 511[M+H]+

The compounds prepared in Examples 1 to 89 are summarized in Table 1 below.

TABLE 1

| Example | Chemical Formula |
|---|---|
| 1 | 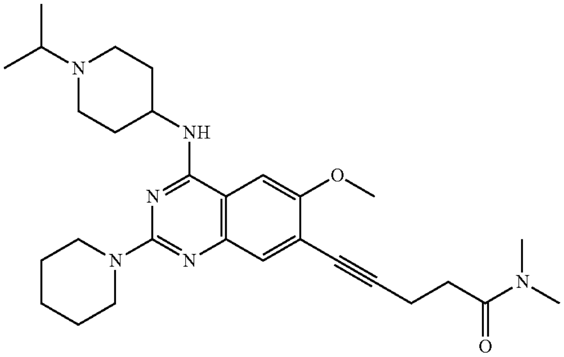 |

TABLE 1-continued
| Example | Chemical Formula |
| --- | --- |
| 2 | 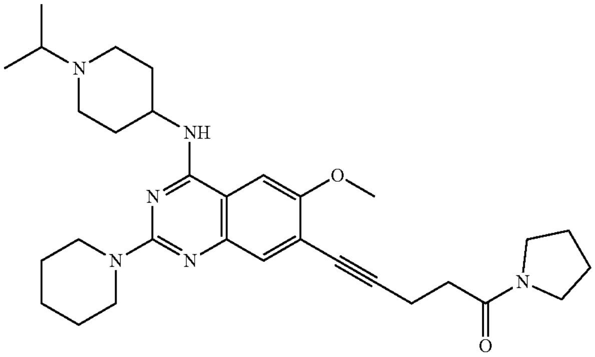 [SMILES: COc1cc2c(NC3CCN(C(C)C)CC3)nc(N3CCCCC3)nc2cc1C#CCCC(=O)N1CCCC1] |
| 3 | 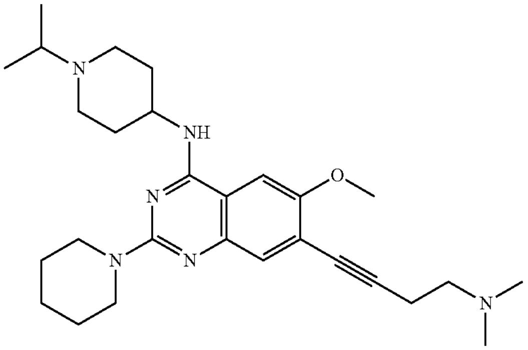 [SMILES: COc1cc2c(NC3CCN(C(C)C)CC3)nc(N3CCCCC3)nc2cc1C#CCCN(C)C] |
| 4 | 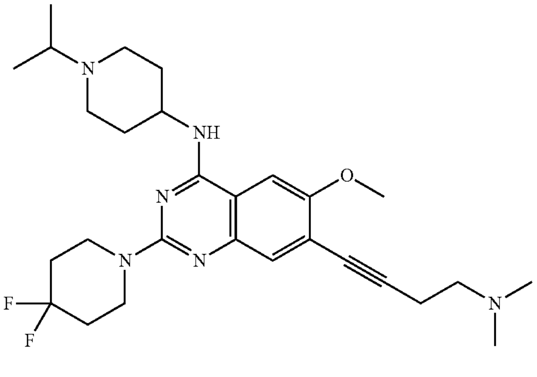 [SMILES: COc1cc2c(NC3CCN(C(C)C)CC3)nc(N3CCC(F)(F)CC3)nc2cc1C#CCCN(C)C] |
| 5 | 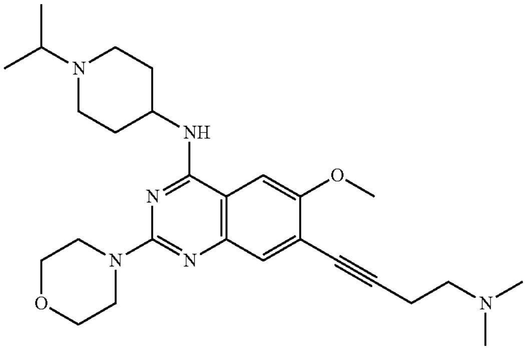 [SMILES: COc1cc2c(NC3CCN(C(C)C)CC3)nc(N3CCOCC3)nc2cc1C#CCCN(C)C] |

TABLE 1-continued
| Example | Chemical Formula |
| --- | --- |
| 6 | 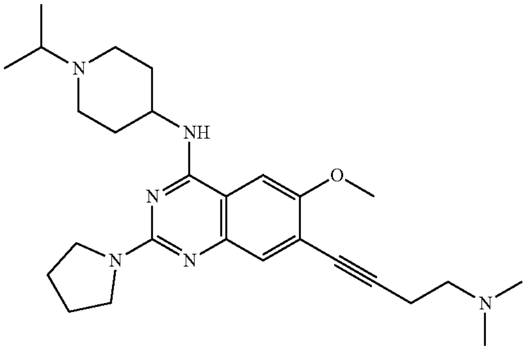 [SMILES: COc1cc2c(NC3CCN(C(C)C)CC3)nc(N3CCCC3)nc2cc1C#CCCN(C)C] |
| 7 | 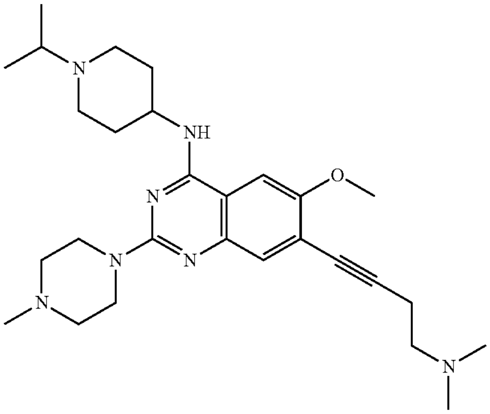 [SMILES: COc1cc2c(NC3CCN(C(C)C)CC3)nc(N3CCN(C)CC3)nc2cc1C#CCCN(C)C] |
| 8 | 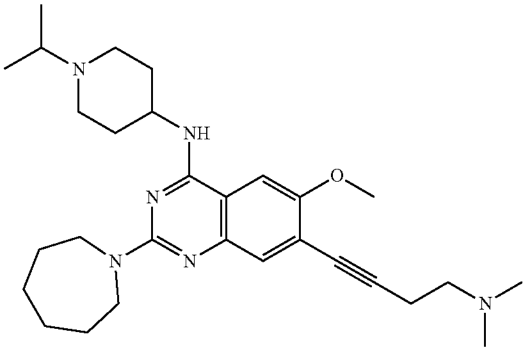 [SMILES: COc1cc2c(NC3CCN(C(C)C)CC3)nc(N3CCCCCC3)nc2cc1C#CCCN(C)C] |
| 9 | 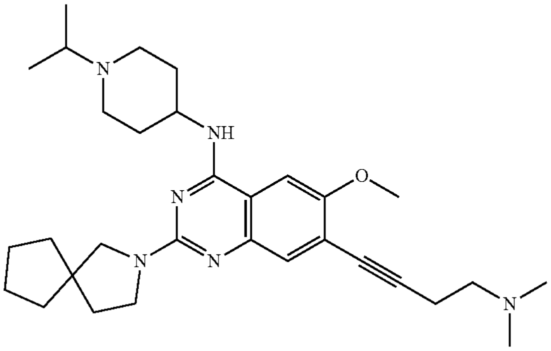 [SMILES: COc1cc2c(NC3CCN(C(C)C)CC3)nc(N3CCC4(CCCC4)C3)nc2cc1C#CCCN(C)C] |

TABLE 1-continued
| Example | Chemical Formula |
| --- | --- |
| 10 | 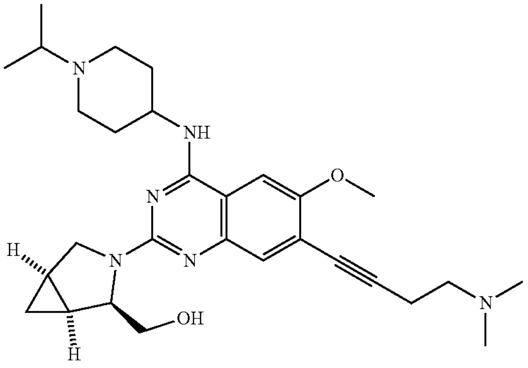 [SMILES: COc1cc2c(NC3CCN(C(C)C)CC3)nc(N3C[C@@H]4C[C@@H]4[C@@H]3CO)nc2cc1C#CCCN(C)C] |
| 11 | 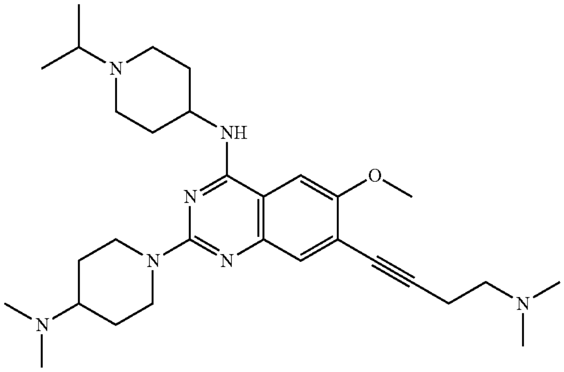 |
| 12 | 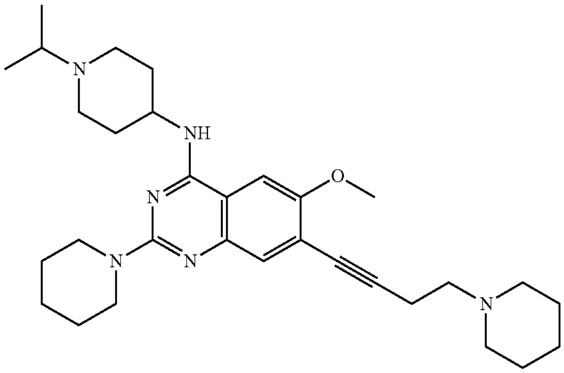 [SMILES: COc1cc2c(NC3CCN(C(C)C)CC3)nc(N3CCCCC3)nc2cc1C#CCCN1CCCCC1] |
| 13 | 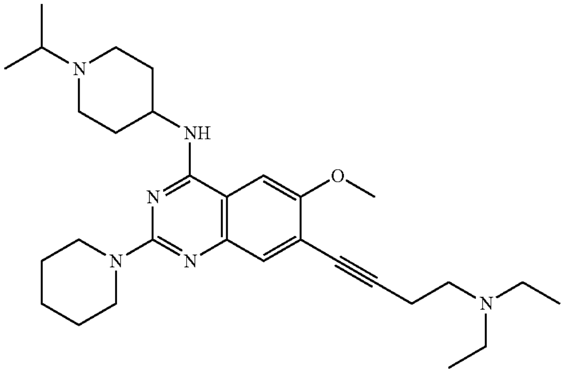 [SMILES: CCN(CC)CCC#Cc1cc2nc(N3CCCCC3)nc(NC3CCN(C(C)C)CC3)c2cc1OC] |

TABLE 1-continued
| Example | Chemical Formula |
| --- | --- |
| 14 | 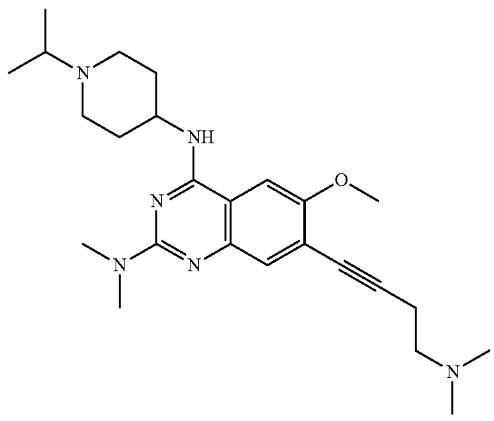 [SMILES: COc1cc2c(NC3CCN(C(C)C)CC3)nc(N(C)C)nc2cc1C#CCCN(C)C] |
| 15 | 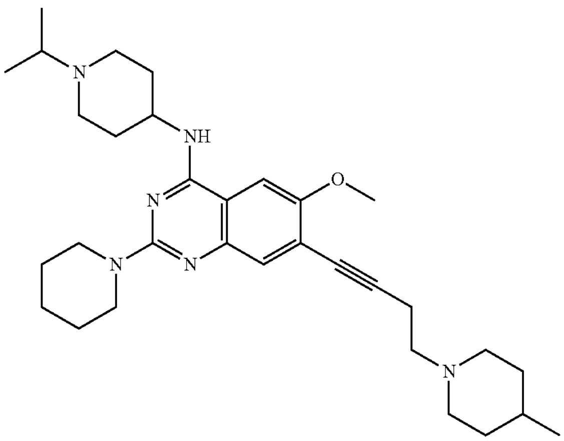 [SMILES: COc1cc2c(NC3CCN(C(C)C)CC3)nc(N3CCCCC3)nc2cc1C#CCCN1CCC(C)CC1] |
| 16 | 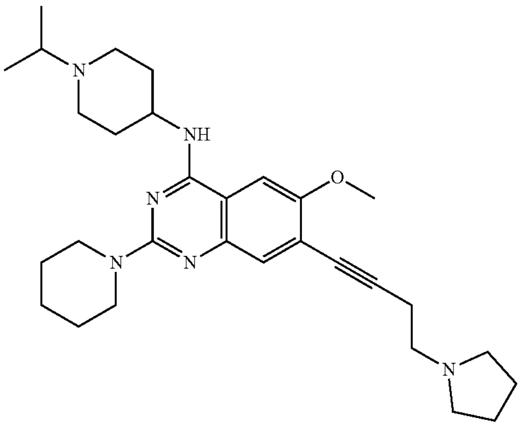 [SMILES: COc1cc2c(NC3CCN(C(C)C)CC3)nc(N3CCCCC3)nc2cc1C#CCCN1CCCC1] |

TABLE 1-continued
| Example | Chemical Formula |
|---|---|
| 17 | 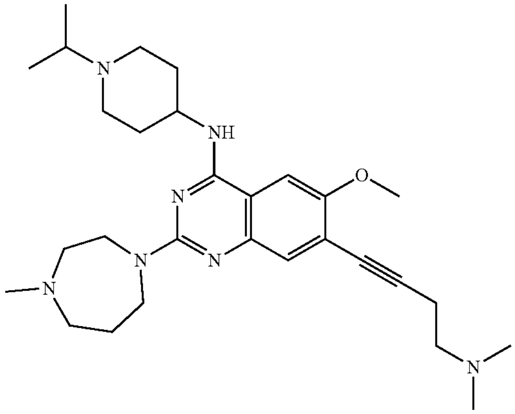 |
| 18 | 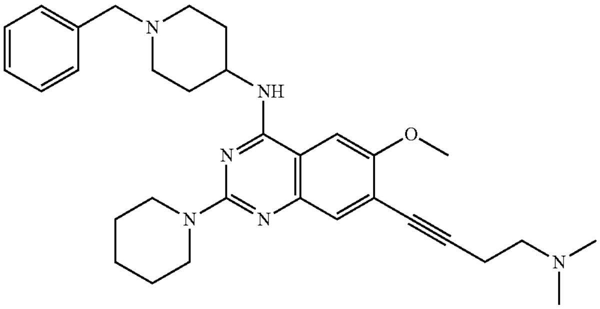 [SMILES: COc1cc2c(NC3CCN(Cc4ccccc4)CC3)nc(N3CCCCC3)nc2cc1C#CCCN(C)C] |
| 19 | 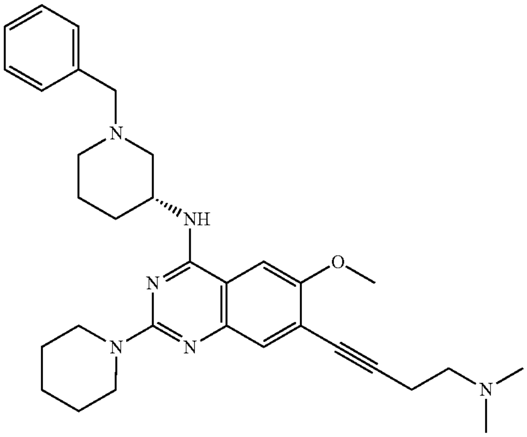 [SMILES: COc1cc2c(N[C@@H]3CCCN(Cc4ccccc4)C3)nc(N3CCCCC3)nc2cc1C#CCCN(C)C] |
| 20 | 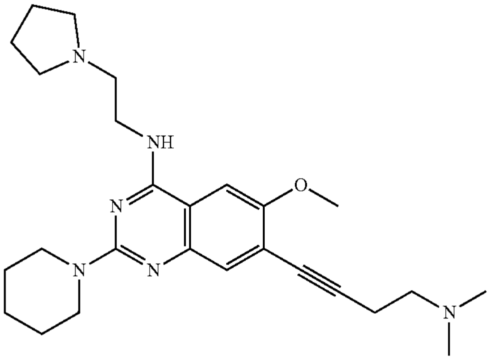 [SMILES: COc1cc2c(NCCN3CCCC3)nc(N3CCCCC3)nc2cc1C#CCCN(C)C] |

TABLE 1-continued
| Example | Chemical Formula |
| --- | --- |
| 21 | 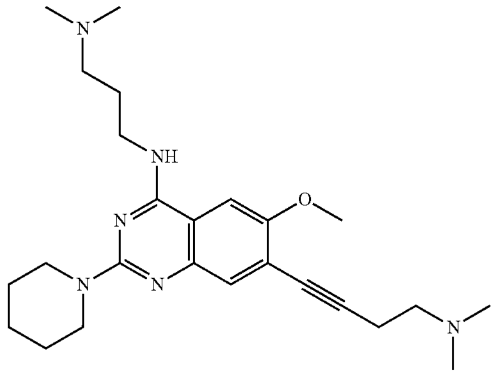 [SMILES: COc1cc2c(NCCCN(C)C)nc(N3CCCCC3)nc2cc1C#CCCN(C)C] |
| 22 | 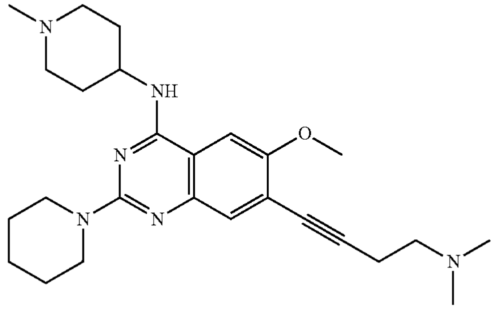 [SMILES: COc1cc2c(NC3CCN(C)CC3)nc(N3CCCCC3)nc2cc1C#CCCN(C)C] |
| 23 | 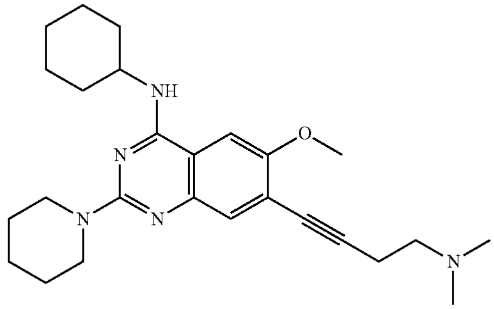 [SMILES: COc1cc2c(NC3CCCCC3)nc(N3CCCCC3)nc2cc1C#CCCN(C)C] |
| 24 | 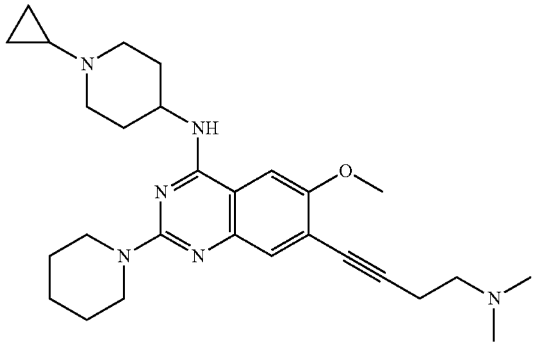 [SMILES: COc1cc2c(NC3CCN(C4CC4)CC3)nc(N3CCCCC3)nc2cc1C#CCCN(C)C] |

TABLE 1-continued
| Example | Chemical Formula |
|---|---|
| 25 | 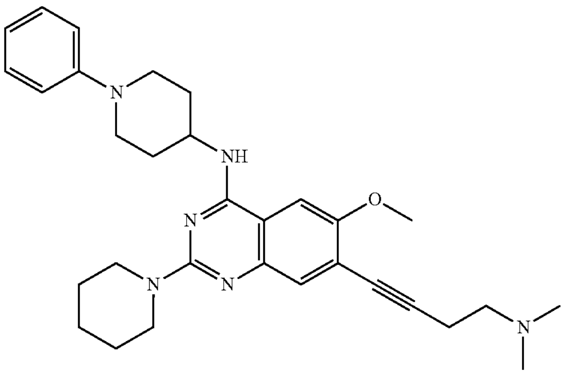 [SMILES: COc1cc2c(NC3CCN(c4ccccc4)CC3)nc(N3CCCCC3)nc2cc1C#CCCN(C)C] |
| 26 | 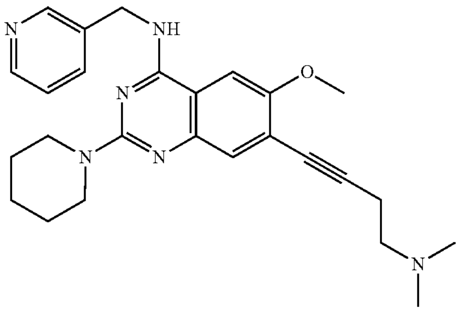 [SMILES: COc1cc2c(NCc3cccnc3)nc(N3CCCCC3)nc2cc1C#CCCN(C)C] |
| 27 | 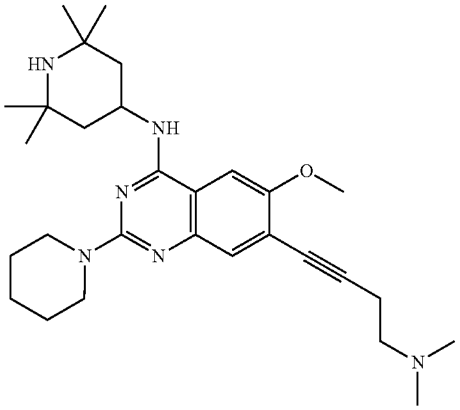 |
| 28 | 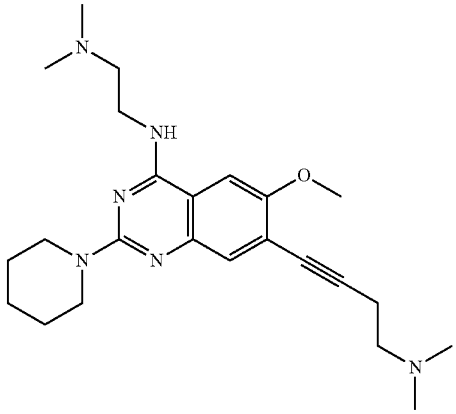 [SMILES: COc1cc2c(NCCN(C)C)nc(N3CCCCC3)nc2cc1C#CCCN(C)C] |

TABLE 1-continued
| Example | Chemical Formula |
| --- | --- |
| 29 | 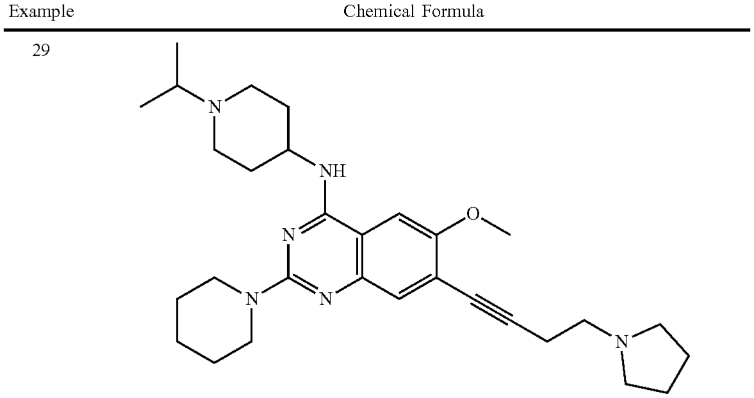 |
| 30 | 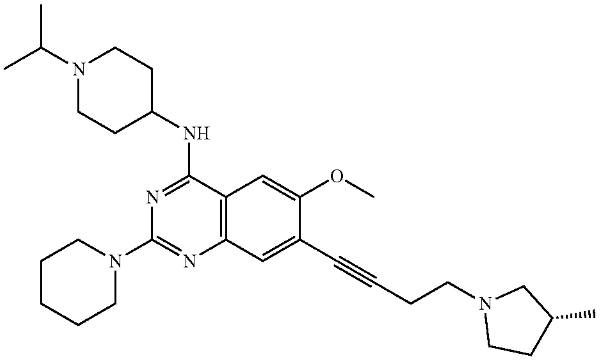 [SMILES: COc1cc2c(NC3CCN(C(C)C)CC3)nc(N3CCCCC3)nc2cc1C#CCCN1CC[C@@H](C)C1] |
| 31 | 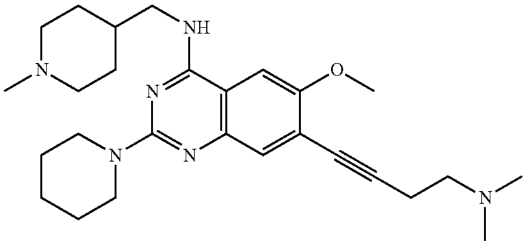 |
| 32 | 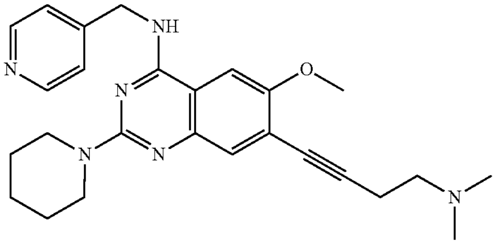 [SMILES: COc1cc2c(NCc3ccncc3)nc(N3CCCCC3)nc2cc1C#CCCN(C)C] |
| 33 | 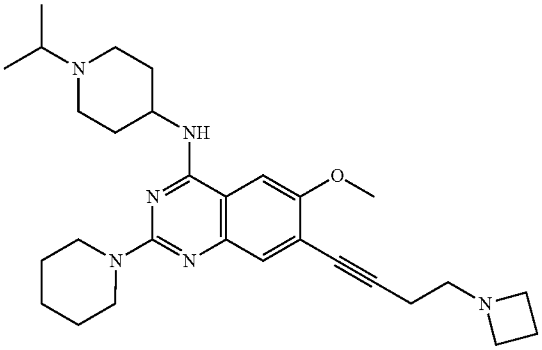 [SMILES: COc1cc2c(NC3CCN(C(C)C)CC3)nc(N3CCCCC3)nc2cc1C#CCCN1CCC1] |

TABLE 1-continued
| Example | Chemical Formula |
|---|---|
| 34 | 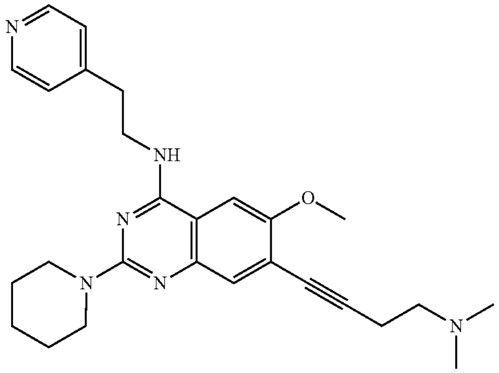 [SMILES: COc1cc2c(NCCc3ccncc3)nc(N3CCCCC3)nc2cc1C#CCCN(C)C] |
| 35 | 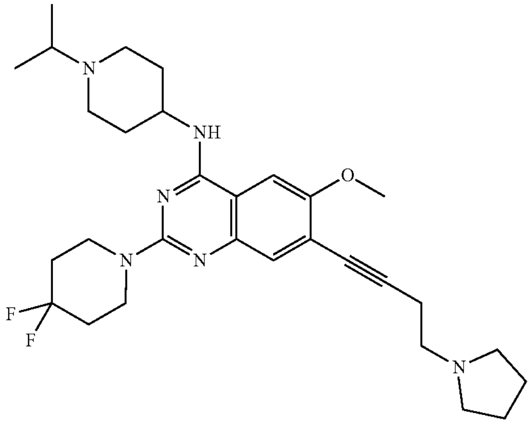 [SMILES: COc1cc2c(NC3CCN(C(C)C)CC3)nc(N3CCC(F)(F)CC3)nc2cc1C#CCCN1CCCC1] |
| 36 | 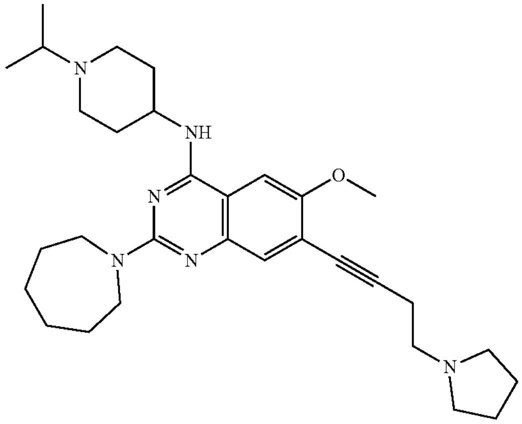 [SMILES: COc1cc2c(NC3CCN(C(C)C)CC3)nc(N3CCCCCC3)nc2cc1C#CCCN1CCCC1] |

TABLE 1-continued
| Example | Chemical Formula |
| --- | --- |
| 37 | 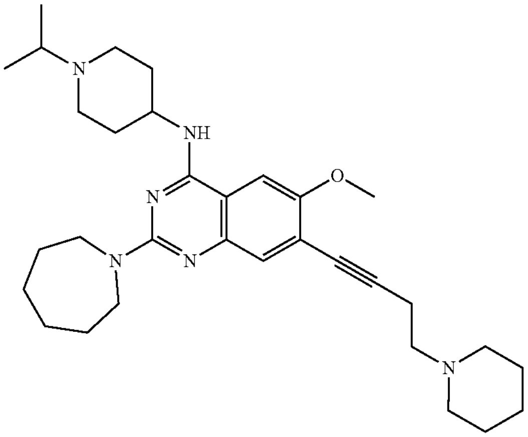 [SMILES: COc1cc2c(NC3CCN(C(C)C)CC3)nc(N3CCCCCC3)nc2cc1C#CCCN1CCCCC1] |
| 38 | 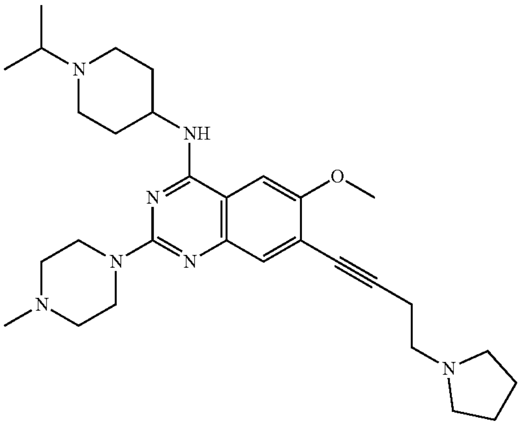 [SMILES: COc1cc2c(NC3CCN(C(C)C)CC3)nc(N3CCN(C)CC3)nc2cc1C#CCCN1CCCC1] |
| 39 | 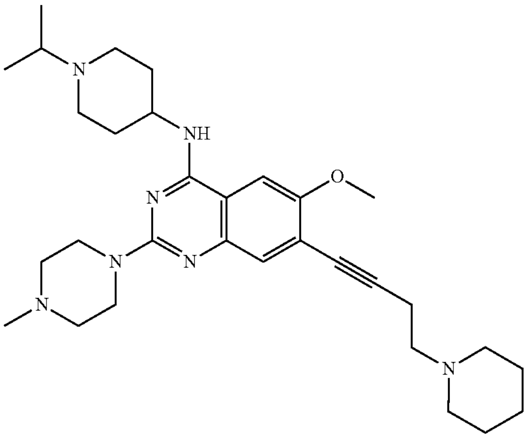 [SMILES: COc1cc2c(NC3CCN(C(C)C)CC3)nc(N3CCN(C)CC3)nc2cc1C#CCCN1CCCCC1] |

TABLE 1-continued
| Example | Chemical Formula |
| --- | --- |
| 40 | 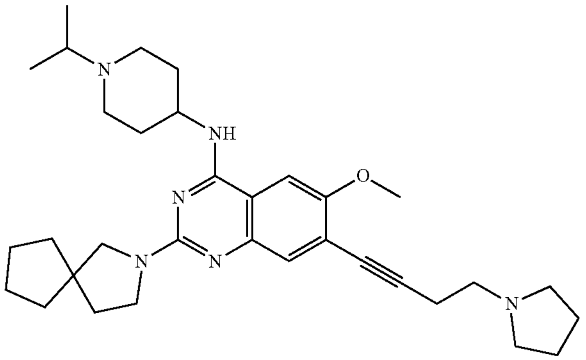 [SMILES: COc1cc2c(NC3CCN(C(C)C)CC3)nc(N3CCC4(CCCC4)C3)nc2cc1C#CCCN1CCCC1] |
| 41 | 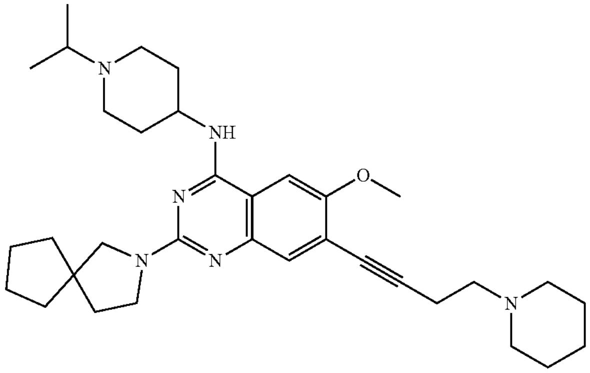 [SMILES: COc1cc2c(NC3CCN(C(C)C)CC3)nc(N3CCC4(CCCC4)C3)nc2cc1C#CCCN1CCCCC1] |
| 42 | 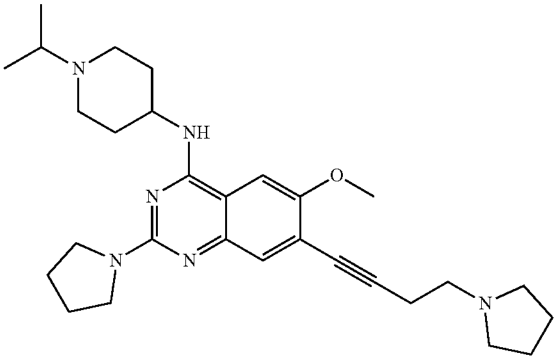 [SMILES: COc1cc2c(NC3CCN(C(C)C)CC3)nc(N3CCCC3)nc2cc1C#CCCN1CCCC1] |
| 43 | 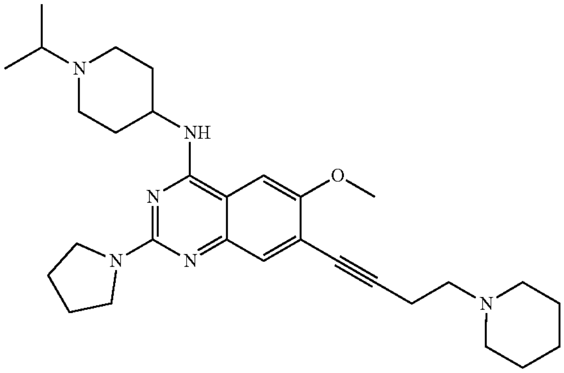 [SMILES: COc1cc2c(NC3CCN(C(C)C)CC3)nc(N3CCCC3)nc2cc1C#CCCN1CCCCC1] |

TABLE 1-continued
| Example | Chemical Formula |
|---|---|
| 44 | 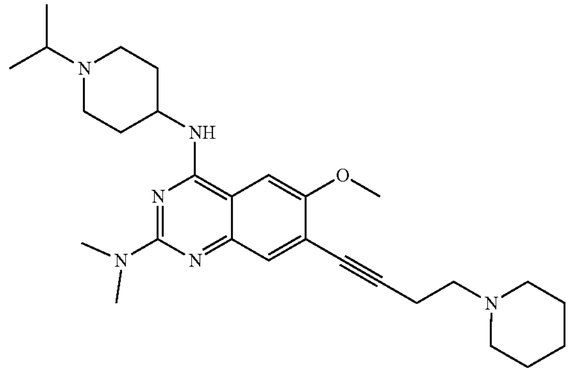 [SMILES: COc1cc2c(NC3CCN(C(C)C)CC3)nc(N(C)C)nc2cc1C#CCCN1CCCCC1] |
| 45 | 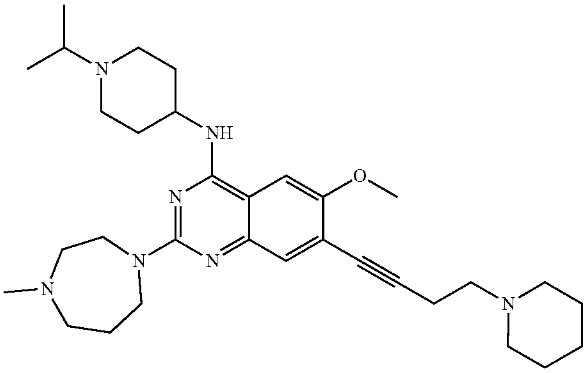 [SMILES: COc1cc2c(NC3CCN(C(C)C)CC3)nc(N3CCCN(C)CC3)nc2cc1C#CCCN1CCCCC1] |
| 46 | 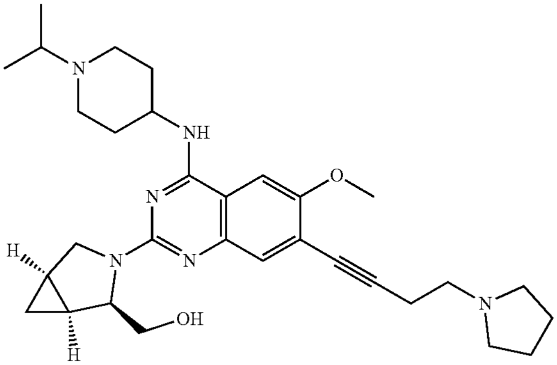 [SMILES: COc1cc2c(NC3CCN(C(C)C)CC3)nc(N3C[C@@H]4C[C@@H]4[C@@H]3CO)nc2cc1C#CCCN1CCCC1] |
| 47 | 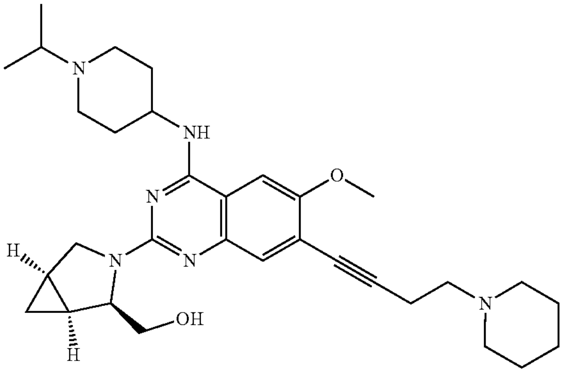 [SMILES: COc1cc2c(NC3CCN(C(C)C)CC3)nc(N3C[C@@H]4C[C@@H]4[C@@H]3CO)nc2cc1C#CCCN1CCCCC1] |

TABLE 1-continued
| Example | Chemical Formula |
| --- | --- |
| 48 | 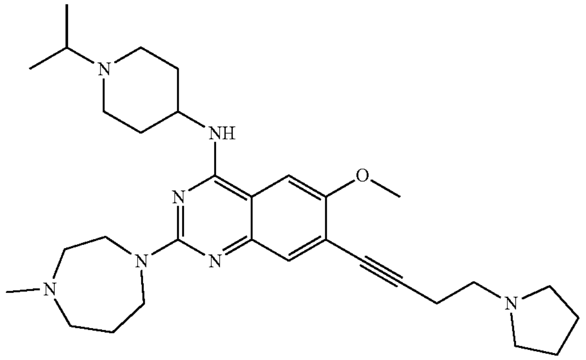 [SMILES: COc1cc2c(NC3CCN(C(C)C)CC3)nc(N3CCCN(C)CC3)nc2cc1C#CCCN1CCCC1] |
| 49 | 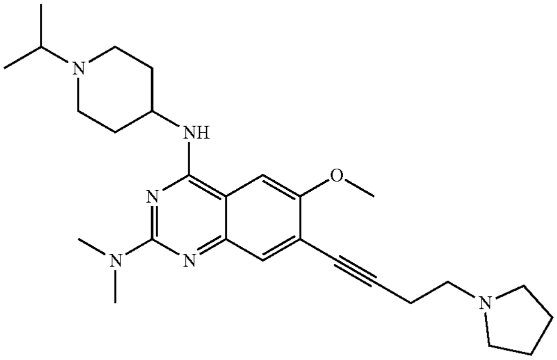 [SMILES: COc1cc2c(NC3CCN(C(C)C)CC3)nc(N(C)C)nc2cc1C#CCCN1CCCC1] |
| 50 | 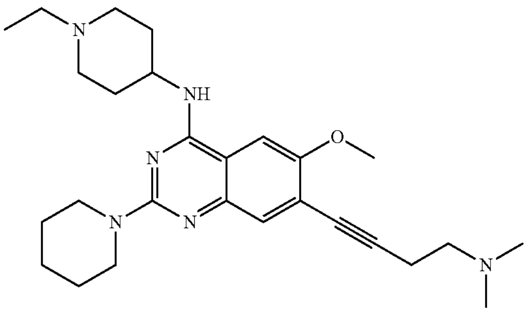 [SMILES: CCN1CCC(Nc2nc(N3CCCCC3)nc3cc(C#CCCN(C)C)c(OC)cc23)CC1] |
| 51 | 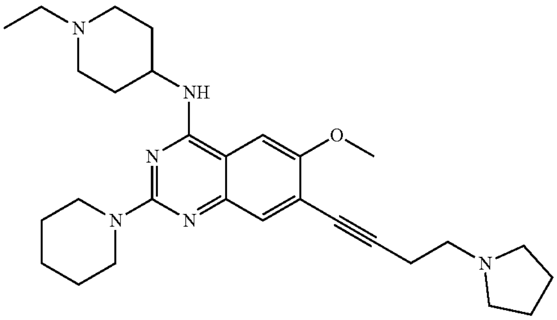 [SMILES: CCN1CCC(Nc2nc(N3CCCCC3)nc3cc(C#CCCN4CCCC4)c(OC)cc23)CC1] |

TABLE 1-continued
| Example | Chemical Formula |
|---|---|
| 52 | 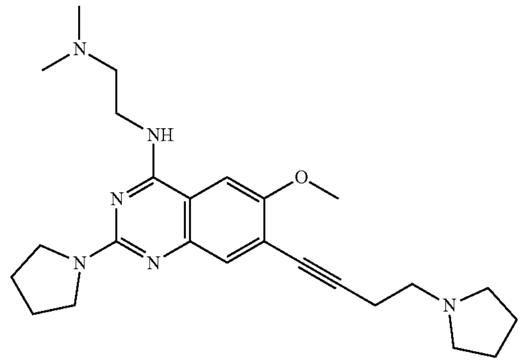 [SMILES: COc1cc2c(NCCN(C)C)nc(N3CCCC3)nc2cc1C#CCCN1CCCC1] |
| 53 | 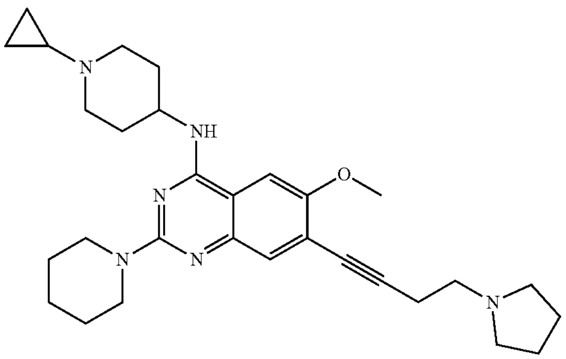 [SMILES: COc1cc2c(NC3CCN(C4CC4)CC3)nc(N3CCCCC3)nc2cc1C#CCCN1CCCC1] |
| 54 | 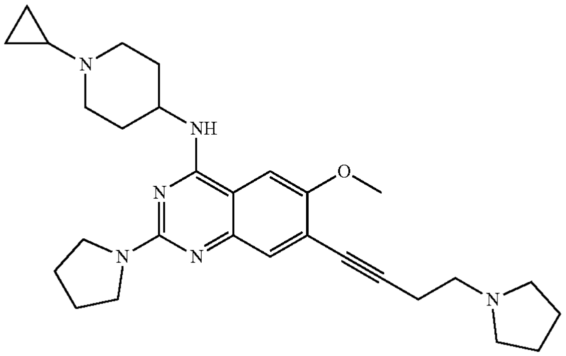 [SMILES: COc1cc2c(NC3CCN(C4CC4)CC3)nc(N3CCCC3)nc2cc1C#CCCN1CCCC1] |
| 55 | 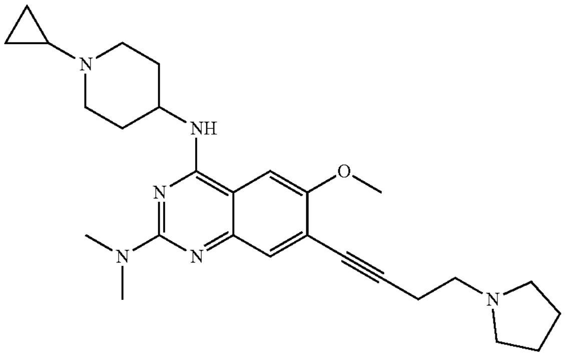 [SMILES: COc1cc2c(NC3CCN(C4CC4)CC3)nc(N(C)C)nc2cc1C#CCCN1CCCC1] |

TABLE 1-continued
| Example | Chemical Formula |
|---|---|
| 56 | 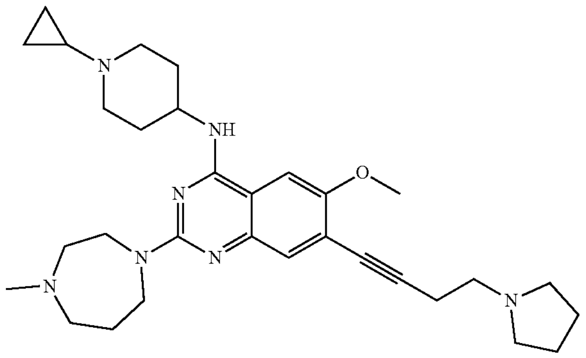 [SMILES: COc1cc2c(NC3CCN(C4CC4)CC3)nc(N3CCCN(C)CC3)nc2cc1C#CCCN1CCCC1] |
| 57 | 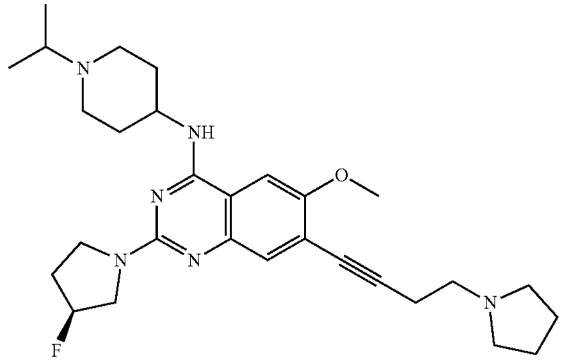 [SMILES: COc1cc2c(NC3CCN(C(C)C)CC3)nc(N3CC[C@H](F)C3)nc2cc1C#CCCN1CCCC1] |
| 58 | 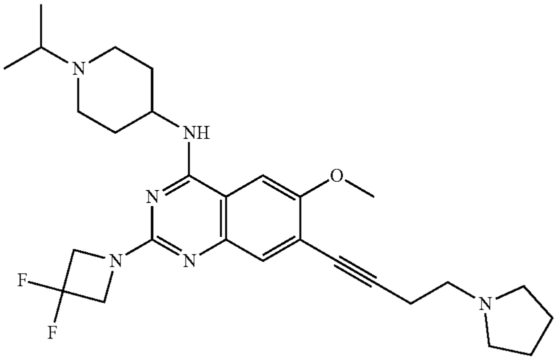 [SMILES: COc1cc2c(NC3CCN(C(C)C)CC3)nc(N3CC(F)(F)C3)nc2cc1C#CCCN1CCCC1] |
| 59 | 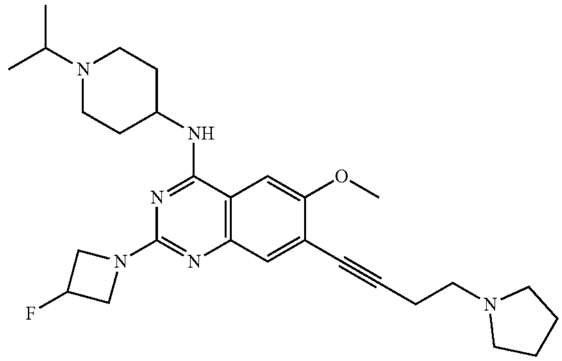 [SMILES: COc1cc2c(NC3CCN(C(C)C)CC3)nc(N3CC(F)C3)nc2cc1C#CCCN1CCCC1] |

TABLE 1-continued
| Example | Chemical Formula |
| --- | --- |
| 60 | 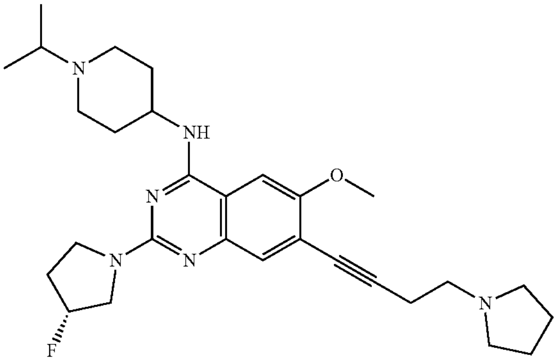 [SMILES: COc1cc2c(NC3CCN(C(C)C)CC3)nc(N3CC[C@@H](F)C3)nc2cc1C#CCCN1CCCC1] |
| 61 | 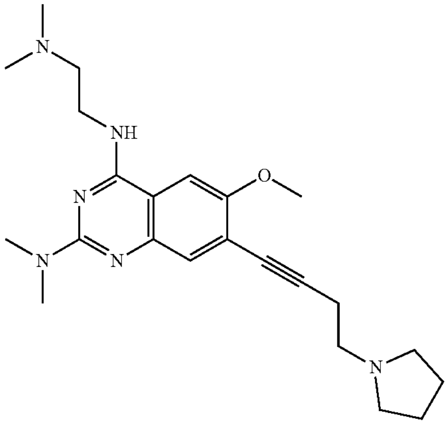 [SMILES: COc1cc2c(NCCN(C)C)nc(N(C)C)nc2cc1C#CCCN1CCCC1] |
| 62 | 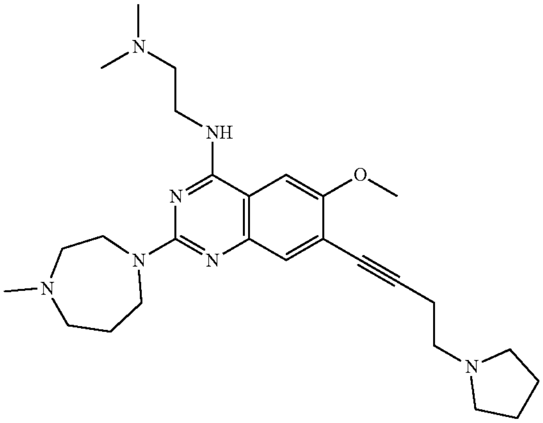 [SMILES: COc1cc2c(NCCN(C)C)nc(N3CCCN(C)CC3)nc2cc1C#CCCN1CCCC1] |
| 63 | 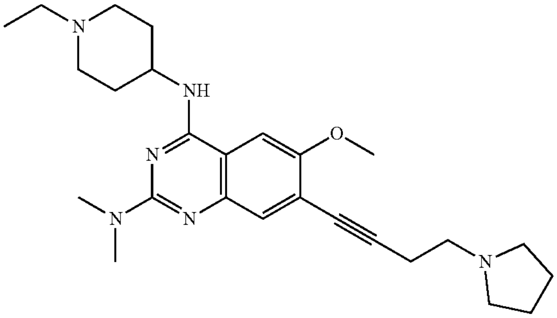 [SMILES: CCN1CCC(Nc2nc(N(C)C)nc3cc(C#CCCN4CCCC4)c(OC)cc23)CC1] |

TABLE 1-continued
| Example | Chemical Formula |
| --- | --- |
| 64 | 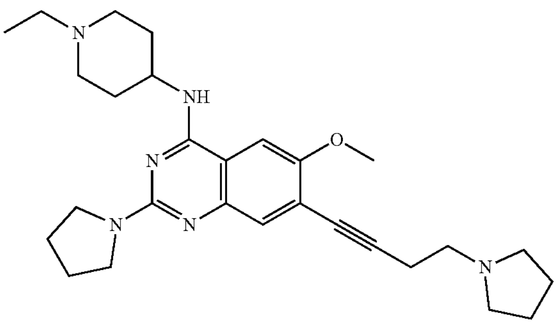 [SMILES: CCN1CCC(Nc2nc(N3CCCC3)nc3cc(C#CCCN4CCCC4)c(OC)cc23)CC1] |
| 65 | 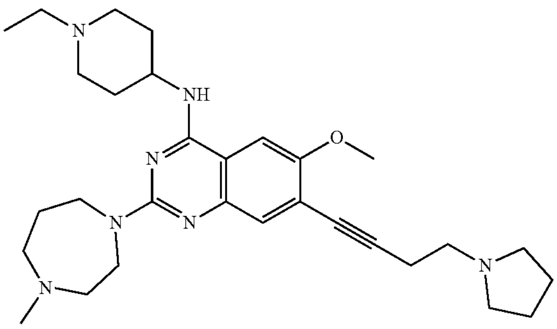 [SMILES: CCN1CCC(Nc2nc(N3CCCN(C)CC3)nc3cc(C#CCCN4CCCC4)c(OC)cc23)CC1] |
| 66 | 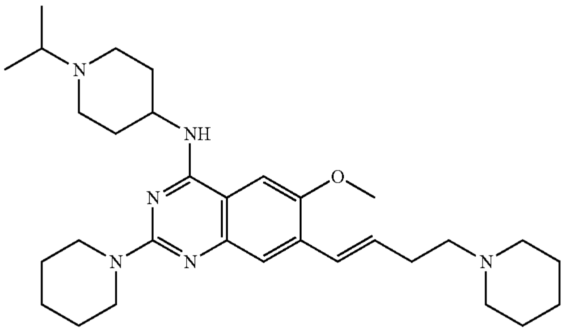 [SMILES: COc1cc2c(NC3CCN(C(C)C)CC3)nc(N3CCCCC3)nc2cc1/C=C/CCN1CCCCC1] |
| 67 | 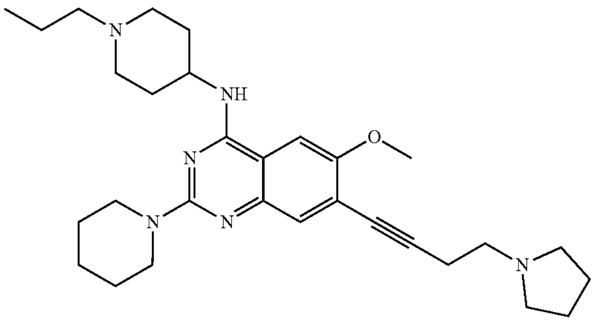 [SMILES: CCCN1CCC(Nc2nc(N3CCCCC3)nc3cc(C#CCCN4CCCC4)c(OC)cc23)CC1] |

TABLE 1-continued
| Example | Chemical Formula |
| --- | --- |
| 68 | 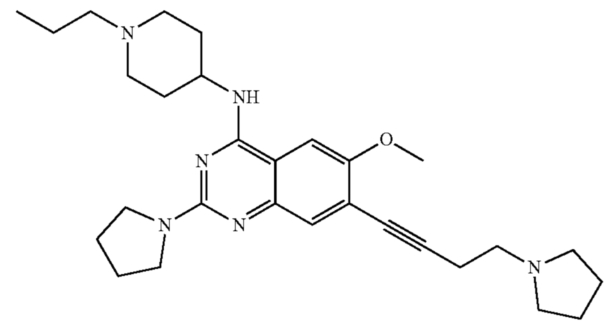 [SMILES: CCCN1CCC(Nc2nc(N3CCCC3)nc3cc(C#CCCN4CCCC4)c(OC)cc23)CC1] |
| 69 | 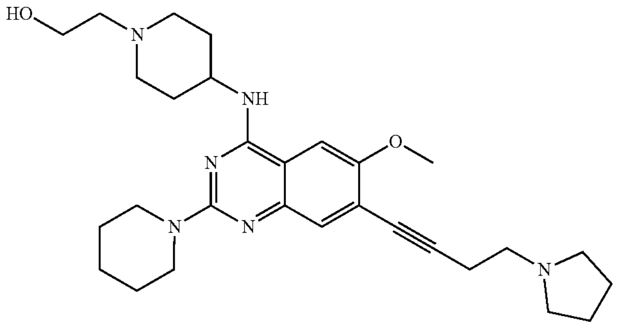 [SMILES: COc1cc2c(NC3CCN(CCO)CC3)nc(N3CCCCC3)nc2cc1C#CCCN1CCCC1] |
| 70 | 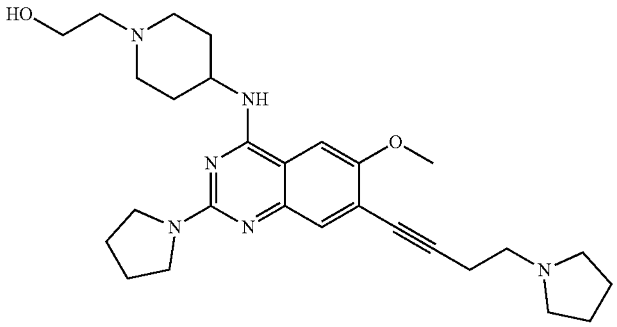 [SMILES: COc1cc2c(NC3CCN(CCO)CC3)nc(N3CCCC3)nc2cc1C#CCCN1CCCC1] |
| 71 | 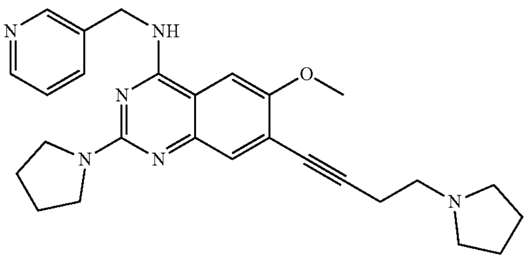 [SMILES: COc1cc2c(NCc3cccnc3)nc(N3CCCC3)nc2cc1C#CCCN1CCCC1] |

TABLE 1-continued
| Example | Chemical Formula |
| --- | --- |
| 72 | 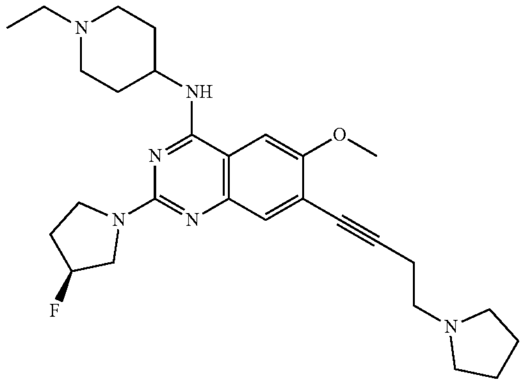 [SMILES: CCN1CCC(Nc2nc(N3CC[C@H](F)C3)nc3cc(C#CCCN4CCCC4)c(OC)cc23)CC1] |
| 73 | 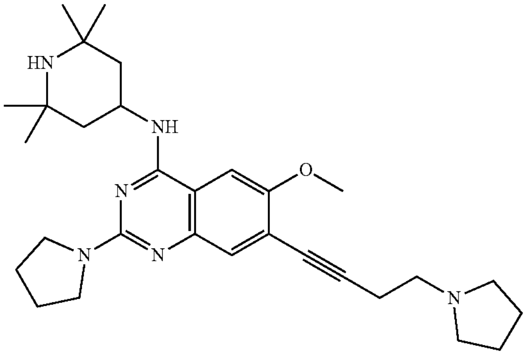 [SMILES: COc1cc2c(NC3CC(C)(C)NC(C)(C)C3)nc(N3CCCC3)nc2cc1C#CCCN1CCCC1] |
| 74 | 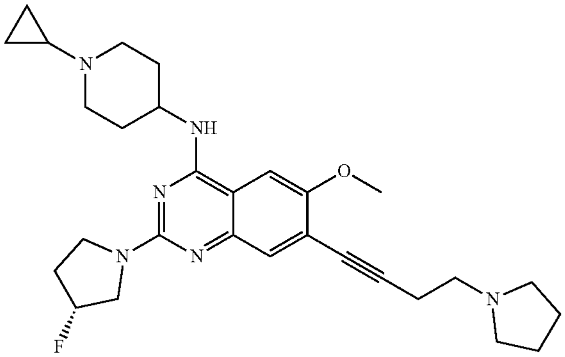 [SMILES: COc1cc2c(NC3CCN(C4CC4)CC3)nc(N3CC[C@@H](F)C3)nc2cc1C#CCCN1CCCC1] |
| 75 | 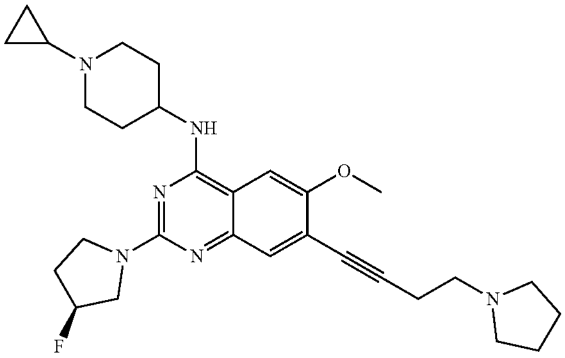 [SMILES: COc1cc2c(NC3CCN(C4CC4)CC3)nc(N3CC[C@H](F)C3)nc2cc1C#CCCN1CCCC1] |

TABLE 1-continued
| Example | Chemical Formula |
|---|---|
| 76 | 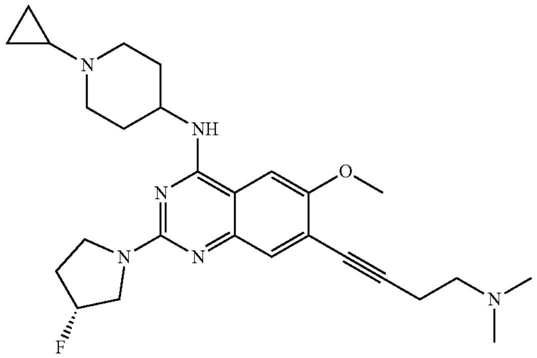 [SMILES: COc1cc2c(NC3CCN(C4CC4)CC3)nc(N3CC[C@@H](F)C3)nc2cc1C#CCCN(C)C] |
| 77 | 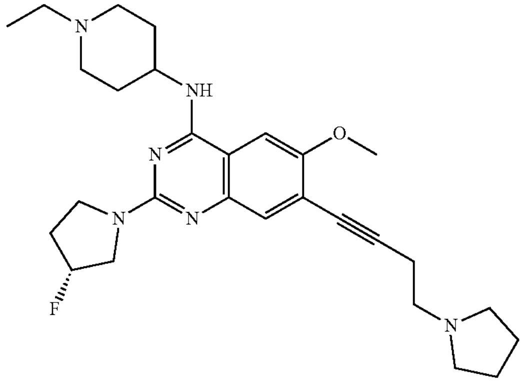 [SMILES: CCN1CCC(Nc2nc(N3CC[C@@H](F)C3)nc3cc(C#CCCN4CCCC4)c(OC)cc23)CC1] |
| 78 | 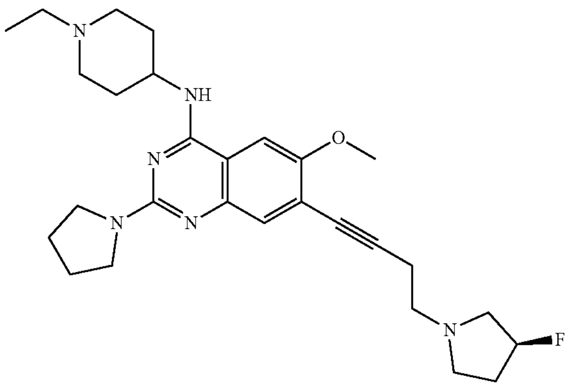 [SMILES: CCN1CCC(Nc2nc(N3CCCC3)nc3cc(C#CCCN4CC[C@H](F)C4)c(OC)cc23)CC1] |
| 79 | 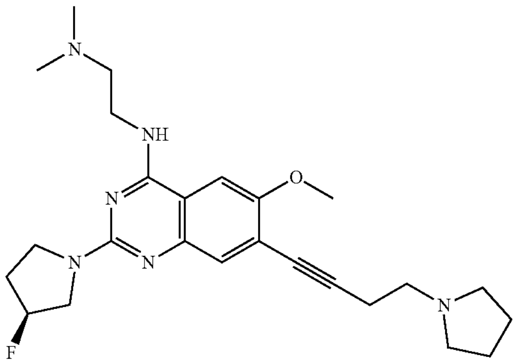 [SMILES: COc1cc2c(NCCN(C)C)nc(N3CC[C@H](F)C3)nc2cc1C#CCCN1CCCC1] |

TABLE 1-continued
| Example | Chemical Formula |
| --- | --- |
| 80 | 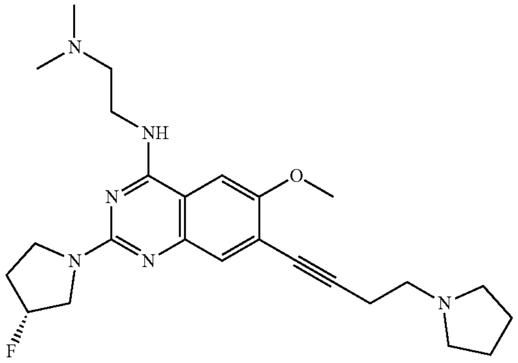 [SMILES: COc1cc2c(NCCN(C)C)nc(N3CC[C@@H](F)C3)nc2cc1C#CCCN1CCCC1] |
| 81 | 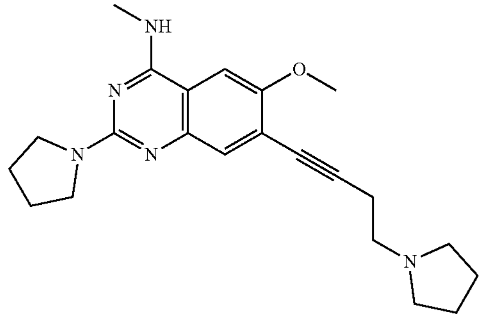 [SMILES: CNc1nc(N2CCCC2)nc2cc(C#CCCN3CCCC3)c(OC)cc12] |
| 82 | 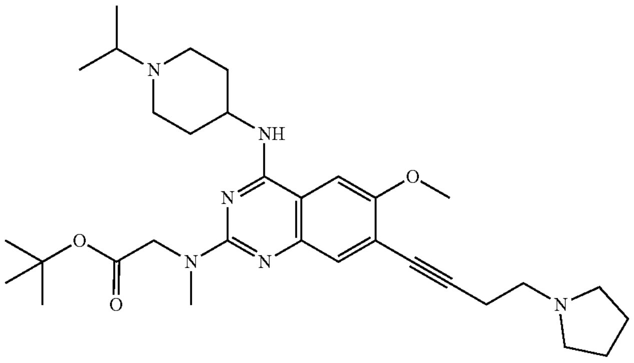 [SMILES: COc1cc2c(NC3CCN(C(C)C)CC3)nc(N(C)CC(=O)OC(C)(C)C)nc2cc1C#CCCN1CCCC1] |
| 83 | 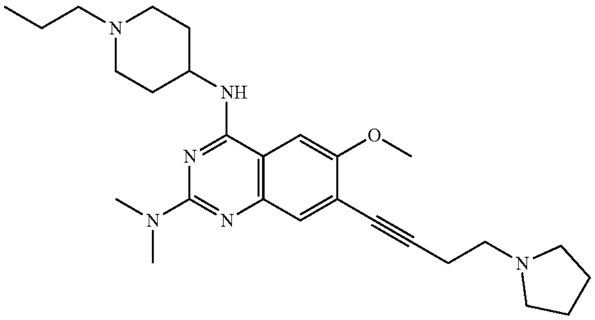 [SMILES: CCCN1CCC(Nc2nc(N(C)C)nc3cc(C#CCCN4CCCC4)c(OC)cc23)CC1] |

TABLE 1-continued
| Example | Chemical Formula |
| --- | --- |
| 84 | 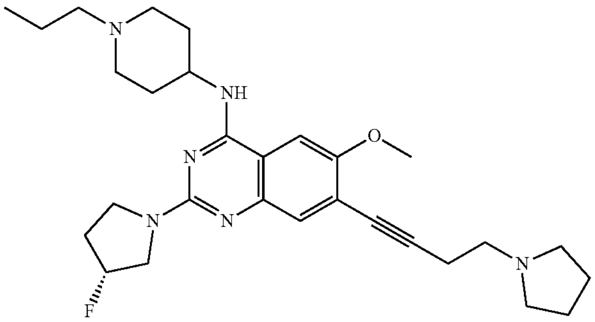 [SMILES: CCCN1CCC(Nc2nc(N3CC[C@@H](F)C3)nc3cc(C#CCCN4CCCC4)c(OC)cc23)CC1] |
| 85 | 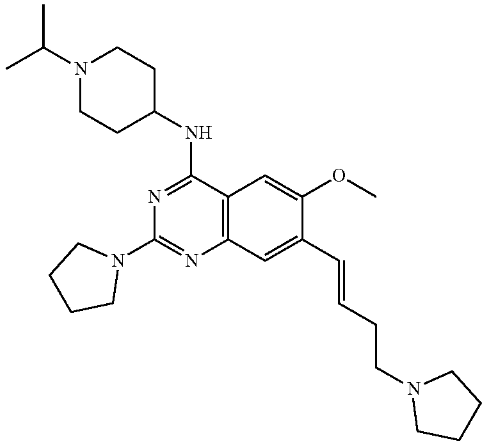 [SMILES: COc1cc2c(NC3CCN(C(C)C)CC3)nc(N3CCCC3)nc2cc1/C=C/CCN1CCCC1] |
| 86 | 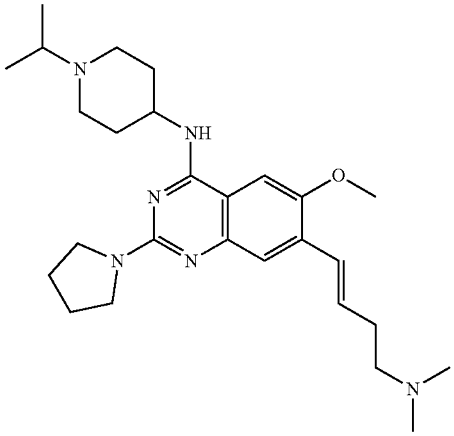 [SMILES: COc1cc2c(NC3CCN(C(C)C)CC3)nc(N3CCCC3)nc2cc1/C=C/CCN(C)C] |
| 87 | 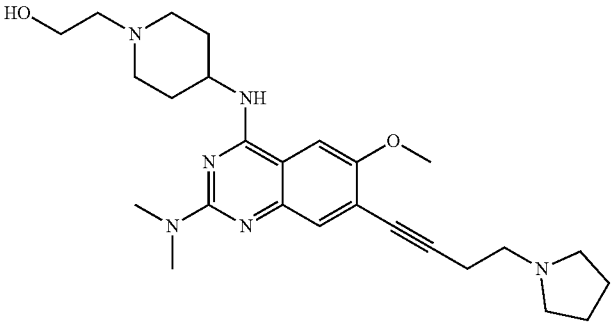 [SMILES: COc1cc2c(NC3CCN(CCO)CC3)nc(N(C)C)nc2cc1C#CCCN1CCCC1] |

TABLE 1-continued

| Example | Chemical Formula |
| --- | --- |
| 88 | 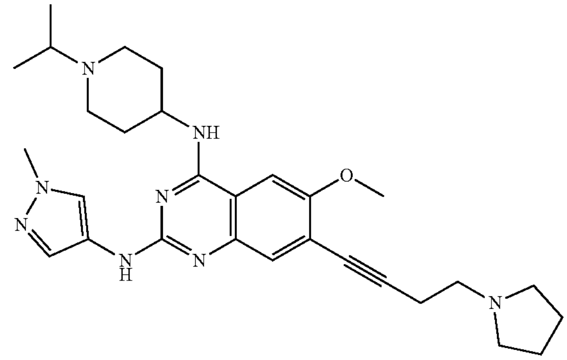 [SMILES: COc1cc2c(NC3CCN(C(C)C)CC3)nc(Nc3cnn(C)c3)nc2cc1C#CCCN1CCCC1] |
| 89 | 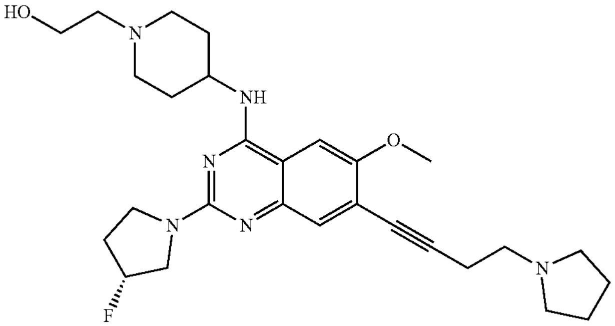 [SMILES: COc1cc2c(NC3CCN(CCO)CC3)nc(N3CC[C@@H](F)C3)nc2cc1C#CCCN1CCCC1] |

<Experimental Example 1> Analysis of Enzyme Inhibitory Efficacy (In Vitro)

In order to analyze the enzyme inhibitory efficacy of the compounds of Examples 1 to 89, EHMT2 (Euchromatic histone-lysine N-methyltransferase 2) enzyme activity was measured using the LANCE TR-FRET™ analysis method of Perkin Elmer. When the EHMT2 enzyme is activated, the $9^{th}$ lysine residue of the biotinylated-histone peptide is methylated and the EU-conjugated antibody is combined to the methylated histone peptide. Then, when the complex is irradiated with light of excitation wavelength, the complex emits light having a wavelength of 665 nm through FRET phenomenon. Accordingly, fluorescence was measured, and $IC_{50}$ values were calculated through a software to evaluate the EHMT2 enzyme activity inhibitory effect of the compounds of Examples 1 to 89.

Specific experimental methods are as follows. First, the compounds of Examples 1 to 89 of 1 nM to 100 μM (4× conc.) were put into a 384 well plate (25 μL/well), and 2 μM EEMT2/G9a enzyme (4× conc.) was put into the 384 well plate (25 μL/well). The plate was then centrifuged at 1,500 rpm for 5 seconds after sealing the plate with plate sealing foil. After incubating the EHMT2/G9a enzyme, SAM, and the compounds of Examples above at room temperature for 10 minutes, 2 μM histone H3 peptide (4× conc.) was added to the 384-well plate (25 μL/well). After sealing the plate with plate sealing foil and centrifuging at 1,500 rpm for 5 seconds, an enzymatic reaction was performed at room temperature for 1 hour. Upon completion of the enzyme reaction, 5 μL each of 200 nM Ulight™-Streptavidin (4× conc.) and 8 nM Eu-antibody (4× conc.) was added to each well of the plate. The plate was sealed with plate sealing foil, centrifuged at 1,500 rpm for 5 seconds and reacted at room temperature for 1 hour. The signal values were measured with Envision (Ex 320 nm, Em 665 nm), and all background values obtained by reacting without enzyme were deleted from the measured raw data values. Then, the EHMT2 enzyme activity inhibitory effect of the compounds of Examples 1 to 89 was converted into % values, and compared with the EHMT2 activity when treated with 4% DMSO vehicle (=0 nM compound) as 100%. $IC_{50}$ values were calculated and shown in Table 2 below.

TABLE 2

| Example | EHMT2 $IC_{50}$ |
| --- | --- |
| 1 | D |
| 2 | D |
| 3 | A |
| 4 | C |
| 5 | D |
| 6 | A |
| 7 | B |
| 8 | A |
| 9 | A |
| 10 | B |
| 11 | C |
| 12 | A |
| 13 | C |
| 14 | A |
| 15 | C |
| 16 | A |
| 17 | A |
| 18 | C |
| 19 | D |
| 20 | C |
| 21 | B |
| 22 | B |
| 23 | D |
| 24 | A |

TABLE 2-continued

| Example | EHMT2 $IC_{50}$ |
|---|---|
| 25 | C |
| 26 | B |
| 27 | B |
| 28 | B |
| 29 | B |
| 30 | B |
| 31 | C |
| 32 | D |
| 33 | D |
| 34 | D |
| 35 | C |
| 36 | A |
| 37 | B |
| 38 | B |
| 39 | C |
| 40 | B |
| 41 | C |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | B |
| 72 | A |
| 73 | A |
| 74 | B |
| 75 | A |
| 76 | C |
| 77 | A |
| 78 | A |
| 79 | B |
| 80 | B |
| 81 | B |
| 82 | A |
| 83 | A |
| 84 | A |
| 85 | A |
| 86 | B |
| 87 | A |
| 88 | B |
| 89 | A |

A: <100 nM
B: 100 nM~1 μM
C: 1 μM~10 μM
D: 10 μM~100 μM

From the above results, it was confirmed that the compounds according to the present invention have excellent inhibitory activity against EHMT2.

<Experimental Example 2> Cancer Cell Growth Inhibition Test (In Vitro)

In order to confirm the effect of reducing cell viability by inhibiting EHMT2 by the compounds of Examples in cells, the effect of inhibiting cancer cell growth was analyzed using CellTiter-glo™ analysis (Promega, cat. G7573) method. Specifically, the amount of ATP in living cells was measured and $IC_{50}$ values were calculated using software to compare the inhibitory effect of the compounds of Examples on cell viability. First, the pancreatic cancer cell line Miapaca 2 was placed in a 96-well cell culture plate at the density of $1\times10^3$ cells/well and cultured overnight, and then each well of the plate was treated with 1 nM to 100 μM of the compounds of Examples 1 to 89 at each concentration for 72 hours (The final concentration of DMSO in each well was 0.5% or less). CellTiter-glo 2.0 reagent was mixed with a medium at 20% of the amount of the medium, reacted at room temperature for 10 minutes, and then 80 μL of the mixture was transferred to each well of a 96-well plate, followed by measuring the degree of luminescence. The results are shown in Table 3 below.

TABLE 3

| Example | MiaPaCa-2 $IC_{50}$ (μM) |
|---|---|
| 3 | 0.655 |
| 14 | 0.338 |
| 42 | 0.304 |
| 49 | 0.333 |
| 52 | 0.464 |
| 55 | 0.307 |
| 56 | 0.192 |
| 60 | 0.669 |

As a result of the above experiment, it was confirmed that the quinazoline-2,4-diamine derivative according to the present invention effectively inhibited EHMT2 and excellently suppressed cancer cell growth.

<Experimental Example 3> Confirmation of Tumor Growth Inhibition Efficacy (In Vivo)

In order to confirm the tumor growth inhibitory effect of the compounds of Examples according to the present invention in a xenograft model in which the human pancreatic cancer cell line was transplanted, a cancer growth inhibition experiment was conducted in the Miapaca2 xenograft model.

Specific experimental methods are as follows. The frozen Miapaca-2 cell line was thawed and cultured in DMEM (Dulbecco's modified Eagle's medium) supplemented with 10% FBS and 1% penicillin-streptomycin in a 37° C., 5% $CO_2$ incubator. The thawed cells were cultured for more than one week, and subcultured at intervals of 2~3 days, confirming that there was no infection with bacteria, yeast (cell image) and mycoplasma. The cells were stained with trypan blue, and those having a survival rate of 90% or more were used for transplantation. The cells were suspended using trypsin-EDTA and then suspended in a cold solution (PBS: matrigel=6:4). Miapaca-2 cells ($4\times10^6$ cells/150 ft) were subcutaneously transplanted under the right scapula of the Athymic nude mouse, which had been acclimated for about 1 week. From the 3rd day after the transplantation, tumor formation and growth were observed, and the volume of the tumor was calculated according to the following equation using the measured tumor length.

[Tumor volume=$(a^2b)/2$, $a$: short diameter, $b$: long diameter]

When the average tumor volume of all mice on the day after tumor transplantation was 80±20 mm3, the mice were grouped by paired-matching. Drugs were dissolved in 40% polyethylene glycol 400+16% 2-hydroxypropyl-b-cyclodextrin. The drugs were intraperitoneally administered at 20 mg/kg once a day for 2 weeks. A tumor growth curve was prepared using the tumor volume from the start date of drug administration to the end of the test. The results are shown in FIG. 1, and the tumor growth inhibition rates of the compounds of Examples to the control group are shown in Table 4.

TABLE 4

| Group | Tumor growth inhibition rate (TGI) (8) |
|---|---|
| Vehicle (n = 5) | 0.00 |
| 20 mg/kg Example 3 (n = 4) | 42.47 |
| 20 mg/kg Example 55 (n = 4) | 31.80 |
| 20 mg/kg Example 52 (n = 4) | 26.39 |

As shown in FIG. 1 and Table 4, it was confirmed that the tumor volume increase rates were low over time when the compounds of Examples of the present invention were treated, compared to the control group. From the above results, it was confirmed that the quinazoline-2,4-diamine derivative according to the present invention has an effect of inhibiting tumor growth in animals.

<Experimental Example 4> Confirmation of Synergistic Efficacy of Combination Therapy with Cancer Immunotherapy Agent (In Vivo)

In order to confirm the synergistic efficacy of the combination therapy of the compounds of Examples of the present invention and a cancer immunotherapy agent (anti CTLA-4) in a syngeneic animal model transplanted with a mouse colorectal cancer cell line, a cancer cell growth inhibition experiment was conducted in the MC38 syngeneic model.

Specific experimental methods are as follows. The frozen MC38 cell line was thawed and cultured in DMEM (Dulbecco's modified Eagle's medium) supplemented with 10% FBS and 1% penicillin-streptomycin in a 37° C., 5% $CO_2$ incubator. The thawed cells were cultured for more than one week, and subcultured at intervals of 2-3 days, confirming that there was no infection with bacteria, yeast (cell image) and mycoplasma. The cells were stained with trypan blue, and those having a survival rate of 90% or more were used for transplantation. The cells were suspended using trypsin-EDTA and then suspended in cold PBS. MC38 cells ($1\times10^5$ cells/150 μl) were subcutaneously transplanted under the right scapula of the C57BL/6 mouse, which had been acclimated for about 1 week. From the 3$^{rd}$ day after the transplantation, tumor formation and growth were observed, and the volume of the tumor was calculated according to the following equation using the measured tumor length.

[Tumor volume=$(a^2b)/2$, $a$: short diameter, $b$: long diameter]

When the average tumor volume of all mice on the day after tumor transplantation was 80±20 mm3, the mice were grouped by paired-matching. Drugs were dissolved in 40% polyethylene glycol 400+16% 2-hydroxypropyl-b-cyclodextrin. The compounds of Examples of the present invention were intraperitoneally administered at 30 mg/kg once a day for 2 weeks, and the CTLA-4 antibody (BioX Cell, cat. BE1031) was intraperitoneally administered at 10 mg/kg three times a week. A tumor growth curve was prepared using the tumor volume from the start date of drug administration to the end of the test. The results are shown in FIG. 2, and the tumor growth inhibition rates of the compounds of Examples to the control group are shown in Table 5.

TABLE 5

| Group | Tumor growth inhibition rate (TGI) (%) |
|---|---|
| Vehicle (n = 7) | 0.00 |
| 30 mg/kg Example 3 (n = 7) | 3.00 |
| 10 mg/kg CTLA-4 (n = 7) | 41.79 |
| 30 mg/kg Example + 10 mg/kg CTLA-4 (n = 7) | 70.12 |

Figure 2:
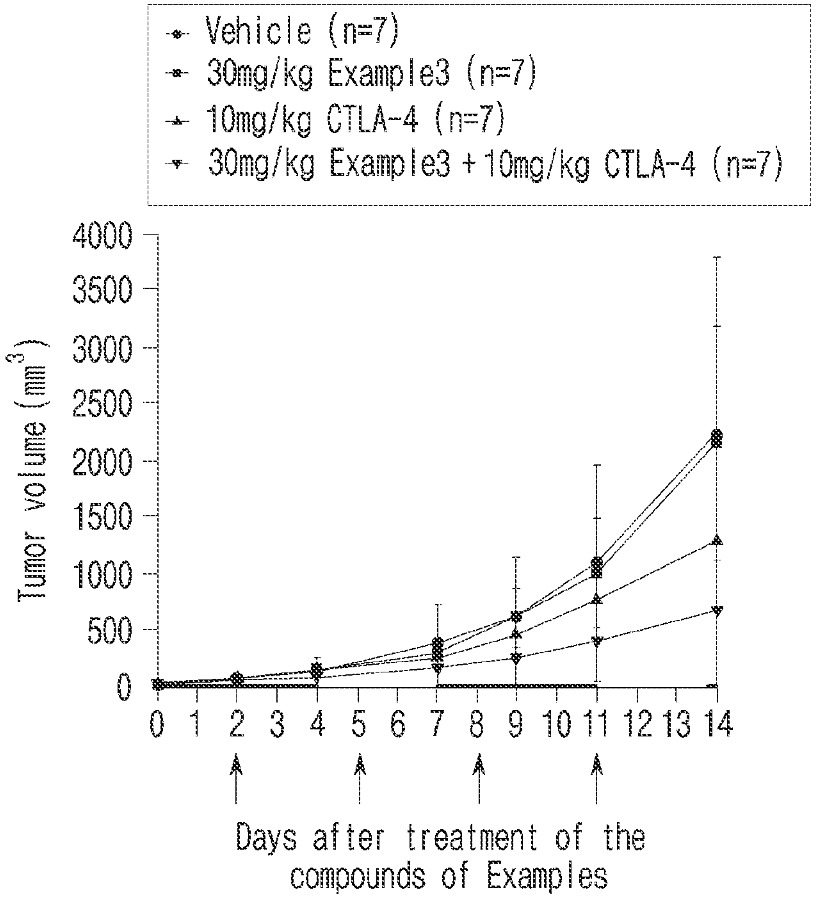
FIG. 2 is a graph showing the results of measuring tumor growth through tumor volume in the case of co-administration of immunotherapeutic agents in the MC38 syngeneic model.

As shown in FIG. 2 and Table 5, it was confirmed that the tumor volume increase rate was lower and the tumor growth inhibition rate was higher when the compounds of Examples of the present invention and the cancer immunotherapy agent (anti CTLA-4) were treated in combination than when the compounds of Examples of the present invention or the cancer immunotherapy agent was treated alone. From the above results, it was confirmed that the combination therapy of the quinazoline-2,4-diamine derivative and the cancer immunotherapy agent had a synergistic effect of inhibiting tumor growth compared to the case of treating each individually.

In particular, the Example compound 3 of the present invention had an anticancer activity that inhibits tumor growth even when treated alone, but had an effect of enhancing the anticancer activity of a cancer immunotherapy agent when treated in combination with a cancer immunotherapy agent. Through this, it can be seen that the quinazoline-2,4-diamine derivative of the present invention can be used as an adjuvant for the cancer immunotherapy agent and enhances the anticancer activity of other anticancer agents, especially cancer immunotherapy agents.

As mentioned above, the present invention has been described in detail through the preferred preparative examples, examples and experimental examples, but the scope of the present invention is not limited to the specific examples, and should be interpreted by the appended claims. In addition, those of ordinary skill in the art should understand that many modifications and variations are possible without departing from the scope of the present invention.

What is claimed is:

1. A compound, a stereoisomer thereof, a hydrate thereof, or a pharmaceutically acceptable salt thereof, wherein the compound is selected from the group consisting of the following compounds:

(3) 7-(4-(dimethylamino)-1-butyne-1-yl)-N-(1-isopropylpiperidine-4-yl)-6-methoxy-2-(piperidine-t-yl)quinazoline-4-amine;

(6) 7-(4-(dimethylamino)-1-butyne-1-yl)-N-(2-isopropylpiperidine-4-yl)-6-methoxy-2-(pyrrolidine-1-yl)quinazoline-4-amine;

(8) 2-(azepane-1-yl)-7-(4-(dimethylamino)-1-butyne-1-yl)-N-(1-isopropylpiperidine-4-yl)-6-methoxyquinazoline-4-amine;

(9) 7-(4-(dimethylamino)-1-butyne-1-yl)-N-(1-isopropylpiperidine-4-yl)-6-methoxy-2-(2-azaspiro[4.4]nonane-2-yl)quinazoline-4-amine;

(12) N-(1-isopropylpiperidine-4-yl)-6-methoxy-2-(piperidine-1-yl)-7-(4-(piperidine-1-yl)-1-butyne-1-yl)quinazoline-4-amine;

(14) 7-(4-(dimethylamino)-1-butyne-1-yl)-N4-(1-isopropylpiperidine-4-yl)-6-methoxy-N2,N2-dimethylquinazoline-2,4-diamine;
(16) N-(1-isopropylpiperidine-4-yl)-6-methoxy-2-(piperidine-1-yl)-7-(4-(pyrrolidine-1-yl)-1-butyne-1-yl) quinazoline-4-amine;
(17) 7-(4-(dimethylamino)-1-butyne-1-yl)-N-(1-isopropylpiperidine-4-yl)-6-methoxy-2-(4-methyl-1,4-diazepane-1-yl)quinazoline-4-amine;
(24) N-(1-cyclopropylpiperidine-4-yl)-7-(4-(dimethylamino)-1-butyne-1-yl)-6-methoxy-2-(piperidine-1-yl) quinazoline-4-amine;
(36) 2-(azepane-1-yl)-N-(1-isopropylpiperidine-4-yl)-6-methoxy-7-(4-(pyrrolidine-1-yl)-1-butyne-1-yl)quinazoline-4-amine;
(42) N-(1-isopropylpiperidine-4-yl)-6-methoxy-2-(pyrrolidine-1-yl)-7-(4-(pyrrolidine-1-yl)-1-butyne-1-yl)quinazoline-4-amine;
(43) N-(1-isopropylpiperidine-4-yl)-6-methoxy-7-(4-(piperidine-1-yl)-1-butyne-1-yl)-2-(pyrrolidine-1-yl)quinazoline-4-amine;
(44) N-(1-isopropylpiperidine-4-yl)-6-methoxy-N2,N2-dimethyl-7-(4-(piperidine-1-yl)-1-butyne-1-yl)quinazoline-2,4-diamine;
(45) N-(1-isopropylpiperidine-4-yl)-6-methoxy-2-(4-methyl1,4-diazepane-1-yl)-7-(4-(piperidine-1-yl)-1-butyne-1-yl)quinazoline-4-amine;
(46) ((1S,2R,5R)-3-(4-((1-isopropylpiperidine-4-yl) amino)-6-methoxy-7-(4-(pyrrolidine-1-yl)-1-butyne-1-yl)quinazoline-2-yl)-3-azabicyclo[3.1.0]hexane-2-yl) methanol;
(47) ((1S,2R,5R)-3-(4-((1-isopropylpiperidine-4-yl) amino)-6-methoxy-7-(4-(piperidine-1-yl)-1-butyne-1-yl)quinazoline-2-yl)-3-azabicyclo[3.1.0]hexane-2-yl) methanol;
(48) N-(1-isopropylpiperidine-4-yl)-6-methoxy-2-(4-methyl-1,4-diazepane-1-yl)-7-(4-(pyrrolidine-1-yl)-1-butyne-1-yl)quinazoline-4-amine;
(49) N4-(1-isopropylpiperidine-4-yl)-6-methoxy-N2,N2-dimethyl-7-(4-(pyrrolidine-1-yl)-1-butyne-1-yl)quinazoline-2,4-diamine;
(50) 7-(4-(dimethylamino)-1-butyne-1-yl)-N-(1-ethylpiperidine-4-yl)-6-methoxy-2-(piperidine-1-yl)quinazoline-4-amine;
(51) N-(1-ethylpiperidine-4-yl)-6-methoxy-2-(piperidine-1-yl)-7-(4-(pyrrolidine-1-yl)-1-butyne-1-yl)quinazoline-4-amine;
(52) N1-(6-methoxy-2-(pyrrolidine-1-yl)-7-(4-(pyrrolidine-1-yl)-1-butyne-1-yl)quinazoline-4-yl)-N2,N2-dimethylethane-1,2-diamine;
(53) N-(1-cyclopropylpiperidine-4-yl)-6-methoxy-2-(piperidine-1-yl)-7-(4-(pyrrolidine-1-yl)-1-butyne-1-yl) quinazoline-4-amine;
(54) N-(1-cyclopropylpiperidine-4-yl)-6-methoxy-2-(pyrrolidine-1-yl)-7-(4-(pyrrolidine-1-yl)-1-butyne-1-yl) quinazoline-4-amine;
(55) N4-(1-cyclopropylpiperidine-4-yl)-6-methoxyN2, N2-dimethyl-7-(4-(pyrrolidine-1-yl)-1-butyne-1-yl) quinazoline-2,4-diamine;
(56) N-(1-cyclopropylpiperidine-4-yl)-6-methoxy-2-(4-methyl-1,4-diazepane-1-yl)-7-(4-(pyrrolidine-1-yl)-1-butyne-1-yl)quinazoline-4-amine;
(57) (S)-2-(3-fluoropyrrolidine-1-yl)-N-(1-isopropylpiperidine-4-yl)-6-methoxy-7-(4-(pyrrolidinel-yl)-1-butyne-1-yl)quinazoline-4-amine;
(58) 2-(3,3-difluoroazetine-1-yl)-N-(1-isopropylpiperidine-4-yl)-6-methoxy-7-(4-(pyrrolidine-1-yl)-1-butyne-1-yl)quinazoline-4-amine;
(59) 2-(3-fluoroazetidine-1-yl)-N-(1-isopropylpiperidine-4-yl)-6-methoxy-7-(4-(pyrrolidine-1-yl)-1-butyne-1-yl)quinazoline-4-amine;
(60) (R)-2-(3-fluoropyrrolidine-1-yl)-N-(1-isopropylpiperidine-4-yl)-6-methoxy-7-(4-(pyrrolidine-1-yl)-1-butyne-1-yl)quinazoline-4-amine;
(61) N4-(2-(dimethylamino)ethyl)-6-methoxy-N2,N2-dimethyl-7-(4-(pyrrolidine-1-yl)-1-butyne-1-yl)quinazoline-2,4-diamine;
(62) N1-(6-methoxy-2-(4-methyl-1,4-diazepane-1-yl)-7-(4-(pyrrolidine-1-yl)-1-butyne-1-yl)quinazoline-4-yl)-N2,N2-dimethylethane-1,2-diamine;
(63) N4-(1-ethylpiperidine-4-yl)-6-methoxy-N2,N2-dimethyl-7-(4-(pyrrolidine-1-yl)-1-butyne-1-yl)quinazoline-2,4-diamine;
(64) N-(1-ethylpiperidine-4-yl)-6-methoxy-2-(pyrrolidine-1-yl)-7-(4-(pyrrolidine-1-yl)-1-butyne-1-yl)quinazoline-4-amine;
(65) N-(1-ethylpiperidine-4-yl)-6-methoxy-2-(4-methyl-1,4-diazepane-1-yl)-7-(4-(pyrrolidine-1-yl)-1-butyne-1-yl)quinazoline-4-amine;
(66) (E)-N-(1-isopropylpiperidine-4-yl)-6-methoxy-2-(piperidine-1-yl)-7-(4-(piperidine-1-yl)-1-butene-1-yl) quinazoline-4-amine;
(67) 6-methoxy-2-(piperidine-1-yl)-N-(1-propylpiperidine-4-yl)-7-(4-(pyrrolidine-1-yl)-1-butyne-1-yl)quinazoline-4-amine;
(68) 6-methoxy-N-(1-propylpiperidine-4-yl)-2-(pyrrolidine-1-yl)-7-(4-(pyrrolidine-1-yl)-1-butyne-1-yl)quinazoline-4-amine;
(69) 2-(4-((6-methoxy-2-(piperidine-1-yl)-7-(4-(pyrrolidine-1-yl)-1-butyne-1-yl)quinazoline-4-yl)amino)piperidine-1-yl)ethanol;
(70) 2-(4-((6-methoxy-2-(pyrrolidine-1-yl)-7-(4-(pyrrolidine-1-yl)-1-butyne-1-yl)quinazoline-4-yl)amino)piperidine-1-yl)ethanol;
(72) (S)—N-(1-ethylpiperidine-4-yl)-2-(3-fluoropyrrolidine-1-yl)-6-methoxy-7-(4-(pyrrolidine-1-yl)-1-butyne-1-yl)quinazoline-4-amine;
(73) 6-methoxy-2-(pyrrolidine-1-yl)-7-(4-(pyrrolidine-1-yl)-1-butyne-1-yl)-N-(2,2,6,6-tetramethylpiperidine-4-yl)quinazoline-4-amine;
(75) (S)—N-(1-cyclopropylpiperidine-4-yl)-2-(3-fluoropyrrolidine-1-yl)-6-methoxy-7-(4-(pyrrolidine-1-yl)-1-butyne-1-yl)quinazoline-4-amine;
(77) (R)—N-(1-ethylpiperidine-4-yl)-2-(3-fluoropyrrolidine-1-yl)-6-methoxy-7-(4-(pyrrolidine-1-yl)-1-butyne-1-yl)quinazoline-4-amine;
(78) (S)—N-(1-ethylpiperidine-4-yl)-7-(4-(3-fluoropyrrolidine-1-yl)-1-butyne-1-yl)-6-methoxy-2-(pyrrolidine-1-yl)quinazoline-4-amine;
(82) tert-butyl 2-((4-((1-isopropylpiperidine-4-yl)amino)-6-methoxy-7-(4-(pyrrolidine-1-yl)-1-butyne-1-yl)quinazoline-2-yl)(methyl)amino)acetate;
(83) 6-methoxy-N2,N2-dimethyl-N4-(1-propylpiperidine-4-yl)-7-(4-(pyrrolidine-1-yl)-1-butyne-1-yl)quinazoline-2,4-diamine;
(84) (R)-2-(3-fluoropyrrolidine-1-yl)-6-methoxy-N-(1-propylpiperidine-4-yl)-7-(4-(pyrrolidine-1-yl)-1-butyne-1-yl)quinazoline-4-amine;
(85) (E)-N-(1-isopropylpiperidine-4-yl)-6-methoxy-2-(pyrrolidine-1-yl)-7-(4-(pyrrolidine-1-yl)-1-butene-1-yl)quinazoline-4-amine;

(87) 2-(4-((2-(dimethylamino)-6-methoxy-7-(4-(pyrrolidine-1-yl)-1-butyne-1-yl)quinazoline-4-yl)amino)piperidine-1-yl)ethanol;

and

(89) (R)-2-(4-((2-(3-(fluoropyrrolidine-1-yl)-6-methoxy-7-(4-(pyrrolidine-1-yl)-1-butyne-1-yl)quinazoline-4-yl)amino)piperidine-1-yl)ethanol.

2. A method of preparing the compound of claim 1 comprising a step of preparing a compound represented by formula 1 by reacting a compound represented by formula 2, as shown in reaction formula 1 below, wherein the compound represented by formula 1 is the compound of claim 1:

[Reaction Formula 1]

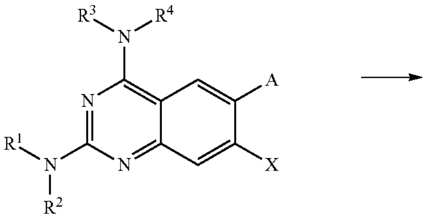

2

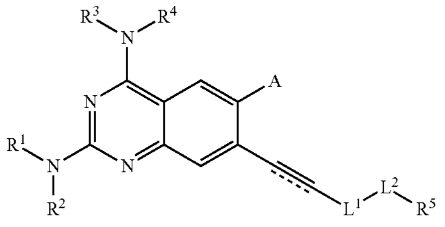

1 wherein:

$\equiv$ is a double bond or a triple bond;

$R^1$ and $R^2$ are independently selected from the group consisting of hydrogen, straight or branched $C_{1-10}$ alkyl, straight or branched $C_{1-10}$ alkoxycarbonyl, straight or branched $C_{1-5}$ alkyl, and nonsubstituted or substituted 3-8 membered heteroaryl containing one or more heteroatoms selected from the group consisting of N, O and S, or $R^1$ and $R^2$ form, together with the nitrogen atom to which they are attached, 3-12 membered nonsubstituted or substituted heterocycloalkyl optionally containing one or more additional heteroatoms selected from the group consisting of N, O and S;

$R^3$ is selected from the group consisting of hydrogen, straight or branched $C_{1-10}$ alkyl, nonsubstituted or substituted $C_{3-10}$ cycloalkyl, nonsubstituted or substituted 3-10 membered heterocycloalkyl containing one or more heteroatoms selected from the group consisting of N, O and S, nonsubstituted or substituted 3-10 membered heterocycloalkyl straight or branched $C_{1-5}$ alkyl containing one or more heteroatoms selected from the group consisting of N, O and S, straight or branched di$C_{1-5}$alkylamino straight or branched $C_{1-5}$ alkyl, and nonsubstituted or substituted 3-8 membered heteroaryl straight or branched $C_{1-5}$ alkyl containing one or more heteroatoms selected from the group consisting of N, O and S;

$R^4$ is selected from the group consisting of hydrogen, and straight or branched $C_{1-5}$ alkyl;

$R^5$ is selected from the group consisting of straight or branched di$C_{1-5}$alkylamino, and nonsubstituted or substituted 3-10 membered heterocycloalkyl containing one or more heteroatoms selected from the group consisting of N, O and S;

wherein each of the substituted heterocycloalkyl, cycloalkyl or heteroaryl is substituted with one or more substituents selected from the group consisting of —OH, —$NH_2$, —$NO_2$, halogen, straight or branched $C_{1-10}$ alkyl, straight or branched $C_{1-5}$ alkoxy, straight or branched di$C_{1-5}$alkylamino, straight or branched $C_{1-5}$ haloalkyl, straight or branched $C_{1-5}$ aminoalkyl, $C_{3-8}$ cycloalkyl, $C_{6-10}$ aryl, $C_{6-8}$ aryl straight or branched $C_{1-3}$ alkyl, and straight or branched $C_{1-5}$ hydroxyalkyl;

A is selected from the group consisting of hydrogen, and straight or branched $C_{1-5}$ alkoxy;

$L^1$ is straight or branched $C_{1-5}$ alkyl; and $L^2$ is selected from the group consisting of a bond, —C(=O)—, or —$SO_2$—; and X is halogen.

3. A pharmaceutical composition for use in preventing or treating cancer comprising the compound of claim 1, the stereoisomer thereof, the hydrate thereof, or the pharmaceutically acceptable salt thereof as an active ingredient.

4. The pharmaceutical composition according to claim 3, wherein the compound inhibits HMT (histone methyl transferase).

5. The pharmaceutical composition according to claim 4, wherein the HMT is EHMT1 (euchromatic histone-lysine N-methyltransferase 1) or EHMT2 (euchromatic histone-lysine N-methyltransferase 2).

6. The pharmaceutical composition according to claim 3, wherein the compound inhibits the growth of cancer cells.

7. The pharmaceutical composition according to claim 3, wherein the cancer is at least one selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myeloid leukemia, acute lymphocytic leukemia, basal cell carcinoma, ovarian epithelial cancer, ovarian germ cell carcinoma, male breast cancer, brain cancer, pituitary adenoma, multiple myeloma, gallbladder cancer, biliary tract cancer, colorectal cancer, chronic myeloid leukemia, chronic lymphocytic leukemia, retinoblastoma, choroidal melanoma, ampullar of vater cancer, bladder cancer, peritoneal cancer, parathyroid cancer, adrenal cancer, rhinosinus cancer, non-small cell lung cancer, tongue cancer, astrocytoma, small cell lung cancer, pediatric brain cancer, childhood lymphoma, childhood leukemia, small intestine cancer, meningioma, esophageal cancer, glioma, renal pelvis cancer, kidney cancer, heart cancer, duodenal cancer, malignant soft tissue cancer, malignant bone cancer, malignant lymphoma, malignant mesothelioma, malignant melanoma, eye cancer, vulvar cancer, ureter cancer, urethral cancer, cancer of unknown primary site, gastric lymphoma, stomach cancer, gastric carcinoid tumor, gastrointestinal interstitial cancer, Wilms' cancer, breast cancer, sarcoma, penile cancer, pharynx cancer, choriocarcinoma of pregnancy, cervical cancer, endometrial cancer, uterine sarcoma, prostate cancer, metastatic bone cancer, metastatic brain cancer, mediastinum cancer, rectal cancer, rectal carcinoid tumor, vaginal cancer, spinal cord cancer, vestibular schwannoma, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleura cancer, and thymus cancer.

8. A health functional food composition for use in preventing or ameliorating cancer comprising the compound of claim 1, the stereoisomer thereof, the hydrate thereof, or the pharmaceutically acceptable salt thereof as an active ingredient.

9. An anticancer adjuvant comprising the compound of claim 1, the stereoisomer thereof, the hydrate thereof, or the pharmaceutically acceptable salt thereof as an active ingredient.

10. The anticancer adjuvant according to claim 9, wherein the compound enhances the anticancer activity of other anticancer agent.

11. An anticancer combination drug comprising the compound of claim 1, the stereoisomer thereof, the hydrate thereof, or the pharmaceutically acceptable salt thereof; and other anticancer agent as active ingredients.

12. The anticancer combination drug according to claim 11, wherein the other anticancer agent is a cancer immunotherapy agent.

13. The anticancer combination drug according to claim 11, wherein the cancer immunotherapy agent is an antibody as an immune checkpoint inhibitor.

14. A method for treating cancer comprising a step of administering the compound of claim 1, the stereoisomer thereof, the hydrate thereof, or the pharmaceutically acceptable salt thereof to an individual or a subject in need thereof.

* * * * *